US009416368B2

(12) United States Patent
Broglie et al.

(10) Patent No.: US 9,416,368 B2
(45) Date of Patent: Aug. 16, 2016

(54) **IDENTIFICATION OF *P. PACHYRHIZI* PROTEIN EFFECTORS AND THEIR USE IN PRODUCING ASIAN SOYBEAN RUST (ASR) RESISTANT PLANTS**

(71) Applicant: E.I. du PONT de NEMOURS and COMPANY, Wilmington, DE (US)

(72) Inventors: Karen E. Broglie, Landenberg, PA (US); Gregory J. Rairdan, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 605 days.

(21) Appl. No.: 13/798,408

(22) Filed: Mar. 13, 2013

(65) Prior Publication Data

US 2014/0283207 A1 Sep. 18, 2014

(51) Int. Cl.
*C12N 15/82* (2006.01)
*C07K 14/37* (2006.01)

(52) U.S. Cl.
CPC ............ *C12N 15/8282* (2013.01); *C07K 14/37* (2013.01)

(58) Field of Classification Search
CPC ........... C12N 15/8279; C12N 15/8282; C12N 15/8216
See application file for complete search history.

(56) References Cited

U.S. PATENT DOCUMENTS

2009/0276922 A1* 11/2009 Fincher ............. C12N 15/8261 800/298

FOREIGN PATENT DOCUMENTS

| | | | |
|---|---|---|---|
| WO | 2007/016680 | A2 | 2/2007 |
| WO | 2008/017706 | A1 | 2/2008 |
| WO | 2011/137414 | A2 | 11/2011 |
| WO | 2013/001435 | A1 | 1/2013 |

OTHER PUBLICATIONS

Stone, Christine L. et al; "Gene expression and proteomic analysis of the formation of *Phakopsora pachyrhizi* appressoria", BMC Genomics, vol. 13 : p. 280 (2012).
Luster, Douglas G. et al; "Proteomic analysis of germinating urediniospores of *Phakopsora pachyrhizi*, causal agent of Asian soybean rust," Protemics, vol. 10, No. 19: pgs. 3549-3557 (2010).
Luster, Douglas G. et al; "Novel *Phakopsora pachyrhizi* Extracellular Proteins Are Ideal Targets for Immunological Diagnostic Assays," Applied and Enviromental Microbiology, vol. 78, No. 11: pp. 3890-3895 (2012).
Wang, Yun et al, "Proteomic Analysis of Differnetially Expressed Proteins in Resistant Soybean Leaves after *Phakospora pachyrhizi* Infection", Journal of Phytopathology, vol. 160, No. 10: pp. 554-560 (2012).
Fang, Zhiwei D. et al; "Combinatorially Selected Peptides for Protection of Soybean Against *PHakopsora pachyrihizi*", Phytopathology, vol. 100, No. 10: pp. 1111-1117 (2010).
International Search Report and Written Opinion for PCT/US2014/024286 mailed on Oct. 13, 2014.

* cited by examiner

*Primary Examiner* — Russell Kallis
*Assistant Examiner* — Weihua Fan
(74) *Attorney, Agent, or Firm* — Pioneer Hi-Bred Int'l

(57) ABSTRACT

The invention relates to novel nucleic acids and their encoded polypeptides from ASR and methods of use that enhance the plant's defensive elicitation response.

4 Claims, No Drawings

IDENTIFICATION OF *P. PACHYRHIZI* PROTEIN EFFECTORS AND THEIR USE IN PRODUCING ASIAN SOYBEAN RUST (ASR) RESISTANT PLANTS

FIELD OF THE INVENTION

This invention relates to the field of plant biotechnology, specifically resistance to Asian Soy Rust.

BACKGROUND OF THE INVENTION

Asian soybean rust (ASR) is a serious disease caused by the fungus *Phakopsora pachyrhizi*. Soybean rust is spread by windblown spores and has caused significant crop losses in many soybean-growing regions of the world. On Nov. 10, 2004 USDA's Animal and Plant Health Inspection Service (APHIS) announced the first confirmation of Asian soybean rust in the continental United States (Louisiana), followed by finds in 8 additional southern states. In 2005, soybean rust was confirmed on soybeans in 29 counties in Georgia, 23 counties in South Carolina, 21 counties in Alabama, 18 counties in North Carolina, 12 counties in Florida, 2 counties in Mississippi, and one county in Louisiana.

Crop loss estimates range from 10-90% of infested fields depending on the growing region, time of epidemic initiation, and environmental conditions. There are currently no commercial soybeans resistant to ASR.

Thus, there is a continuing need for compositions and methods for conferring resistance to Asian Soy Rust.

DETAILED DESCRIPTION OF THE INVENTION

Disease in plants is caused by biotic and abiotic causes. Biotic causes include fungi, viruses, bacteria, and nematodes. An example of the importance of plant disease is illustrated by phytopathogenic fungi, which cause significant annual crop yield losses as well as devastating epidemics. Plant disease outbreaks have resulted in catastrophic crop failures that have triggered famines and caused major social change. All of the approximately 300,000 species of flowering plants are attacked by pathogenic fungi; however, a single plant species can be host to only a few fungal species, and similarly, most fungi usually have a limited host range. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Molecular methods of crop protection have the potential to implement novel mechanisms for disease resistance and can also be implemented more quickly than traditional breeding methods. Accordingly, molecular methods are needed to supplement traditional breeding methods to protect plants from pathogen attack.

A host of cellular processes enable plants to defend themselves against diseases caused by pathogenic agents. These defense mechanisms are activated by initial pathogen infection in a process known as elicitation. In elicitation, the host plant recognizes a pathogen-derived compound known as an elicitor; the plant then activates disease gene expression to limit further spread of the invading organism. It is generally believed that to overcome these plant defense mechanisms, plant pathogens must find a way to suppress elicitation as well as to overcome more physically-based barriers to infection, such as reinforcement of the plant cell wall and/or rearrangement of the actin filament networks near the cell's plasma membrane.

Thus, the present invention solves the need for enhancement of the plant's defensive elicitation response via a molecularly based mechanism which can be quickly incorporated into commercial crops.

Pathogens secrete protein molecules that are either localized to the plant apoplast or are taken up into the plant cell. These proteins, termed effectors, can have either an avirulence or virulence function. In the former case, recognition by the cognate plant R protein activates host defense responses, ultimately leading to programmed cell death and resistance to the pathogen.

The virulence activity of effectors is associated with the manipulation of normal host cell functions or the suppression of host defense responses by the pathogen in order to establish successful infection.

Major gene resistance which relies on the gene-for-gene relationship between pathogen avirulence and plant resistance genes, has been widely used in breeding approaches. However, such resistance is typically race-specific and easily overcome by single mutations in the pathogen avr gene as a consequence of diversifying selection to avoid recognition by the host. Thus the durability of such qualitative resistance is of concern. Attempts have been made to introduce novel antimicrobial/antifungal genes or to modify expression of endogenous defense-related genes in transgenic plants. However, in many cases, the effect is partial and comes at a cost to plant yield and or vigor.

In the present invention, the resistance strategy is focused on the inactivation of pathogen molecules that are essential to establishment of Asian soybean rust infection. Different approaches are being taken to inhibit the activity of these critical soy rust molecules, termed "effectors". Random high throughput screening of phage display or peptide antibody libraries may be performed to identify short sequences that bind the fungal effector and block its functional activity. These may be high affinity peptide sequences that prevent interaction of the effector with its host target.

Alternatively, sequences identified through this approach may exhibit tight binding with effector moieties that specify uptake into host cells. In the latter case inhibition would derive from blocking entry of pathogen factors into the host cell, while in the former, effectors that are delivered into the host cytoplasm are prevented from interacting with and interfering with host target proteins. High affinity, inhibitory peptides may be over-expressed in transgenic plants and their effectiveness tested in ASR disease assays.

In a second approach, effector inhibitors may be designed based upon the targets of those pathogen molecules. Host targets may first be identified by yeast-2-hybrid screens, and then variants generated that exhibit altered effector binding activity. Of particular interest may be host target variants that fail to bind effector, but retain normal activity in the plant, or variants with significantly enhanced binding affinity that prevent interaction of the effector with the native target. The native target and the variants may be overexpressed in transgenic plants and the sensitivity to rust infection evaluated in comparison to wild type plants.

It is expected that through such approaches, it may be possible to inactivate several pathogen effectors and thus to interfere with the ability of the pathogen to infect soybean. Such a strategy can be used alone or in combination with other strategies to produce transgenic Asian soybean rust resistant plants.

These additional strategies include but are no means limited to modified expression of endogenous plant defense molecules or ectopic expression of novel molecules from other plant, microbial or animal sources. These protein molecules can include plant immune receptors such as intracellular NB-LRR proteins or extracellular pattern recognition receptors, or antifungal proteins such as plant or microbial defensins Sequences of *Phakopsora* candidate effectors can be introduced into plants as part of overexpression or silencing constructs. In both cases, in planta expression can provide information about functional activity of the pathogen protein or virulence activity. Overexpression of bacterial or oomycete effectors in plants has been associated with visible phenotypes such as leaf chlorosis, induction of cell death, plant stunting, etc. In planta expression can additionally produce an alteration in plant susceptibility to pathogen infection. In the latter case, enhanced plant resistance might be expected if in planta expression of the pathogen effector leads to elicitation of plant defense responses. Silencing constructs of pathogen genes would be expected to be processed by the plant RNAi machinery to produce small RNA molecules that are taken up by the pathogen, and interact with the RISC complex to target the pathogen mRNA for degradation. Gene silencing and a loss of function phenotype can thus give important clues to the role of the pathogen genes in determining pathogen virulence and infectivity. In addition, down regulation of critical virulence genes can lead to compromised pathogenicity and therefore, increased plant resistance.

The compositions and methods of the invention are useful for modulating the levels of at least one protein in a plant. By “modulate” is defined herein as an increase or decrease in the level of a protein within a genetically altered plant relative to the level of that protein from the corresponding wild-type plant (i.e., a plant not genetically altered in accordance with the methods of the present invention).

The terms “inhibit,” “inhibition,” “inhibiting”, “reduced”, “reduction” and the like as used herein refer to any decrease in the expression or function of a target gene product, including any relative decrease in expression or function up to and including complete abrogation of expression or function of the target gene product. The term “expression” as used herein in the context of a gene product refers to the biosynthesis of that gene product, including the transcription and/or translation of the gene product. Inhibition of expression or function of a target gene product (i.e., a gene product of interest) can be in the context of a comparison between any two plants, for example, expression or function of a target gene product in a genetically altered plant versus the expression or function of that target gene product in a corresponding wild-type plant. Alternatively, inhibition of expression or function of the target gene product can be in the context of a comparison between plant cells, organelles, organs, tissues, or plant parts within the same plant or between plants, and includes comparisons between developmental or temporal stages within the same plant or between plants. Any method or composition that down-regulates expression of a target gene product, either at the level of transcription or translation, or down-regulates functional activity of the target gene product can be used to achieve inhibition of expression or function of the target gene product.

The term “inhibitory sequence” encompasses any polynucleotide or polypeptide sequence that is capable of inhibiting the expression of a target gene product, for example, at the level of transcription or translation, or which is capable of inhibiting the function of a target gene product. Examples of inhibitory sequences include, but are not limited to, full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term “polynucleotide sequence” includes sequences of RNA, DNA, chemically modified nucleic acids, nucleic acid analogs, combinations thereof, and the like.

Methods for inhibiting gene expression are well known in the art. Although any method known in the art for reducing the level of protein in a plant could be used, possible methods for reducing protein include, but are not limited to, homology-dependent gene silencing, antisense technology, co-suppression including, for example, RNA interference (RNAi), micro RNA and the like, site-specific recombination, site-specific integration, mutagenesis including transposon tagging, and biosynthetic competition, homologous recombination, and gene targeting, alone or in combination. Depending upon the intended goal, the level of at least one protein may be increased, decreased, or eliminated entirely as described below.

The invention encompasses isolated or substantially purified nucleic acid or protein compositions. An “isolated” or “purified” nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an “isolated” nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the present invention. By “fragment” is intended a portion of the nucleotide sequence or a portion of the amino acid sequence and hence protein encoded thereby. Fragments of a nucleotide sequence may encode protein fragments that retain the biological activity of the native protein and hence have effector-like activity and thereby affect development, developmental pathways, and defense responses. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

The sequences of the invention are provided in expression cassettes or DNA constructs for expression in the plant of interest. The cassette can include 5' and 3' regulatory sequences operably linked to a sequence of the invention. By "operably linked" a functional linkage between a promoter and a second sequence, wherein the promoter sequence initiates and mediates transcription of the DNA sequence corresponding to the second sequence is intended. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the nucleotide sequence to be under the transcriptional regulation of the regulatory regions. The expression cassette may additionally contain selectable marker genes.

The expression cassette can include in the 5'-3' direction of transcription, a transcriptional and translational initiation region, a DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, native promoter sequences may be used. Such constructs would change expression levels in the host cell (i.e., plant or plant cell). Thus, the phenotype of the host cell (i.e., plant or plant cell) is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acid Res. 15:9627-9639.

Where appropriate, the gene(s) may be optimized for increased expression in the transformed plant. That is, the genes can be synthesized using plant-preferred codons for improved expression. See, for example, Campbell and Gowri (1990) Plant Physiol. 92:1-11 for a discussion of host-preferred codon usage. Methods are available in the art for synthesizing plant-preferred genes. See, for example, U.S. Pat. Nos. 5,380,831, 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy Stein et al. (1989) PNAS USA 86:6126 6130); potyvirus leaders, for example, TEV leader (Tobacco Etch Virus) (Allison et al. (1986); MDMV leader (Maize Dwarf Mosaic Virus); Virology 154:9 20), and human immunoglobulin heavy chain binding protein (BiP), (Macejak et al. (1991) Nature 353:90 94); untranslated leader from the coat protein mRNA of alfalfa mosaic virus (AMV RNA 4) (Jobling et al. (1987) Nature 325:622 625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382 385). See also, Della Cioppa et al. (1987) Plant Physiol. 84:965 968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette can comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, imidazolinones, and 2,4-dichlorophenoxyacetate (2,4-D). See generally, Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Sci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl. Acad. Sci. USA 89:3952-3956; Baim et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985)

Handbook of Experimental Pharmacology, Vol. 78 (Springer-Verlag, Berlin); Gill et al. (1988) Nature 334:721-724. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611, herein incorporated by reference.

Generally, it may be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) Neth. J. Plant Pathol. 89:245-254; Uknes et al. (1992) Plant Cell 4:645-656; and Van Loon (1985) Plant Mol. Virol. 4:111-116. See also WO 99/43819 published Sep. 9, 1999, herein incorporated by reference.

Of interest are promoters that are expressed locally at or near the site of pathogen infection. See, for example, Marineau et al. (1987) Plant Mol. Biol. 9:335-342; Matton et al. (1989) Molecular Plant-Microbe Interactions 2:325-331; Somsisch et al. (1986) Proc. Natl. Acad. Sci. USA 83:2427-2430; Somsisch et al. (1988) Mol. Gen. Genet. 2:93-98; and Yang (1996) Proc. Natl. Acad. Sci. USA 93:14972-14977. See also, Chen et al. (1996) Plant J. 10:955-966; Zhang et al. (1994) Proc. Natl. Acad. Sci. USA 91:2507-2511; Warner et al. (1993) Plant J. 3:191-201; Siebertz et al. (1989) Plant Cell 1:961-968; U.S. Pat. No. 5,750,386 (nematode-inducible); and the references cited therein. Of particular interest is the inducible promoter for the maize PRms gene, whose expression is induced by the pathogen Fusarium moniliforme (see, for example, Cordero et al. (1992) Physiol. Mol. Plant Path. 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) Ann. Rev. Phytopath. 28:425-449; Duan et al. (1996) Nature Biotechnology 14:494-498); wun1 and wun2, U.S. Pat. No. 5,428,148; win1 and win2 (Stanford et al. (1989) Mol. Gen. Genet. 215:200-208); systemin (McGurl et al. (1992) Science 225:1570-1573); WIP1 (Rohmeier et al. (1993) Plant Mol. Biol. 22:783-792; Eckelkamp et al. (1993) FEBS Letters 323:73-76); MPI gene (Corderok et al. (1994) Plant J. 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible and tetracycline-repressible promoters (see, for example, Gatz et al. (1991) Mol. Gen. Genet. 227:229-237, and U.S. Pat. Nos. 5,814,618 and 5,789,156), herein incorporated by reference.

Tissue-preferred promoters can be utilized to target enhanced expression within a particular plant tissue. Tissue-preferred promoters include Yamamoto et al. (1997) Plant J. 12(2):255-265; Kawamata et al. (1997) Plant Cell Physiol. 38(7):792-803; Hansen et al. (1997) Mol. Gen Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol Biol. 23(6):1129-1138; Matsuoka et al. (1993) Proc Natl. Acad. Sci. USA 90(20):9586-9590; and Guevara-Garcia et al. (1993) Plant J. 4(3):495-505. Such promoters can be modified, if necessary, for weak expression.

Leaf-specific promoters are known in the art. See, for example, Yamamoto et al. (1997) Plant J. 12(2):255-265; Kwon et al. (1994) Plant Physiol. 105:357-67; Yamamoto et al. (1994) Plant Cell Physiol. 35(5):773-778; Gotor et al. (1993) Plant J. 3:509-18; Orozco et al. (1993) Plant Mol. Biol. 23(6):1129-1138; and Matsuoka et al. (1993) Proc. Natl. Acad. Sci. USA 90(20):9586-9590.

"Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see WO 00/11177, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection may be employed.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320 334), electroporation (Riggs et al. (1986) Proc. Natl. Acad. Sci. USA 83:5602 5606, Agrobacterium-mediated transformation (Townsend et al., U.S. Pat. No. 5,563,055; Zhao et al., U.S. Pat. No. 5,981,840), direct gene transfer (Paszkowski et al. (1984) EMBO J. 3:2717 2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; McCabe et al. (1988) Biotechnology 6:923 926); and Led transformation (WO 00/28058). Also see Weissinger et al. (1988) Ann. Rev. Genet. 22:421 477; Sanford et al. (1987) Particulate Science and Technology 5:27 37 (onion); Christou et al. (1988) Plant Physiol. 87:671 674 (soybean); McCabe et al. (1988) Bio/Technology 6:923 926 (soybean); Finer and McMullen (1991) In Vitro Cell Dev. Biol. 27P:175-182 (soybean); Singh et al. (1998) Theor. Appl. Genet. 96:319-324 (soybean); Datta et al. (1990) Biotechnology 8:736 740 (rice); Klein et al. (1988) Proc. Natl. Acad. Sci. USA 85:4305 4309 (maize); Klein et al. (1988) Biotechnology 6:559 563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91:440 444 (maize); Fromm et al. (1990) Biotechnology 8:833 839 (maize); Hooykaas-Van Slogteren et al. (1984) Nature (London) 311:763-764; Bowen et al., U.S. Pat. No. 5,736,369 (cereals); Bytebier et al. (1987) Proc. Natl. Acad. Sci. USA 84:5345-5349 (Liliaceae); De Wet et al. (1985) in The Experimental Manipulation of Ovule Tissues, ed. Chapman et al. (Longman, New York), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via Agrobacterium tumefaciens); all of which are herein incorporated by reference.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The present invention may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), *citrus* trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

The following examples are offered by way of illustration and not by way of limitation.

EXAMPLES

Example 1

Effector Identification

To isolate transcripts present in *Phakopsora pachyrhizi* haustoria we harvested infected soy leaves 6 days post inoculation, homogenized them (4C) in buffer (0.3M Sorbitol, 20 mM MOPS, 0.2% PVP, 1 mM, DTT (add fresh), 0.1% BSA, pH 7.2). The homogenate was passed through a 100 um Nytex fliter, then a 25 um Nytex filter. Homogenate was centrifuged (3700 g for 10 mins, 4C). Resuspend pellet in 3 ml buffer (0.3M Sorbitol, 10 mM MOPS, 0.2% BSA, 1 mM CaCl2, 1 mM MnCl2, 0.2% Protect RNA pH 5.4).

Streptavidin-paramagnetic beads which had been pre-incubated with concanavilin A-biotin were added to the suspended homogenate and incubated on ice with rotation for 30 minutes. Beads were captured with a magnetic stand, washed 1× with suspension buffer and then RNA was extracted from haustoria captured on the beads using a standard trizol extraction method.

Total RNA was quantified and a cDNA library was generated from total RNA using the SMART cDNA library kit and protocols (Clontech®).

We obtained 5' sequence reads from these clones and identified clones that contained an open reading frame that encoded a protein predicted to have a signal peptide by the SignalP algorithm. Clones with predicted signal peptides were fully sequenced and the predicted protein sequence was blasted against the NCBI non-redundant protein database. Predicted proteins that appeared to have clear homologs in organisms that were not within the order Pucciniales (Uredinales) were removed from the collection.

To isolate candidate *phakopsora* effector sequences from soy infected with soy rust, we harvested total RNA from three samples using a standard trizol RNA preparation protocol: a soybean plant eight days after inoculation with *Phakopsora pachyrhizi*, a native soybean plant, and germinating *Phakopsora pachyrhizi* spores. Messenger RNAs are isolated using the Qiagen® RNeasy isolation kit for total RNA isolation, followed by mRNA isolation and fragment library construction using the Illumina TruSeq RNA sample preparation kit (Illumina, Inc. San Diego, Calif.). In this method, mRNAs are isolated via oligo dT beads, fragmented, and reverse transcribed into cDNA fragments using random primers. The resulting cDNA fragments are end repaired, 3' A-Tailed, ligated with Illumina TruSeq adapters and amplified using Illumina TruSeq specific primers. PCR products are purified by binding to Ampure XP beads (Beckman Genomics, Danvers, Mass.) and initial library quality is assessed by the Agilent Bioanalyzer DNA 7500 chip. To reduce the presence of abundant cDNAs, the fragment libraries are denatured and reannealed at 68° C. for five hours followed by treatment with Duplex Specific Nuclease (Evrogen, Moscow, Russia) for 25 minutes. Digested libraries are purified with AmpureXP beads (Beckman Coulter Genomics), amplified with Illumina TruSeq primers, and checked for final quality and quantity on the Agilent Bioanalyzer DNA 7500 chip prior to sequencing on the Illumina HiSeq2000.

After Illumina sequencing, reads from the rust-infected soy sample were searched for soy sequences which were subsequently removed. The remaining sequences were assembled into contigs using Velvet and Oasis. This set of contigs represents the *Phakopsora pachyrhizi* transcriptome.

These contigs were screened for open reading frames. These open reading frames were screened for secretory signal peptides using SignalP, and then blasted (blastn and tblastx) against complete NA and protein databases. ORFS that did not have a signal peptide or returned significant similarity to sequences outside of the order Pucciniales were eliminated. The relative abundance of the remaining sequences was compared to their abundance in germinating spores. If the abundance of the transcript was higher in germinating spores, it was regarded as less likely to be a haustoria-associated effector transcript encoding an effector. The ORFs remaining were considered to be strong candidate effectors.

All publications, patents and patent applications mentioned in the specification are indicative of the level of those skilled in the art to which this invention pertains. All publications, patents and patent applications are herein incorporated by reference to the same extent as if each individual publication, patent, or patent application was specifically and individually indicated to be incorporated by reference.

Although the foregoing invention has been described in some detail by way of illustration and example, for purposes of clarity of understanding, it will be obvious that certain changes and modifications may be practiced within the scope of the appended claims.

What is claimed is:

1. An isolated polynucleotide comprising a nucleic acid sequence selected from the group consisting of:

(a) the nucleic acid sequence set forth in SEQ ID NO: 75 or the complement thereof; and, (b) a nucleotide sequence encoding a polypeptide having the amino acid sequence set forth in SEQ ID NO: 76, wherein the polynucleotide is operably linked to a heterologous regulatory element.

2. An expression cassette comprising the isolated polynucleotide of claim 1.

3. A non-human host cell comprising the expression cassette of claim 2.

4. The host cell of claim 3 wherein the cell is a plant cell.

* * * * *

SEQUENCE LISTING

```
<160> NUMBER OF SEQ ID NOS: 378

<210> SEQ ID NO 1
<211> LENGTH: 168
<212> TYPE: DNA
<213> ORGANISM: Phakopsora pachyrhizi
<220> FEATURE:
<221> NAME/KEY: misc_feature
<222> LOCATION: (1)..(168)
<223> OTHER INFORMATION: 01-c18

<400> SEQUENCE: 1

atgatttcca aggttattta caactcgtta tattacctaa atgcttcgat ggtaatggtg      60

gcggtcagtc ttcaaaattc ggcgcttcat aagagagctg tttcaagcag cgagccatgt     120

tgttgcgctg ggtgtggaga gttcctttct caatgttctg ttatctga                  168


<210> SEQ ID NO 2
<211> LENGTH: 55
<212> TYPE: PRT
<213> ORGANISM: Phakopsora pachyrhizi
<220> FEATURE:
<221> NAME/KEY: VARIANT
<222> LOCATION: (1)..(55)
<223> OTHER INFORMATION: 01-e12

<400> SEQUENCE: 2

Met Ile Ser Lys Val Ile Tyr Asn Ser Leu Tyr Tyr Leu Asn Ala Ser
1               5                   10                  15

Met Val Met Val Ala Val Ser Leu Gln Asn Ser Ala Leu His Lys Arg
            20                  25                  30

Ala Val Ser Ser Ser Glu Pro Cys Cys Cys Ala Gly Cys Gly Glu Phe
        35                  40                  45

Leu Ser Gln Cys Ser Val Ile
    50                  55


<210> SEQ ID NO 3
<211> LENGTH: 429
<212> TYPE: DNA
<213> ORGANISM: Phakopsora pachyrhizi
<220> FEATURE:
<221> NAME/KEY: misc_feature
```

<222> LOCATION: (1)..(429)
<223> OTHER INFORMATION: 01-e12

<400> SEQUENCE: 3
atgcatgctg ctaatatgaa agtttcaacc cttatgatag tagtgttaag ttttatccag 60
ctatattctt ttactttatc tcaaatcacc aatgggggca ttacgcagga tccaaatgat 120
aaatacaggg ttcgatgttt agccgactct aaatcagggg atataatttc tgatgactgc 180
tatgattcat tggatgactt ttcccaagat gatggaatta ttaaattcaa tgcaaaagga 240
gaagataatg atgaagactc ttgtaggttg gagttagttg gttatcctaa tcaaatcacc 300
aataatgatg aaatcaaagt gccaaaaaca tctgtgatca gcgcaatcaa ttttggctta 360
gatggctgta aaaattcttc agccatagtt gaagcaacag gctttattct caacatttac 420
aaaaattaa 429

<210> SEQ ID NO 4
<211> LENGTH: 142
<212> TYPE: PRT
<213> ORGANISM: Phakopsora pachyrhizi
<220> FEATURE:
<221> NAME/KEY: VARIANT
<222> LOCATION: (1)..(142)
<223> OTHER INFORMATION: 01-e12

<400> SEQUENCE: 4

Met His Ala Ala Asn Met Lys Val Ser Thr Leu Met Ile Val Val Leu
1 5 10 15

Ser Phe Ile Gln Leu Tyr Ser Phe Thr Leu Ser Gln Ile Thr Asn Gly
20 25 30

Gly Ile Thr Gln Asp Pro Asn Asp Lys Tyr Arg Val Arg Cys Leu Ala
35 40 45

Asp Ser Lys Ser Gly Asp Ile Ile Ser Asp Asp Cys Tyr Asp Ser Leu
50 55 60

Asp Asp Phe Ser Gln Asp Asp Gly Ile Ile Lys Phe Asn Ala Lys Gly
65 70 75 80

Glu Asp Asn Asp Glu Asp Ser Cys Arg Leu Glu Leu Val Gly Tyr Pro
85 90 95

Asn Gln Ile Thr Asn Asn Asp Glu Ile Lys Val Pro Lys Thr Ser Val
100 105 110

Ile Ser Ala Ile Asn Phe Gly Leu Asp Gly Cys Lys Asn Ser Ser Ala
115 120 125

Ile Val Glu Ala Thr Gly Phe Ile Leu Asn Ile Tyr Lys Asn
130 135 140

<210> SEQ ID NO 5
<211> LENGTH: 294
<212> TYPE: DNA
<213> ORGANISM: Phakopsora pachyrhizi
<220> FEATURE:
<221> NAME/KEY: misc_feature
<222> LOCATION: (1)..(294)
<223> OTHER INFORMATION: 02-g20

<400> SEQUENCE: 5
atgaccttct tcaacatgct cctccttctg tggagagtcc gtgtccccag gaaaacctcc 60
aacatcatgt tcatgtccat caaaatgatt ttcaggaaaa ttggcatcct ccaccaaatt 120
gcctgcatca tcttcatcag gcagcaggtg aggaaatcca gagctatcaa tcacagtccc 180
tacatcatgt tcatcagaat gattctgagg aaaattaggg tcctcgggca catatcctac 240
aacatgtcca tcaaaatcgt gctcggccat gagtatattt tctgcgaaaa ataa 294

<210> SEQ ID NO 6
<211> LENGTH: 97
<212> TYPE: PRT
<213> ORGANISM: Phakopsora pachyrhizi
<220> FEATURE:
<221> NAME/KEY: VARIANT
<222> LOCATION: (1)..(97)
<223> OTHER INFORMATION: 02-g20

<400> SEQUENCE: 6

Met Thr Phe Phe Asn Met Leu Leu Leu Leu Trp Arg Val Arg Val Pro
1 5 10 15

Arg Lys Thr Ser Asn Ile Met Phe Met Ser Ile Lys Met Ile Phe Arg
20 25 30

Lys Ile Gly Ile Leu His Gln Ile Ala Cys Ile Ile Phe Ile Arg Gln
35 40 45

Gln Val Arg Lys Ser Arg Ala Ile Asn His Ser Pro Tyr Ile Met Phe
50 55 60

Ile Arg Met Ile Leu Arg Lys Ile Arg Val Leu Gly His Ile Ser Tyr
65 70 75 80

Asn Met Ser Ile Lys Ile Val Leu Gly His Glu Tyr Ile Phe Cys Glu
85 90 95

Lys

<210> SEQ ID NO 7
<211> LENGTH: 483
<212> TYPE: DNA
<213> ORGANISM: Phakopsora pachyrhizi
<220> FEATURE:
<221> NAME/KEY: misc_feature
<222> LOCATION: (1)..(483)
<223> OTHER INFORMATION: 04-a13

<400> SEQUENCE: 7
atgatcttca aaccagtctt actacgtcag agcatggtta cagtctcagg acctagtcga 60
ttgttgagat cgactatcag aagatcaacc atctcacatc tcaatcacac cccgatcatc 120
tccaaacagt ggatccaatc agctttctac agtgctggtc atgatacagc tgatgaatcg 180
tatccagcct tcaacgagag gtacactaag ttctttgagg gagttcaaga cctttttgag 240
cttcaaagag gtttgaataa ctgctttgcc tatgacttgg ttcctgcggt ttcaactgta 300
gaagcagccc tcaaggcggc caggcgtgtg aatgatctgc ctactgcgat tcgaatattt 360
gaaggtctca aagaaaaggt tgagaacaag acacagtaca aggcatattt agaagagtta 420
aaacctttga gagatgaact tggtgttcct accaaagaag aactatacgg tcaaactatt 480
taa 483

<210> SEQ ID NO 8
<211> LENGTH: 160
<212> TYPE: PRT
<213> ORGANISM: Phakopsora pachyrhizi
<220> FEATURE:
<221> NAME/KEY: VARIANT
<222> LOCATION: (1)..(160)
<223> OTHER INFORMATION: 04-a13

<400> SEQUENCE: 8

Met Ile Phe Lys Pro Val Leu Leu Arg Gln Ser Met Val Thr Val Ser
1 5 10 15

-continued

Gly Pro Ser Arg Leu Leu Arg Ser Thr Ile Arg Arg Ser Thr Ile Ser
20 25 30

His Leu Asn His Thr Pro Ile Ile Ser Lys Gln Trp Ile Gln Ser Ala
35 40 45

Phe Tyr Ser Ala Gly His Asp Thr Ala Asp Glu Ser Tyr Pro Ala Phe
50 55 60

Asn Glu Arg Tyr Thr Lys Phe Phe Glu Gly Val Gln Asp Leu Phe Glu
65 70 75 80

Leu Gln Arg Gly Leu Asn Asn Cys Phe Ala Tyr Asp Leu Val Pro Ala
85 90 95

Val Ser Thr Val Glu Ala Ala Leu Lys Ala Ala Arg Arg Val Asn Asp
100 105 110

Leu Pro Thr Ala Ile Arg Ile Phe Glu Gly Leu Lys Glu Lys Val Glu
115 120 125

Asn Lys Thr Gln Tyr Lys Ala Tyr Leu Glu Glu Leu Lys Pro Leu Arg
130 135 140

Asp Glu Leu Gly Val Pro Thr Lys Glu Glu Leu Tyr Gly Gln Thr Ile
145 150 155 160

<210> SEQ ID NO 9
<211> LENGTH: 954
<212> TYPE: DNA
<213> ORGANISM: Phakopsora pachyrhizi
<220> FEATURE:
<221> NAME/KEY: misc_feature
<222> LOCATION: (1)..(954)
<223> OTHER INFORMATION: 04-f24

<400> SEQUENCE: 9
atgaaaaata tttttagagg ttctttatat atatttttga cactccttaa tttgattgta 60
agcctcgaag cagccttagt agcatttgac gaggaagtta gcttgttgag gaatacggat 120
cgcataagcc aaactcaacc caagacttta gagctccaaa aatattcaaa ggcttataat 180
ggtcctttga tatatgcccc atccagctct gtagaagtct tcaaaagtgc agctcagttg 240
cacactagtc caaaatctga taaatctttt actcgagatt ggagaagtat ccacatgaat 300
gatttattaa atccaaggat tactcaacct ataaaatcta aaaaagggtc tttactttta 360
tacttattta gaaaaaaacc taaaactcaa tatgaggtta aaaagacatt agttctttcc 420
gacaaaggtt ctaccgatac ttcatcttta ttcaataaag aatctttagc gctaagttac 480
cccagaaaag aaaaaaattc cggaaactac ttagagggct tagagattga agttccaacg 540
ctcagtgatg aagcattagt agatctaaga gactggaagc ggagcacatc agtgttatat 600
tttatagaac agatcgagct aagaacaaat aaggttgtag atttactaaa aaggccagat 660
ttaaatatag aagatgtaga gggtctctca aactttttga aagacttaaa cgttgatgag 720
aatggagatt tgaaagacct cagggagggt gaaacgatct atctgatgat tcaagacgtt 780
tggaaggctt caaagtctaa cttccctgcc gaggtaaaaa ctcaaatctt ttatagatac 840
gagtatagac tcaaaaagat cttcgataag ctctcagagc aaaggttttt cattaaaaag 900
ggtaaaaagg aaactctaat caaggaatca atggagatag ttctatacag gctg 954

<210> SEQ ID NO 10
<211> LENGTH: 318
<212> TYPE: PRT
<213> ORGANISM: Phakopsora pachyrhizi
<220> FEATURE:
<221> NAME/KEY: VARIANT
<222> LOCATION: (1)..(318)
<223> OTHER INFORMATION: 04-f24

<400> SEQUENCE: 10

Met Lys Asn Ile Phe Arg Gly Ser Leu Tyr Ile Phe Leu Thr Leu Leu
1               5                   10                  15

Asn Leu Ile Val Ser Leu Glu Ala Ala Leu Val Ala Phe Asp Glu Glu
            20                  25                  30

Val Ser Leu Leu Arg Asn Thr Asp Arg Ile Ser Gln Thr Gln Pro Lys
        35                  40                  45

Thr Leu Glu Leu Gln Lys Tyr Ser Lys Ala Tyr Asn Gly Pro Leu Ile
    50                  55                  60

Tyr Ala Pro Ser Ser Ser Val Glu Val Phe Lys Ser Ala Ala Gln Leu
65                  70                  75                  80

His Thr Ser Pro Lys Ser Asp Lys Ser Phe Thr Arg Asp Trp Arg Ser
                85                  90                  95

Ile His Met Asn Asp Leu Leu Asn Pro Arg Ile Thr Gln Pro Ile Lys
            100                 105                 110

Ser Lys Lys Gly Ser Leu Leu Leu Tyr Leu Phe Arg Lys Lys Pro Lys
        115                 120                 125

Thr Gln Tyr Glu Val Lys Lys Thr Leu Val Leu Ser Asp Lys Gly Ser
    130                 135                 140

Thr Asp Thr Ser Ser Leu Phe Asn Lys Glu Ser Leu Ala Leu Ser Tyr
145                 150                 155                 160

Pro Arg Lys Glu Lys Asn Ser Gly Asn Tyr Leu Glu Gly Leu Glu Ile
                165                 170                 175

Glu Val Pro Thr Leu Ser Asp Glu Ala Leu Val Asp Leu Arg Asp Trp
            180                 185                 190

Lys Arg Ser Thr Ser Val Leu Tyr Phe Ile Glu Gln Ile Glu Leu Arg
        195                 200                 205

Thr Asn Lys Val Val Asp Leu Leu Lys Arg Pro Asp Leu Asn Ile Glu
    210                 215                 220

Asp Val Glu Gly Leu Ser Asn Phe Leu Lys Asp Leu Asn Val Asp Glu
225                 230                 235                 240

Asn Gly Asp Leu Lys Asp Leu Arg Glu Gly Glu Thr Ile Tyr Leu Met
                245                 250                 255

Ile Gln Asp Val Trp Lys Ala Ser Lys Ser Asn Phe Pro Ala Glu Val
            260                 265                 270

Lys Thr Gln Ile Phe Tyr Arg Tyr Glu Tyr Arg Leu Lys Lys Ile Phe
        275                 280                 285

Asp Lys Leu Ser Glu Gln Arg Phe Phe Ile Lys Lys Gly Lys Lys Glu
    290                 295                 300

Thr Leu Ile Lys Glu Ser Met Glu Ile Val Leu Tyr Arg Leu
305                 310                 315

<210> SEQ ID NO 11
<211> LENGTH: 1065
<212> TYPE: DNA
<213> ORGANISM: Phakopsora pachyrhizi
<220> FEATURE:
<221> NAME/KEY: misc_feature
<222> LOCATION: (1)..(1065)
<223> OTHER INFORMATION: 04-i14

<400> SEQUENCE: 11
atgaatcagc actatagaga aattatggtt ttcagaaaag cagttatata tctgtgctta      60

```
ggagcactta aaatattatc taccaatgca gcgttttcaa agagtaacga tatcaaaact     120

ttagatgata ttgctgaagg ctctatgcct gaaaaccctt ttttcagcca agataatttt     180

atttcctgta ctaaaaatac atcgcaaatc gagaaacagt cacaagcaga aggttacatt     240

aattttccag ataaaaatgt agttatcact cagtttgtcg ctaataacaa aagggatttc     300

aaggaaacat tagagaatag agaggccaag ccagttcatt cacctgttaa cttagaagag     360

cataaattaa cgcctagcat tgtaactgac caggttgatg atttaatgtt tttcgctact     420

gagttggatg attttccaac ttatttgatg gaatttcatc cagctgagat acagcctaat     480

tctgctactg cgtctgatgg tttggaactc agctatcatg actatcacct tcaggacaat     540

gattttgggg aaaataattc ttggttgata aaccaatctg aaccattagg atttcaaagt     600

agtactgtcc taaatggtgc ggcagaaatt ccagtcccag agcatcaaaa tttaggagct     660

ccgagtctcg acaataatca gcttttctgt agcttatttg aagcggagcc cacagctgtc     720

tcagaagaaa acacttacaa cgcttgggca agcaattttg gacctactct tcaggaggaa     780

gcaagagaat cgtataaaga agggcaaatt tcaaatgaat caattgaaaa ccttcattca     840

ctgaatttca attacgactc caatatttta aagattagac tttcaaaagc acaaaatgac     900

gtatttgaat tagaagacct tccggtttta gaaaaacagc tatctcaaac attgagccca     960

ggagaaaaat atataataga aaacgaatca ttacttaaaa gcaggcggag tcactcaaaa    1020

gcccctggta gtaaaagtcg caagatcacg aaaaacacta aagat                    1065
```

<210> SEQ ID NO 12
<211> LENGTH: 355
<212> TYPE: PRT
<213> ORGANISM: Phakopsora pachyrhizi
<220> FEATURE:
<221> NAME/KEY: VARIANT
<222> LOCATION: (1)..(355)
<223> OTHER INFORMATION: 04-i14

<400> SEQUENCE: 12

```
Met Asn Gln His Tyr Arg Glu Ile Met Val Phe Arg Lys Ala Val Ile
1               5                   10                  15

Tyr Leu Cys Leu Gly Ala Leu Lys Ile Leu Ser Thr Asn Ala Ala Phe
            20                  25                  30

Ser Lys Ser Asn Asp Ile Lys Thr Leu Asp Asp Ile Ala Glu Gly Ser
        35                  40                  45

Met Pro Glu Asn Pro Phe Phe Ser Gln Asp Asn Phe Ile Ser Cys Thr
    50                  55                  60

Lys Asn Thr Ser Gln Ile Glu Lys Gln Ser Gln Ala Glu Gly Tyr Ile
65                  70                  75                  80

Asn Phe Pro Asp Lys Asn Val Val Ile Thr Gln Phe Val Ala Asn Asn
                85                  90                  95

Lys Arg Asp Phe Lys Glu Thr Leu Glu Asn Arg Glu Ala Lys Pro Val
            100                 105                 110

His Ser Pro Val Asn Leu Glu Glu His Lys Leu Thr Pro Ser Ile Val
        115                 120                 125

Thr Asp Gln Val Asp Asp Leu Met Phe Phe Ala Thr Glu Leu Asp Asp
    130                 135                 140

Phe Pro Thr Tyr Leu Met Glu Phe His Pro Ala Glu Ile Gln Pro Asn
145                 150                 155                 160

Ser Ala Thr Ala Ser Asp Gly Leu Glu Leu Ser Tyr His Asp Tyr His
                165                 170                 175
```

-continued

```
Leu Gln Asp Asn Asp Phe Gly Glu Asn Asn Ser Trp Leu Ile Asn Gln
            180                 185                 190

Ser Glu Pro Leu Gly Phe Gln Ser Ser Thr Val Leu Asn Gly Ala Ala
        195                 200                 205

Glu Ile Pro Val Pro Glu His Gln Asn Leu Gly Ala Pro Ser Leu Asp
    210                 215                 220

Asn Asn Gln Leu Phe Cys Ser Leu Phe Glu Ala Glu Pro Thr Ala Val
225                 230                 235                 240

Ser Glu Glu Asn Thr Tyr Asn Ala Trp Ala Ser Asn Phe Gly Pro Thr
                245                 250                 255

Leu Gln Glu Glu Ala Arg Glu Ser Tyr Lys Glu Gly Gln Ile Ser Asn
            260                 265                 270

Glu Ser Ile Glu Asn Leu His Ser Leu Asn Phe Asn Tyr Asp Ser Asn
        275                 280                 285

Ile Leu Lys Ile Arg Leu Ser Lys Ala Gln Asn Asp Val Phe Glu Leu
    290                 295                 300

Glu Asp Leu Pro Val Leu Glu Lys Gln Leu Ser Gln Thr Leu Ser Pro
305                 310                 315                 320

Gly Glu Lys Tyr Ile Ile Glu Asn Glu Ser Leu Leu Lys Ser Arg Arg
                325                 330                 335

Ser His Ser Lys Ala Pro Gly Ser Lys Ser Arg Lys Ile Thr Lys Asn
            340                 345                 350

Thr Lys Asp
        355


<210> SEQ ID NO 13
<211> LENGTH: 984
<212> TYPE: DNA
<213> ORGANISM: Phakopsora pachyrhizi
<220> FEATURE:
<221> NAME/KEY: misc_feature
<222> LOCATION: (1)..(984)
<223> OTHER INFORMATION: 04-L8

<400> SEQUENCE: 13

atgaaaaaag cccagtgtac gataatatgc ctcgcactga gctttcaggt gtttctagaa      60

gctgggtcaa cctatttgac cgagcccatg agaagtattg atggcgaggc cagcttcggc     120

tcatgtagca cttcctggat gtctaatgct gggaacgcca aggccaatgg tgtaaatccg     180

aatggtgtgc tggataaagt ggtataccct ttctctaaac aatgttactg gtctggcaag     240

gacatgaaaa accttgagag ctttaatttt tgtggtaata aacaaattgc cgctcagtac     300

agagacctta ttaacagcta catatcgcca aggcagataa tccttcataa tgaaaataaa     360

gaaaaattag ctttattaaa cagaaattta aaagagctta gccctgaaga caaagaagca     420

ctagaattat gggcaagcaa aaactttcag cctaacaacg tattaataga aaatgaaagc     480

ccaaatgaat tccgaagtgc taaggctgct ttagaatgga atctaaagag ggcttctgct     540

aagcaagatg tatggtggac caaagaggat cttcaacgtt gggctcatca cgattctgat     600

gaaacagtta tcattaaatt tggtgatata ctaaagtttg atcagaaaag ggaggatttt     660

gtgatcaaag atagtccagt acaattagct tcaagacttt tcagagcgct agataaatca     720

actggtggta attcttttaa caagcgagtt gcttggccct ctgaagaaat tcaatccttg     780

agattaatca aagccgaaga ctcaaacaaa tctttatttc atatgaggtt ggatcaaatg     840

ttaaagaatt ataaaagatt taaagatcat aaaagtcaag aaaatggaaa ttttaaggaa     900

ttcagtgatt ttattggttt atcaaaaact gataaaactg aacctcaaaa taaattacac     960
```

-continued

```
caaaagaaca ttgaattaaa ataa                                         984


<210> SEQ ID NO 14
<211> LENGTH: 327
<212> TYPE: PRT
<213> ORGANISM: Phakopsora pachyrhizi
<220> FEATURE:
<221> NAME/KEY: VARIANT
<222> LOCATION: (1)..(327)
<223> OTHER INFORMATION: 04-L8

<400> SEQUENCE: 14

Met Lys Lys Ala Gln Cys Thr Ile Ile Cys Leu Ala Leu Ser Phe Gln
1               5                   10                  15

Val Phe Leu Glu Ala Gly Ser Thr Tyr Leu Thr Glu Pro Met Arg Ser
            20                  25                  30

Ile Asp Gly Glu Ala Ser Phe Gly Ser Cys Ser Thr Ser Trp Met Ser
        35                  40                  45

Asn Ala Gly Asn Ala Lys Ala Asn Gly Val Asn Pro Asn Gly Val Leu
    50                  55                  60

Asp Lys Val Val Tyr Pro Phe Ser Lys Gln Cys Tyr Trp Ser Gly Lys
65                  70                  75                  80

Asp Met Lys Asn Leu Glu Ser Phe Asn Phe Cys Gly Asn Lys Gln Ile
                85                  90                  95

Ala Ala Gln Tyr Arg Asp Leu Ile Asn Ser Tyr Ile Ser Pro Arg Gln
            100                 105                 110

Ile Ile Leu His Asn Glu Asn Lys Glu Lys Leu Ala Leu Leu Asn Arg
        115                 120                 125

Asn Leu Lys Glu Leu Ser Pro Glu Asp Lys Glu Ala Leu Glu Leu Trp
    130                 135                 140

Ala Ser Lys Asn Phe Gln Pro Asn Asn Val Leu Ile Glu Asn Glu Ser
145                 150                 155                 160

Pro Asn Glu Phe Arg Ser Ala Lys Ala Ala Leu Glu Trp Asn Leu Lys
                165                 170                 175

Arg Ala Ser Ala Lys Gln Asp Val Trp Trp Thr Lys Glu Asp Leu Gln
            180                 185                 190

Arg Trp Ala His His Asp Ser Asp Glu Thr Val Ile Ile Lys Phe Gly
        195                 200                 205

Asp Ile Leu Lys Phe Asp Gln Lys Arg Glu Asp Phe Val Ile Lys Asp
    210                 215                 220

Ser Pro Val Gln Leu Ala Ser Arg Leu Phe Arg Ala Leu Asp Lys Ser
225                 230                 235                 240

Thr Gly Gly Asn Ser Phe Asn Lys Arg Val Ala Trp Pro Ser Glu Glu
                245                 250                 255

Ile Gln Ser Leu Arg Leu Ile Lys Ala Glu Asp Ser Asn Lys Ser Leu
            260                 265                 270

Phe His Met Arg Leu Asp Gln Met Leu Lys Asn Tyr Lys Arg Phe Lys
        275                 280                 285

Asp His Lys Ser Gln Glu Asn Gly Asn Phe Lys Glu Phe Ser Asp Phe
    290                 295                 300

Ile Gly Leu Ser Lys Thr Asp Lys Thr Glu Pro Gln Asn Lys Leu His
305                 310                 315                 320

Gln Lys Asn Ile Glu Leu Lys
                325
```

-continued

<210> SEQ ID NO 15
<211> LENGTH: 1101
<212> TYPE: DNA
<213> ORGANISM: Phakopsora pachyrhizi
<220> FEATURE:
<221> NAME/KEY: misc_feature
<222> LOCATION: (1)..(1101)
<223> OTHER INFORMATION: 09-d10

<400> SEQUENCE: 15
atggcttttt ggaagaatag ttgttttgta tttttaaata ccttagcaaa gttaacatgt 60
ggaatgcttc cggaaggcaa ccaaataaaa cacctcagtg atgtaaccag tggttctcaa 120
tttcttatcc cgtttgcagc agaggatagt ttggggacac aagcaaatga tgctctgcac 180
gtagcaactt catcaaggaa tacccagaac acgccctgga cggcagatag ctcgattaag 240
gaacacgtaa acatgggtga tataatgcat caagatgaag catttaggat taataaaata 300
ttttctccat taccccttt tccaattgct tacaacccgc ctggttataa tcaacacatg 360
gttggtttta cttcaagtcc ttatttaaat ctagattatg ttacacatcc ttctatctta 420
tcgcacccag ctgcgaataa acatgacttt gataataggg tggagaagag cttcgattat 480
tttcaacaaa ttccaaaata caactttcaa gacattcaat acaggtttgc ggatcagcca 540
cagaatagtg atgttaataa tcatcaaaaa aatttgaagg atgcagaagg aagtagtcag 600
caattcattc attatcttac ctccgatgag ttttcagcca tttacccaaa tttagaacag 660
ctacaggtat accaaagcca ccatattcca agcaatccaa atgagctaat cagaaatcaa 720
ctttctccag ttaattcaga ggaattgagg ggcatcaaaa ataaagctat tagtcaatat 780
tccgaaacta gaaaaggaaa agaaatgttg gaaagtagct tacaccatac agaccagttc 840
aatcaattta ttcgaagcaa agaaaatgtt atacaccaag gcgaagaaaa cagcttggtt 900
gtagcaccgc atgaatcatc tttatctcat ttacaaagtg atctgaatga atctgatgga 960
aggagattca agaattccaa gaacggtgat aaaggtgatt cgcacagcca aatcgctact 1020
tcatccagac gaataccacc gaaaaagcat cgattcaaaa cttctttaag atcactacca 1080
gtcgatgaaa actcaaatga c 1101

<210> SEQ ID NO 16
<211> LENGTH: 367
<212> TYPE: PRT
<213> ORGANISM: Phakopsora pachyrhizi
<220> FEATURE:
<221> NAME/KEY: VARIANT
<222> LOCATION: (1)..(367)
<223> OTHER INFORMATION: 09-d10

<400> SEQUENCE: 16

Met Ala Phe Trp Lys Asn Ser Cys Phe Val Phe Leu Asn Thr Leu Ala
1 5 10 15

Lys Leu Thr Cys Gly Met Leu Pro Glu Gly Asn Gln Ile Lys His Leu
20 25 30

Ser Asp Val Thr Ser Gly Ser Gln Phe Leu Ile Pro Phe Ala Ala Glu
35 40 45

Asp Ser Leu Gly Thr Gln Ala Asn Asp Ala Leu His Val Ala Thr Ser
50 55 60

Ser Arg Asn Thr Gln Asn Thr Pro Trp Thr Ala Asp Ser Ser Ile Lys
65 70 75 80

Glu His Val Asn Met Gly Asp Ile Met His Gln Asp Glu Ala Phe Arg
85 90 95

-continued

```
Ile Asn Lys Ile Phe Ser Pro Leu Pro Leu Phe Pro Ile Ala Tyr Asn
            100                 105                 110

Pro Pro Gly Tyr Asn Gln His Met Val Gly Phe Thr Ser Ser Pro Tyr
        115                 120                 125

Leu Asn Leu Asp Tyr Val Thr His Pro Ser Ile Leu Ser His Pro Ala
    130                 135                 140

Ala Asn Lys His Asp Phe Asp Asn Arg Val Glu Lys Ser Phe Asp Tyr
145                 150                 155                 160

Phe Gln Gln Ile Pro Lys Tyr Asn Phe Gln Asp Ile Gln Tyr Arg Phe
                165                 170                 175

Ala Asp Gln Pro Gln Asn Ser Asp Val Asn Asn His Gln Lys Asn Leu
            180                 185                 190

Lys Asp Ala Glu Gly Ser Ser Gln Gln Phe Ile His Tyr Leu Thr Ser
        195                 200                 205

Asp Glu Phe Ser Ala Ile Tyr Pro Asn Leu Glu Gln Leu Gln Val Tyr
    210                 215                 220

Gln Ser His His Ile Pro Ser Asn Pro Asn Glu Leu Ile Arg Asn Gln
225                 230                 235                 240

Leu Ser Pro Val Asn Ser Glu Glu Leu Arg Gly Ile Lys Asn Lys Ala
                245                 250                 255

Ile Ser Gln Tyr Ser Glu Thr Arg Lys Gly Lys Glu Met Leu Glu Ser
            260                 265                 270

Ser Leu His His Thr Asp Gln Phe Asn Gln Phe Ile Arg Ser Lys Glu
        275                 280                 285

Asn Val Ile His Gln Gly Glu Glu Asn Ser Leu Val Val Ala Pro His
    290                 295                 300

Glu Ser Ser Leu Ser His Leu Gln Ser Asp Leu Asn Glu Ser Asp Gly
305                 310                 315                 320

Arg Arg Phe Lys Asn Ser Lys Asn Gly Asp Lys Gly Asp Ser His Ser
                325                 330                 335

Gln Ile Ala Thr Ser Ser Arg Arg Ile Pro Pro Lys Lys His Arg Phe
            340                 345                 350

Lys Thr Ser Leu Arg Ser Leu Pro Val Asp Glu Asn Ser Asn Asp
        355                 360                 365
```

```
<210> SEQ ID NO 17
<211> LENGTH: 316
<212> TYPE: DNA
<213> ORGANISM: Phakopsora pachyrhizi
<220> FEATURE:
<221> NAME/KEY: misc_feature
<222> LOCATION: (1)..(316)
<223> OTHER INFORMATION: 09-j15

<400> SEQUENCE: 17

aggatttcag caaaattttg ctgaaggaac tcttgagttt aaacttccta atcgttcttt      60

aggtaataat caagctgcat tcaaaactct atcgtcgtac tccaaagaca acaacaactt     120

ggaggcaggc ctcgtttggc cattaagtga accaaagatc acaatcatta aacttgacct     180

caaacagtta ttagaagaat ttaaaacaaa attaacagaa gcgcttacga ttattgagga     240

actgtgcagc tataaaccga acacttataa agaaatcagc aatcaaataa tacaagttta     300

taaacatatt acccga                                                     316


<210> SEQ ID NO 18
<211> LENGTH: 157
<212> TYPE: PRT
```

<213> ORGANISM: Phakopsora pachyrhizi
<220> FEATURE:
<221> NAME/KEY: VARIANT
<222> LOCATION: (1)..(157)
<223> OTHER INFORMATION: 09-j15

<400> SEQUENCE: 18

Met His Leu His Ser Leu Thr Ile Lys Leu Ser Met Arg Leu Leu Tyr
1 5 10 15

Phe Cys Ser Ala Trp Phe Ser Leu Ile Phe Asn Asn Phe Ser Cys Phe
20 25 30

Asn Asp Phe Val Pro Ser Glu Phe Thr Arg Asp Leu Gln Leu Gly Lys
35 40 45

Gly Asn Phe Arg Gly Phe Gln Gln Asn Phe Ala Glu Gly Thr Leu Glu
50 55 60

Phe Lys Leu Pro Asn Arg Ser Leu Gly Asn Asn Gln Ala Ala Phe Lys
65 70 75 80

Thr Leu Ser Ser Tyr Ser Lys Asp Asn Asn Asn Leu Glu Ala Gly Leu
85 90 95

Val Trp Pro Leu Ser Glu Pro Lys Ile Thr Ile Ile Lys Leu Asp Leu
100 105 110

Lys Gln Leu Leu Glu Glu Phe Lys Thr Lys Leu Thr Glu Ala Leu Thr
115 120 125

Ile Ile Glu Glu Leu Cys Ser Tyr Lys Pro Asn Thr Tyr Lys Glu Ile
130 135 140

Ser Asn Gln Ile Ile Gln Val Tyr Lys His Ile Thr Arg
145 150 155

<210> SEQ ID NO 19
<211> LENGTH: 183
<212> TYPE: DNA
<213> ORGANISM: Phakopsora pachyrhizi
<220> FEATURE:
<221> NAME/KEY: misc_feature
<222> LOCATION: (1)..(183)
<223> OTHER INFORMATION: 10-c2

<400> SEQUENCE: 19
atgctggttc atgtaagatt tgtagcaatg aggctggtgc attttatctt tgttccacct 60
agacgacaaa agaattcatt catgtactta caggcgacgc atgctaaatg cgcattttgt 120
tattttctct ctaatgcttc ttctctttat caatattctc agaccttttt attttggtat 180
taa 183

<210> SEQ ID NO 20
<211> LENGTH: 60
<212> TYPE: PRT
<213> ORGANISM: Phakopsora pachyrhizi
<220> FEATURE:
<221> NAME/KEY: VARIANT
<222> LOCATION: (1)..(60)
<223> OTHER INFORMATION: 10-c2

<400> SEQUENCE: 20

Met Leu Val His Val Arg Phe Val Ala Met Arg Leu Val His Phe Ile
1 5 10 15

Phe Val Pro Pro Arg Arg Gln Lys Asn Ser Phe Met Tyr Leu Gln Ala
20 25 30

Thr His Ala Lys Cys Ala Phe Cys Tyr Phe Leu Ser Asn Ala Ser Ser
35 40 45

```
Leu Tyr Gln Tyr Ser Gln Thr Phe Leu Phe Trp Tyr
    50                  55                  60


<210> SEQ ID NO 21
<211> LENGTH: 258
<212> TYPE: DNA
<213> ORGANISM: Phakopsora pachyrhizi
<220> FEATURE:
<221> NAME/KEY: misc_feature
<222> LOCATION: (1)..(258)
<223> OTHER INFORMATION: 10-e18

<400> SEQUENCE: 21

atgatttttt ggaaaatatt tatatgcttg tgcttagttg aatttaacat aatattaatt      60

gttgcagcat tatcagaggg tagctctgtc aaaaccttag aggatataat tgagggctct     120

aagttacaaa actctctggc gggccagcaa aaccttgctt ttcgttcaaa taacgcagat     180

aacatcggga atcgattaca aggcaaacat caaattagct tcaccactag agatgtagat     240

atcactccgt tccccacc                                                   258


<210> SEQ ID NO 22
<211> LENGTH: 86
<212> TYPE: PRT
<213> ORGANISM: Phakopsora pachyrhizi
<220> FEATURE:
<221> NAME/KEY: VARIANT
<222> LOCATION: (1)..(86)
<223> OTHER INFORMATION: 10-e18

<400> SEQUENCE: 22

Met Ile Phe Trp Lys Ile Phe Ile Cys Leu Cys Leu Val Glu Phe Asn
1               5                   10                  15

Ile Ile Leu Ile Val Ala Ala Leu Ser Glu Gly Ser Ser Val Lys Thr
            20                  25                  30

Leu Glu Asp Ile Ile Glu Gly Ser Lys Leu Gln Asn Ser Leu Ala Gly
        35                  40                  45

Gln Gln Asn Leu Ala Phe Arg Ser Asn Asn Ala Asp Asn Ile Gly Asn
    50                  55                  60

Arg Leu Gln Gly Lys His Gln Ile Ser Phe Thr Thr Arg Asp Val Asp
65                  70                  75                  80

Ile Thr Pro Phe Pro Thr
                85


<210> SEQ ID NO 23
<211> LENGTH: 966
<212> TYPE: DNA
<213> ORGANISM: Phakopsora pachyrhizi
<220> FEATURE:
<221> NAME/KEY: misc_feature
<222> LOCATION: (1)..(966)
<223> OTHER INFORMATION: 10-g13

<400> SEQUENCE: 23

atggtttttc taaaatgtat gacaattttc atctttggtc tcttggaatt aaaccaaata      60

atttgtacag tcgaaccagc gcttttaaat tttaaccgga tcaagaaatc ttatgatgaa     120

gctgatgtgc gagtgtttat gcttgactat gatggaacac taccaatagc ccctaaatcg     180

gatgccaatt accttaggaa tcttataggt caacttgcaa aagatgataa gaatttagta     240

tacataaaca ctgctcgtcc tatctactat gcaatcaaag aatttgaaaa tcttaaaaat     300

gtaataattg ttggtgaact tgggttgtac caagcaaaag ctactgaaga agtactagaa     360
```

```
gctgaaaaaa ataatcaatt ttggatagtc aataacgata ttgttcagtc tacaatcaaa    420

agacttatta aatcaggcca aataaataat ctgactacat ttaagtgtag gatggttggt    480

catggaactt ttggaggaat aattgtcaca gataagaatc tttctgtaaa tgaaaaagaa    540

gaaatttatc agaaggttgt taaagagtta agagaagaga tcggtgatgt aaggtttcaa    600

cctgctcagg gaacctcaaa tgataaatat cttactagta taggagttga tctatctgga    660

gagaacaaat acagggttga tgtatctggt gaatttataa atataatacc taaggatcaa    720

cacaagggga agtttgtgaa ggattttatg aaaaaatttg tcaaagagaa cagtggaaag    780

aggatctttg gtctaagtat tggaaatgag gatgcagatg aggcaatgca ccttgtcatg    840

aattcttatg gactatactc agcacttgtt ggtgatttag tagacttaca agaaaccttg    900

gcaacttttc acctagcaaa tgaacaggaa actggacagc tcatcctaca gctttcaagt    960

cactga                                                               966
```

```
<210> SEQ ID NO 24
<211> LENGTH: 321
<212> TYPE: PRT
<213> ORGANISM: Phakopsora pachyrhizi
<220> FEATURE:
<221> NAME/KEY: VARIANT
<222> LOCATION: (1)..(321)
<223> OTHER INFORMATION: 10-g13

<400> SEQUENCE: 24

Met Val Phe Leu Lys Cys Met Thr Ile Phe Ile Phe Gly Leu Leu Glu
1               5                   10                  15

Leu Asn Gln Ile Ile Cys Thr Val Glu Pro Ala Leu Leu Asn Phe Asn
            20                  25                  30

Arg Ile Lys Lys Ser Tyr Asp Glu Ala Asp Val Arg Val Phe Met Leu
        35                  40                  45

Asp Tyr Asp Gly Thr Leu Pro Ile Ala Pro Lys Ser Asp Ala Asn Tyr
    50                  55                  60

Leu Arg Asn Leu Ile Gly Gln Leu Ala Lys Asp Asp Lys Asn Leu Val
65                  70                  75                  80

Tyr Ile Asn Thr Ala Arg Pro Ile Tyr Tyr Ala Ile Lys Glu Phe Glu
                85                  90                  95

Asn Leu Lys Asn Val Ile Ile Val Gly Glu Leu Gly Leu Tyr Gln Ala
            100                 105                 110

Lys Ala Thr Glu Glu Val Leu Glu Ala Glu Lys Asn Asn Gln Phe Trp
        115                 120                 125

Ile Val Asn Asn Asp Ile Val Gln Ser Thr Ile Lys Arg Leu Ile Lys
    130                 135                 140

Ser Gly Gln Ile Asn Asn Leu Thr Thr Phe Lys Cys Arg Met Val Gly
145                 150                 155                 160

His Gly Thr Phe Gly Gly Ile Ile Val Thr Asp Lys Asn Leu Ser Val
                165                 170                 175

Asn Glu Lys Glu Glu Ile Tyr Gln Lys Val Val Lys Glu Leu Arg Glu
            180                 185                 190

Glu Ile Gly Asp Val Arg Phe Gln Pro Ala Gln Gly Thr Ser Asn Asp
        195                 200                 205

Lys Tyr Leu Thr Ser Ile Gly Val Asp Leu Ser Gly Glu Asn Lys Tyr
    210                 215                 220

Arg Val Asp Val Ser Gly Glu Phe Ile Asn Ile Ile Pro Lys Asp Gln
225                 230                 235                 240
```

-continued

His Lys Gly Lys Phe Val Lys Asp Phe Met Lys Lys Phe Val Lys Glu
245 250 255

Asn Ser Gly Lys Arg Ile Phe Gly Leu Ser Ile Gly Asn Glu Asp Ala
260 265 270

Asp Glu Ala Met His Leu Val Met Asn Ser Tyr Gly Leu Tyr Ser Ala
275 280 285

Leu Val Gly Asp Leu Val Asp Leu Gln Glu Thr Leu Ala Thr Phe His
290 295 300

Leu Ala Asn Glu Gln Glu Thr Gly Gln Leu Ile Leu Gln Leu Ser Ser
305 310 315 320

His

<210> SEQ ID NO 25
<211> LENGTH: 465
<212> TYPE: DNA
<213> ORGANISM: Phakopsora pachyrhizi
<220> FEATURE:
<221> NAME/KEY: misc_feature
<222> LOCATION: (1)..(465)
<223> OTHER INFORMATION: 12-L21

<400> SEQUENCE: 25
atgcaatcca actttctcct cgctttttgc ttgattgctg ctgtctctgt tccagttagc 60
agggctcacg gtgttattac ttcagttgag ggcgcaaatg gtcaaactgg atctgccttt 120
ggaatggtag agtccactcc tcgtgatggc actcgaacga acccattcca aactgacagt 180
tccatcattc gagaccgtga ggtttcaagc ggaaaggcgt ctgcttgtgg acgcactctt 240
gcgggcggaa acaacgatat tgctagtgac atgtcatcgg ctgaatctgc cggattggcc 300
agtattggac ctgacggaaa agtcagaatg actcttcacc aggtcaacgg tgacggtgga 360
ggcccataca gctgtgaagt tgacaccacc gccactggtg acaacttcaa gaaaatgaac 420
atcgacacaa acgttcctgg caagaacagt cgatcaaggg catag 465

<210> SEQ ID NO 26
<211> LENGTH: 154
<212> TYPE: PRT
<213> ORGANISM: Phakopsora pachyrhizi
<220> FEATURE:
<221> NAME/KEY: VARIANT
<222> LOCATION: (1)..(154)
<223> OTHER INFORMATION: 12-L21

<400> SEQUENCE: 26

Met Gln Ser Asn Phe Leu Leu Ala Phe Cys Leu Ile Ala Ala Val Ser
1 5 10 15

Val Pro Val Ser Arg Ala His Gly Val Ile Thr Ser Val Glu Gly Ala
20 25 30

Asn Gly Gln Thr Gly Ser Ala Phe Gly Met Val Glu Ser Thr Pro Arg
35 40 45

Asp Gly Thr Arg Thr Asn Pro Phe Gln Thr Asp Ser Ser Ile Ile Arg
50 55 60

Asp Arg Glu Val Ser Ser Gly Lys Ala Ser Ala Cys Gly Arg Thr Leu
65 70 75 80

Ala Gly Gly Asn Asn Asp Ile Ala Ser Asp Met Ser Ser Ala Glu Ser
85 90 95

Ala Gly Leu Ala Ser Ile Gly Pro Asp Gly Lys Val Arg Met Thr Leu
100 105 110

His Gln Val Asn Gly Asp Gly Gly Gly Pro Tyr Ser Cys Glu Val Asp

-continued

```
        115                 120                 125

Thr Thr Ala Thr Gly Asp Asn Phe Lys Lys Met Asn Ile Asp Thr Asn
    130                 135                 140

Val Pro Gly Lys Asn Ser Arg Ser Arg Ala
145                 150


<210> SEQ ID NO 27
<211> LENGTH: 906
<212> TYPE: DNA
<213> ORGANISM: Phakopsora pachyrhizi
<220> FEATURE:
<221> NAME/KEY: misc_feature
<222> LOCATION: (1)..(906)
<223> OTHER INFORMATION: 15-d2

<400> SEQUENCE: 27

atgtactcaa aaatctcaaa cctttctatt ctcttagtga cttcaagttt tattttctta      60

aattgtgcag attgctttac cacaaatttt caatcaagga ctagtgagta caagcctgct     120

tcaaactcag tgcagaacgt aacgataaaa gattctggag ataaaaaata ttttcctgtt     180

cgttttgtca ctgtctacgc accggcctct caacatcaag caacgtcctc tgatcaaaac     240

attagtcaag taaccaaagg tgaaaatgta acaagtaccc cttcaaatga gaagcagaga     300

gatactgttt acgtcaacga atcagaagtt ggtaacttga ttccgatggc aacccaagga     360

attcttgatg aagtctatgt gatgaataga gaattggatt ggaccaataa cgagtttccg     420

atctacaact caacaggggg aatcgcttat acgattacca ataagataaa cggctctcag     480

ttggcagagt cacagttcgc aatcatcggt cctgaccgtt ggttagttct aacttctgat     540

acgaaatctg gtctctgtgg tttttcaaat gagtactctt cctccgacca cgttttatac     600

agcttaagac caagactttt catgccagat cgttggtacc tatctggtga cttggtcagt     660

ccactgaaag atcatgctta cgaatttcgc cggggtgctc taagttttga gggtgatata     720

ctcactttgg gaactcatac cagacatgct aagatcagca atggtaaatt ggctcaaggg     780

tggatcgata agaagattcc gggtggccgc acaatttccg tctttactga tggtactatt     840

cctttgccaa acttaatttc tctgatagtg ataagcgtga caagaattaa aaaatgcggt     900

ttttag                                                                906


<210> SEQ ID NO 28
<211> LENGTH: 301
<212> TYPE: PRT
<213> ORGANISM: Phakopsora pachyrhizi
<220> FEATURE:
<221> NAME/KEY: VARIANT
<222> LOCATION: (1)..(301)
<223> OTHER INFORMATION: 15-d2

<400> SEQUENCE: 28

Met Tyr Ser Lys Ile Ser Asn Leu Ser Ile Leu Leu Val Thr Ser Ser
1               5                   10                  15

Phe Ile Phe Leu Asn Cys Ala Asp Cys Phe Thr Thr Asn Phe Gln Ser
            20                  25                  30

Arg Thr Ser Glu Tyr Lys Pro Ala Ser Asn Ser Val Gln Asn Val Thr
        35                  40                  45

Ile Lys Asp Ser Gly Asp Lys Lys Tyr Phe Pro Val Arg Phe Val Thr
    50                  55                  60

Val Tyr Ala Pro Ala Ser Gln His Gln Ala Thr Ser Ser Asp Gln Asn
65                  70                  75                  80
```

-continued

```
Ile Ser Gln Val Thr Lys Gly Glu Asn Val Thr Ser Thr Pro Ser Asn
                85                  90                  95

Glu Lys Gln Arg Asp Thr Val Tyr Val Asn Glu Ser Glu Val Gly Asn
            100                 105                 110

Leu Ile Pro Met Ala Thr Gln Gly Ile Leu Asp Glu Val Tyr Val Met
        115                 120                 125

Asn Arg Glu Leu Asp Trp Thr Asn Asn Glu Phe Pro Ile Tyr Asn Ser
    130                 135                 140

Thr Gly Gly Ile Ala Tyr Thr Ile Thr Asn Lys Ile Asn Gly Ser Gln
145                 150                 155                 160

Leu Ala Glu Ser Gln Phe Ala Ile Ile Gly Pro Asp Arg Trp Leu Val
                165                 170                 175

Leu Thr Ser Asp Thr Lys Ser Gly Leu Cys Gly Phe Ser Asn Glu Tyr
            180                 185                 190

Ser Ser Ser Asp His Val Leu Tyr Ser Leu Arg Pro Arg Leu Phe Met
        195                 200                 205

Pro Asp Arg Trp Tyr Leu Ser Gly Asp Leu Val Ser Pro Leu Lys Asp
    210                 215                 220

His Ala Tyr Glu Phe Arg Arg Gly Ala Leu Ser Phe Glu Gly Asp Ile
225                 230                 235                 240

Leu Thr Leu Gly Thr His Thr Arg His Ala Lys Ile Ser Asn Gly Lys
                245                 250                 255

Leu Ala Gln Gly Trp Ile Asp Lys Lys Ile Pro Gly Gly Arg Thr Ile
            260                 265                 270

Ser Val Phe Thr Asp Gly Thr Ile Pro Leu Pro Asn Leu Ile Ser Leu
        275                 280                 285

Ile Val Ile Ser Val Thr Arg Ile Lys Lys Cys Gly Phe
    290                 295                 300
```

<210> SEQ ID NO 29
<211> LENGTH: 243
<212> TYPE: DNA
<213> ORGANISM: Phakopsora pachyrhizi
<220> FEATURE:
<221> NAME/KEY: misc_feature
<222> LOCATION: (1)..(243)
<223> OTHER INFORMATION: 15-i14

<400> SEQUENCE: 29

```
atgttgttgc agaaaataat caccttaatc caaatagaaa gaatcatatt tatcaccaga     60

cttaaaacat tcagcgaacc atatacaaaa cagaaattag ttatatatat tacaaatagc    120

agcttaaatt ttaagcttgt gtcatgtcct gaacaatttc atttcatttg tcaacaaatg    180

gagaatcaaa caagagctaa taagtatcta gaaaccttca atagagtaac aagccaaatt    240

tga                                                                  243
```

<210> SEQ ID NO 30
<211> LENGTH: 80
<212> TYPE: PRT
<213> ORGANISM: Phakopsora pachyrhizi
<220> FEATURE:
<221> NAME/KEY: VARIANT
<222> LOCATION: (1)..(80)
<223> OTHER INFORMATION: 15-i14

<400> SEQUENCE: 30

```
Met Leu Leu Gln Lys Ile Ile Thr Leu Ile Gln Ile Glu Arg Ile Ile
1               5                   10                  15
```

```
Phe Ile Thr Arg Leu Lys Thr Phe Ser Glu Pro Tyr Thr Lys Gln Lys
            20                  25                  30

Leu Val Ile Tyr Ile Thr Asn Ser Ser Leu Asn Phe Lys Leu Val Ser
        35                  40                  45

Cys Pro Glu Gln Phe His Phe Ile Cys Gln Gln Met Glu Asn Gln Thr
    50                  55                  60

Arg Ala Asn Lys Tyr Leu Glu Thr Phe Asn Arg Val Thr Ser Gln Ile
65                  70                  75                  80


<210> SEQ ID NO 31
<211> LENGTH: 529
<212> TYPE: DNA
<213> ORGANISM: Phakopsora pachyrhizi
<220> FEATURE:
<221> NAME/KEY: misc_feature
<222> LOCATION: (1)..(529)
<223> OTHER INFORMATION: 19-o21

<400> SEQUENCE: 31

atggcaattg gggtttaaca cgatgatgat ctcacgcccc ttgtcgaccc gatcattgct      60

ctatggtaca gtgatttcac caatatttat aaccattcta ttactgttcc tatccggact     120

accgacggct gagaagccag ttcaagagtc aatctttatc aaatcttaca aagccaagcg     180

atcgaactca caggaccagc agaacggaca ggggcagccg agcaatcagt cagtcaatcc     240

tcaatttgga gaaaatgcga agaatgatga tggcggtgag agagtgtata gcggagtcca     300

gaaggcatcg gatctaggag agggaaaagc agaggggcaa gtttggaagg actacaaaga     360

ttatctggac caaacatcaa tcctcttacc gatccctcaa tcaatctaca ggaagattcc     420

aacaagcata aagtctacgg ttcttttgga ctggcccatc tacagatttg atgaaaactc     480

tgagagggct cagcatctga tcaaccagat taacgacgaa ataaattga                 529


<210> SEQ ID NO 32
<211> LENGTH: 174
<212> TYPE: PRT
<213> ORGANISM: Phakopsora pachyrhizi
<220> FEATURE:
<221> NAME/KEY: VARIANT
<222> LOCATION: (1)..(174)
<223> OTHER INFORMATION: 19-o21

<400> SEQUENCE: 32

Met Ala Ile Gly Ser Ala Arg Asn Pro Gly Thr Pro Glu Ser Thr Arg
1               5                   10                  15

Ser Leu Leu Tyr Gly Thr Val Ile Ser Pro Ile Phe Ile Thr Ile Leu
            20                  25                  30

Leu Leu Phe Leu Ser Gly Leu Pro Thr Ala Glu Lys Pro Val Gln Glu
        35                  40                  45

Ser Ile Phe Ile Lys Ser Tyr Lys Ala Lys Arg Ser Asn Ser Gln Asp
    50                  55                  60

Gln Gln Asn Gly Gln Gly Gln Pro Ser Asn Gln Ser Val Asn Pro Gln
65                  70                  75                  80

Phe Gly Glu Asn Ala Lys Asn Asp Asp Gly Gly Glu Arg Val Tyr Ser
                85                  90                  95

Gly Val Gln Lys Ala Ser Asp Leu Gly Glu Gly Lys Ala Glu Gly Gln
            100                 105                 110

Val Trp Lys Asp Tyr Lys Asp Tyr Leu Asp Gln Thr Ser Ile Leu Leu
        115                 120                 125

Pro Ile Pro Gln Ser Ile Tyr Arg Lys Ile Pro Thr Ser Ile Lys Ser
```

-continued

```
    130                 135                 140

Thr Val Leu Leu Asp Trp Pro Ile Tyr Arg Phe Asp Glu Asn Ser Glu
145                 150                 155                 160

Arg Ala Gln His Leu Ile Asn Gln Ile Asn Asp Glu Ile Asn
                165                 170
```

<210> SEQ ID NO 33
<211> LENGTH: 876
<212> TYPE: DNA
<213> ORGANISM: Phakopsora pachyrhizi
<220> FEATURE:
<221> NAME/KEY: misc_feature
<222> LOCATION: (1)..(876)
<223> OTHER INFORMATION: 20-g1

<400> SEQUENCE: 33

```
atgtatcact taacctttgt cctcttttca ctcttttttt tgtccgctaa cggagcttct      60

acttcggagc caagcggaca gaccctagat tgctcccact acactggcgc gaacaccaaa     120

gaagcaactt gtaacgaatt ccctggcaga atttgtcacg gaggttgcac tggagcagtt     180

gtggccagta attgtacctt gaaccccggc gaagaaccaa aagatcaaac ctacaccata     240

gcttttggaa aatcttcagc tacgatttca atctgtcgca atgagaaggg atcgtattct     300

tgcacaggac ctatcaaagg aagcgcaaag tgctctgttt gtgttgaccc tccaacaggt     360

tccgatcaaa gcccaaccac gcctgctcct gctccaggaa acaacggatc gacttcaaaa     420

gaaggccaaa ctctacagtg cactcatttt actggtgcta atactcaaag cgcaacttgt     480

aacgaggttc ctggcagagt ttgcaacaag ggttgtacct catcagtcgt tgccaccaag     540

tgtacgttga atcctggtga ccaagagagt caacaaaact gtacccaagc tttcgggaaa     600

tcctcagctg cgatatccat ttgcatcaat gacaaagggt cattttcatg cacgggaagc     660

gtcagcggaa atgccacttg ctctggatgt accgatcaat catcatctgg ttcctctgaa     720

taccctggtt cttctggaac caccaagccc cctactgacc ctacaggtgg tgaaaacaaa     780

gaccaagaca agaaggccga agcaaccagc ttgcaattcg ccatgagctc tttctgctta     840

gctttgtctc taatgattgg tgtcgccgtg ctctag                               876
```

<210> SEQ ID NO 34
<211> LENGTH: 291
<212> TYPE: PRT
<213> ORGANISM: Phakopsora pachyrhizi
<220> FEATURE:
<221> NAME/KEY: VARIANT
<222> LOCATION: (1)..(291)
<223> OTHER INFORMATION: 20-g1

<400> SEQUENCE: 34

```
Met Tyr His Leu Thr Phe Val Leu Phe Ser Leu Phe Phe Leu Ser Ala
1               5                   10                  15

Asn Gly Ala Ser Thr Ser Glu Pro Ser Gly Gln Thr Leu Asp Cys Ser
            20                  25                  30

His Tyr Thr Gly Ala Asn Thr Lys Glu Ala Thr Cys Asn Glu Phe Pro
        35                  40                  45

Gly Arg Ile Cys His Gly Gly Cys Thr Gly Ala Val Val Ala Ser Asn
    50                  55                  60

Cys Thr Leu Asn Pro Gly Glu Glu Pro Lys Asp Gln Thr Tyr Thr Ile
65                  70                  75                  80

Ala Phe Gly Lys Ser Ser Ala Thr Ile Ser Ile Cys Arg Asn Glu Lys
                85                  90                  95
```

```
Gly Ser Tyr Ser Cys Thr Gly Pro Ile Lys Gly Ser Ala Lys Cys Ser
            100                 105                 110

Val Cys Val Asp Pro Pro Thr Gly Ser Asp Gln Ser Pro Thr Thr Pro
        115                 120                 125

Ala Pro Ala Pro Gly Asn Asn Gly Ser Thr Ser Lys Glu Gly Gln Thr
    130                 135                 140

Leu Gln Cys Thr His Phe Thr Gly Ala Asn Thr Gln Ser Ala Thr Cys
145                 150                 155                 160

Asn Glu Val Pro Gly Arg Val Cys Asn Lys Gly Cys Thr Ser Ser Val
                165                 170                 175

Val Ala Thr Lys Cys Thr Leu Asn Pro Gly Asp Gln Glu Ser Gln Gln
            180                 185                 190

Asn Cys Thr Gln Ala Phe Gly Lys Ser Ser Ala Ala Ile Ser Ile Cys
        195                 200                 205

Ile Asn Asp Lys Gly Ser Phe Ser Cys Thr Gly Ser Val Ser Gly Asn
    210                 215                 220

Ala Thr Cys Ser Gly Cys Thr Asp Gln Ser Ser Ser Gly Ser Ser Glu
225                 230                 235                 240

Tyr Pro Gly Ser Ser Gly Thr Thr Lys Pro Pro Thr Asp Pro Thr Gly
                245                 250                 255

Gly Glu Asn Lys Asp Gln Asp Lys Lys Ala Glu Ala Thr Ser Leu Gln
            260                 265                 270

Phe Ala Met Ser Ser Phe Cys Leu Ala Leu Ser Leu Met Ile Gly Val
        275                 280                 285

Ala Val Leu
    290
```

<210> SEQ ID NO 35
<211> LENGTH: 270
<212> TYPE: DNA
<213> ORGANISM: Phakopsora pachyrhizi
<220> FEATURE:
<221> NAME/KEY: misc_feature
<222> LOCATION: (1)..(270)
<223> OTHER INFORMATION: 20-h7

<400> SEQUENCE: 35

```
atgtgtggcc tgaaaatgag agctacatgt agatcggtta agttggggag ctgcaggtgt      60

ttgggatgtg gaacaatgct caagtgtagg aggaattggt tgcccaatag gatgtgtcag     120

ttgagaagta gaaggttgtg gcaaaatagt acctctacct ctccctcttc ccctacctct     180

actaatccct ctaccagtac ctcttcctct accactcata ttctgattat ttgccattta     240

tatgcatata aaaataatta cctaatgtag                                      270
```

<210> SEQ ID NO 36
<211> LENGTH: 89
<212> TYPE: PRT
<213> ORGANISM: Phakopsora pachyrhizi
<220> FEATURE:
<221> NAME/KEY: VARIANT
<222> LOCATION: (1)..(89)
<223> OTHER INFORMATION: 20-h7

<400> SEQUENCE: 36

```
Met Cys Gly Leu Lys Met Arg Ala Thr Cys Arg Ser Val Lys Leu Gly
1               5                   10                  15

Ser Cys Arg Cys Leu Gly Cys Gly Thr Met Leu Lys Cys Arg Arg Asn
            20                  25                  30
```

-continued

```
Trp Leu Pro Asn Arg Met Cys Gln Leu Arg Ser Arg Arg Leu Trp Gln
        35                  40                  45

Asn Ser Thr Ser Thr Ser Pro Ser Ser Pro Thr Ser Thr Asn Pro Ser
    50                  55                  60

Thr Ser Thr Ser Ser Ser Thr Thr His Ile Leu Ile Ile Cys His Leu
65                  70                  75                  80

Tyr Ala Tyr Lys Asn Asn Tyr Leu Met
                85


<210> SEQ ID NO 37
<211> LENGTH: 996
<212> TYPE: DNA
<213> ORGANISM: Phakopsora pachyrhizi
<220> FEATURE:
<221> NAME/KEY: misc_feature
<222> LOCATION: (1)..(996)
<223> OTHER INFORMATION: 20-j15

<400> SEQUENCE: 37

atggtttgtc aatgggagcc ttggactcag tacggtcatg atgccgtggt gcagtatgag      60

ggttgcttct acaagatcat tcaacctcac aggtccgagc ccaactggca acccacaaac     120

acacctgctc tatggtcgag agttcctgat gattgctgcc atcagtacag gtctggtgag     180

aatcaccatg gggccaaga gcataatcga ccacagtttg tagatcaatc aggtggtgct     240

ccaggaggag gctaccaaga aaggccccaa ggcggtggtt ggggacaaga caacaacggt     300

ggaaatcaac tacaagaaaa tcaaggctgg ctagacgaga aaagaaaaca tcaattggag     360

attgggggtg ggattttggg cgctgtggct atcggagccg gcgcatatgc ttacagtaag     420

cacaagagcg aagaaaagga agaggctaag aaacaagctt ggcaaaacga atctaatcat     480

gaaacgtggt tgagaggtgc acatgcgcat actcaacatt acatgtctgg tggacaaagt     540

ccaccagtct attgggtttt ggtcgacaga aatgatccga tacctaataa cgctatcgaa     600

ggcggacgtg aaggcggtca ctcactttac attggtaggg tgttcttcaa gtccggtcta     660

catatcggaa aagtgtctag ccatgtaggt ggtattgcta tcggatgggg tggcaaggag     720

cacaatgact ttgataagtt tgaggttctc tgtggtgaca atcgtgccat tcgttggata     780

aatcactcat cgcaccaagg aaatattact gtccaaggtt ggcagcccgt agaaggagga     840

agagaggcag atggaagatt cttgtttgtt agtcaagtcc aacatgatgg tggtgttcat     900

ccttgcaagg cccaagatac caccgatttt gcgatctttt cttacggagg taaagaacac     960

acctccaaag aattcaacat cttggcttat gcgtga                              996


<210> SEQ ID NO 38
<211> LENGTH: 331
<212> TYPE: PRT
<213> ORGANISM: Phakopsora pachyrhizi
<220> FEATURE:
<221> NAME/KEY: VARIANT
<222> LOCATION: (1)..(331)
<223> OTHER INFORMATION: 20-j15

<400> SEQUENCE: 38

Met Val Cys Gln Trp Glu Pro Trp Thr Gln Tyr Gly His Asp Ala Val
1               5                   10                  15

Val Gln Tyr Glu Gly Cys Phe Tyr Lys Ile Ile Gln Pro His Arg Ser
            20                  25                  30

Glu Pro Asn Trp Gln Pro Thr Asn Thr Pro Ala Leu Trp Ser Arg Val
        35                  40                  45
```

-continued

```
Pro Asp Asp Cys Cys His Gln Tyr Arg Ser Gly Glu Asn His His Gly
    50                  55                  60

Gly Gln Glu His Asn Arg Pro Gln Phe Val Asp Gln Ser Gly Gly Ala
65                  70                  75                  80

Pro Gly Gly Gly Tyr Gln Glu Arg Pro Gln Gly Gly Gly Trp Gly Gln
                85                  90                  95

Asp Asn Asn Gly Gly Asn Gln Leu Gln Glu Asn Gln Gly Trp Leu Asp
            100                 105                 110

Glu Lys Arg Lys His Gln Leu Glu Ile Gly Gly Gly Ile Leu Gly Ala
        115                 120                 125

Val Ala Ile Gly Ala Gly Ala Tyr Ala Tyr Ser Lys His Lys Ser Glu
    130                 135                 140

Glu Lys Glu Glu Ala Lys Lys Gln Ala Trp Gln Asn Glu Ser Asn His
145                 150                 155                 160

Glu Thr Trp Leu Arg Gly Ala His Ala His Thr Gln His Tyr Met Ser
                165                 170                 175

Gly Gly Gln Ser Pro Pro Val Tyr Trp Val Leu Val Asp Arg Asn Asp
            180                 185                 190

Pro Ile Pro Asn Asn Ala Ile Glu Gly Gly Arg Glu Gly Gly His Ser
        195                 200                 205

Leu Tyr Ile Gly Arg Val Phe Phe Lys Ser Gly Leu His Ile Gly Lys
    210                 215                 220

Val Ser Ser His Val Gly Gly Ile Ala Ile Gly Trp Gly Gly Lys Glu
225                 230                 235                 240

His Asn Asp Phe Asp Lys Phe Glu Val Leu Cys Gly Asp Asn Arg Ala
                245                 250                 255

Ile Arg Trp Ile Asn His Ser Ser His Gln Gly Asn Ile Thr Val Gln
            260                 265                 270

Gly Trp Gln Pro Val Glu Gly Gly Arg Glu Ala Asp Gly Arg Phe Leu
        275                 280                 285

Phe Val Ser Gln Val Gln His Asp Gly Gly Val His Pro Cys Lys Ala
    290                 295                 300

Gln Asp Thr Thr Asp Phe Ala Ile Phe Ser Tyr Gly Gly Lys Glu His
305                 310                 315                 320

Thr Ser Lys Glu Phe Asn Ile Leu Ala Tyr Ala
                325                 330
```

<210> SEQ ID NO 39
<211> LENGTH: 255
<212> TYPE: DNA
<213> ORGANISM: Phakopsora pachyrhizi
<220> FEATURE:
<221> NAME/KEY: misc_feature
<222> LOCATION: (1)..(255)
<223> OTHER INFORMATION: 21-b5

<400> SEQUENCE: 39

```
atgagctata ggctgagggt ccagggtttt ttggtgaaga tatcagccag ttggggggtt      60

ttttttttt taaaaaaaaa aaaaaaaatt atacttttat ttcaaagtta tagaataatg      120

atttgtgtaa taaaattctc atatgatatg ttagattttt ttactgaaaa tttttatcta     180

tgtaaatttg agttgaaact agtgttatca cattctaata ttattaagtc taaggtgata     240

aaaccagcca gatag                                                      255
```

<210> SEQ ID NO 40

<211> LENGTH: 84
<212> TYPE: PRT
<213> ORGANISM: Phakopsora pachyrhizi
<220> FEATURE:
<221> NAME/KEY: VARIANT
<222> LOCATION: (1)..(84)
<223> OTHER INFORMATION: 21-b5

<400> SEQUENCE: 40

Met Ser Tyr Arg Leu Arg Val Gln Gly Phe Leu Val Lys Ile Ser Ala
1 5 10 15

Ser Trp Gly Val Phe Phe Phe Leu Lys Lys Lys Lys Lys Ile Ile Leu
20 25 30

Leu Phe Gln Ser Tyr Arg Ile Met Ile Cys Val Ile Lys Phe Ser Tyr
35 40 45

Asp Met Leu Asp Phe Phe Thr Glu Asn Phe Tyr Leu Cys Lys Phe Glu
50 55 60

Leu Lys Leu Val Leu Ser His Ser Asn Ile Ile Lys Ser Lys Val Ile
65 70 75 80

Lys Pro Ala Arg

<210> SEQ ID NO 41
<211> LENGTH: 330
<212> TYPE: DNA
<213> ORGANISM: Phakopsora pachyrhizi
<220> FEATURE:
<221> NAME/KEY: misc_feature
<222> LOCATION: (1)..(330)
<223> OTHER INFORMATION: 21-k6

<400> SEQUENCE: 41
atgttcgaat atcgaataaa attttcaaaa aaactgttcc tctttgtaat aagtagcttt 60
attactctaa actttcaact attagaagct aagaaaccgg cccatggact tgcaaagatt 120
ggcaatagct cagtaacagg atcgaagtta aaacctcctc gtcgagttgt accgctcgga 180
attcttcccg tagtgacaca tactagcaca cccttagaaa gagtacaaaa ggcacaacac 240
catcacgaat ttcacaggaa tagacctcaa aatagagatt ctacattaca ttctagtatc 300
aagcacacca ggaaatctta ttctccctaa 330

<210> SEQ ID NO 42
<211> LENGTH: 109
<212> TYPE: PRT
<213> ORGANISM: Phakopsora pachyrhizi
<220> FEATURE:
<221> NAME/KEY: VARIANT
<222> LOCATION: (1)..(109)
<223> OTHER INFORMATION: 21-k6

<400> SEQUENCE: 42

Met Phe Glu Tyr Arg Ile Lys Phe Ser Lys Lys Leu Phe Leu Phe Val
1 5 10 15

Ile Ser Ser Phe Ile Thr Leu Asn Phe Gln Leu Leu Glu Ala Lys Lys
20 25 30

Pro Ala His Gly Leu Ala Lys Ile Gly Asn Ser Ser Val Thr Gly Ser
35 40 45

Lys Leu Lys Pro Pro Arg Arg Val Val Pro Leu Gly Ile Leu Pro Val
50 55 60

Val Thr His Thr Ser Thr Pro Leu Glu Arg Val Gln Lys Ala Gln His
65 70 75 80

His His Glu Phe His Arg Asn Arg Pro Gln Asn Arg Asp Ser Thr Leu

-continued

```
                85                  90                  95

His Ser Ser Ile Lys His Thr Arg Lys Ser Tyr Ser Pro
            100                 105


<210> SEQ ID NO 43
<211> LENGTH: 876
<212> TYPE: DNA
<213> ORGANISM: Phakopsora pachyrhizi
<220> FEATURE:
<221> NAME/KEY: misc_feature
<222> LOCATION: (1)..(876)
<223> OTHER INFORMATION: 30-L16

<400> SEQUENCE: 43

atgttgcact tttctagttt aacttctcta ggaatttttg cgtgccaaac tgcttggctc      60

gttgcagttt caaacgcctt cgtagcggaa catgcagtta tccaggacat aaccaatctt     120

gcttttagtc ctaataagat tgtagataga acacttggac aaaaaaaccc aaattttgcc     180

aagttcgtca atgcagaacc attactttat cgtgaaatgg ctcgcaaagc tggacgatct     240

gttggaacag tcttaactga ctctcgagga accaatcttc ctctactcat ccgtgacctt     300

cgagtcaccg actggattca tagcgatccg gtaattaagg gaatgccacc aaacaatcta     360

cctcaaaatg ctattgaact tgcccagaac tccttcgcat ctcgtctagt ggacattcgg     420

aacgcaaatg ataaagccaa gttcgaccag cacgcattaa tagcacgtaa ccacttagct     480

aaggtactgt tttacatcat aagtgagatg catatatcta tgcttccgaa acttgatgta     540

gtcaatgtag ctgcgtggca gaaagaaagg gcaggccgcg tcgctctttt gatgacacaa     600

aatcctttcc tcaagcggct ttattccgtc caccaacaaa tcggaaatcc ggatcaatac     660

attactcctg agactgcgga tgcagctttt atgaaacttt ttcctcatca aaattcaaac     720

aaacagggtc atccttcaca atcggcaaca tctgaaaaaa tgaaaactca ccctgagggc     780

gaaggaaact ttcctgccca tcgccctgtg gatgaaaata aagagggcat tgtccctgga     840

actcacccta atgctgcaac tgtttcttct tcttaa                              876


<210> SEQ ID NO 44
<211> LENGTH: 291
<212> TYPE: PRT
<213> ORGANISM: Phakopsora pachyrhizi
<220> FEATURE:
<221> NAME/KEY: VARIANT
<222> LOCATION: (1)..(291)
<223> OTHER INFORMATION: 30-L16

<400> SEQUENCE: 44

Met Leu His Phe Ser Ser Leu Thr Ser Leu Gly Ile Phe Ala Cys Gln
1               5                   10                  15

Thr Ala Trp Leu Val Ala Val Ser Asn Ala Phe Val Ala Glu His Ala
            20                  25                  30

Val Ile Gln Asp Ile Thr Asn Leu Ala Phe Ser Pro Asn Lys Ile Val
        35                  40                  45

Asp Arg Thr Leu Gly Gln Lys Asn Pro Asn Phe Ala Lys Phe Val Asn
    50                  55                  60

Ala Glu Pro Leu Leu Tyr Arg Glu Met Ala Arg Lys Ala Gly Arg Ser
65                  70                  75                  80

Val Gly Thr Val Leu Thr Asp Ser Arg Gly Thr Asn Leu Pro Leu Leu
                85                  90                  95

Ile Arg Asp Leu Arg Val Thr Asp Trp Ile His Ser Asp Pro Val Ile
            100                 105                 110
```

-continued

```
Lys Gly Met Pro Pro Asn Asn Leu Pro Gln Asn Ala Ile Glu Leu Ala
        115                 120                 125

Gln Asn Ser Phe Ala Ser Arg Leu Val Asp Ile Arg Asn Ala Asn Asp
    130                 135                 140

Lys Ala Lys Phe Asp Gln His Ala Leu Ile Ala Arg Asn His Leu Ala
145                 150                 155                 160

Lys Val Leu Phe Tyr Ile Ile Ser Glu Met His Ile Ser Met Leu Pro
                165                 170                 175

Lys Leu Asp Val Val Asn Val Ala Ala Trp Gln Lys Glu Arg Ala Gly
            180                 185                 190

Arg Val Ala Leu Leu Met Thr Gln Asn Pro Phe Leu Lys Arg Leu Tyr
        195                 200                 205

Ser Val His Gln Gln Ile Gly Asn Pro Asp Gln Tyr Ile Thr Pro Glu
    210                 215                 220

Thr Ala Asp Ala Ala Phe Met Lys Leu Phe Pro His Gln Asn Ser Asn
225                 230                 235                 240

Lys Gln Gly His Pro Ser Gln Ser Ala Thr Ser Glu Lys Met Lys Thr
                245                 250                 255

His Pro Glu Gly Glu Gly Asn Phe Pro Ala His Arg Pro Val Asp Glu
            260                 265                 270

Asn Lys Glu Gly Ile Val Pro Gly Thr His Pro Asn Ala Ala Thr Val
        275                 280                 285

Ser Ser Ser
    290
```

<210> SEQ ID NO 45
<211> LENGTH: 936
<212> TYPE: DNA
<213> ORGANISM: Phakopsora pachyrhizi
<220> FEATURE:
<221> NAME/KEY: misc_feature
<222> LOCATION: (1)..(936)
<223> OTHER INFORMATION: 28-L20

<400> SEQUENCE: 45

```
atgagaatca gtttatacac cctcatatgc gtttctttaa accttcatag cctaggttgt     60

gttaattttc tccaaatttc ccacaatcca acatttacgt tgggtaataa tgaaattagt    120

gttttgccac acgcggtaaa tcaaccttgg ttacgaagcc aacgcacgat aattactcca    180

gagggtgagg ttactgtgaa tatgctgcgt ggccataatt ctgttgatca gaaatcgcta    240

caaatgcaaa acgttataat accttataga gacttgatct gcagctatga aagatcagac    300

tctttagcac tgagcaaatc tacgcaaggt caatacaaac aattagctca agagttagat    360

aacttcaaga atgagaagga aggaaaatca atggaagctt tagaatcatt ggcgaaaaaa    420

acttttaata aactaaagtt tcatcatcct aactcggacg gtgaaacttt tgaaaatgct    480

aagctgatgg cggaatggac cataaataga gcagcttcaa agcaaggcgt ttggtggagc    540

aaaaaggact tgacacgctg gaacaaaaat tcgattgata aaatgacagc tataaagatt    600

ggcgatcttc tagactttga cattatgact tccaatcata agctctcatt aaccaacaaa    660

ttaaaagatg atttgtctga agctttaaag tctctcaaac tagaaggact ttcgacggag    720

ggaagccctc tactactttc accagttata attgatttac gtaagtttaa ggcaaacgat    780

ggtcagactt tatttgacat ccgccttaga caatttcaag aactacagga gaaaccaagt    840

agttcaatgc ggggggcaaa tgcgattctc aaacagcctc aaatcaatgg ggatgaccaa    900
```

-continued

```
attataaaaa ctctatgctc ttatctatca acttag                           936


<210> SEQ ID NO 46
<211> LENGTH: 311
<212> TYPE: PRT
<213> ORGANISM: Phakopsora pachyrhizi
<220> FEATURE:
<221> NAME/KEY: VARIANT
<222> LOCATION: (1)..(311)
<223> OTHER INFORMATION: 28-L20

<400> SEQUENCE: 46

Met Arg Ile Ser Leu Tyr Thr Leu Ile Cys Val Ser Leu Asn Leu His
1               5                   10                  15

Ser Leu Gly Cys Val Asn Phe Leu Gln Ile Ser His Asn Pro Thr Phe
            20                  25                  30

Thr Leu Gly Asn Asn Glu Ile Ser Val Leu Pro His Ala Val Asn Gln
        35                  40                  45

Pro Trp Leu Arg Ser Gln Arg Thr Ile Ile Thr Pro Glu Gly Glu Val
    50                  55                  60

Thr Val Asn Met Leu Arg Gly His Asn Ser Val Asp Gln Lys Ser Leu
65                  70                  75                  80

Gln Met Gln Asn Val Ile Ile Pro Tyr Arg Asp Leu Ile Cys Ser Tyr
                85                  90                  95

Glu Arg Ser Asp Ser Leu Ala Leu Ser Lys Ser Thr Gln Gly Gln Tyr
            100                 105                 110

Lys Gln Leu Ala Gln Glu Leu Asp Asn Phe Lys Asn Glu Lys Glu Gly
        115                 120                 125

Lys Ser Met Glu Ala Leu Glu Ser Leu Ala Lys Lys Thr Phe Asn Lys
    130                 135                 140

Leu Lys Phe His His Pro Asn Ser Asp Gly Glu Thr Phe Glu Asn Ala
145                 150                 155                 160

Lys Leu Met Ala Glu Trp Thr Ile Asn Arg Ala Ala Ser Lys Gln Gly
                165                 170                 175

Val Trp Trp Ser Lys Lys Asp Leu Thr Arg Trp Asn Lys Asn Ser Ile
            180                 185                 190

Asp Lys Met Thr Ala Ile Lys Ile Gly Asp Leu Leu Asp Phe Asp Ile
        195                 200                 205

Met Thr Ser Asn His Lys Leu Ser Leu Thr Asn Lys Leu Lys Asp Asp
    210                 215                 220

Leu Ser Glu Ala Leu Lys Ser Leu Lys Leu Glu Gly Leu Ser Thr Glu
225                 230                 235                 240

Gly Ser Pro Leu Leu Leu Ser Pro Val Ile Ile Asp Leu Arg Lys Phe
                245                 250                 255

Lys Ala Asn Asp Gly Gln Thr Leu Phe Asp Ile Arg Leu Arg Gln Phe
            260                 265                 270

Gln Glu Leu Gln Glu Lys Pro Ser Ser Ser Met Arg Gly Ala Asn Ala
        275                 280                 285

Ile Leu Lys Gln Pro Gln Ile Asn Gly Asp Asp Gln Ile Ile Lys Thr
    290                 295                 300

Leu Cys Ser Tyr Leu Ser Thr
305                 310


<210> SEQ ID NO 47
<211> LENGTH: 1047
<212> TYPE: DNA
<213> ORGANISM: Phakopsora pachyrhizi
```

-continued

<220> FEATURE:
<221> NAME/KEY: misc_feature
<222> LOCATION: (1)..(1047)
<223> OTHER INFORMATION: 26-k11

<400> SEQUENCE: 47

```
atgcactcga gagcatctta ttggtcgagc tttgccttag ctctagccac aataactatc     60

ccctctcctg cgacgagcaa acaatgcgct gcggatccca ctaacacggg ttgcgttatg    120

tgcccggaat ctgaactaat ggaatggtgg aacaaaggcc ttgaacacaa caaaaagtgc    180

agcgatgttg atgatgttac caagaaggcg aaatgttact gcaaaggata cgctacctta    240

gcctacgctt ggtctaaagg cagatgctgc actgaatact cccccacatt acaagcctcg    300

gaaaatatct gcaatcttgc tacctatccc gaatatcata taaagatgca tttagatcat    360

catttaaccg acgctaagcg agtgcaagac ggtatctggc acaatgactc tggtgttaaa    420

gtgcccaaag tctacgagca cgttgatgtt tacaggggcg ataaccctga ggttggtgaa    480

ggctactcag aaaaagacgc aaaagcccaa tcctctgaaa aaacttaccg ggaatccaag    540

gttgttaaga ctcatcaatc cgcccccaat tctttggagg accaatccac gaaaaaggag    600

ctatcttcat atagcgggca acaagctacc aattttgggt cgcaagcacc ccgggtcaat    660

tttatgagcg aggggaagtc taatgtagaa aaacataaac cttcaagctg gacagagaaa    720

cgtaataaaa agcatgttca gtataacccc tcgtcctgga gctaccctca tgctcgtctc    780

tatgctggca ctaggcatca caaagctaga gtgagcaaaa agccccgcaa ttgtgtcaat    840

gagcaggaga agtatcacaa ttatgttaaa tatcattcta agcgatccac tttggaaaca    900

aagccaaccc taggcatcac gaaagcagag tcattaattg cgaagaaact gcaaaagcga    960

ggtgtgattt gtgggataga ttttcaaaac gttccatatc ctaaatctgt acctacagct   1020

gtgcttaagg tttatgctga actttga                                       1047
```

<210> SEQ ID NO 48
<211> LENGTH: 348
<212> TYPE: PRT
<213> ORGANISM: Phakopsora pachyrhizi
<220> FEATURE:
<221> NAME/KEY: VARIANT
<222> LOCATION: (1)..(348)
<223> OTHER INFORMATION: 26-k11

<400> SEQUENCE: 48

```
Met His Ser Arg Ala Ser Tyr Trp Ser Ser Phe Ala Leu Ala Leu Ala
1               5                   10                  15

Thr Ile Thr Ile Pro Ser Pro Ala Thr Ser Lys Gln Cys Ala Ala Asp
            20                  25                  30

Pro Thr Asn Thr Gly Cys Val Met Cys Pro Glu Ser Glu Leu Met Glu
        35                  40                  45

Trp Trp Asn Lys Gly Leu Glu His Asn Lys Lys Cys Ser Asp Val Asp
    50                  55                  60

Asp Val Thr Lys Lys Ala Lys Cys Tyr Cys Lys Gly Tyr Ala Thr Leu
65                  70                  75                  80

Ala Tyr Ala Trp Ser Lys Gly Arg Cys Cys Thr Glu Tyr Ser Pro Thr
                85                  90                  95

Leu Gln Ala Ser Glu Asn Ile Cys Asn Leu Ala Thr Tyr Pro Glu Tyr
            100                 105                 110

His Ile Lys Met His Leu Asp His His Leu Thr Asp Ala Lys Arg Val
        115                 120                 125
```

```
Gln Asp Gly Ile Trp His Asn Asp Ser Gly Val Lys Val Pro Lys Val
    130                 135                 140

Tyr Glu His Val Asp Val Tyr Arg Gly Asp Asn Pro Glu Val Gly Glu
145                 150                 155                 160

Gly Tyr Ser Glu Lys Asp Ala Lys Ala Gln Ser Ser Glu Lys Thr Tyr
                165                 170                 175

Arg Glu Ser Lys Val Val Lys Thr His Gln Ser Ala Pro Asn Ser Leu
            180                 185                 190

Glu Asp Gln Ser Thr Lys Lys Glu Leu Ser Ser Tyr Ser Gly Gln Gln
        195                 200                 205

Ala Thr Asn Phe Gly Ser Gln Ala Pro Arg Val Asn Phe Met Ser Glu
    210                 215                 220

Gly Lys Ser Asn Val Glu Lys His Lys Pro Ser Ser Trp Thr Glu Lys
225                 230                 235                 240

Arg Asn Lys Lys His Val Gln Tyr Asn Pro Ser Ser Trp Ser Tyr Pro
                245                 250                 255

His Ala Arg Leu Tyr Ala Gly Thr Arg His His Lys Ala Arg Val Ser
            260                 265                 270

Lys Lys Pro Arg Asn Cys Val Asn Glu Gln Glu Lys Tyr His Asn Tyr
        275                 280                 285

Val Lys Tyr His Ser Lys Arg Ser Thr Leu Glu Thr Lys Pro Thr Leu
    290                 295                 300

Gly Ile Thr Lys Ala Glu Ser Leu Ile Ala Lys Lys Leu Gln Lys Arg
305                 310                 315                 320

Gly Val Ile Cys Gly Ile Asp Phe Gln Asn Val Pro Tyr Pro Lys Ser
                325                 330                 335

Val Pro Thr Ala Val Leu Lys Val Tyr Ala Glu Leu
            340                 345
```

<210> SEQ ID NO 49
<211> LENGTH: 312
<212> TYPE: DNA
<213> ORGANISM: Phakopsora pachyrhizi
<220> FEATURE:
<221> NAME/KEY: misc_feature
<222> LOCATION: (1)..(312)
<223> OTHER INFORMATION: 21-L24

<400> SEQUENCE: 49

```
atggttggat gtgagagcgg tgcaacgaaa aagtctatga taatcaagat gattggattc      60

ttgtgcattt ggtttcaact attagaaata gttttgactc aatctactgc tgcaactact     120

agtgccactg agactaaaaa ttataatagt tattttaaaa ggcttgaaaa aagaagccca     180

tcgaccagct ctggtcgaat tgagaaaaga catcgcagat gtggaccgcc atatggggga     240

tattatggac ctggatatag tagtggttat tataactatg gctattactc tggatataag     300

aaaaagcaat aa                                                         312
```

<210> SEQ ID NO 50
<211> LENGTH: 103
<212> TYPE: PRT
<213> ORGANISM: Phakopsora pachyrhizi
<220> FEATURE:
<221> NAME/KEY: VARIANT
<222> LOCATION: (1)..(103)
<223> OTHER INFORMATION: 21-L24

<400> SEQUENCE: 50

```
Met Val Gly Cys Glu Ser Gly Ala Thr Lys Lys Ser Met Ile Ile Lys
```

-continued

```
1               5                   10                  15

Met Ile Gly Phe Leu Cys Ile Trp Phe Gln Leu Leu Glu Ile Val Leu
            20                  25                  30

Thr Gln Ser Thr Ala Ala Thr Thr Ser Ala Thr Glu Thr Lys Asn Tyr
        35                  40                  45

Asn Ser Tyr Phe Lys Arg Leu Glu Lys Arg Ser Pro Ser Thr Ser Ser
    50                  55                  60

Gly Arg Ile Glu Lys Arg His Arg Arg Cys Gly Pro Pro Tyr Gly Gly
65                  70                  75                  80

Tyr Tyr Gly Pro Gly Tyr Ser Ser Gly Tyr Tyr Asn Tyr Gly Tyr Tyr
                85                  90                  95

Ser Gly Tyr Lys Lys Lys Gln
            100


<210> SEQ ID NO 51
<211> LENGTH: 174
<212> TYPE: DNA
<213> ORGANISM: Phakopsora pachyrhizi
<220> FEATURE:
<221> NAME/KEY: misc_feature
<222> LOCATION: (1)..(174)
<223> OTHER INFORMATION: 21-k22

<400> SEQUENCE: 51

atgctttcgc ttcaagtatt gcgcctgtcg ttgctctatt gtttgagtga agatttacag      60

ctaacggagt tgttaaaaaa ttgccatgtc ttttatttgg aagctatcaa caaactagaa     120

agatacaaga agaaacaaaa gtattttaaa attcacttca aatatttatc ctga           174


<210> SEQ ID NO 52
<211> LENGTH: 57
<212> TYPE: PRT
<213> ORGANISM: Phakopsora pachyrhizi
<220> FEATURE:
<221> NAME/KEY: VARIANT
<222> LOCATION: (1)..(57)
<223> OTHER INFORMATION: 21-k22

<400> SEQUENCE: 52

Met Leu Ser Leu Gln Val Leu Arg Leu Ser Leu Leu Tyr Cys Leu Ser
1               5                   10                  15

Glu Asp Leu Gln Leu Thr Glu Leu Leu Lys Asn Cys His Val Phe Tyr
            20                  25                  30

Leu Glu Ala Ile Asn Lys Leu Glu Arg Tyr Lys Lys Lys Gln Lys Tyr
        35                  40                  45

Phe Lys Ile His Phe Lys Tyr Leu Ser
    50                  55


<210> SEQ ID NO 53
<211> LENGTH: 636
<212> TYPE: DNA
<213> ORGANISM: Phakopsora pachyrhizi
<220> FEATURE:
<221> NAME/KEY: misc_feature
<222> LOCATION: (1)..(636)
<223> OTHER INFORMATION: 20-a22

<400> SEQUENCE: 53

atgaatcacg ctttgatcat ctgtctactt ggacttgcct cctttggctt gatctcgggg      60

cattttacca tggactatcc tccaacccga ggttttatgg aggatgacga ggataaattc     120

tgtggaggat tccctaccaa tgctaccggt agacatccgt tcccgatatc cggtcctgct     180
```

```
catgttgcgc tcatggctca ccacgggtcc cccaaaatca gtatttccat aagctttaag    240

cacaatttta ctagtgaagc cgagtttaac ggcactgagt tgatatctaa cgctcctctg    300

cctcatcctg gaaatgcttg ttttgaaatt gatctgtcga acgttactag taagatgacg    360

cctaaacctt ccaacggaac attagcaact ctagaggtta aatatgatgc cggaggtgag    420

gctttgtacc agtgttcaga yttagttctg gtccaggatg ctgcggtgac aaatcaaagc    480

cttagcagct gctctgccgg ccgtggcagt aatggcggaa gcggctctga tgccaagcaa    540

aatgctcaaa atagctctgc taactctttg tggttccaac ctactccgac tatgatctgc    600

cttagtctaa ttcttttatc gctctccatt ctttaa                              636
```

<210> SEQ ID NO 54
<211> LENGTH: 211
<212> TYPE: PRT
<213> ORGANISM: Phakopsora pachyrhizi
<220> FEATURE:
<221> NAME/KEY: VARIANT
<222> LOCATION: (1)..(211)
<223> OTHER INFORMATION: 20-a22

<400> SEQUENCE: 54

```
Met Asn His Ala Leu Ile Ile Cys Leu Leu Gly Leu Ala Ser Phe Gly
1               5                   10                  15

Leu Ile Ser Gly His Phe Thr Met Asp Tyr Pro Pro Thr Arg Gly Phe
            20                  25                  30

Met Glu Asp Asp Glu Asp Lys Phe Cys Gly Gly Phe Pro Thr Asn Ala
        35                  40                  45

Thr Gly Arg His Pro Phe Pro Ile Ser Gly Pro Ala His Val Ala Leu
    50                  55                  60

Met Ala His His Gly Ser Pro Lys Ile Ser Ile Ser Ile Ser Phe Lys
65                  70                  75                  80

His Asn Phe Thr Ser Glu Ala Glu Phe Asn Gly Thr Glu Leu Ile Ser
                85                  90                  95

Asn Ala Pro Leu Pro His Pro Gly Asn Ala Cys Phe Glu Ile Asp Leu
            100                 105                 110

Ser Asn Val Thr Ser Lys Met Thr Pro Lys Pro Ser Asn Gly Thr Leu
        115                 120                 125

Ala Thr Leu Glu Val Lys Tyr Asp Ala Gly Gly Glu Ala Leu Tyr Gln
    130                 135                 140

Cys Ser Asp Leu Val Leu Val Gln Asp Ala Ala Val Thr Asn Gln Ser
145                 150                 155                 160

Leu Ser Ser Cys Ser Ala Gly Arg Gly Ser Asn Gly Gly Ser Gly Ser
                165                 170                 175

Asp Ala Lys Gln Asn Ala Gln Asn Ser Ser Ala Asn Ser Leu Trp Phe
            180                 185                 190

Gln Pro Thr Pro Thr Met Ile Cys Leu Ser Leu Ile Leu Leu Ser Leu
        195                 200                 205

Ser Ile Leu
    210
```

<210> SEQ ID NO 55
<211> LENGTH: 639
<212> TYPE: DNA
<213> ORGANISM: Phakopsora pachyrhizi
<220> FEATURE:
<221> NAME/KEY: misc_feature
<222> LOCATION: (1)..(639)

<223> OTHER INFORMATION: 19-o13

<400> SEQUENCE: 55

```
atggccaaaa ttttgtttca atttattttg ctaataattg gcttgttaag ttcgtgtggt     60
agagcgatgg agtcggtgga actgcctaag gtttccaagc aagctaaagt ggcttccacc    120
tccaccatcc ccgtggtggg cgttgagcta aagaacactg gccatttcac aaatgagatt    180
cccactcaat cgttaaattt aaactataaa tcttttaaac aagaactggg aaaagtgcag    240
gaaaggatta aaaagcatag ctttgaaacc caaagatatc taaagaatga ctttaatccc    300
attcaaaatt tgatcgaaaa attattgaga gtagccgaag agtacaaaaa tggagaaaaa    360
ataagctttg actcaaagaa gcatttgaca aacattagcg catcagatat ggtattgaat    420
ggaatcttgg atgaagttag aaagtttctg tcrgatttat ataagatacc caatatacct    480
tggaatactg gtatgagtcg gaaatgggta atcatgtcag gcatcttgca agtactagac    540
ccactcataa aacatggctt tttaaacaaa gtgcaaatgc agcagtggtt tgaagattca    600
gaagtcctcc gaaatttctg cctatgttct aagcaatga                           639
```

<210> SEQ ID NO 56
<211> LENGTH: 312
<212> TYPE: PRT
<213> ORGANISM: Phakopsora pachyrhizi
<220> FEATURE:
<221> NAME/KEY: VARIANT
<222> LOCATION: (1)..(312)
<223> OTHER INFORMATION: 19-o13

<400> SEQUENCE: 56

```
Met Ala Lys Ile Leu Phe Gln Phe Ile Leu Leu Ile Ile Gly Leu Leu
1               5                   10                  15

Ser Ser Cys Gly Arg Ala Met Glu Ser Val Glu Leu Pro Lys Val Ser
            20                  25                  30

Lys Gln Ala Lys Val Ala Ser Thr Ser Thr Ile Pro Val Val Gly Val
        35                  40                  45

Glu Leu Lys Asn Thr Gly His Phe Thr Asn Glu Ile Pro Thr Gln Ser
    50                  55                  60

Leu Asn Leu Asn Tyr Lys Ser Phe Lys Gln Glu Leu Gly Lys Val Gln
65                  70                  75                  80

Glu Arg Ile Lys Lys His Ser Phe Glu Thr Gln Arg Tyr Leu Lys Asn
                85                  90                  95

Asp Phe Asn Pro Ile Gln Asn Leu Ile Glu Lys Leu Leu Arg Val Ala
            100                 105                 110

Glu Glu Tyr Lys Asn Gly Glu Lys Ile Ser Phe Asp Ser Lys Lys His
        115                 120                 125

Leu Thr Asn Ile Ser Ala Ser Asp Met Val Leu Asn Gly Ile Leu Asp
    130                 135                 140

Glu Val Arg Lys Phe Leu Ser Asp Leu Tyr Lys Ile Pro Asn Ile Pro
145                 150                 155                 160

Trp Asn Thr Gly Met Ser Arg Lys Trp Val Ile Met Ser Gly Ile Leu
                165                 170                 175

Gln Val Leu Asp Pro Leu Ile Lys His Gly Phe Leu Asn Lys Val Gln
            180                 185                 190

Met Gln Gln Trp Phe Glu Asp Ser Glu Val Leu Arg Asn Ser Ala Tyr
        195                 200                 205

Val Leu Ser Asn Glu Phe Gly Leu His Ser Ser Tyr Trp Leu Pro Ser
    210                 215                 220
```

```
Val Glu Lys Leu Ile Asn Leu Thr Ala Asp Glu Phe Leu Trp Leu Ser
225                 230                 235                 240

Leu Leu Asn Glu Gln Glu Ala Lys Asn Phe Leu Arg Gln Leu Ile Gly
                245                 250                 255

Phe Thr Tyr Asn Ser Asn Glu Ser Cys Asn Ile Ser His Pro Lys Phe
            260                 265                 270

Thr Pro Ile Val Asn Leu Phe Ile Gly Asp Ser Gly Val Thr Lys Asp
        275                 280                 285

Thr Phe Asn Ala Leu Ile Glu Ala Ile Asp Ser Ser Glu Lys Phe Ser
    290                 295                 300

Glu Ser Thr Glu Gln Glu Ser Ser
305                 310


<210> SEQ ID NO 57
<211> LENGTH: 405
<212> TYPE: DNA
<213> ORGANISM: Phakopsora pachyrhizi
<220> FEATURE:
<221> NAME/KEY: misc_feature
<222> LOCATION: (1)..(405)
<223> OTHER INFORMATION: 19-L7

<400> SEQUENCE: 57

atggagcaga agaaaagttt taaagcttta gttgttcttc tatttgccct gctcaatctc      60

ttggtatcga tcagctctgc accgatgagc aagataacaa cagagacctc aaaaatctta     120

aacccagaga ccaacctgag cttgatcgaa aaatctacgg aaaataatag agtcgaaggc     180

ctgactgact taaaaagtgt cgaaaataat ccagcctcca aaacacaatc tgctccaagc     240

tatcagccac tatcagtggt tgattcttca aaatcacagg gctcaactgc acctatccta     300

tacaattatc agacgcctac tacacaaacg ttcacatacc aaaacccgga aatcccattg     360

tatggcaaga ttaaatatgg aactaccagt agaacttata agtag                     405


<210> SEQ ID NO 58
<211> LENGTH: 134
<212> TYPE: PRT
<213> ORGANISM: Phakopsora pachyrhizi
<220> FEATURE:
<221> NAME/KEY: VARIANT
<222> LOCATION: (1)..(134)
<223> OTHER INFORMATION: 19-L7

<400> SEQUENCE: 58

Met Glu Gln Lys Lys Ser Phe Lys Ala Leu Val Val Leu Leu Phe Ala
1               5                   10                  15

Leu Leu Asn Leu Leu Val Ser Ile Ser Ser Ala Pro Met Ser Lys Ile
            20                  25                  30

Thr Thr Glu Thr Ser Lys Ile Leu Asn Pro Glu Thr Asn Leu Ser Leu
        35                  40                  45

Ile Glu Lys Ser Thr Glu Asn Asn Arg Val Glu Gly Leu Thr Asp Leu
    50                  55                  60

Lys Ser Val Glu Asn Asn Pro Ala Ser Lys Thr Gln Ser Ala Pro Ser
65                  70                  75                  80

Tyr Gln Pro Leu Ser Val Val Asp Ser Ser Lys Ser Gln Gly Ser Thr
                85                  90                  95

Ala Pro Ile Leu Tyr Asn Tyr Gln Thr Pro Thr Thr Gln Thr Phe Thr
            100                 105                 110

Tyr Gln Asn Pro Glu Ile Pro Leu Tyr Gly Lys Ile Lys Tyr Gly Thr
```

115 120 125

Thr Ser Arg Thr Tyr Lys
130

<210> SEQ ID NO 59
<211> LENGTH: 906
<212> TYPE: DNA
<213> ORGANISM: Phakopsora pachyrhizi
<220> FEATURE:
<221> NAME/KEY: misc_feature
<222> LOCATION: (1)..(906)
<223> OTHER INFORMATION: 21-c12

<400> SEQUENCE: 59
atgaaaatcc ccatgatcta ccgttgcgca atcgcccttt tggccttttt tccaagcagc 60
ttgaaggctt attttttgtt gaaaaaacct ttatcacttc tagagtcaga tgaaaaaata 120
ttttattgca ctgcgcccat acaatctgga tacacagata ttctcaagta cttaccaata 180
aacaaaaaac cagacccctc accttatgtc aaaacggaga actcggtcat aactcaaatg 240
agcggagatg atgcatgtct aaaatatcga aaaaatttaa tatcctcccc gcctaaagat 300
ctcgtaaatc taagggcata taaaacatta cttttgagat cagtttatat gaaccttgag 360
ggcgtgttta agacatataa acataattct ggccctcaaa ccattttata tcatttgctt 420
gaagcacgcc ctgcggcctg taggctctta caaataaacg aaaaccgggc ggaccttaag 480
gctgacacag cacgaattat atgtgatcat ctggcaaaca taaaacatac agaagaagat 540
tttttcgaat ttgccggctg gatgcacttt attgccatga ttatcgatat tggagatgtt 600
gtgaaaatct cgccagaagc atttgcagcc gacattgctt ttcatgtcgg actcttgtcc 660
cttgagcaga agtttaattc ggatccggac cggtccaaaa tcataaaagc tttgctaaca 720
attcttgatg aacgtcgtca gaaatttcag cggtataaaa cctttcttaa gaatttttttc 780 aaagattatg atgaaaaact gccttggatg cgagaatatt attttccaaa aaacgggttg 840
ccagaaaatt tttgtaagac tttcttccta tcgagcaatc tatgtcaaga taataaaata 900
aaataa 906

<210> SEQ ID NO 60
<211> LENGTH: 301
<212> TYPE: PRT
<213> ORGANISM: Phakopsora pachyrhizi
<220> FEATURE:
<221> NAME/KEY: VARIANT
<222> LOCATION: (1)..(301)
<223> OTHER INFORMATION: 21-c12

<400> SEQUENCE: 60

Met Lys Ile Pro Met Ile Tyr Arg Cys Ala Ile Ala Leu Leu Ala Phe
1 5 10 15

Phe Pro Ser Ser Leu Lys Ala Tyr Phe Leu Leu Lys Lys Pro Leu Ser
20 25 30

Leu Leu Glu Ser Asp Glu Lys Ile Phe Tyr Cys Thr Ala Pro Ile Gln
35 40 45

Ser Gly Tyr Thr Asp Ile Leu Lys Tyr Leu Pro Ile Asn Lys Lys Pro
50 55 60

Asp Pro Ser Pro Tyr Val Lys Thr Glu Asn Ser Val Ile Thr Gln Met
65 70 75 80

Ser Gly Asp Asp Ala Cys Leu Lys Tyr Arg Lys Asn Leu Ile Ser Ser
85 90 95

-continued

```
Pro Pro Lys Asp Leu Val Asn Leu Arg Ala Tyr Lys Thr Leu Leu Leu
            100                 105                 110

Arg Ser Val Tyr Met Asn Leu Glu Gly Val Phe Lys Thr Tyr Lys His
        115                 120                 125

Asn Ser Gly Pro Gln Thr Ile Leu Tyr His Leu Leu Glu Ala Arg Pro
    130                 135                 140

Ala Ala Cys Arg Leu Leu Gln Ile Asn Glu Asn Arg Ala Asp Leu Lys
145                 150                 155                 160

Ala Asp Thr Ala Arg Ile Ile Cys Asp His Leu Ala Asn Ile Lys His
                165                 170                 175

Thr Glu Glu Asp Phe Phe Glu Phe Ala Gly Trp Met His Phe Ile Ala
            180                 185                 190

Met Ile Ile Asp Ile Gly Asp Val Val Lys Ile Ser Pro Glu Ala Phe
        195                 200                 205

Ala Ala Asp Ile Ala Phe His Val Gly Leu Leu Ser Leu Glu Gln Lys
    210                 215                 220

Phe Asn Ser Asp Pro Asp Arg Ser Lys Ile Ile Lys Ala Leu Leu Thr
225                 230                 235                 240

Ile Leu Asp Glu Arg Arg Gln Lys Phe Gln Arg Tyr Lys Thr Phe Leu
                245                 250                 255

Lys Asn Phe Phe Lys Asp Tyr Asp Glu Lys Leu Pro Trp Met Arg Glu
            260                 265                 270

Tyr Tyr Phe Pro Lys Asn Gly Leu Pro Glu Asn Phe Cys Lys Thr Phe
        275                 280                 285

Phe Leu Ser Ser Asn Leu Cys Gln Asp Asn Lys Ile Lys
    290                 295                 300
```

```
<210> SEQ ID NO 61
<211> LENGTH: 723
<212> TYPE: DNA
<213> ORGANISM: Phakopsora pachyrhizi
<220> FEATURE:
<221> NAME/KEY: misc_feature
<222> LOCATION: (1)..(723)
<223> OTHER INFORMATION: 16-n11

<400> SEQUENCE: 61

atgaagatga atatgcttca ccattctttg ttgctcttca ctttcttctg tataaaactg      60

ttgatttgct tacccatgaa tggtaagact ccagcagttg ttgccgatgc cgtttcagca     120

attcaggaaa ccggaaaagt tgcaagcacc agcatagaag taccaagcgc aaatttgggt     180

gcggaagtca aggaactttc agcgattgat gcgtctgtgt tcacaaatgt tcctgctatc     240

aatccgaagg attcggccca agtagaaaat ctggggcaat caactttgca ggagaaagaa     300

agcccagtta tattgaaggg tgatgtaaat catgagaaaa aaaatctaat aaaaaaccgaa    360

tctaaatctg cagatagtga aataaaaaaa gaagttgatg aaaaaccctt gaaagaaaaa     420

tcacagggtg aagacggtcc tgatggccct gaaaaaaaaa acattgaggg cgaaggagga     480

gatctgaaaa atgacaaaaa tttgaatcaa tcagaacaaa aaactaggtt gagcaggatt     540

aagaactggt ttataaggca ataccttatg ttgaaaaaca atgtataccc taaaataaaa     600

gaaaaaagtc aacaattttg ggcttggaca aagaaaaaat tttcaagagg caataacaag     660

gtagctacaa atgaaattga attaaagcca tgttgccgag gaaaaaagac acatttcagc     720

taa                                                                   723
```

```
<210> SEQ ID NO 62
```

<211> LENGTH: 240
<212> TYPE: PRT
<213> ORGANISM: Phakopsora pachyrhizi
<220> FEATURE:
<221> NAME/KEY: VARIANT
<222> LOCATION: (1)..(240)
<223> OTHER INFORMATION: 16-n11

<400> SEQUENCE: 62

```
Met Lys Met Asn Met Leu His His Ser Leu Leu Leu Phe Thr Phe Phe
1               5                   10                  15

Cys Ile Lys Leu Leu Ile Cys Leu Pro Met Asn Gly Lys Thr Pro Ala
            20                  25                  30

Val Val Ala Asp Ala Val Ser Ala Ile Gln Glu Thr Gly Lys Val Ala
        35                  40                  45

Ser Thr Ser Ile Glu Val Pro Ser Ala Asn Leu Gly Ala Glu Val Lys
    50                  55                  60

Glu Leu Ser Ala Ile Asp Ala Ser Val Phe Thr Asn Val Pro Ala Ile
65                  70                  75                  80

Asn Pro Lys Asp Ser Ala Gln Val Glu Asn Leu Gly Gln Ser Thr Leu
                85                  90                  95

Gln Glu Lys Glu Ser Pro Val Ile Leu Lys Gly Asp Val Asn His Glu
            100                 105                 110

Lys Lys Asn Leu Ile Lys Thr Glu Ser Lys Ser Ala Asp Ser Glu Ile
        115                 120                 125

Lys Lys Glu Val Asp Glu Lys Pro Leu Lys Glu Lys Ser Gln Gly Glu
    130                 135                 140

Asp Gly Pro Asp Gly Pro Glu Lys Lys Asn Ile Glu Gly Glu Gly Gly
145                 150                 155                 160

Asp Leu Lys Asn Asp Lys Asn Leu Asn Gln Ser Glu Gln Lys Thr Arg
                165                 170                 175

Leu Ser Arg Ile Lys Asn Trp Phe Ile Arg Gln Tyr Leu Met Leu Lys
            180                 185                 190

Asn Asn Val Tyr Pro Lys Ile Lys Glu Lys Ser Gln Gln Phe Trp Ala
        195                 200                 205

Trp Thr Lys Lys Lys Phe Ser Arg Gly Asn Asn Lys Val Ala Thr Asn
    210                 215                 220

Glu Ile Glu Leu Lys Pro Cys Cys Arg Gly Lys Lys Thr His Phe Ser
225                 230                 235                 240
```

<210> SEQ ID NO 63
<211> LENGTH: 654
<212> TYPE: DNA
<213> ORGANISM: Phakopsora pachyrhizi
<220> FEATURE:
<221> NAME/KEY: misc_feature
<222> LOCATION: (1)..(654)
<223> OTHER INFORMATION: 15-m3

<400> SEQUENCE: 63

```
atgaagcttt tcagctgtac aaatgagtgg aacattttgc cctttgtatt attaagcgcg      60

tggtatacca gaaccgttct tggaatgcat tttgccgaaa gctcaaagga aaatattatc     120

agctctgcaa agggtctact acaggaacag cctccggaaa atataccaat tacacaagga     180

attagcatta ggactgaggg acaagattct ctttcgataa atgcagaagt aaaagagccc     240

aaatggcatt cggtttctca aaaggatgaa aatttccccg atgtaagaac ttggaaagag     300

attttgtatg gtagaacgaa tgcacacaat tatggttatt cagatgatga aataacgcct     360
```

```
gaaataaggc aaatactgaa aaatcgcctt ccaaagtttc tcccaccccc agcagaccca    420

aaactcgaaa ggatcaaaga taacttcgaa tttttaatga gaaacaatga tcccgctcga    480

aattataatt taaattttca aataaataca catcttaggg atctgcttga caattttaaa    540

gtgaatgctc agttaccaac cgaattggat gagcaattta gtgatgtaat aaaatttctc    600

aaagattcaa cttttaagaa tgataacgaa aaacatgtaa ttgagaatat tcac          654


<210> SEQ ID NO 64
<211> LENGTH: 218
<212> TYPE: PRT
<213> ORGANISM: Phakopsora pachyrhizi
<220> FEATURE:
<221> NAME/KEY: VARIANT
<222> LOCATION: (1)..(218)
<223> OTHER INFORMATION: 15-m3

<400> SEQUENCE: 64

Met Lys Leu Phe Ser Cys Thr Asn Glu Trp Asn Ile Leu Pro Phe Val
1               5                   10                  15

Leu Leu Ser Ala Trp Tyr Thr Arg Thr Val Leu Gly Met His Phe Ala
            20                  25                  30

Glu Ser Ser Lys Glu Asn Ile Ile Ser Ser Ala Lys Gly Leu Leu Gln
        35                  40                  45

Glu Gln Pro Pro Glu Asn Ile Pro Ile Thr Gln Gly Ile Ser Ile Arg
    50                  55                  60

Thr Glu Gly Gln Asp Ser Leu Ser Ile Asn Ala Glu Val Lys Glu Pro
65                  70                  75                  80

Lys Trp His Ser Val Ser Gln Lys Asp Glu Asn Phe Pro Asp Val Arg
                85                  90                  95

Thr Trp Lys Glu Ile Leu Tyr Gly Arg Thr Asn Ala His Asn Tyr Gly
            100                 105                 110

Tyr Ser Asp Asp Glu Ile Thr Pro Glu Ile Arg Gln Ile Leu Lys Asn
        115                 120                 125

Arg Leu Pro Lys Phe Leu Pro Pro Pro Ala Asp Pro Lys Leu Glu Arg
    130                 135                 140

Ile Lys Asp Asn Phe Glu Phe Leu Met Arg Asn Asn Asp Pro Ala Arg
145                 150                 155                 160

Asn Tyr Asn Leu Asn Phe Gln Ile Asn Thr His Leu Arg Asp Leu Leu
                165                 170                 175

Asp Asn Phe Lys Val Asn Ala Gln Leu Pro Thr Glu Leu Asp Glu Gln
            180                 185                 190

Phe Ser Asp Val Ile Lys Phe Leu Lys Asp Ser Thr Phe Lys Asn Asp
        195                 200                 205

Asn Glu Lys His Val Ile Glu Asn Ile His
    210                 215


<210> SEQ ID NO 65
<211> LENGTH: 486
<212> TYPE: DNA
<213> ORGANISM: Phakopsora pachyrhizi
<220> FEATURE:
<221> NAME/KEY: misc_feature
<222> LOCATION: (1)..(486)
<223> OTHER INFORMATION: 27-e12

<400> SEQUENCE: 65

atgaagatga atatgcttca ccattctttg ttgctcttca ctttcttctg tataaaactg     60

ttgatttgct tacccatgaa tggtaagact ccagcagttg ttgccgatgc cgtttcagca    120
```

```
attcaggaaa ccggaaaagt tgcaagtacc agcatagaag taccaagcgc aaatttgggt    180

gcggaagtca aggaactttc agcgattgat gcgtctgtgt tcacaaatgt tcctgctatc    240

aatccgaagg attcggccca agtagaaaat ctggggcaat caactttgca ggagaaagaa    300

agcccagtta tattgaaggg tgatgtaaat catgagaaaa aaaatctaat aaaaaccgaa    360

tctaaatctg cagatagtga aataaaaaaa gaagttgatg aaaaaccctt gaaagaaaaa    420

tcacagggtg aagacggtcc tgatggccct gaaaaaaaaa cattgagggc gaaggaggag    480

atctga                                                               486


<210> SEQ ID NO 66
<211> LENGTH: 161
<212> TYPE: PRT
<213> ORGANISM: Phakopsora pachyrhizi
<220> FEATURE:
<221> NAME/KEY: VARIANT
<222> LOCATION: (1)..(161)
<223> OTHER INFORMATION: 27-e12

<400> SEQUENCE: 66

Met Lys Met Asn Met Leu His His Ser Leu Leu Leu Phe Thr Phe Phe
1               5                   10                  15

Cys Ile Lys Leu Leu Ile Cys Leu Pro Met Asn Gly Lys Thr Pro Ala
            20                  25                  30

Val Val Ala Asp Ala Val Ser Ala Ile Gln Glu Thr Gly Lys Val Ala
        35                  40                  45

Ser Thr Ser Ile Glu Val Pro Ser Ala Asn Leu Gly Ala Glu Val Lys
    50                  55                  60

Glu Leu Ser Ala Ile Asp Ala Ser Val Phe Thr Asn Val Pro Ala Ile
65                  70                  75                  80

Asn Pro Lys Asp Ser Ala Gln Val Glu Asn Leu Gly Gln Ser Thr Leu
                85                  90                  95

Gln Glu Lys Glu Ser Pro Val Ile Leu Lys Gly Asp Val Asn His Glu
            100                 105                 110

Lys Lys Asn Leu Ile Lys Thr Glu Ser Lys Ser Ala Asp Ser Glu Ile
        115                 120                 125

Lys Lys Glu Val Asp Glu Lys Pro Leu Lys Glu Lys Ser Gln Gly Glu
    130                 135                 140

Asp Gly Pro Asp Gly Pro Glu Lys Lys Thr Leu Arg Ala Lys Glu Glu
145                 150                 155                 160

Ile


<210> SEQ ID NO 67
<211> LENGTH: 552
<212> TYPE: DNA
<213> ORGANISM: Phakopsora pachyrhizi
<220> FEATURE:
<221> NAME/KEY: misc_feature
<222> LOCATION: (1)..(552)
<223> OTHER INFORMATION: 24-i9

<400> SEQUENCE: 67

atgctgttct gcaaattttt attaattttt tcgttgatgt gctatggcgc tctagctgct     60

ccgataatga gagttttttg ggcggctttt ccactttttaa atcttccagt cttcaaattc    120

ctcattcacc cccaagagtc tttgaagtta cttcttggtt tagagagagg ayttcaggaa    180

attaaagatc tagaattgag taagagtgct tttagacttc aaaagttgat tttaggtgat    240
```

-continued

```
cagaaagtgt ttctgaagga aattgacggc aaaattgaaa acgaagcaac aaccttcgca    300

aatgtcatga gacttgataa taaaaagcag tttgaaaaca tacccttcag actacctcta    360

aatacaaagg atttgcatga aagtatttat aattctttag tagaagtagt taatgatcct    420

aaaattattg gcctccaaag gattcccaac ccaaaattga cgcaaaaacg tttaagtgaa    480

ttgaaaccca tatcggagcc cattgcagat attaatatac ttcgtactgc agtggcgcat    540

tcaaaattat aa                                                         552
```

<210> SEQ ID NO 68
<211> LENGTH: 182
<212> TYPE: PRT
<213> ORGANISM: Phakopsora pachyrhizi
<220> FEATURE:
<221> NAME/KEY: VARIANT
<222> LOCATION: (1)..(182)
<223> OTHER INFORMATION: 24-i9

<400> SEQUENCE: 68

```
Met Leu Phe Cys Lys Phe Leu Leu Ile Phe Ser Leu Met Cys Tyr Gly
1               5                   10                  15

Ala Leu Ala Ala Pro Ile Met Arg Val Phe Trp Ala Ala Phe Pro Leu
            20                  25                  30

Leu Asn Leu Pro Val Phe Lys Phe Leu Ile His Pro Gln Glu Ser Leu
        35                  40                  45

Lys Leu Leu Leu Gly Leu Glu Arg Gly Gln Glu Ile Lys Asp Leu Glu
    50                  55                  60

Leu Ser Lys Ser Ala Phe Arg Leu Gln Lys Leu Ile Leu Gly Asp Gln
65                  70                  75                  80

Lys Val Phe Leu Lys Glu Ile Asp Gly Lys Ile Glu Asn Glu Ala Thr
                85                  90                  95

Thr Phe Ala Asn Val Met Arg Leu Asp Asn Lys Lys Gln Phe Glu Asn
            100                 105                 110

Ile Pro Phe Arg Leu Pro Leu Asn Thr Lys Asp Leu His Glu Ser Ile
        115                 120                 125

Tyr Asn Ser Leu Val Glu Val Val Asn Asp Pro Lys Ile Ile Gly Leu
    130                 135                 140

Gln Arg Ile Pro Asn Pro Lys Leu Thr Gln Lys Arg Leu Ser Glu Leu
145                 150                 155                 160

Lys Pro Ile Ser Glu Pro Ile Ala Asp Ile Asn Ile Leu Arg Thr Ala
                165                 170                 175

Val Ala His Ser Lys Leu
            180
```

<210> SEQ ID NO 69
<211> LENGTH: 1074
<212> TYPE: DNA
<213> ORGANISM: Phakopsora pachyrhizi
<220> FEATURE:
<221> NAME/KEY: misc_feature
<222> LOCATION: (1)..(1074)
<223> OTHER INFORMATION: 23-m13

<400> SEQUENCE: 69

```
atgctatcgc ttttgaaact ttgttgtttc ttgactttta tttacagctg gggtctgca     60

aggccaatgt ttaaactatg tcggggtatg gattataaat tatgcatagt cgagaacgcg    120

ggcaatctgg gtataaaccc aagtaaggac accggaagtt ttatgaaatt tatgactgct    180

aattcgccag atgcgttcag ctccagtagc tcggcttcaa gcgttgtttc taaaaaagta    240
```

```
agggcaggct ctacgaaaaa acagagaaat attccaagca atttgttaac tcaaggtgag    300

cagctagaga gcagaagaga aattaacatt ccaagggcgc cccaaaaatt aaaaaccaaa    360

gaaaaaaact tgaatttaag ttcagaaaaa atcaacccga aatctctcag ggtttcggaa    420

aattcaactg ctgatcgaca ttctagatcc ctaccgcctg ggaaatcttc tcctttggta    480

accaacaaca acaataaaaa atcaaaatca ttaccaaagt caaagccgaa caagagttta    540

acaaaagttt atgagactca ttatgcaaaa agtcccaccc gagttcctat aaaagccccc    600

atgataaacc agattttgcc accaaaacgc aaaatattta tctcacctac tttaactagc    660

ggcaataaac ctgctgctga gcttaaatct ccagaaaact caaaacgctt ctctaccatt    720

aaagataaaa aactatcccc gccggtctct tttgactcta aatccccaga aaactcgaga    780

cgcttctcta ccaataaaga taaaagtcta tccccgccgg tcacttttga ctccacaaaa    840

attccgcatt ctaagcagac taatacaaat atccttgtta aacctcataa cttacctaat    900

aatgacatca aagactctcg tgaagtcaat cgattgacaa aagaaaaaaa tattggagaa    960

gtatccttca gaattcatcc agatgatgat gaatctttta agtttccaaa tttgaaagaa   1020

acacatatag gtaataaaaa tcacttttgg aatttcaatg aagaaaatca ataa         1074
```

```
<210> SEQ ID NO 70
<211> LENGTH: 357
<212> TYPE: PRT
<213> ORGANISM: Phakopsora pachyrhizi
<220> FEATURE:
<221> NAME/KEY: VARIANT
<222> LOCATION: (1)..(357)
<223> OTHER INFORMATION: 23-m13

<400> SEQUENCE: 70

Met Leu Ser Leu Leu Lys Leu Cys Cys Phe Leu Thr Phe Ile Tyr Ser
1               5                   10                  15

Trp Gly Ser Ala Arg Pro Met Phe Lys Leu Cys Arg Gly Met Asp Tyr
            20                  25                  30

Lys Leu Cys Ile Val Glu Asn Ala Gly Asn Leu Gly Ile Asn Pro Ser
        35                  40                  45

Lys Asp Thr Gly Ser Phe Met Lys Phe Met Thr Ala Asn Ser Pro Asp
    50                  55                  60

Ala Phe Ser Ser Ser Ser Ser Ala Ser Ser Val Val Ser Lys Lys Val
65                  70                  75                  80

Arg Ala Gly Ser Thr Lys Lys Gln Arg Asn Ile Pro Ser Asn Leu Leu
                85                  90                  95

Thr Gln Gly Glu Gln Leu Glu Ser Arg Arg Glu Ile Asn Ile Pro Arg
            100                 105                 110

Ala Pro Gln Lys Leu Lys Thr Lys Glu Lys Asn Leu Asn Leu Ser Ser
        115                 120                 125

Glu Lys Ile Asn Pro Lys Ser Leu Arg Val Ser Glu Asn Ser Thr Ala
    130                 135                 140

Asp Arg His Ser Arg Ser Leu Pro Pro Gly Lys Ser Ser Pro Leu Val
145                 150                 155                 160

Thr Asn Asn Asn Asn Lys Lys Ser Lys Ser Leu Pro Lys Ser Lys Pro
                165                 170                 175

Asn Lys Ser Leu Thr Lys Val Tyr Glu Thr His Tyr Ala Lys Ser Pro
            180                 185                 190

Thr Arg Val Pro Ile Lys Ala Pro Met Ile Asn Gln Ile Leu Pro Pro
        195                 200                 205
```

```
Lys Arg Lys Ile Phe Ile Ser Pro Thr Leu Thr Ser Gly Asn Lys Pro
    210                 215                 220

Ala Ala Glu Leu Lys Ser Pro Glu Asn Ser Lys Arg Phe Ser Thr Ile
225                 230                 235                 240

Lys Asp Lys Lys Leu Ser Pro Pro Val Ser Phe Asp Ser Lys Ser Pro
                245                 250                 255

Glu Asn Ser Arg Arg Phe Ser Thr Asn Lys Asp Lys Ser Leu Ser Pro
            260                 265                 270

Pro Val Thr Phe Asp Ser Thr Lys Ile Pro His Ser Lys Gln Thr Asn
        275                 280                 285

Thr Asn Ile Leu Val Lys Pro His Asn Leu Pro Asn Asn Asp Ile Lys
    290                 295                 300

Asp Ser Arg Glu Val Asn Arg Leu Thr Lys Glu Lys Asn Ile Gly Glu
305                 310                 315                 320

Val Ser Phe Arg Ile His Pro Asp Asp Asp Glu Ser Phe Lys Phe Pro
                325                 330                 335

Asn Leu Lys Glu Thr His Ile Gly Asn Lys Asn His Phe Trp Asn Phe
            340                 345                 350

Asn Glu Glu Asn Gln
        355
```

<210> SEQ ID NO 71
<211> LENGTH: 627
<212> TYPE: DNA
<213> ORGANISM: Phakopsora pachyrhizi
<220> FEATURE:
<221> NAME/KEY: misc_feature
<222> LOCATION: (1)..(627)
<223> OTHER INFORMATION: 02-f1 (01-G4)

<400> SEQUENCE: 71

```
atgcgttcac ttatcgttcc caccctttta tgcgtgctat ttattcacaa atcttgcgca     60

accgttcaca ctcagtgcta caactatttt ttacaaaagg atggatgcgt tttctctgca    120

gctgatgaca gaaatcgatg ttctgcagat cccaagccca gtacagccgt tggagtggtt    180

caagaaagca acaaaaatgt taaaagacac actctggcac gccgttatga tactacttta    240

ccatctcctt ctatacaggg tgaaggaatt tgcggacact atgacacagc aacagctgag    300

ggagccagtc tttgggttgg tcctaaccca ggtagcacaa gacctgagga ggcaggctgg    360

cttaacaggg gaaagacatc taattgcaat aagagattat atgtaataaa ccctcgcaca    420

ggaaaaaccg tctacgtaaa ggtcatagat ggccgcgatt ttcagacaac acagcctgat    480

gtgggatgct tccagattgc actcacccaa aagaccattc ttgagcttga tccgactgat    540

gaagaaaagg caaagggtgc cataggatct ctcacatggg acttcgacaa cctgcatgga    600

attagttctc agcaaggtcc tgtatga                                         627
```

<210> SEQ ID NO 72
<211> LENGTH: 208
<212> TYPE: PRT
<213> ORGANISM: Phakopsora pachyrhizi
<220> FEATURE:
<221> NAME/KEY: VARIANT
<222> LOCATION: (1)..(208)
<223> OTHER INFORMATION: 02-f1 (01-G4)

<400> SEQUENCE: 72

```
Met Arg Ser Leu Ile Val Pro Thr Leu Leu Cys Val Leu Phe Ile His
1               5                   10                  15
```

```
Lys Ser Cys Ala Thr Val His Thr Gln Cys Tyr Asn Tyr Phe Leu Gln
            20                  25                  30

Lys Asp Gly Cys Val Phe Ser Ala Ala Asp Asp Arg Asn Arg Cys Ser
        35                  40                  45

Ala Asp Pro Lys Pro Ser Thr Ala Val Gly Val Val Gln Glu Ser Asn
    50                  55                  60

Lys Asn Val Lys Arg His Thr Leu Ala Arg Arg Tyr Asp Thr Thr Leu
65                  70                  75                  80

Pro Ser Pro Ser Ile Gln Gly Glu Gly Ile Cys Gly His Tyr Asp Thr
                85                  90                  95

Ala Thr Ala Glu Gly Ala Ser Leu Trp Val Gly Pro Asn Pro Gly Ser
            100                 105                 110

Thr Arg Pro Glu Glu Ala Gly Trp Leu Asn Arg Gly Lys Thr Ser Asn
        115                 120                 125

Cys Asn Lys Arg Leu Tyr Val Ile Asn Pro Arg Thr Gly Lys Thr Val
    130                 135                 140

Tyr Val Lys Val Ile Asp Gly Arg Asp Phe Gln Thr Thr Gln Pro Asp
145                 150                 155                 160

Val Gly Cys Phe Gln Ile Ala Leu Thr Gln Lys Thr Ile Leu Glu Leu
                165                 170                 175

Asp Pro Thr Asp Glu Glu Lys Ala Lys Gly Ala Ile Gly Ser Leu Thr
            180                 185                 190

Trp Asp Phe Asp Asn Leu His Gly Ile Ser Ser Gln Gln Gly Pro Val
        195                 200                 205
```

<210> SEQ ID NO 73
<211> LENGTH: 597
<212> TYPE: DNA
<213> ORGANISM: Phakopsora pachyrhizi
<220> FEATURE:
<221> NAME/KEY: misc_feature
<222> LOCATION: (1)..(597)
<223> OTHER INFORMATION: 02-c11

<400> SEQUENCE: 73

```
atgtatcgat ttccactcat ttcccttgcc atttatgctt cagtcgtata tggtcaagga     60

actaccgtca ctcctactac gaacgtcaac ccaaacacat caggtaatcc gccaaaccaa    120

cccactaatg gtacccctac caatccggca actcctacgg catctcctac gacgactcct    180

actcccaaaa ttcttgctgt taattgtaca cagtcttact ttgagatcac tgatgattca    240

atgaacggaa cttctatcgg tgcatgtacg aagattggag acggagaaaa aggcggttcc    300

ttctgccaaa ccaaagagtg ttttggcttt gccacttgcc aagattgtaa cctagcaacc    360

cctggtccta ataatacgac tgtaatctca aacaccacta tcaaagcagt accctgcaac    420

aagggctact atatccctgg accaggagat aacgttactg tgacttattg ctccgcccaa    480

aacaatgcga atccggatga ctacatttgc aagggcccat gcacaagttt tacagcgtgt    540

ggagattgta tcaatataaa cgatccagcg attgcgggcc tgaaagatac tccttaa       597
```

<210> SEQ ID NO 74
<211> LENGTH: 198
<212> TYPE: PRT
<213> ORGANISM: Phakopsora pachyrhizi
<220> FEATURE:
<221> NAME/KEY: VARIANT
<222> LOCATION: (1)..(198)
<223> OTHER INFORMATION: 02-c11

<400> SEQUENCE: 74

Met Tyr Arg Phe Pro Leu Ile Ser Leu Ala Ile Tyr Ala Ser Val Val
1 5 10 15

Tyr Gly Gln Gly Thr Thr Val Thr Pro Thr Thr Asn Val Asn Pro Asn
20 25 30

Thr Ser Gly Asn Pro Pro Asn Gln Pro Thr Asn Gly Thr Pro Thr Asn
35 40 45

Pro Ala Thr Pro Thr Ala Ser Pro Thr Thr Thr Pro Thr Pro Lys Ile
50 55 60

Leu Ala Val Asn Cys Thr Gln Ser Tyr Phe Glu Ile Thr Asp Asp Ser
65 70 75 80

Met Asn Gly Thr Ser Ile Gly Ala Cys Thr Lys Ile Gly Asp Gly Glu
85 90 95

Lys Gly Gly Ser Phe Cys Gln Thr Lys Glu Cys Phe Gly Phe Ala Thr
100 105 110

Cys Gln Asp Cys Asn Leu Ala Thr Pro Gly Pro Asn Asn Thr Thr Val
115 120 125

Ile Ser Asn Thr Thr Ile Lys Ala Val Pro Cys Asn Lys Gly Tyr Tyr
130 135 140

Ile Pro Gly Pro Gly Asp Asn Val Thr Val Thr Tyr Cys Ser Ala Gln
145 150 155 160

Asn Asn Ala Asn Pro Asp Asp Tyr Ile Cys Lys Gly Pro Cys Thr Ser
165 170 175

Phe Thr Ala Cys Gly Asp Cys Ile Asn Ile Asn Asp Pro Ala Ile Ala
180 185 190

Gly Leu Lys Asp Thr Pro
195

<210> SEQ ID NO 75
<211> LENGTH: 318
<212> TYPE: DNA
<213> ORGANISM: Phakopsora pachyrhizi
<220> FEATURE:
<221> NAME/KEY: misc_feature
<222> LOCATION: (1)..(318)
<223> OTHER INFORMATION: 02-p12

<400> SEQUENCE: 75
atgaagttaa tgcagctaat attctatatg ctcaacatac tagcactcac gatggcccat 60
aactgttgtg agctgtcaaa gatgccaact cttcctgaga taggcgtgat gtcctcgaag 120
cctgttagac caaagccaat ccaatccacg gcatcgaaag gcacaaagtt cttgcctact 180
acgctctgta tcatcaagtg caagtttaac atctgtctgg ctcatgctaa tgtcataaac 240
tccgtacaaa ttggtaatcg gatgagggag agtaagggag ctgtcaactt gaatgctcca 300
cgccaccatt cattttaa 318

<210> SEQ ID NO 76
<211> LENGTH: 105
<212> TYPE: PRT
<213> ORGANISM: Phakopsora pachyrhizi
<220> FEATURE:
<221> NAME/KEY: VARIANT
<222> LOCATION: (1)..(105)
<223> OTHER INFORMATION: 02-p12

<400> SEQUENCE: 76

Met Lys Leu Met Gln Leu Ile Phe Tyr Met Leu Asn Ile Leu Ala Leu
1 5 10 15

```
Thr Met Ala His Asn Cys Cys Glu Leu Ser Lys Met Pro Thr Leu Pro
            20                  25                  30

Glu Ile Gly Val Met Ser Ser Lys Pro Val Arg Pro Lys Pro Ile Gln
        35                  40                  45

Ser Thr Ala Ser Lys Gly Thr Lys Phe Leu Pro Thr Thr Leu Cys Ile
    50                  55                  60

Ile Lys Cys Lys Phe Asn Ile Cys Leu Ala His Ala Asn Val Ile Asn
65                  70                  75                  80

Ser Val Gln Ile Gly Asn Arg Met Arg Glu Ser Lys Gly Ala Val Asn
                85                  90                  95

Leu Asn Ala Pro Arg His His Ser Phe
            100                 105


<210> SEQ ID NO 77
<211> LENGTH: 588
<212> TYPE: DNA
<213> ORGANISM: Phakopsora pachyrhizi
<220> FEATURE:
<221> NAME/KEY: misc_feature
<222> LOCATION: (1)..(588)
<223> OTHER INFORMATION: 03-c8

<400> SEQUENCE: 77

atgaaaagag aaattaaatt gatattattg attgctgtaa ctttactaag tgcacccttt      60

gtagtgaaca atttgccgtt taatagcaac tcactaatct ctgttagtga atgtagcaac     120

aaaacccctc tacttgaaaa cagggtcgcg gagattgggt ttaaacgccc agagatactc     180

gacggtcagg agaaagagtt tttttcccaa cagaggattg gttgcttacc aaacattttt     240

aggaaggcta taggatcatg ttgctttggg aacgaggaaa ataaaaatat aaaatatagg     300

cttctgaagc cagagtattc ttcttgggat gaaataaggt atatctttga tccaaaattc     360

ctacttgttc atcgaaattc tgataatttt ttggagaaca ttgatttaga aaaatttgag     420

aaaaagcttc ttggtaatcc ggacggaaat caagcacatt tgtttagtcg tccaaagttt     480

gcagaccttg aaaacgcttg ggtgaaatat ctcagacaag tagttctatt agtcgtagag     540

ttagggagct tatgttacat tggccagcgt ttttgcggaa gggtttga                  588


<210> SEQ ID NO 78
<211> LENGTH: 195
<212> TYPE: PRT
<213> ORGANISM: Phakopsora pachyrhizi
<220> FEATURE:
<221> NAME/KEY: VARIANT
<222> LOCATION: (1)..(195)
<223> OTHER INFORMATION: 03-c8

<400> SEQUENCE: 78

Met Lys Arg Glu Ile Lys Leu Ile Leu Leu Ile Ala Val Thr Leu Leu
1               5                   10                  15

Ser Ala Pro Phe Val Val Asn Asn Leu Pro Phe Asn Ser Asn Ser Leu
            20                  25                  30

Ile Ser Val Ser Glu Cys Ser Asn Lys Thr Pro Leu Leu Glu Asn Arg
        35                  40                  45

Val Ala Glu Ile Gly Phe Lys Arg Pro Glu Ile Leu Asp Gly Gln Glu
    50                  55                  60

Lys Glu Phe Phe Ser Gln Gln Arg Ile Gly Cys Leu Pro Asn Ile Phe
65                  70                  75                  80

Arg Lys Ala Ile Gly Ser Cys Cys Phe Gly Asn Glu Glu Asn Lys Asn
```

```
                85                  90                  95

Ile Lys Tyr Arg Leu Leu Lys Pro Glu Tyr Ser Ser Trp Asp Glu Ile
            100                 105                 110

Arg Tyr Ile Phe Asp Pro Lys Phe Leu Leu Val His Arg Asn Ser Asp
        115                 120                 125

Asn Phe Leu Glu Asn Ile Asp Leu Glu Lys Phe Glu Lys Lys Leu Leu
    130                 135                 140

Gly Asn Pro Asp Gly Asn Gln Ala His Leu Phe Ser Arg Pro Lys Phe
145                 150                 155                 160

Ala Asp Leu Glu Asn Ala Trp Val Lys Tyr Leu Arg Gln Val Val Leu
                165                 170                 175

Leu Val Val Glu Leu Gly Ser Leu Cys Tyr Ile Gly Gln Arg Phe Cys
            180                 185                 190

Gly Arg Val
        195
```

<210> SEQ ID NO 79
<211> LENGTH: 444
<212> TYPE: DNA
<213> ORGANISM: Phakopsora pachyrhizi
<220> FEATURE:
<221> NAME/KEY: misc_feature
<222> LOCATION: (1)..(444)
<223> OTHER INFORMATION: 02-a6

<400> SEQUENCE: 79

```
atgctgctag gtctacattt ttcctccctt atgaattgga ctacaataat tctgtccaca     60

actctgcttc ttagactgtc taaatgcgaa cttttcgatg ccagtttggc agtaagaggg    120

atcactcatg gcactccaag tttaggtcat gattctaaga ctcttcatat cacctcacag    180

ggagggctca atagtccatc tcaccatgtg aagcagcttt caactaaagc cagaaaaccc    240

cctaaggttc caaatgcaaa agattccggt tgggaaatta ttgacccaaa acttccagag    300

tgggaactga ttgaaaagcc aaaagtaaaa aaaaaactcc ccaaaattta tgtcccagag    360

gccaagtttt attcttctga tggtagttca gaaaccatca atttcataga agatcattat    420

gcgattaaag aatctacacc gtaa                                            444
```

<210> SEQ ID NO 80
<211> LENGTH: 147
<212> TYPE: PRT
<213> ORGANISM: Phakopsora pachyrhizi
<220> FEATURE:
<221> NAME/KEY: VARIANT
<222> LOCATION: (1)..(147)
<223> OTHER INFORMATION: 02-a6

<400> SEQUENCE: 80

```
Met Leu Leu Gly Leu His Phe Ser Ser Leu Met Asn Trp Thr Thr Ile
1               5                   10                  15

Ile Leu Ser Thr Thr Leu Leu Leu Arg Leu Ser Lys Cys Glu Leu Phe
            20                  25                  30

Asp Ala Ser Leu Ala Val Arg Gly Ile Thr His Gly Thr Pro Ser Leu
        35                  40                  45

Gly His Asp Ser Lys Thr Leu His Ile Thr Ser Gln Gly Gly Leu Asn
    50                  55                  60

Ser Pro Ser His His Val Lys Gln Leu Ser Thr Lys Ala Arg Lys Pro
65                  70                  75                  80

Pro Lys Val Pro Asn Ala Lys Asp Ser Gly Trp Glu Ile Ile Asp Pro
```

```
                85                  90                  95

Lys Leu Pro Glu Trp Glu Leu Ile Glu Lys Pro Lys Val Lys Lys Lys
            100                 105                 110

Leu Pro Lys Ile Tyr Val Pro Glu Ala Lys Phe Tyr Ser Ser Asp Gly
        115                 120                 125

Ser Ser Glu Thr Ile Asn Phe Ile Glu Asp His Tyr Ala Ile Lys Glu
    130                 135                 140

Ser Thr Pro
145


<210> SEQ ID NO 81
<211> LENGTH: 231
<212> TYPE: DNA
<213> ORGANISM: Phakopsora pachyrhizi
<220> FEATURE:
<221> NAME/KEY: misc_feature
<222> LOCATION: (1)..(231)
<223> OTHER INFORMATION: 02-c24

<400> SEQUENCE: 81

atggctggaa aagagattta tgaaccaaga aagtcaatga tgattaaaat gattgggttc      60

ttatgcattt ggtttcaact attaggagta gtttttacac aatctactgc tgcaactaca     120

agtgccacta aggccaaaac ttatgatact tatttcaaga ggcttgcaaa aagaagccca     180

ttgactaact ctggccgaat tgagagaagg cataaatgtg gaccgccata g              231


<210> SEQ ID NO 82
<211> LENGTH: 76
<212> TYPE: PRT
<213> ORGANISM: Phakopsora pachyrhizi
<220> FEATURE:
<221> NAME/KEY: VARIANT
<222> LOCATION: (1)..(76)
<223> OTHER INFORMATION: 02-c24

<400> SEQUENCE: 82

Met Ala Gly Lys Glu Ile Tyr Glu Pro Arg Lys Ser Met Met Ile Lys
1               5                   10                  15

Met Ile Gly Phe Leu Cys Ile Trp Phe Gln Leu Leu Gly Val Val Phe
            20                  25                  30

Thr Gln Ser Thr Ala Ala Thr Thr Ser Ala Thr Lys Ala Lys Thr Tyr
        35                  40                  45

Asp Thr Tyr Phe Lys Arg Leu Ala Lys Arg Ser Pro Leu Thr Asn Ser
    50                  55                  60

Gly Arg Ile Glu Arg Arg His Lys Cys Gly Pro Pro
65                  70                  75


<210> SEQ ID NO 83
<211> LENGTH: 1389
<212> TYPE: DNA
<213> ORGANISM: Phakopsora pachyrhizi
<220> FEATURE:
<221> NAME/KEY: misc_feature
<222> LOCATION: (1)..(1389)
<223> OTHER INFORMATION: 02-h8

<400> SEQUENCE: 83

atgcaaaata aattccagcc attcaagctt ttgttagctt tgagtttgtt cattgcaggc      60

tcatcagcaa accaagatga tggctccgca atcactgtga attacagcga gaacaaagct     120

agcacatctg cttctgtaga aactcgatcc atcggtgtac aattcaaccc agggtacaaa     180
```

```
agttccaata gcacggttgt ccccaccaag aacaaaaaaa caggaaacgg gagggtcagc    240

gcatattttc ctagctacaa cgcagatcat gattctgtct ctaaaatcag atatgatctt    300

tacgatgatt taatcttctt cgtggccact acaacgtcga acttcaccat tggccttggt    360

aatctcaccc aaaacgaatg ggattcctta gcttatgaat ttgttaacag aagcaaggaa    420

gctggagttt ctccgtcatg cagtattgga ggctggacag gatctgttta tttctctgcg    480

ctcgcatcta ccgctgagaa tcgaaccacc tttgcaaatt ctgccattaa ttttgctaag    540

aaatatggct tcgagggtat tgacattgat tgggagtatc cacttatcca aggaatcgga    600

tgcaatatta ttcaagattc tgatgcagaa aattatcagt tgctcttgaa ggaaattaaa    660

agaatctggc ctgagggaaa gcttagcaca gccgtaagca tcgcaggaat tcgtgcgtcg    720

gactacagtg cccttcctgc tgccaattta accaccttag caagtgtcgt tgacattttg    780

aaaattatgg catacgatgt ctatggaggc tggtcaatta cgactggacc acatgctccg    840

ttaagaagca catgtgcgga ccccaatgat aatttgtcgg ttgaaaccgc tatcgacgtt    900

tatatccggc aaggctttag cccgagtcaa ctttccctag gattgcctgg ttacggtaga    960

agctggctgt tagagagtcc aacccttgtt cccaagactg ttcaaaacta cacaagttat   1020

tactatcaaa atttcactgg attgcctcaa ggcgggaact ttgatgataa acctggagta   1080

gttgacgttt gtggtcagac atctactagc tggggcggta ctatccttgt ctcagaattg   1140

gtttcgcgtg gttatttgaa cgaagacgaa actaaggcag gttctggatt tgttcgatac   1200

tatgacgagt gcagtggaca gcctttcatt gccaatggca cccatttgat ttcctacgac   1260

gatacccaaa gtacattgca aaaagtaaaa tacgcaaaat cgcgaaacat atcacatatc   1320

tatttctttg actcatttgg cccaacagac tctactgtta aggctgcaag agaagcatta   1380

ctagcataa                                                           1389
```

<210> SEQ ID NO 84
<211> LENGTH: 462
<212> TYPE: PRT
<213> ORGANISM: Phakopsora pachyrhizi
<220> FEATURE:
<221> NAME/KEY: VARIANT
<222> LOCATION: (1)..(462)
<223> OTHER INFORMATION: 02-h8

<400> SEQUENCE: 84

```
Met Gln Asn Lys Phe Gln Pro Phe Lys Leu Leu Leu Ala Leu Ser Leu
1               5                   10                  15

Phe Ile Ala Gly Ser Ser Ala Asn Gln Asp Asp Gly Ser Ala Ile Thr
            20                  25                  30

Val Asn Tyr Ser Glu Asn Lys Ala Ser Thr Ser Ala Ser Val Glu Thr
        35                  40                  45

Arg Ser Ile Gly Val Gln Phe Asn Pro Gly Tyr Lys Ser Ser Asn Ser
    50                  55                  60

Thr Val Val Pro Thr Lys Asn Lys Lys Thr Gly Asn Gly Arg Val Ser
65                  70                  75                  80

Ala Tyr Phe Pro Ser Tyr Asn Ala Asp His Asp Ser Val Ser Lys Ile
                85                  90                  95

Arg Tyr Asp Leu Tyr Asp Asp Leu Ile Phe Phe Val Ala Thr Thr Thr
            100                 105                 110

Ser Asn Phe Thr Ile Gly Leu Gly Asn Leu Thr Gln Asn Glu Trp Asp
        115                 120                 125

Ser Leu Ala Tyr Glu Phe Val Asn Arg Ser Lys Glu Ala Gly Val Ser
```

```
    130                 135                 140

Pro Ser Cys Ser Ile Gly Gly Trp Thr Gly Ser Val Tyr Phe Ser Ala
145                 150                 155                 160

Leu Ala Ser Thr Ala Glu Asn Arg Thr Thr Phe Ala Asn Ser Ala Ile
                165                 170                 175

Asn Phe Ala Lys Lys Tyr Gly Phe Glu Gly Ile Asp Ile Asp Trp Glu
            180                 185                 190

Tyr Pro Leu Ile Gln Gly Ile Gly Cys Asn Ile Ile Gln Asp Ser Asp
        195                 200                 205

Ala Glu Asn Tyr Gln Leu Leu Leu Lys Glu Ile Lys Arg Ile Trp Pro
    210                 215                 220

Glu Gly Lys Leu Ser Thr Ala Val Ser Ile Ala Gly Ile Arg Ala Ser
225                 230                 235                 240

Asp Tyr Ser Ala Leu Pro Ala Ala Asn Leu Thr Thr Leu Ala Ser Val
                245                 250                 255

Val Asp Ile Leu Lys Ile Met Ala Tyr Asp Val Tyr Gly Gly Trp Ser
            260                 265                 270

Ile Thr Thr Gly Pro His Ala Pro Leu Arg Ser Thr Cys Ala Asp Pro
        275                 280                 285

Asn Asp Asn Leu Ser Val Glu Thr Ala Ile Asp Val Tyr Ile Arg Gln
    290                 295                 300

Gly Phe Ser Pro Ser Gln Leu Ser Leu Gly Leu Pro Gly Tyr Gly Arg
305                 310                 315                 320

Ser Trp Leu Leu Glu Ser Pro Thr Leu Val Pro Lys Thr Val Gln Asn
                325                 330                 335

Tyr Thr Ser Tyr Tyr Tyr Gln Asn Phe Thr Gly Leu Pro Gln Gly Gly
            340                 345                 350

Asn Phe Asp Asp Lys Pro Gly Val Val Asp Val Cys Gly Gln Thr Ser
        355                 360                 365

Thr Ser Trp Gly Gly Thr Ile Leu Val Ser Glu Leu Val Ser Arg Gly
    370                 375                 380

Tyr Leu Asn Glu Asp Glu Thr Lys Ala Gly Ser Gly Phe Val Arg Tyr
385                 390                 395                 400

Tyr Asp Glu Cys Ser Gly Gln Pro Phe Ile Ala Asn Gly Thr His Leu
                405                 410                 415

Ile Ser Tyr Asp Asp Thr Gln Ser Thr Leu Gln Lys Val Lys Tyr Ala
            420                 425                 430

Lys Ser Arg Asn Ile Ser His Ile Tyr Phe Phe Asp Ser Phe Gly Pro
        435                 440                 445

Thr Asp Ser Thr Val Lys Ala Ala Arg Glu Ala Leu Leu Ala
    450                 455                 460


<210> SEQ ID NO 85
<211> LENGTH: 615
<212> TYPE: DNA
<213> ORGANISM: Phakopsora pachyrhizi
<220> FEATURE:
<221> NAME/KEY: misc_feature
<222> LOCATION: (1)..(615)
<223> OTHER INFORMATION: 04-c1

<400> SEQUENCE: 85

atgatgagag ctagcaagtc aatcgttttt atttcagcat gtttttacct gttttctgga     60

gaaacacttg cagcctcagc tttaaaagga gtcgaaactg aggccaacag tattcctgat    120

gcggcaaagt ttggcgagag tctttcaatc aagacagata gtctttccga gctgccgtta    180
```

```
aaatcgtctc ctacaattcc aagtacaccg tctggtttag atggcaatcc tcaaagttca    240

ctgctagata aaagtgcaat gaaagaaatt gatgcttcag aatcagcaga aaaaataaag    300

agccatcctt ttacatctgg tatctctgcc aaaaggccta caaagtcgct tgacgcgtca    360

gcaacaggct ccgacggact agttcaacag gtgcacgtcg gtgattcgca aatagctgtt    420

gatgcgaaaa cggagattcc acccgcagcc gcttatgaac acaataaagt aactcggaaa    480

tgtaaccatg atcatgatca tgatcaccac catcaccatc accatcatca tggccctggt    540

gacgatcatg atcatgatca tcatcaccat caccatcacc atcatggtca tgatcatgac    600

catgaccatg cataa                                                      615
```

<210> SEQ ID NO 86
<211> LENGTH: 204
<212> TYPE: PRT
<213> ORGANISM: Phakopsora pachyrhizi
<220> FEATURE:
<221> NAME/KEY: VARIANT
<222> LOCATION: (1)..(204)
<223> OTHER INFORMATION: 04-c1

<400> SEQUENCE: 86

```
Met Met Arg Ala Ser Lys Ser Ile Val Phe Ile Ser Ala Cys Phe Tyr
1               5                   10                  15

Leu Phe Ser Gly Glu Thr Leu Ala Ala Ser Ala Leu Lys Gly Val Glu
            20                  25                  30

Thr Glu Ala Asn Ser Ile Pro Asp Ala Ala Lys Phe Gly Glu Ser Leu
        35                  40                  45

Ser Ile Lys Thr Asp Ser Leu Ser Glu Leu Pro Leu Lys Ser Ser Pro
    50                  55                  60

Thr Ile Pro Ser Thr Pro Ser Gly Leu Asp Gly Asn Pro Gln Ser Ser
65                  70                  75                  80

Leu Leu Asp Lys Ser Ala Met Lys Glu Ile Asp Ala Ser Glu Ser Ala
                85                  90                  95

Glu Lys Ile Lys Ser His Pro Phe Thr Ser Gly Ile Ser Ala Lys Arg
            100                 105                 110

Pro Thr Lys Ser Leu Asp Ala Ser Ala Thr Gly Ser Asp Gly Leu Val
        115                 120                 125

Gln Gln Val His Val Gly Asp Ser Gln Ile Ala Val Asp Ala Lys Thr
    130                 135                 140

Glu Ile Pro Pro Ala Ala Ala Tyr Glu His Asn Lys Val Thr Arg Lys
145                 150                 155                 160

Cys Asn His Asp His Asp His Asp His His His His His His His His
                165                 170                 175

His Gly Pro Gly Asp Asp His Asp His Asp His His His His His His
            180                 185                 190

His His His Gly His Asp His Asp His Asp His Ala
        195                 200
```

<210> SEQ ID NO 87
<211> LENGTH: 549
<212> TYPE: DNA
<213> ORGANISM: Phakopsora pachyrhizi
<220> FEATURE:
<221> NAME/KEY: misc_feature
<222> LOCATION: (1)..(549)
<223> OTHER INFORMATION: 04-d11

<400> SEQUENCE: 87

-continued

```
atgcaaggtt tttttcttgt ttccattgca gttcaggttg ctctcgtagt tgctcaagga     60

aacaccccca ccaaagttac tgctcagcct caggtaaaca actcgtctgc tccggcaaac    120

gcatctgcta ttgatctgcc aaaaataata gctgttaatt gtacacaagc ctacatcgaa    180

ataactgaca gctcaattaa cggaactact attggcgctt gcaaaaggtt tgaagattct    240

gaaggatctt tttgcaagcc tgatgattgc attggcagtg ccacttgctt atcctgcaaa    300

aaagttaccg ttggtgccac tgcgaatagc accgttgtct cgaactcaac agtagactct    360

gtggtgtgcc gcaaggacta cttctttcca ggaccgggtt ctaaatccaa ccagtccctt    420

tgtacggatg agaaggatga taactacatc tgcagtggtg tttgcacaag ttttgctagc    480

tgctctcatt gcgtcagcgc taaagaccca gcacttgcaa aattaaaaga gaagtctcca    540

aaaaattaa                                                            549


<210> SEQ ID NO 88
<211> LENGTH: 182
<212> TYPE: PRT
<213> ORGANISM: Phakopsora pachyrhizi
<220> FEATURE:
<221> NAME/KEY: VARIANT
<222> LOCATION: (1)..(182)
<223> OTHER INFORMATION: 04-d11

<400> SEQUENCE: 88

Met Gln Gly Phe Phe Leu Val Ser Ile Ala Val Gln Val Ala Leu Val
1               5                   10                  15

Val Ala Gln Gly Asn Thr Pro Thr Lys Val Thr Ala Gln Pro Gln Val
            20                  25                  30

Asn Asn Ser Ser Ala Pro Ala Asn Ala Ser Ala Ile Asp Leu Pro Lys
        35                  40                  45

Ile Ile Ala Val Asn Cys Thr Gln Ala Tyr Ile Glu Ile Thr Asp Ser
    50                  55                  60

Ser Ile Asn Gly Thr Thr Ile Gly Ala Cys Lys Arg Phe Glu Asp Ser
65                  70                  75                  80

Glu Gly Ser Phe Cys Lys Pro Asp Asp Cys Ile Gly Ser Ala Thr Cys
                85                  90                  95

Leu Ser Cys Lys Lys Val Thr Val Gly Ala Thr Ala Asn Ser Thr Val
            100                 105                 110

Val Ser Asn Ser Thr Val Asp Ser Val Val Cys Arg Lys Asp Tyr Phe
        115                 120                 125

Phe Pro Gly Pro Gly Ser Lys Ser Asn Gln Ser Leu Cys Thr Asp Glu
    130                 135                 140

Lys Asp Asp Asn Tyr Ile Cys Ser Gly Val Cys Thr Ser Phe Ala Ser
145                 150                 155                 160

Cys Ser His Cys Val Ser Ala Lys Asp Pro Ala Leu Ala Lys Leu Lys
                165                 170                 175

Glu Lys Ser Pro Lys Asn
            180


<210> SEQ ID NO 89
<211> LENGTH: 1326
<212> TYPE: DNA
<213> ORGANISM: Phakopsora pachyrhizi
<220> FEATURE:
<221> NAME/KEY: misc_feature
<222> LOCATION: (1)..(1326)
<223> OTHER INFORMATION: 27i10
```

<400> SEQUENCE: 89
atggttctcc gtacttctgt tcttgtgatt gcaatcgcag cagtaaacct gtgctttttc 60
cagacaaatg ctacagatat ccttggaaga gataatcaac tcatccgtcg gcagacactc 120
agtccaccgc cagcgagact caatacaaca gaatgcccgg atctacctat aagtccccaa 180
acctggaagt ctctgaatct cgatgattac ttaaagcaat acccaggtgg tgttaacata 240
tcacttcagg aatacgcatt tgcacatcat gcccaaaact tcatctgcgg tgtaggagaa 300
gggtgcaacg ccggccagct ttgcaatcca atcacagcac ccgactggta tgtcttatat 360
gccacccaag agtggaacgc aatgcagaac gcaatctata ctgcagtagg gtttgccgta 420
tcaatggtcc aagctactgc tgcagctatg gtcactgact tctatccacc agagcataaa 480
tcggtactat acaagctcaa tgacttgttt gtaatgctta gtgctgtagc attcactgta 540
gcagttttat cattgctact tgactggcca gtggccgtat ttgtaggagc ggcaattggt 600
ggttctttgg ccgccggtac ttccgcagtc ttaactggag tcaatcttgc aaattcttgg 660
aatataaagc cagacggatt tactaagtgg tctaattacg cctactacct atcccaatgg 720
caatcaaaag tccaagacga gctggctaac aatgctgcat cagtgatttc agccggaatt 780
tcaagcactg ctggaatttc tgaagcactt aaggggggga atttccttac cgatgtccaa 840
attaggccaa cctctgaaat tgaagatgag ataaaatata caatgagtgc ccgaatttta 900
gttgatatta ttcgtaacca gggtggttac gttacttatg gaagtgaccc gtgcgacggg 960
aaaggaccga atggggcatg ggatggcgaa gacgtgattt ctttctgcaa aaacggaact 1020
atgatgaaca ttgttagagc aaagggaaac aagacgaaga aaaagtggta caatgcccgc 1080
cttatagctt caaagtacgg cctcactgct gaatatctta ctactcaatc tgtggaatgc 1140
caaaagaaat ataagacttt tggatacgat ccttacagga atggatctct tcctaaatca 1200
gcatccgaag aatgtattgt taatttacct gtctgcgatt gcactagtcc agaaataaaa 1260
cgtgctagaa agaaaggaca cacaacaact gttgcatgcc gtgaggttgg gaagcttcct 1320
atctga 1326

<210> SEQ ID NO 90
<211> LENGTH: 441
<212> TYPE: PRT
<213> ORGANISM: Phakopsora pachyrhizi
<220> FEATURE:
<221> NAME/KEY: VARIANT
<222> LOCATION: (1)..(441)
<223> OTHER INFORMATION: 27i10

<400> SEQUENCE: 90

Met Val Leu Arg Thr Ser Val Leu Val Ile Ala Ile Ala Ala Val Asn
1 5 10 15

Leu Cys Phe Phe Gln Thr Asn Ala Thr Asp Ile Leu Gly Arg Asp Asn
20 25 30

Gln Leu Ile Arg Arg Gln Thr Leu Ser Pro Pro Pro Ala Arg Leu Asn
35 40 45

Thr Thr Glu Cys Pro Asp Leu Pro Ile Ser Pro Gln Thr Trp Lys Ser
50 55 60

Leu Asn Leu Asp Asp Tyr Leu Lys Gln Tyr Pro Gly Gly Val Asn Ile
65 70 75 80

Ser Leu Gln Glu Tyr Ala Phe Ala His His Ala Gln Asn Phe Ile Cys
85 90 95

Gly Val Gly Glu Gly Cys Asn Ala Gly Gln Leu Cys Asn Pro Ile Thr

```
            100                 105                 110
Ala Pro Asp Trp Tyr Val Leu Tyr Ala Thr Gln Glu Trp Asn Ala Met
        115                 120                 125

Gln Asn Ala Ile Tyr Thr Ala Val Gly Phe Ala Val Ser Met Val Gln
    130                 135                 140

Ala Thr Ala Ala Ala Met Val Thr Asp Phe Tyr Pro Pro Glu His Lys
145                 150                 155                 160

Ser Val Leu Tyr Lys Leu Asn Asp Leu Phe Val Met Leu Ser Ala Val
                165                 170                 175

Ala Phe Thr Val Ala Val Leu Ser Leu Leu Leu Asp Trp Pro Val Ala
            180                 185                 190

Val Phe Val Gly Ala Ala Ile Gly Gly Ser Leu Ala Ala Gly Thr Ser
        195                 200                 205

Ala Val Leu Thr Gly Val Asn Leu Ala Asn Ser Trp Asn Ile Lys Pro
    210                 215                 220

Asp Gly Phe Thr Lys Trp Ser Asn Tyr Ala Tyr Tyr Leu Ser Gln Trp
225                 230                 235                 240

Gln Ser Lys Val Gln Asp Glu Leu Ala Asn Asn Ala Ala Ser Val Ile
                245                 250                 255

Ser Ala Gly Ile Ser Ser Thr Ala Gly Ile Ser Glu Ala Leu Lys Gly
            260                 265                 270

Gly Asn Phe Leu Thr Asp Val Gln Ile Arg Pro Thr Ser Glu Ile Glu
        275                 280                 285

Asp Glu Ile Lys Tyr Thr Met Ser Ala Arg Ile Leu Val Asp Ile Ile
    290                 295                 300

Arg Asn Gln Gly Gly Tyr Val Thr Tyr Gly Ser Asp Pro Cys Asp Gly
305                 310                 315                 320

Lys Gly Pro Asn Gly Ala Trp Asp Gly Glu Asp Val Ile Ser Phe Cys
                325                 330                 335

Lys Asn Gly Thr Met Met Asn Ile Val Arg Ala Lys Gly Asn Lys Thr
            340                 345                 350

Lys Lys Lys Trp Tyr Asn Ala Arg Leu Ile Ala Ser Lys Tyr Gly Leu
        355                 360                 365

Thr Ala Glu Tyr Leu Thr Thr Gln Ser Val Glu Cys Gln Lys Lys Tyr
    370                 375                 380

Lys Thr Phe Gly Tyr Asp Pro Tyr Arg Asn Gly Ser Leu Pro Lys Ser
385                 390                 395                 400

Ala Ser Glu Glu Cys Ile Val Asn Leu Pro Val Cys Asp Cys Thr Ser
                405                 410                 415

Pro Glu Ile Lys Arg Ala Arg Lys Lys Gly His Thr Thr Thr Val Ala
            420                 425                 430

Cys Arg Glu Val Gly Lys Leu Pro Ile
        435                 440

<210> SEQ ID NO 91
<211> LENGTH: 219
<212> TYPE: DNA
<213> ORGANISM: Phakopsora pachyrhizi
<220> FEATURE:
<221> NAME/KEY: misc_feature
<222> LOCATION: (1)..(219)
<223> OTHER INFORMATION: 17j13

<400> SEQUENCE: 91

atgatcgttc gaactttttt taatgctctc atagcaggtg ggatagccgg tacaaccgtc      60
```

```
gatctggtct tctaccctct ggataccatc aagactaggc tacaatcatc gcagggtttt    120

ctgaattccg gcggtctgag aggagtttac aaagggttgg gtagcgttgc tgtcggtagt    180

gctcctggtg gttgctgccc tattttttac tacttatga                           219
```

<210> SEQ ID NO 92
<211> LENGTH: 72
<212> TYPE: PRT
<213> ORGANISM: Phakopsora pachyrhizi
<220> FEATURE:
<221> NAME/KEY: VARIANT
<222> LOCATION: (1)..(72)
<223> OTHER INFORMATION: 17j13

<400> SEQUENCE: 92

```
Met Ile Val Arg Thr Phe Phe Asn Ala Leu Ile Ala Gly Gly Ile Ala
1               5                   10                  15

Gly Thr Thr Val Asp Leu Val Phe Tyr Pro Leu Asp Thr Ile Lys Thr
            20                  25                  30

Arg Leu Gln Ser Ser Gln Gly Phe Leu Asn Ser Gly Gly Leu Arg Gly
        35                  40                  45

Val Tyr Lys Gly Leu Gly Ser Val Ala Val Gly Ser Ala Pro Gly Gly
    50                  55                  60

Cys Cys Pro Ile Phe Tyr Tyr Leu
65                  70
```

<210> SEQ ID NO 93
<211> LENGTH: 606
<212> TYPE: DNA
<213> ORGANISM: Phakopsora pachyrhizi
<220> FEATURE:
<221> NAME/KEY: misc_feature
<222> LOCATION: (1)..(606)
<223> OTHER INFORMATION: 17k20

<400> SEQUENCE: 93

```
atgcaattcc ttaccctagt cactcttttg atcacatctc agctggcatc gtcggtgcca     60

cttgttgagc gagctgaaac tcgcacctct gcagagcatg tgaatcaaaa aggattcttt    120

ggaggactac cttgcgcacc tatcggtgga atgcttcctc ctccagtggg cggtttcttg    180

cccccaccac caattggcgg gtttcttcct ccaccaccaa tcggaggctt cggaggcttc    240

ggtggcctag gtggctttgg cctaccccct ccaccaattg gcggattcgg tggtcttgga    300

ttcggtggac taccacctcc cccgatcgga ggtctaggct ttggtggctt acctccccct    360

atgattggtg gttttggagg tctaggaggt ggaattggcg gtatgggtgg tttcggtgga    420

atkggtggtg gtggtttcgg tggtgccagc ggattcaacc gaaactcttt cagctctgtt    480

caatctggct cttcatctaa cggattcaaa gctggtggtg gccaatttgg cggagctggt    540

ggtttaggtg gaattggtgg aatgggtggt ttcttgaaaa acaacaaaga gaagagcgaa    600

gcataa                                                               606
```

<210> SEQ ID NO 94
<211> LENGTH: 201
<212> TYPE: PRT
<213> ORGANISM: Phakopsora pachyrhizi
<220> FEATURE:
<221> NAME/KEY: VARIANT
<222> LOCATION: (1)..(201)
<223> OTHER INFORMATION: 17k20

<400> SEQUENCE: 94

-continued

```
Met Gln Phe Leu Thr Leu Val Thr Leu Leu Ile Thr Ser Gln Leu Ala
1               5                   10                  15

Ser Ser Val Pro Leu Val Glu Arg Ala Glu Thr Arg Thr Ser Ala Glu
            20                  25                  30

His Val Asn Gln Lys Gly Phe Phe Gly Gly Leu Pro Cys Ala Pro Ile
        35                  40                  45

Gly Gly Met Leu Pro Pro Pro Val Gly Gly Phe Leu Pro Pro Pro Pro
    50                  55                  60

Ile Gly Gly Phe Leu Pro Pro Pro Pro Ile Gly Gly Phe Gly Gly Phe
65                  70                  75                  80

Gly Gly Leu Gly Gly Phe Gly Leu Pro Pro Pro Pro Ile Gly Gly Phe
                85                  90                  95

Gly Gly Leu Gly Phe Gly Gly Leu Pro Pro Pro Pro Ile Gly Gly Leu
            100                 105                 110

Gly Phe Gly Gly Leu Pro Pro Pro Met Ile Gly Gly Phe Gly Gly Leu
        115                 120                 125

Gly Gly Gly Ile Gly Gly Met Gly Gly Phe Gly Gly Met Gly Gly Gly
    130                 135                 140

Gly Phe Gly Gly Ala Ser Gly Phe Asn Arg Asn Ser Phe Ser Ser Val
145                 150                 155                 160

Gln Ser Gly Ser Ser Ser Asn Gly Phe Lys Ala Gly Gly Gly Gln Phe
                165                 170                 175

Gly Gly Ala Gly Gly Leu Gly Gly Ile Gly Gly Met Gly Gly Phe Leu
            180                 185                 190

Lys Asn Asn Lys Glu Lys Ser Glu Ala
        195                 200
```

<210> SEQ ID NO 95
<211> LENGTH: 663
<212> TYPE: DNA
<213> ORGANISM: Phakopsora pachyrhizi
<220> FEATURE:
<221> NAME/KEY: misc_feature
<222> LOCATION: (1)..(663)
<223> OTHER INFORMATION: 15L1

<400> SEQUENCE: 95

```
atgaaagtaa aactgttttc attgaagatc attataagtc ttgctacttt atctcgtgcg      60

acgtttttttg attccaagaa agcattatta tctgtgaagg actctgagcc atctttctca    120

cagagtggcg aacaaagctt gcaacattgg aactctcaag tggggtcttc taaatcacca     180

accgccaact tattcccaag agaatcagat tatattccac aagccaatca acagcaactt     240

ggggagaagc gaagcaggga aggtgttctc ttagacgcgt tcactaaaga ccctgaatcc     300

cgtcctgctc tacacctagg tctctcacaa tcagcattcc ctgaaactga aaatcaaaca     360

tcagagatta aaaagcttcg tcttagcagt ctttctacac ctgagcatgg actaaaacat     420

tcggacattg tctttgaatc agctcataat gagcctggat cacataatga tctgagtcta     480

gatcttctac gatcggatat ggagaaaaga catagttcta ccagtgatac tctcgatcaa     540

ggactaaaaa atccgcaatt tagttctaca tcctcaagta aagatcgaga agtagataat     600

caccacattg atgctgcgca cttcgatttt tttaaagtct atgaaaaaat ccaccttgat     660

aaa                                                                   663
```

<210> SEQ ID NO 96
<211> LENGTH: 221
<212> TYPE: PRT

<213> ORGANISM: Phakopsora pachyrhizi
<220> FEATURE:
<221> NAME/KEY: VARIANT
<222> LOCATION: (1)..(221)
<223> OTHER INFORMATION: 15L1

<400> SEQUENCE: 96

Met Lys Val Lys Leu Phe Ser Leu Lys Ile Ile Ile Ser Leu Ala Thr
1 5 10 15

Leu Ser Arg Ala Thr Phe Phe Asp Ser Lys Lys Ala Leu Leu Ser Val
20 25 30

Lys Asp Ser Glu Pro Ser Phe Ser Gln Ser Gly Glu Gln Ser Leu Gln
35 40 45

His Trp Asn Ser Gln Val Gly Ser Ser Lys Ser Pro Thr Ala Asn Leu
50 55 60

Phe Pro Arg Glu Ser Asp Tyr Ile Pro Gln Ala Asn Gln Gln Gln Leu
65 70 75 80

Gly Glu Lys Arg Ser Arg Glu Gly Val Leu Leu Asp Ala Phe Thr Lys
85 90 95

Asp Pro Glu Ser Arg Pro Ala Leu His Leu Gly Leu Ser Gln Ser Ala
100 105 110

Phe Pro Glu Thr Glu Asn Gln Thr Ser Glu Ile Lys Lys Leu Arg Leu
115 120 125

Ser Ser Leu Ser Thr Pro Glu His Gly Leu Lys His Ser Asp Ile Val
130 135 140

Phe Glu Ser Ala His Asn Glu Pro Gly Ser His Asn Asp Leu Ser Leu
145 150 155 160

Asp Leu Leu Arg Ser Asp Met Glu Lys Arg His Ser Ser Thr Ser Asp
165 170 175

Thr Leu Asp Gln Gly Leu Lys Asn Pro Gln Phe Ser Ser Thr Ser Ser
180 185 190

Ser Lys Asp Arg Glu Val Asp Asn His His Ile Asp Ala Ala His Phe
195 200 205

Asp Phe Phe Lys Val Tyr Glu Lys Ile His Leu Asp Lys
210 215 220

<210> SEQ ID NO 97
<211> LENGTH: 810
<212> TYPE: DNA
<213> ORGANISM: Phakopsora pachyrhizi
<220> FEATURE:
<221> NAME/KEY: misc_feature
<222> LOCATION: (1)..(810)
<223> OTHER INFORMATION: 30d13

<400> SEQUENCE: 97
atggctttga cctcggaggg taaccatgcg atcgctatca agatcctcaa cgtcttagtc 60
ttcttcttct ttttcggttc taacgtctat agctctcttg gtggtccttc gaccggttac 120
tattctcaga aggaaaccta cattactcct gcccctgaaa cgttttggat atggacggtc 180
atcaacctcc ttttccttgg ctttgtaatc tttcaattct ttgaagcggg cacaaaggcc 240
attgttgacg ttgtcagttg gcgttttgcg gcgattggag ttttacaatc gatctggatt 300
catctatccg ttggccatca ttacatctta gcctttgtat tctctctgat tgtggcatca 360
cttgtctcac atgtttattg ggacctgaaa tcctctgact tgaaatccaa ggccgagtta 420
attttcgttc atctaccatt cagcctctta catgcctacc tggtattttt gttggtttta 480
agtgctttta cagcttttgg agttgataag gcagaacatc cagccggtat catcacccag 540
atccttgtat caatcgcact agtagcactt gctttaaccg gaatgggata tgccttccac 600
agcgatcaag gcgacatagc cggcgctgtc gtcatcgcac ttgagcttgc cggtgtattt 660
gctcgtcaga gtaagcctga taccattcac tgggttgctt tcgtgtcttt cttggtcact 720
ttggttgcgg ttctcaaggc aatttacttt actgttaagg gcggaagaat ccgtctcgag 780
gattctgagc gcgcaccatt gattggctga 810

<210> SEQ ID NO 98
<211> LENGTH: 269
<212> TYPE: PRT
<213> ORGANISM: Phakopsora pachyrhizi
<220> FEATURE:
<221> NAME/KEY: VARIANT
<222> LOCATION: (1)..(269)
<223> OTHER INFORMATION: 30d13

<400> SEQUENCE: 98

Met Ala Leu Thr Ser Glu Gly Asn His Ala Ile Ala Ile Lys Ile Leu
1 5 10 15

Asn Val Leu Val Phe Phe Phe Phe Phe Gly Ser Asn Val Tyr Ser Ser
20 25 30

Leu Gly Gly Pro Ser Thr Gly Tyr Tyr Ser Gln Lys Glu Thr Tyr Ile
35 40 45

Thr Pro Ala Pro Glu Thr Phe Trp Ile Trp Thr Val Ile Asn Leu Leu
50 55 60

Phe Leu Gly Phe Val Ile Phe Gln Phe Phe Glu Ala Gly Thr Lys Ala
65 70 75 80

Ile Val Asp Val Val Ser Trp Arg Phe Ala Ala Ile Gly Val Leu Gln
85 90 95

Ser Ile Trp Ile His Leu Ser Val Gly His His Tyr Ile Leu Ala Phe
100 105 110

Val Phe Ser Leu Ile Val Ala Ser Leu Val Ser His Val Tyr Trp Asp
115 120 125

Leu Lys Ser Ser Asp Leu Lys Ser Lys Ala Glu Leu Ile Phe Val His
130 135 140

Leu Pro Phe Ser Leu Leu His Ala Tyr Leu Val Phe Leu Leu Val Leu
145 150 155 160

Ser Ala Phe Thr Ala Phe Gly Val Asp Lys Ala Glu His Pro Ala Gly
165 170 175

Ile Ile Thr Gln Ile Leu Val Ser Ile Ala Leu Val Ala Leu Ala Leu
180 185 190

Thr Gly Met Gly Tyr Ala Phe His Ser Asp Gln Gly Asp Ile Ala Gly
195 200 205

Ala Val Val Ile Ala Leu Glu Leu Ala Gly Val Phe Ala Arg Gln Ser
210 215 220

Lys Pro Asp Thr Ile His Trp Val Ala Phe Val Ser Phe Leu Val Thr
225 230 235 240

Leu Val Ala Val Leu Lys Ala Ile Tyr Phe Thr Val Lys Gly Gly Arg
245 250 255

Ile Arg Leu Glu Asp Ser Glu Arg Ala Pro Leu Ile Gly
260 265

<210> SEQ ID NO 99
<211> LENGTH: 813
<212> TYPE: DNA
<213> ORGANISM: Phakopsora pachyrhizi -continued
<220> FEATURE:
<221> NAME/KEY: misc_feature
<222> LOCATION: (1)..(813)
<223> OTHER INFORMATION: HESP-735

<400> SEQUENCE: 99

```
atgaaccgaa ttaggatagc catcgtctta gcttctttaa gcttggcgaa ctgccaattt     60

ttatttgggg atcctgcagc agatgctcag aacagctcaa caaatcaggc taattcaaca    120

ggctctaaac tttcacccac tcaaagcagt gaccaaactg ttcctttgac ttattcctca    180

aattccagtg atacaaactc attgaactca gctaatggca cagctactaa tagctctatc    240

ctaacaggcg gcacgaacgc ttttgacaat actggttcta atagttccat caaaacaaac    300

agcagcagcc tttttaacgg tactgctacc aacagctcta ttcaatccac agggctcatt    360

ggtagctata atgggacaat ctcaccctcc aaaaacactt caatgttttc agaagtctac    420

actttagact acagtattaa atgggatgaa agtgatttca atgtctatgg ccaaaatggt    480

aaagttgaat ataccattag taacaaagtg gagggagtca acatgtcaaa gaaagaattt    540

gttgtgaaag aagccaccga tggacaagca agagttagaa ttgacgccaa taataaattc    600

tgtggatttg gtaaaactta cacatcagat gatggggcaa gctttacaat cgacccacgc    660

atgtttttac ctgatcgctg gtttatcagg caaagcaatg ttacgtacgt ttttaaacgc    720

ttcgccatga gtcttaatgg agatatcttg gatgtcgaaa acaagcgcct tgtagcgcag    780

gtcaaagtcg acaaagctaa tactacgagt taa                                 813
```

<210> SEQ ID NO 100
<211> LENGTH: 270
<212> TYPE: PRT
<213> ORGANISM: Phakopsora pachyrhizi
<220> FEATURE:
<221> NAME/KEY: VARIANT
<222> LOCATION: (1)..(270)
<223> OTHER INFORMATION: HESP-735

<400> SEQUENCE: 100

```
Met Asn Arg Ile Arg Ile Ala Ile Val Leu Ala Ser Leu Ser Leu Ala
1               5                   10                  15

Asn Cys Gln Phe Leu Phe Gly Asp Pro Ala Ala Asp Ala Gln Asn Ser
            20                  25                  30

Ser Thr Asn Gln Ala Asn Ser Thr Gly Ser Lys Leu Ser Pro Thr Gln
        35                  40                  45

Ser Ser Asp Gln Thr Val Pro Leu Thr Tyr Ser Ser Asn Ser Ser Asp
    50                  55                  60

Thr Asn Ser Leu Asn Ser Ala Asn Gly Thr Ala Thr Asn Ser Ser Ile
65                  70                  75                  80

Leu Thr Gly Gly Thr Asn Ala Phe Asp Asn Thr Gly Ser Asn Ser Ser
                85                  90                  95

Ile Lys Thr Asn Ser Ser Ser Leu Phe Asn Gly Thr Ala Thr Asn Ser
            100                 105                 110

Ser Ile Gln Ser Thr Gly Leu Ile Gly Ser Tyr Asn Gly Thr Ile Ser
        115                 120                 125

Pro Ser Lys Asn Thr Ser Met Phe Ser Glu Val Tyr Thr Leu Asp Tyr
    130                 135                 140

Ser Ile Lys Trp Asp Glu Ser Asp Phe Asn Val Tyr Gly Gln Asn Gly
145                 150                 155                 160

Lys Val Glu Tyr Thr Ile Ser Asn Lys Val Glu Gly Val Asn Met Ser
                165                 170                 175
```

```
Lys Lys Glu Phe Val Val Lys Glu Ala Thr Asp Gly Gln Ala Arg Val
            180                 185                 190

Arg Ile Asp Ala Asn Asn Lys Phe Cys Gly Phe Gly Lys Thr Tyr Thr
        195                 200                 205

Ser Asp Asp Gly Ala Ser Phe Thr Ile Asp Pro Arg Met Phe Leu Pro
    210                 215                 220

Asp Arg Trp Phe Ile Arg Gln Ser Asn Val Thr Tyr Val Phe Lys Arg
225                 230                 235                 240

Phe Ala Met Ser Leu Asn Gly Asp Ile Leu Asp Val Glu Asn Lys Arg
                245                 250                 255

Leu Val Ala Gln Val Lys Val Asp Lys Ala Asn Thr Thr Ser
            260                 265                 270


<210> SEQ ID NO 101
<211> LENGTH: 885
<212> TYPE: DNA
<213> ORGANISM: Phakopsora pachyrhizi
<220> FEATURE:
<221> NAME/KEY: misc_feature
<222> LOCATION: (1)..(885)
<223> OTHER INFORMATION: 04-m23

<400> SEQUENCE: 101

atgaagcttt tcagctgtac aaatgagtgg aacattttgc cctttgtatt attaagcgcg      60

tggtatacca gaaccgttct tggaatgcat tttgccgaaa gctcaaagga aaatattatc     120

agctctgcaa agggtctact acaggaacag cctccggaaa atatactaat tacaaaaggt     180

cgcttaggcc ctaaaccaga tgactcagca tttactttta aaagtggaaa acgttataca     240

cacgtagagg aacaaaaaac tagtgatatt cctgatccta cacgagtgcc aaaatttgat     300

agaattgaag aaaagatctc aatgctatac aagcaaaaca attttaaaag gaacatgcat     360

ctggacgata ttgttaggaa agaccttcta gtttatctca acaatatcaa aaataaagca     420

ataaaagata atctgccaac cttggatgcc gaattaggca caatatttac acttcttgct     480

ttaaaattga ggggcatttc agataataat ataacattaa aaatttctgc tacttttgaa     540

actcttagtg aaaaaatttt aagcaaaata ttttcaaaag tcgaattgaa agaagatgat     600

ctattgaaat acaaaatatt gagtgaaatg gttacagtgc tgatggctct ctttgccaat     660

cgagattatt tagcaattca gtcattagtt gaaggtaaaa acgttatcag gctcctagct     720

agcgaattaa attttataac tagaaataaa ttagaattac tggtattaga taaatcttat     780

attgattttt tcttgaagtc taaagcaacg gaaaatttcc ataagatctt gaattatctc     840

aagagtgaaa aaactcaaga aaagttacat agtttgttag agtaa                     885


<210> SEQ ID NO 102
<211> LENGTH: 294
<212> TYPE: PRT
<213> ORGANISM: Phakopsora pachyrhizi
<220> FEATURE:
<221> NAME/KEY: VARIANT
<222> LOCATION: (1)..(294)
<223> OTHER INFORMATION: 04-m23

<400> SEQUENCE: 102

Met Lys Leu Phe Ser Cys Thr Asn Glu Trp Asn Ile Leu Pro Phe Val
1               5                   10                  15

Leu Leu Ser Ala Trp Tyr Thr Arg Thr Val Leu Gly Met His Phe Ala
            20                  25                  30
```

-continued

```
Glu Ser Ser Lys Glu Asn Ile Ile Ser Ser Ala Lys Gly Leu Leu Gln
        35                  40                  45

Glu Gln Pro Pro Glu Asn Ile Leu Ile Thr Lys Gly Arg Leu Gly Pro
    50                  55                  60

Lys Pro Asp Asp Ser Ala Phe Thr Phe Lys Ser Gly Lys Arg Tyr Thr
65                  70                  75                  80

His Val Glu Glu Gln Lys Thr Ser Asp Ile Pro Asp Pro Thr Arg Val
                85                  90                  95

Pro Lys Phe Asp Arg Ile Glu Glu Lys Ile Ser Met Leu Tyr Lys Gln
            100                 105                 110

Asn Asn Phe Lys Arg Asn Met His Leu Asp Asp Ile Val Arg Lys Asp
        115                 120                 125

Leu Leu Val Tyr Leu Asn Asn Ile Lys Asn Lys Ala Ile Lys Asp Asn
    130                 135                 140

Leu Pro Thr Leu Asp Ala Glu Leu Gly Thr Ile Phe Thr Leu Leu Ala
145                 150                 155                 160

Leu Lys Leu Arg Gly Ile Ser Asp Asn Asn Ile Thr Leu Lys Ile Ser
                165                 170                 175

Ala Thr Phe Glu Thr Leu Ser Glu Lys Ile Leu Ser Lys Ile Phe Ser
            180                 185                 190

Lys Val Glu Leu Lys Glu Asp Asp Leu Leu Lys Tyr Lys Ile Leu Ser
        195                 200                 205

Glu Met Val Thr Val Leu Met Ala Leu Phe Ala Asn Arg Asp Tyr Leu
    210                 215                 220

Ala Ile Gln Ser Leu Val Glu Gly Lys Asn Val Ile Arg Leu Leu Ala
225                 230                 235                 240

Ser Glu Leu Asn Phe Ile Thr Arg Asn Lys Leu Glu Leu Leu Val Leu
                245                 250                 255

Asp Lys Ser Tyr Ile Asp Phe Phe Leu Lys Ser Lys Ala Thr Glu Asn
            260                 265                 270

Phe His Lys Ile Leu Asn Tyr Leu Lys Ser Glu Lys Thr Gln Glu Lys
        275                 280                 285

Leu His Ser Leu Leu Glu
    290
```

```
<210> SEQ ID NO 103
<211> LENGTH: 351
<212> TYPE: DNA
<213> ORGANISM: Phakopsora pachyrhizi
<220> FEATURE:
<221> NAME/KEY: misc_feature
<222> LOCATION: (1)..(351)
<223> OTHER INFORMATION: 13o11

<400> SEQUENCE: 103

atggcaactt tcttggcaaa gaacgtagcc cttgtacctc tcttcgttgc cgtggggtta      60

ggtctaggag gtggaatagg atttggaatc cattatttaa agaataacca agacgtcgtt     120

ttaagaaaaa agtcaaaccc agacccatgg aacaaagttc cacaggacaa caacacgaag     180

ttgttctctt ttaatccgga cttctggcga gctagagccc aattgactga tccaagatta     240

agttttatgg aaagtaaacc agagaatgag agaactttac atgaacaagc catggtcgaa     300

agggctaagc agatcagact gaatgacaag gaacgtacca ttcacagttg a              351


<210> SEQ ID NO 104
<211> LENGTH: 116
<212> TYPE: PRT
```

<213> ORGANISM: Phakopsora pachyrhizi
<220> FEATURE:
<221> NAME/KEY: VARIANT
<222> LOCATION: (1)..(116)
<223> OTHER INFORMATION: 13o11

<400> SEQUENCE: 104

```
Met Ala Thr Phe Leu Ala Lys Asn Val Ala Leu Val Pro Leu Phe Val
1               5                   10                  15

Ala Val Gly Leu Gly Leu Gly Gly Gly Ile Gly Phe Gly Ile His Tyr
            20                  25                  30

Leu Lys Asn Asn Gln Asp Val Val Leu Arg Lys Lys Ser Asn Pro Asp
        35                  40                  45

Pro Trp Asn Lys Val Pro Gln Asp Asn Asn Thr Lys Leu Phe Ser Phe
    50                  55                  60

Asn Pro Asp Phe Trp Arg Ala Arg Ala Gln Leu Thr Asp Pro Arg Leu
65                  70                  75                  80

Ser Phe Met Glu Ser Lys Pro Glu Asn Glu Arg Thr Leu His Glu Gln
                85                  90                  95

Ala Met Val Glu Arg Ala Lys Gln Ile Arg Leu Asn Asp Lys Glu Arg
            100                 105                 110

Thr Ile His Ser
        115
```

<210> SEQ ID NO 105
<211> LENGTH: 1602
<212> TYPE: DNA
<213> ORGANISM: Phakopsora pachyrhizi
<220> FEATURE:
<221> NAME/KEY: misc_feature
<222> LOCATION: (1)..(1602)
<223> OTHER INFORMATION: 14c16

<400> SEQUENCE: 105

```
atggcgcttc gtcaatttaa cacatgcttt gttctctatt gcactacgtt gatcttattg     60

tcaacgatcg ttatgagtgg catggtaccg aaatctgaag gcgctgaaaa aataattggc    120

gacggcgtca aaattgaaga cgtcacgttt aaagatatca acgaagcatc ctctggcggc    180

tggagggagt accaggaggg ttttttagca tctggcagtc ctgccacgag ttatgatgat    240

aatactaaaa ccacaagaca tattcctata cgcgaatttc ctctatcaaa gccaagaaaa    300

tcgttgggga ccgcgaaaca tatggctgat caatttttcg aagctaaaag tcgccaatta    360

agaagttgta cccaactgct tgccaagctt caaaattcaa gagaagaaat ccaaaactct    420

atagataaag aagtttttaa caatctacag agcttgcttg cgcagctaaa tgattataca    480

gacaaatact taaacgaact gaaacgccgt aagagtgcta atcttttatt gaatgaaaga    540

tttgtaaatt tgattttgga agactttgcc aaagtcttcg agcacatatc tcaacatttt    600

tatccagctt ttaagataga gaattcgcca gcaacatctt ttacgtttca tatcattaat    660

tggcttgccg aaaatgtgca agatatgcac ttaattttgt tcaaactatt aaatagggaa    720

aagatgatgg aaggactaga gtggtacact tcttctcaga ttattcttaa aaggggctat    780

attgattttt ttaaaacgga tgatataaaa aactatttgc tgaatcatca agacttaaga    840

gaaataaaga acatattaaa atatctaggg gaaaaacatt ggaaaaagct tgaacttggg    900

ttcattaagt ctcatctgaa cccatcattt aatatggaaa caaatcgccc aatggtaaat    960

ttaaacactg ttaacgattt taatgaaatt ctaaaatcga tagagaatgc ccagagcttt   1020

aatcctgaat ggctgaaaaa actaagtatg gattcgaaag agaaaaacgt tgctttctat   1080
```

```
ttcacagaga agatatttgt gcttcatatc ctaagttatt gccaaaaata cttcggaact   1140

ataaaagagg accagctgat gatgcaaaaa gtagattatt tcaagagaat tgttgagctg   1200

tatagaaaac agttagagat gtatgaagag ctcgtagatt ctggaaattt aagcagaatt   1260

atactttcag aaaaattttc ggttatgaat cacattcttg cactaaaacc atcggaaata   1320

gagaaaagtt ttccggtaga cgtggtctta ataggcgact ccaagtttga attccttaaa   1380

acacgtaata ctttaggtga acattggaag tctagatata caaaccagtg cagcatttta   1440

gagacagctc aaaaatatat acaagatcat cattacttaa ttcaaatcaa cataaatgga   1500

atgacattta acctcaggtc aaagcccact ctatccgaac aattttatga tgaatttttt   1560

tctttaagta aagtttacac ggagcttacc aaatatttat ag                       1602
```

<210> SEQ ID NO 106
<211> LENGTH: 533
<212> TYPE: PRT
<213> ORGANISM: Phakopsora pachyrhizi
<220> FEATURE:
<221> NAME/KEY: VARIANT
<222> LOCATION: (1)..(533)
<223> OTHER INFORMATION: 14c16

<400> SEQUENCE: 106

```
Met Ala Leu Arg Gln Phe Asn Thr Cys Phe Val Leu Tyr Cys Thr Thr
1               5                   10                  15

Leu Ile Leu Leu Ser Thr Ile Val Met Ser Gly Met Val Pro Lys Ser
            20                  25                  30

Glu Gly Ala Glu Lys Ile Ile Gly Asp Gly Val Lys Ile Glu Asp Val
        35                  40                  45

Thr Phe Lys Asp Ile Asn Glu Ala Ser Ser Gly Gly Trp Arg Glu Tyr
    50                  55                  60

Gln Glu Gly Phe Leu Ala Ser Gly Ser Pro Ala Thr Ser Tyr Asp Asp
65                  70                  75                  80

Asn Thr Lys Thr Thr Arg His Ile Pro Ile Arg Glu Phe Pro Leu Ser
                85                  90                  95

Lys Pro Arg Lys Ser Leu Gly Thr Ala Lys His Met Ala Asp Gln Phe
            100                 105                 110

Phe Glu Ala Lys Ser Arg Gln Leu Arg Ser Cys Thr Gln Leu Leu Ala
        115                 120                 125

Lys Leu Gln Asn Ser Arg Glu Glu Ile Gln Asn Ser Ile Asp Lys Glu
    130                 135                 140

Val Phe Asn Asn Leu Gln Ser Leu Leu Ala Gln Leu Asn Asp Tyr Thr
145                 150                 155                 160

Asp Lys Tyr Leu Asn Glu Leu Lys Arg Arg Lys Ser Ala Asn Leu Leu
                165                 170                 175

Leu Asn Glu Arg Phe Val Asn Leu Ile Leu Glu Asp Phe Ala Lys Val
            180                 185                 190

Phe Glu His Ile Ser Gln His Phe Tyr Pro Ala Phe Lys Ile Glu Asn
        195                 200                 205

Ser Pro Ala Thr Ser Phe Thr Phe His Ile Ile Asn Trp Leu Ala Glu
    210                 215                 220

Asn Val Gln Asp Met His Leu Ile Leu Phe Lys Leu Leu Asn Arg Glu
225                 230                 235                 240

Lys Met Met Glu Gly Leu Glu Trp Tyr Thr Ser Ser Gln Ile Ile Leu
                245                 250                 255
```

-continued

```
Lys Arg Gly Tyr Ile Asp Phe Phe Lys Thr Asp Asp Ile Lys Asn Tyr
            260                 265                 270

Leu Leu Asn His Gln Asp Leu Arg Glu Ile Lys Asn Ile Leu Lys Tyr
        275                 280                 285

Leu Gly Glu Lys His Trp Lys Lys Leu Glu Leu Gly Phe Ile Lys Ser
    290                 295                 300

His Leu Asn Pro Ser Phe Asn Met Glu Thr Asn Arg Pro Met Val Asn
305                 310                 315                 320

Leu Asn Thr Val Asn Asp Phe Asn Glu Ile Leu Lys Ser Ile Glu Asn
                325                 330                 335

Ala Gln Ser Phe Asn Pro Glu Trp Leu Lys Lys Leu Ser Met Asp Ser
            340                 345                 350

Lys Glu Lys Asn Val Ala Phe Tyr Phe Thr Glu Lys Ile Phe Val Leu
        355                 360                 365

His Ile Leu Ser Tyr Cys Gln Lys Tyr Phe Gly Thr Ile Lys Glu Asp
    370                 375                 380

Gln Leu Met Met Gln Lys Val Asp Tyr Phe Lys Arg Ile Val Glu Leu
385                 390                 395                 400

Tyr Arg Lys Gln Leu Glu Met Tyr Glu Glu Leu Val Asp Ser Gly Asn
                405                 410                 415

Leu Ser Arg Ile Ile Leu Ser Glu Lys Phe Ser Val Met Asn His Ile
            420                 425                 430

Leu Ala Leu Lys Pro Ser Glu Ile Glu Lys Ser Phe Pro Val Asp Val
        435                 440                 445

Val Leu Ile Gly Asp Ser Lys Phe Glu Phe Leu Lys Thr Arg Asn Thr
    450                 455                 460

Leu Gly Glu His Trp Lys Ser Arg Tyr Thr Asn Gln Cys Ser Ile Leu
465                 470                 475                 480

Glu Thr Ala Gln Lys Tyr Ile Gln Asp His His Tyr Leu Ile Gln Ile
                485                 490                 495

Asn Ile Asn Gly Met Thr Phe Asn Leu Arg Ser Lys Pro Thr Leu Ser
            500                 505                 510

Glu Gln Phe Tyr Asp Glu Phe Phe Ser Leu Ser Lys Val Tyr Thr Glu
        515                 520                 525

Leu Thr Lys Tyr Leu
    530
```

<210> SEQ ID NO 107
<211> LENGTH: 396
<212> TYPE: DNA
<213> ORGANISM: Phakopsora pachyrhizi
<220> FEATURE:
<221> NAME/KEY: misc_feature
<222> LOCATION: (1)..(396)
<223> OTHER INFORMATION: 15o4

<400> SEQUENCE: 107

```
atgaaacatg atcaaagtta tagagctcta gtttttcttt tgtttgcctt gctaaatctc      60

ttggtatcaa tcagttcagc accaatgggc aagataacaa cagaagcttc aaaaatctcc     120

accccagtag ctgaactgaa caaatttgaa ggcatgagag acgtaaaaat tgttgaaaac     180

aatccaagaa ttgaaacaca aggaacagct tccaaccacc agacaccagt agactttgaa     240

tcttccaaaa cagatgactc aattggtcca cttctggtca atcatcaaac atctttaagc     300

aaaactttta caaacaaaaa ctcattgatt aaacaaccat caccaggatt aaaactggat     360

caactcttag atcgtataac aatgagcatt atttaa                               396
```

<210> SEQ ID NO 108
<211> LENGTH: 131
<212> TYPE: PRT
<213> ORGANISM: Phakopsora pachyrhizi
<220> FEATURE:
<221> NAME/KEY: VARIANT
<222> LOCATION: (1)..(131)
<223> OTHER INFORMATION: 15o4

<400> SEQUENCE: 108

```
Met Lys His Asp Gln Ser Tyr Arg Ala Leu Val Phe Leu Leu Phe Ala
1               5                   10                  15

Leu Leu Asn Leu Leu Val Ser Ile Ser Ser Ala Pro Met Gly Lys Ile
            20                  25                  30

Thr Thr Glu Ala Ser Lys Ile Ser Thr Pro Val Ala Glu Leu Asn Lys
        35                  40                  45

Phe Glu Gly Met Arg Asp Val Lys Ile Val Glu Asn Asn Pro Arg Ile
    50                  55                  60

Glu Thr Gln Gly Thr Ala Ser Asn His Gln Thr Pro Val Asp Phe Glu
65                  70                  75                  80

Ser Ser Lys Thr Asp Asp Ser Ile Gly Pro Leu Leu Val Asn His Gln
                85                  90                  95

Thr Ser Leu Ser Lys Thr Phe Thr Asn Lys Asn Ser Leu Ile Lys Gln
            100                 105                 110

Pro Ser Pro Gly Leu Lys Leu Asp Gln Leu Leu Asp Arg Ile Thr Met
        115                 120                 125

Ser Ile Ile
    130
```

<210> SEQ ID NO 109
<211> LENGTH: 972
<212> TYPE: DNA
<213> ORGANISM: Phakopsora pachyrhizi
<220> FEATURE:
<221> NAME/KEY: misc_feature
<222> LOCATION: (1)..(972)
<223> OTHER INFORMATION: 16a8

<400> SEQUENCE: 109

```
atgttatggg gaaaaaatat ctatcgactg tcatgcatct cctcgggaat gagcctcttc      60

tctaatctca tgtatatatc tttcatttac tctatatctg caaaaaattc agattctgat     120

gcccaaggat tggtacatcc aatccgtgac cctcgtttgc tttctggagt caggcctgga     180

attacctcga gccaaggcac tagcttgcaa gggagttatt accttagaaa ttcttatcta     240

cgtcacaacc ttaaagaaaa ccaaactggt gttcccttgt tccttacgat ttctgtaact     300

gacaccaatt catgttcccc gattgaaaat gctctcgtgg agctgtgggg cgcaaacaat     360

catgggctgt actcaggctt tagcaaaagt ggcagccctt ctagtgactg ctcctcttgg     420

ctgagaggcg caatggagac agattctgag ggtttggcta agtttgaaac cttataccct     480

ggtcaagaag aaaaccgatc tttgcacttg tatgcgatta ttcgaacgga ttggtacgag     540

cacagcaaga accaaacagt ggattcggat tctagacata atgcagctgc catcgttcaa     600

atttttttcc cagacagttt gaatcaccaa gtcttgaata gaactgatta taaaattaca     660

gggagacaat ttgttaagaa caagcaggac ttcattttct cttctggtca aggagtgtta     720

aaggctaaag ctgaacttcc taaaagcagc atctgtggtg gtgttcaggc tcacgtacag     780

atctctgtgg atgcccatgc atcacagaat attactgtca ctgaatctcc ttatcagtgt     840
```

```
aagaccaatt gcaaagctta ccaaaacacc actgagcaaa caactacaat ttcagcaact    900

tcaaaacaca agccacattt tataccgctt gcagtaatct tttttgcctc tacttatgtt    960

ttctatggct ga                                                        972


<210> SEQ ID NO 110
<211> LENGTH: 323
<212> TYPE: PRT
<213> ORGANISM: Phakopsora pachyrhizi
<220> FEATURE:
<221> NAME/KEY: VARIANT
<222> LOCATION: (1)..(323)
<223> OTHER INFORMATION: 16a8

<400> SEQUENCE: 110

Met Leu Trp Gly Lys Asn Ile Tyr Arg Leu Ser Cys Ile Ser Ser Gly
1               5                   10                  15

Met Ser Leu Phe Ser Asn Leu Met Tyr Ile Ser Phe Ile Tyr Ser Ile
            20                  25                  30

Ser Ala Lys Asn Ser Asp Ser Asp Ala Gln Gly Leu Val His Pro Ile
        35                  40                  45

Arg Asp Pro Arg Leu Leu Ser Gly Val Arg Pro Gly Ile Thr Ser Ser
    50                  55                  60

Gln Gly Thr Ser Leu Gln Gly Ser Tyr Tyr Leu Arg Asn Ser Tyr Leu
65                  70                  75                  80

Arg His Asn Leu Lys Glu Asn Gln Thr Gly Val Pro Leu Phe Leu Thr
                85                  90                  95

Ile Ser Val Thr Asp Thr Asn Ser Cys Ser Pro Ile Glu Asn Ala Leu
            100                 105                 110

Val Glu Leu Trp Gly Ala Asn Asn His Gly Leu Tyr Ser Gly Phe Ser
        115                 120                 125

Lys Ser Gly Ser Pro Ser Ser Asp Cys Ser Ser Trp Leu Arg Gly Ala
    130                 135                 140

Met Glu Thr Asp Ser Glu Gly Leu Ala Lys Phe Glu Thr Leu Tyr Pro
145                 150                 155                 160

Gly Gln Glu Glu Asn Arg Ser Leu His Leu Tyr Ala Ile Ile Arg Thr
                165                 170                 175

Asp Trp Tyr Glu His Ser Lys Asn Gln Thr Val Asp Ser Asp Ser Arg
            180                 185                 190

His Asn Ala Ala Ala Ile Val Gln Ile Phe Phe Pro Asp Ser Leu Asn
        195                 200                 205

His Gln Val Leu Asn Arg Thr Asp Tyr Lys Ile Thr Gly Arg Gln Phe
    210                 215                 220

Val Lys Asn Lys Gln Asp Phe Ile Phe Ser Ser Gly Gln Gly Val Leu
225                 230                 235                 240

Lys Ala Lys Ala Glu Leu Pro Lys Ser Ser Ile Cys Gly Gly Val Gln
                245                 250                 255

Ala His Val Gln Ile Ser Val Asp Ala His Ala Ser Gln Asn Ile Thr
            260                 265                 270

Val Thr Glu Ser Pro Tyr Gln Cys Lys Thr Asn Cys Lys Ala Tyr Gln
        275                 280                 285

Asn Thr Thr Glu Gln Thr Thr Thr Ile Ser Ala Thr Ser Lys His Lys
    290                 295                 300

Pro His Phe Ile Pro Leu Ala Val Ile Phe Phe Ala Ser Thr Tyr Val
305                 310                 315                 320
```

-continued

Phe Tyr Gly

<210> SEQ ID NO 111
<211> LENGTH: 360
<212> TYPE: DNA
<213> ORGANISM: Phakopsora pachyrhizi
<220> FEATURE:
<221> NAME/KEY: misc_feature
<222> LOCATION: (1)..(360)
<223> OTHER INFORMATION: 22-e10

<400> SEQUENCE: 111
atgcagtcct ttatcttgtc agccattgtc tttatggtaa ttgctcaatt gactgttgcg 60
tccccatttt tcggtggagg tttaggcggc ctaggaggtg ccggtggttt tggtggtgct 120
catggtggtg gtgcatccgg ttacaaccac aattccttta gctcctccca aagtggctcg 180
tcgtcttccg gtttcagcgg aggacaaggt ggctctgtca gaggtggtgg tatcggcgga 240
atgggtggta ttggcggtat tggtcccatc ggtggacttg gaccattcgg ccccggaatt 300
ggcggacttg gtggaccatt cctcaaggat aatgaacaca aaaacaagaa tgttcaataa 360

<210> SEQ ID NO 112
<211> LENGTH: 119
<212> TYPE: PRT
<213> ORGANISM: Phakopsora pachyrhizi
<220> FEATURE:
<221> NAME/KEY: VARIANT
<222> LOCATION: (1)..(119)
<223> OTHER INFORMATION: 22-e10

<400> SEQUENCE: 112

Met Gln Ser Phe Ile Leu Ser Ala Ile Val Phe Met Val Ile Ala Gln
1 5 10 15

Leu Thr Val Ala Ser Pro Phe Phe Gly Gly Gly Leu Gly Gly Leu Gly
20 25 30

Gly Ala Gly Gly Phe Gly Gly Ala His Gly Gly Gly Ala Ser Gly Tyr
35 40 45

Asn His Asn Ser Phe Ser Ser Ser Gln Ser Gly Ser Ser Ser Ser Gly
50 55 60

Phe Ser Gly Gly Gln Gly Gly Ser Val Arg Gly Gly Gly Ile Gly Gly
65 70 75 80

Met Gly Gly Ile Gly Gly Ile Gly Pro Ile Gly Gly Leu Gly Pro Phe
85 90 95

Gly Pro Gly Ile Gly Gly Leu Gly Gly Pro Phe Leu Lys Asp Asn Glu
100 105 110

His Lys Asn Lys Asn Val Gln
115

<210> SEQ ID NO 113
<211> LENGTH: 429
<212> TYPE: DNA
<213> ORGANISM: Phakopsora pachyrhizi
<220> FEATURE:
<221> NAME/KEY: misc_feature
<222> LOCATION: (1)..(429)
<223> OTHER INFORMATION: 14-a18

<400> SEQUENCE: 113
atgtttgttt ccctcaaggc cataatttcg accacaatcg ctacccttgc ggtgatcgga 60
gtcgtttcag ggcagaatat tactatagtc tctccacaga gcgggcaagt catcagggca 120
ggtgatgtgt taacagttga actagcccaa caatctacca catcatcggt ccaaagcatc 180
gcattcagca ccggtttcag ttcaaggccc acagatacta tttccttggg cagaccttta 240
ggcggaaccc agtttttgac tgccagagga aacataacct ttcaaattaa tgtgcccaaa 300
gcaagtgaat ttattgacgg gatttccaat gtcccttacg aattcaaagt agcccattac 360
tatttccttg gtgccacctc tactcccacg attgatatag ccagcgttcc agttagcgta 420
caacaataa 429

<210> SEQ ID NO 114
<211> LENGTH: 142
<212> TYPE: PRT
<213> ORGANISM: Phakopsora pachyrhizi
<220> FEATURE:
<221> NAME/KEY: VARIANT
<222> LOCATION: (1)..(142)
<223> OTHER INFORMATION: 14-a18

<400> SEQUENCE: 114

Met Phe Val Ser Leu Lys Ala Ile Ile Ser Thr Thr Ile Ala Thr Leu
1 5 10 15

Ala Val Ile Gly Val Val Ser Gly Gln Asn Ile Thr Ile Val Ser Pro
20 25 30

Gln Ser Gly Gln Val Ile Arg Ala Gly Asp Val Leu Thr Val Glu Leu
35 40 45

Ala Gln Gln Ser Thr Thr Ser Ser Val Gln Ser Ile Ala Phe Ser Thr
50 55 60

Gly Phe Ser Ser Arg Pro Thr Asp Thr Ile Ser Leu Gly Arg Pro Leu
65 70 75 80

Gly Gly Thr Gln Phe Leu Thr Ala Arg Gly Asn Ile Thr Phe Gln Ile
85 90 95

Asn Val Pro Lys Ala Ser Glu Phe Ile Asp Gly Ile Ser Asn Val Pro
100 105 110

Tyr Glu Phe Lys Val Ala His Tyr Tyr Phe Leu Gly Ala Thr Ser Thr
115 120 125

Pro Thr Ile Asp Ile Ala Ser Val Pro Val Ser Val Gln Gln
130 135 140

<210> SEQ ID NO 115
<211> LENGTH: 657
<212> TYPE: DNA
<213> ORGANISM: Phakopsora pachyrhizi
<220> FEATURE:
<221> NAME/KEY: misc_feature
<222> LOCATION: (1)..(657)
<223> OTHER INFORMATION: 02-d23

<400> SEQUENCE: 115
atgctttttg ctacactaat agccgtttgc ttacttgctc tgggaggcaa agctgagagt 60
gatgtccaaa gtgataccgc atctaaactt cagcgacgag gacatgatga ctctctacct 120
cctgtgacat ttattatgag agatagcaac gagcatgtag gcggaaagct gttgatctac 180
aattctgatg gaacactagc tttcaccttt cgcagagcag ttttgaactc tgatggcctt 240
tccaacgttg aagtcagaga tgtgcgaaat aatttttcga taaacttaga atctaacgat 300
gacacctgct ttaaaaagtc tcactatgtt gaaagagaaa aaaatctggg tcaattcaaa 360
attgatccac gaggtgcaaa agcagacaga tggcatttca ctaggaaaac tccacacgga 420
gatttcaagt atgactttca tcgcaagtat ttttcgaagg acggtaatat ttacataaaa 480
gacacccatg tgcgagtggc ttccctgaca tccgaaattc gacatgaagc ttggctccaa 540
ccggggaaac atggtgttcc aacattctca ttgcatcttc aatataacac tgagcctatc 600 tttttgtag ctttgatggg cttagatctc accagagtag acacatgtgg actttga 657

<210> SEQ ID NO 116
<211> LENGTH: 218
<212> TYPE: PRT
<213> ORGANISM: Phakopsora pachyrhizi
<220> FEATURE:
<221> NAME/KEY: VARIANT
<222> LOCATION: (1)..(218)
<223> OTHER INFORMATION: 02-d23

<400> SEQUENCE: 116

Met Leu Phe Ala Thr Leu Ile Ala Val Cys Leu Leu Ala Leu Gly Gly
1 5 10 15

Lys Ala Glu Ser Asp Val Gln Ser Asp Thr Ala Ser Lys Leu Gln Arg
20 25 30

Arg Gly His Asp Asp Ser Leu Pro Pro Val Thr Phe Ile Met Arg Asp
35 40 45

Ser Asn Glu His Val Gly Gly Lys Leu Leu Ile Tyr Asn Ser Asp Gly
50 55 60

Thr Leu Ala Phe Thr Phe Arg Arg Ala Val Leu Asn Ser Asp Gly Leu
65 70 75 80

Ser Asn Val Glu Val Arg Asp Val Arg Asn Asn Phe Ser Ile Asn Leu
85 90 95

Glu Ser Asn Asp Asp Thr Cys Phe Lys Lys Ser His Tyr Val Glu Arg
100 105 110

Glu Lys Asn Leu Gly Gln Phe Lys Ile Asp Pro Arg Gly Ala Lys Ala
115 120 125

Asp Arg Trp His Phe Thr Arg Lys Thr Pro His Gly Asp Phe Lys Tyr
130 135 140

Asp Phe His Arg Lys Tyr Phe Ser Lys Asp Gly Asn Ile Tyr Ile Lys
145 150 155 160

Asp Thr His Val Arg Val Ala Ser Leu Thr Ser Glu Ile Arg His Glu
165 170 175

Ala Trp Leu Gln Pro Gly Lys His Gly Val Pro Thr Phe Ser Leu His
180 185 190

Leu Gln Tyr Asn Thr Glu Pro Ile Phe Phe Val Ala Leu Met Gly Leu
195 200 205

Asp Leu Thr Arg Val Asp Thr Cys Gly Leu
210 215

<210> SEQ ID NO 117
<211> LENGTH: 381
<212> TYPE: DNA
<213> ORGANISM: Phakopsora pachyrhizi
<220> FEATURE:
<221> NAME/KEY: misc_feature
<222> LOCATION: (1)..(381)
<223> OTHER INFORMATION: 02-L20

<400> SEQUENCE: 117
atgagggcaa tcttaatatt cctgattgga ttctgctttt tatacaacgg cgtcaggtcc 60
atcgaatcca taataaaaaa agcacaaagc gaaataaaaa gtctagggag ctatggaaaa 120
tcagaagctg tcaagcagcc acttactcag gcaagctctc atctaaatgg tttgcgagga 180
gcgaaagggc aaaaaaaggc agcagtgaaa caattgatcc aagagcaatt gaacaattat 240

-continued

```
agtgaaaatc tatataatga atgtaaaata aaaacttctg aaaaaagttc aagtaaagaa    300

gaaatacgta ctttactttc agataagaag aaggtagaca aagcaattga aaatataatg    360

aaagggcttg aaaaagctta a                                              381
```

```
<210> SEQ ID NO 118
<211> LENGTH: 126
<212> TYPE: PRT
<213> ORGANISM: Phakopsora pachyrhizi
<220> FEATURE:
<221> NAME/KEY: VARIANT
<222> LOCATION: (1)..(126)
<223> OTHER INFORMATION: 02-L20

<400> SEQUENCE: 118

Met Arg Ala Ile Leu Ile Phe Leu Ile Gly Phe Cys Phe Leu Tyr Asn
1               5                   10                  15

Gly Val Arg Ser Ile Glu Ser Ile Ile Lys Lys Ala Gln Ser Glu Ile
            20                  25                  30

Lys Ser Leu Gly Ser Tyr Gly Lys Ser Glu Ala Val Lys Gln Pro Leu
        35                  40                  45

Thr Gln Ala Ser Ser His Leu Asn Gly Leu Arg Gly Ala Lys Gly Gln
    50                  55                  60

Lys Lys Ala Ala Val Lys Gln Leu Ile Gln Glu Gln Leu Asn Asn Tyr
65                  70                  75                  80

Ser Glu Asn Leu Tyr Asn Glu Cys Lys Ile Lys Thr Ser Glu Lys Ser
                85                  90                  95

Ser Ser Lys Glu Glu Ile Arg Thr Leu Leu Ser Asp Lys Lys Lys Val
            100                 105                 110

Asp Lys Ala Ile Glu Asn Ile Met Lys Gly Leu Glu Lys Ala
        115                 120                 125
```

```
<210> SEQ ID NO 119
<211> LENGTH: 579
<212> TYPE: DNA
<213> ORGANISM: Phakopsora pachyrhizi
<220> FEATURE:
<221> NAME/KEY: misc_feature
<222> LOCATION: (1)..(579)
<223> OTHER INFORMATION: 03-c18

<400> SEQUENCE: 119

atgaggttaa tccctgtctt aattttgctt tttgcctctg cgctcaatgc ctcaccatgt     60

gataaatcta aagttgcgaa aggcgaagat gtcactatga gcgtcatatt ttcagagacc    120

tccatcgcat acgcatcagg gctcaccgtc atccaggaaa gttgccataa cggagaatat    180

gagaaagttg aacaatctac tcttactatt caccagcaaa tgacgataat cacagagact    240

gtgaaaagta aagactttaa caaagattct gcggttcaat acgagggaac tgtagcatct    300

tacatcgtag actatagcaa agtagtacag actgttgttg attatccaga aactgaacct    360

tgccatagta ccttggtaga gattcatcaa aaaattcaaa ctgttattaa tacgtacgcc    420

tccgaatata acatttctct caagaaggaa gtagacaggc aaggtggaat tgatcccaaa    480

tctctagaaa aactgaatct caaatttgat tttcacgaag cgcgtacgca tcaagaaaat    540

gaagtcgatg aatatcaaat atctgaatac aagaattaa                           579
```

```
<210> SEQ ID NO 120
<211> LENGTH: 192
<212> TYPE: PRT
<213> ORGANISM: Phakopsora pachyrhizi
```

```
<220> FEATURE:
<221> NAME/KEY: VARIANT
<222> LOCATION: (1)..(192)
<223> OTHER INFORMATION: 03-c18

<400> SEQUENCE: 120

Met Arg Leu Ile Pro Val Leu Ile Leu Leu Phe Ala Ser Ala Leu Asn
1               5                   10                  15

Ala Ser Pro Cys Asp Lys Ser Lys Val Ala Lys Gly Glu Asp Val Thr
            20                  25                  30

Met Ser Val Ile Phe Ser Glu Thr Ser Ile Ala Tyr Ala Ser Gly Leu
        35                  40                  45

Thr Val Ile Gln Glu Ser Cys His Asn Gly Glu Tyr Glu Lys Val Glu
    50                  55                  60

Gln Ser Thr Leu Thr Ile His Gln Gln Met Thr Ile Ile Thr Glu Thr
65                  70                  75                  80

Val Lys Ser Lys Asp Phe Asn Lys Asp Ser Ala Val Gln Tyr Glu Gly
                85                  90                  95

Thr Val Ala Ser Tyr Ile Val Asp Tyr Ser Lys Val Val Gln Thr Val
            100                 105                 110

Val Asp Tyr Pro Glu Thr Glu Pro Cys His Ser Thr Leu Val Glu Ile
        115                 120                 125

His Gln Lys Ile Gln Thr Val Ile Asn Thr Tyr Ala Ser Glu Tyr Asn
    130                 135                 140

Ile Ser Leu Lys Lys Glu Val Asp Arg Gln Gly Gly Ile Asp Pro Lys
145                 150                 155                 160

Ser Leu Glu Lys Leu Asn Leu Lys Phe Asp Phe His Glu Ala Arg Thr
                165                 170                 175

His Gln Glu Asn Glu Val Asp Glu Tyr Gln Ile Ser Glu Tyr Lys Asn
            180                 185                 190


<210> SEQ ID NO 121
<211> LENGTH: 885
<212> TYPE: DNA
<213> ORGANISM: Phakopsora pachyrhizi
<220> FEATURE:
<221> NAME/KEY: misc_feature
<222> LOCATION: (1)..(885)
<223> OTHER INFORMATION: 04-a4

<400> SEQUENCE: 121

atgaactcca agtctaccct cgcgatactt gtcgtggtca ccgccagttt gttaccatac      60

agctggggat ttaatcagga tagctcagaa actcaaacat ttgagcatcc ctcctccgcg     120

aaggaatcac aatcttcatt cagttatgag agtaatgaaa gcaagtcatc ttactcaagc     180

aatcaaatat cgacaaaaaa tcaatatggg cctagtagta gcttaggagg aagcactgaa     240

gacggctttg atcctgaatt cgatccaaca gaggaagaca caattacagc agagactcca     300

actaaaacaa tcttttgtcc aggaccaatt aataccggaa cgggagaggg tgtatggata     360

gatggacatt gtgaaattat gtgcttcaac aatctcgtac tggatggaga tcgatgtacc     420

tgccccccaa cctatcactt tgaccacaaa aatgtgaaat gcgtttgcag acctccactc     480

tgtgaacaag gcggtaagtg tatcttgaag ccatcgcagt atcctggcgt ccacaactct     540

gcccatagaa agaggtcaat gcctgcgcag cttcgattaa ccccacaagt ttataatgga     600

aatcatgctc gaacatcttt cgatgataag cactgcattt caaatgagat cgcctgtcgc     660

attggtagta tgactggtgg agttcaatgc gttgatccca caagtgacct ggaacactgt     720
```

gggggggtgct ccaacaccac agaaggcata aactgcaatc aaattcccgg ggtagataac 780
gctggatgca atcagtcaaa atgtgtcatt ttttcttgca aagatgggca cagactggtg 840
aataacgtat gcgtgaaagc gctaaataac aaaagaaggc tgtaa 885

<210> SEQ ID NO 122
<211> LENGTH: 294
<212> TYPE: PRT
<213> ORGANISM: Phakopsora pachyrhizi
<220> FEATURE:
<221> NAME/KEY: VARIANT
<222> LOCATION: (1)..(294)
<223> OTHER INFORMATION: 04-a4

<400> SEQUENCE: 122

Met Asn Ser Lys Ser Thr Leu Ala Ile Leu Val Val Val Thr Ala Ser
1 5 10 15

Leu Leu Pro Tyr Ser Trp Gly Phe Asn Gln Asp Ser Ser Glu Thr Gln
20 25 30

Thr Phe Glu His Pro Ser Ser Ala Lys Glu Ser Gln Ser Ser Phe Ser
35 40 45

Tyr Glu Ser Asn Glu Ser Lys Ser Ser Tyr Ser Ser Asn Gln Ile Ser
50 55 60

Thr Lys Asn Gln Tyr Gly Pro Ser Ser Ser Leu Gly Gly Ser Thr Glu
65 70 75 80

Asp Gly Phe Asp Pro Glu Phe Asp Pro Thr Glu Glu Asp Thr Ile Thr
85 90 95

Ala Glu Thr Pro Thr Lys Thr Ile Phe Cys Pro Gly Pro Ile Asn Thr
100 105 110

Gly Thr Gly Glu Gly Val Trp Ile Asp Gly His Cys Glu Ile Met Cys
115 120 125

Phe Asn Asn Leu Val Leu Asp Gly Asp Arg Cys Thr Cys Pro Pro Thr
130 135 140

Tyr His Phe Asp His Lys Asn Val Lys Cys Val Cys Arg Pro Pro Leu
145 150 155 160

Cys Glu Gln Gly Gly Lys Cys Ile Leu Lys Pro Ser Gln Tyr Pro Gly
165 170 175

Val His Asn Ser Ala His Arg Lys Arg Ser Met Pro Ala Gln Leu Arg
180 185 190

Leu Thr Pro Gln Val Tyr Asn Gly Asn His Ala Arg Thr Ser Phe Asp
195 200 205

Asp Lys His Cys Ile Ser Asn Glu Ile Ala Cys Arg Ile Gly Ser Met
210 215 220

Thr Gly Gly Val Gln Cys Val Asp Pro Thr Ser Asp Leu Glu His Cys
225 230 235 240

Gly Gly Cys Ser Asn Thr Thr Glu Gly Ile Asn Cys Asn Gln Ile Pro
245 250 255

Gly Val Asp Asn Ala Gly Cys Asn Gln Ser Lys Cys Val Ile Phe Ser
260 265 270

Cys Lys Asp Gly His Arg Leu Val Asn Asn Val Cys Val Lys Ala Leu
275 280 285

Asn Asn Lys Arg Arg Leu
290

<210> SEQ ID NO 123
<211> LENGTH: 642
<212> TYPE: DNA

<213> ORGANISM: Phakopsora pachyrhizi
<220> FEATURE:
<221> NAME/KEY: misc_feature
<222> LOCATION: (1)..(642)
<223> OTHER INFORMATION: 12d21

<400> SEQUENCE: 123
atggtttact caaaggcaac cttcaccctg gtctcactcc tacctatgat cctggcccag 60
cagagcatca acaacagtga taccacaacc acggctgcta ccccggccag tcccaccaac 120
agcagcagct ctaccactac ttccactacc acctctaaca ctgccagtgg agctgctcag 180
tccttccctg cgccaacagt ctcaggaaca tcctgtggta cagcccagca gaactttaac 240
cagtgtgtta ccaaagtatc aaaggatatc tcctcatgtc cctctaccga taacacctgt 300
ctttgccaaa cgtatgcaaa cctagcctac tgttacaacg cctgtccaga tctggcatca 360
tcaggggccg gatacctgca gcagtccaca gtgaactgtg atgcagcagg tatcaagcca 420
aacgctactt ccaacgtcac caccacccct gtcacctcca ccactaacag gaacaccacc 480
aacacctcac ccatctctaa cacaaacaag aacaattcta cctcgggcaa cactgctgct 540
acatttgctg ctggaaactc caaggcaagt gggattgagg ccccgttact gagcgttgct 600
gttgttgggc tgtgtggtat cattgctagc ctatttgcat ga 642

<210> SEQ ID NO 124
<211> LENGTH: 213
<212> TYPE: PRT
<213> ORGANISM: Phakopsora pachyrhizi
<220> FEATURE:
<221> NAME/KEY: VARIANT
<222> LOCATION: (1)..(213)
<223> OTHER INFORMATION: 12d21

<400> SEQUENCE: 124

Met Val Tyr Ser Lys Ala Thr Phe Thr Leu Val Ser Leu Leu Pro Met
1               5                   10                  15

Ile Leu Ala Gln Gln Ser Ile Asn Asn Ser Asp Thr Thr Thr Thr Ala
            20                  25                  30

Ala Thr Pro Ala Ser Pro Thr Asn Ser Ser Ser Ser Thr Thr Thr Ser
        35                  40                  45

Thr Thr Thr Ser Asn Thr Ala Ser Gly Ala Ala Gln Ser Phe Pro Ala
    50                  55                  60

Pro Thr Val Ser Gly Thr Ser Cys Gly Thr Ala Gln Gln Asn Phe Asn
65                  70                  75                  80

Gln Cys Val Thr Lys Val Ser Lys Asp Ile Ser Ser Cys Pro Ser Thr
                85                  90                  95

Asp Asn Thr Cys Leu Cys Gln Thr Tyr Ala Asn Leu Ala Tyr Cys Tyr
            100                 105                 110

Asn Ala Cys Pro Asp Leu Ala Ser Ser Gly Ala Gly Tyr Leu Gln Gln
        115                 120                 125

Ser Thr Val Asn Cys Asp Ala Ala Gly Ile Lys Pro Asn Ala Thr Ser
    130                 135                 140

Asn Val Thr Thr Thr Pro Val Thr Ser Thr Thr Asn Arg Asn Thr Thr
145                 150                 155                 160

Asn Thr Ser Pro Ile Ser Asn Thr Asn Lys Asn Asn Ser Thr Ser Gly
                165                 170                 175

Asn Thr Ala Ala Thr Phe Ala Ala Gly Asn Ser Lys Ala Ser Gly Ile
            180                 185                 190

Glu Ala Pro Leu Leu Ser Val Ala Val Val Gly Leu Cys Gly Ile Ile

```
        195                 200                 205

Ala Ser Leu Phe Ala
    210


<210> SEQ ID NO 125
<211> LENGTH: 465
<212> TYPE: DNA
<213> ORGANISM: Phakopsora pachyrhizi
<220> FEATURE:
<221> NAME/KEY: misc_feature
<222> LOCATION: (1)..(465)
<223> OTHER INFORMATION: 12L21

<400> SEQUENCE: 125

atgcaatcca actttctcct cgctttttgc ttgattgctg ctgtctctgt tccagttagc      60

agggctcacg gtgttattac ttcagttgag ggcgcaaatg gtcaaactgg atctgccttt     120

ggaatggtag agtccactcc tcgtgatggc actcgaacga acccattcca aactgacagt     180

tccatcattc gagaccgtga ggtttcaagc ggaaaggcgt ctgcttgtgg acgcactctt     240

gcgggcggaa acaacgatat tgctagtgac atgtcatcgg ctgaatctgc cggattggcc     300

agtattggac ctgacggaaa agtcagaatg actcttcacc aggtcaacgg tgacggtgga     360

ggcccataca gctgtgaagt tgacaccacc gccactggtg acaacttcaa gaaaatgaac     420

atcgacacaa acgttcctgg caagaacagt cgatcaaggg catag                     465


<210> SEQ ID NO 126
<211> LENGTH: 154
<212> TYPE: PRT
<213> ORGANISM: Phakopsora pachyrhizi
<220> FEATURE:
<221> NAME/KEY: VARIANT
<222> LOCATION: (1)..(154)
<223> OTHER INFORMATION: 12L21

<400> SEQUENCE: 126

Met Gln Ser Asn Phe Leu Leu Ala Phe Cys Leu Ile Ala Ala Val Ser
1               5                   10                  15

Val Pro Val Ser Arg Ala His Gly Val Ile Thr Ser Val Glu Gly Ala
            20                  25                  30

Asn Gly Gln Thr Gly Ser Ala Phe Gly Met Val Glu Ser Thr Pro Arg
        35                  40                  45

Asp Gly Thr Arg Thr Asn Pro Phe Gln Thr Asp Ser Ser Ile Ile Arg
    50                  55                  60

Asp Arg Glu Val Ser Ser Gly Lys Ala Ser Ala Cys Gly Arg Thr Leu
65                  70                  75                  80

Ala Gly Gly Asn Asn Asp Ile Ala Ser Asp Met Ser Ser Ala Glu Ser
                85                  90                  95

Ala Gly Leu Ala Ser Ile Gly Pro Asp Gly Lys Val Arg Met Thr Leu
            100                 105                 110

His Gln Val Asn Gly Asp Gly Gly Gly Pro Tyr Ser Cys Glu Val Asp
        115                 120                 125

Thr Thr Ala Thr Gly Asp Asn Phe Lys Lys Met Asn Ile Asp Thr Asn
    130                 135                 140

Val Pro Gly Lys Asn Ser Arg Ser Arg Ala
145                 150


<210> SEQ ID NO 127
<211> LENGTH: 486
<212> TYPE: DNA
```

<213> ORGANISM: Phakopsora pachyrhizi
<220> FEATURE:
<221> NAME/KEY: misc_feature
<222> LOCATION: (1)..(486)
<223> OTHER INFORMATION: 15m10

<400> SEQUENCE: 127
atgcttttca actcaaacgt gatcctcttt gcattaactt ttgctctggg atcgttatac 60
cagggatcag aagctcagga tctggccgga ctacctaact gtggtcagaa ctgtctattg 120
acagccttta cgacatcgag cgatggttgc acacagaccg actttgcatg tctttgcaag 180
tcgcaaaagt ttactggtac atcaaattcg tgctactcct cgtcctgtac ctccactgaa 240
gcagcgactg ccaagagctg gggtgccaag acttgtgctt ctgtaggagt taatgtgacg 300
gccacccttg gaaacaccac ttccgttgga actgtcatcg gaaatggaac taatcctaac 360
accaactcta cgcttcataa tggcacaact gcctctacac atgcacagaa ctctggaggc 420
ctcatcaacg tgcaacccat ctttttcatg tctttagtct ctgtcctggc tgcagtcttc 480
atgtga 486

<210> SEQ ID NO 128
<211> LENGTH: 161
<212> TYPE: PRT
<213> ORGANISM: Phakopsora pachyrhizi
<220> FEATURE:
<221> NAME/KEY: VARIANT
<222> LOCATION: (1)..(161)
<223> OTHER INFORMATION: 15m10

<400> SEQUENCE: 128

Met Leu Phe Asn Ser Asn Val Ile Leu Phe Ala Leu Thr Phe Ala Leu
1 5 10 15

Gly Ser Leu Tyr Gln Gly Ser Glu Ala Gln Asp Leu Ala Gly Leu Pro
20 25 30

Asn Cys Gly Gln Asn Cys Leu Leu Thr Ala Phe Thr Thr Ser Ser Asp
35 40 45

Gly Cys Thr Gln Thr Asp Phe Ala Cys Leu Cys Lys Ser Gln Lys Phe
50 55 60

Thr Gly Thr Ser Asn Ser Cys Tyr Ser Ser Ser Cys Thr Ser Thr Glu
65 70 75 80

Ala Ala Thr Ala Lys Ser Trp Gly Ala Lys Thr Cys Ala Ser Val Gly
85 90 95

Val Asn Val Thr Ala Thr Leu Gly Asn Thr Thr Ser Val Gly Thr Val
100 105 110

Ile Gly Asn Gly Thr Asn Pro Asn Thr Asn Ser Thr Leu His Asn Gly
115 120 125

Thr Thr Ala Ser Thr His Ala Gln Asn Ser Gly Gly Leu Ile Asn Val
130 135 140

Gln Pro Ile Phe Phe Met Ser Leu Val Ser Val Leu Ala Ala Val Phe
145 150 155 160

Met

<210> SEQ ID NO 129
<211> LENGTH: 591
<212> TYPE: DNA
<213> ORGANISM: Phakopsora pachyrhizi
<220> FEATURE:
<221> NAME/KEY: misc_feature
<222> LOCATION: (1)..(591)
<223> OTHER INFORMATION: 24o10

<400> SEQUENCE: 129

```
atgattcatc tattgcttaa aaaatttgtt tgcgcattat gtttattcct gatacgagga     60
aacccttcta agtcagcctt aactagaatt gccaatggag gcgcagttaa aggactctcg    120
actccagatt gggtactaga tttagctact aaaaaacatc ccacaaattt attagctgct    180
aatgagctca aattttcaga gacggtcact aggccacctc caatacaaga tatgaatttc    240
aggcaccctt cacctgagca aacagaaata ataaaaaact ttatcagaaa acacccaagt    300
ggccaaacct atagactaga tgagaaaggg aactttatag atgtaccaaa ggagaattgg    360
acgttaaaat actactgtgg tagggtaatc gtggtagacg atcacggcaa tgagctatat    420
aatactggct gttgttattg caatgcgtct tcacagacca atttaaactc agcagagata    480
ttggtaaaca aatgtgtata tggatttgga aaaattgctt tagagataat ttctgcactc    540
cttggccatg aagacaggaa tcggtctagc aaaaggtatg gtggaaagta a             591
```

<210> SEQ ID NO 130
<211> LENGTH: 196
<212> TYPE: PRT
<213> ORGANISM: Phakopsora pachyrhizi
<220> FEATURE:
<221> NAME/KEY: VARIANT
<222> LOCATION: (1)..(196)
<223> OTHER INFORMATION: 24o10

<400> SEQUENCE: 130

```
Met Ile His Leu Leu Leu Lys Lys Phe Val Cys Ala Leu Cys Leu Phe
1               5                   10                  15

Leu Ile Arg Gly Asn Pro Ser Lys Ser Ala Leu Thr Arg Ile Ala Asn
            20                  25                  30

Gly Gly Ala Val Lys Gly Leu Ser Thr Pro Asp Trp Val Leu Asp Leu
        35                  40                  45

Ala Thr Lys Lys His Pro Thr Asn Leu Leu Ala Ala Asn Glu Leu Lys
    50                  55                  60

Phe Ser Glu Thr Val Thr Arg Pro Pro Pro Ile Gln Asp Met Asn Phe
65                  70                  75                  80

Arg His Pro Ser Pro Glu Gln Thr Glu Ile Ile Lys Asn Phe Ile Arg
                85                  90                  95

Lys His Pro Ser Gly Gln Thr Tyr Arg Leu Asp Glu Lys Gly Asn Phe
            100                 105                 110

Ile Asp Val Pro Lys Glu Asn Trp Thr Leu Lys Tyr Tyr Cys Gly Arg
        115                 120                 125

Val Ile Val Val Asp Asp His Gly Asn Glu Leu Tyr Asn Thr Gly Cys
    130                 135                 140

Cys Tyr Cys Asn Ala Ser Ser Gln Thr Asn Leu Asn Ser Ala Glu Ile
145                 150                 155                 160

Leu Val Asn Lys Cys Val Tyr Gly Phe Gly Lys Ile Ala Leu Glu Ile
                165                 170                 175

Ile Ser Ala Leu Leu Gly His Glu Asp Arg Asn Arg Ser Ser Lys Arg
            180                 185                 190

Tyr Gly Gly Lys
        195
```

<210> SEQ ID NO 131
<211> LENGTH: 486
<212> TYPE: DNA
<213> ORGANISM: Phakopsora pachyrhizi
<220> FEATURE:
<221> NAME/KEY: misc_feature
<222> LOCATION: (1)..(486)
<223> OTHER INFORMATION: 19n19

<400> SEQUENCE: 131
atgatgacaa agtttaacac gatgatgatc tcacgcccct tatccctcct gctaggtatt 60
atccttctga caaccatcgt atccatcaga gcttctgaga aggagaaact tcagatcggg 120
gtcaaacata aaccgagctc atgtccaatc aaatctcaga agaatgatga attatcgatg 180
cattataccg gaacgctcaa gtcagatgga agcgtttttg attcgtctgt ccaaaggaat 240
gaaccgtttg ttttcactct tggattaggc caagtaataa agggatggga ccaaggtcta 300
ttagatatgt gcattggaga aaagaggaag ttggtcatac cttcaaactt ggcgtatggt 360
gataggggag ctggtggaaa aattcccggc ggtgcgacgc tgatctttga ggttgaactc 420
ttggatattc ttaatcgaaa agcacctgcc tcggaagatc aaaaagagca taaagatgaa 480
ctttaa 486

<210> SEQ ID NO 132
<211> LENGTH: 161
<212> TYPE: PRT
<213> ORGANISM: Phakopsora pachyrhizi
<220> FEATURE:
<221> NAME/KEY: VARIANT
<222> LOCATION: (1)..(161)
<223> OTHER INFORMATION: 19n19

<400> SEQUENCE: 132

Met Met Thr Lys Phe Asn Thr Met Met Ile Ser Arg Pro Leu Ser Leu
1 5 10 15

Leu Leu Gly Ile Ile Leu Leu Thr Thr Ile Val Ser Ile Arg Ala Ser
20 25 30

Glu Lys Glu Lys Leu Gln Ile Gly Val Lys His Lys Pro Ser Ser Cys
35 40 45

Pro Ile Lys Ser Gln Lys Asn Asp Glu Leu Ser Met His Tyr Thr Gly
50 55 60

Thr Leu Lys Ser Asp Gly Ser Val Phe Asp Ser Ser Val Gln Arg Asn
65 70 75 80

Glu Pro Phe Val Phe Thr Leu Gly Leu Gly Gln Val Ile Lys Gly Trp
85 90 95

Asp Gln Gly Leu Leu Asp Met Cys Ile Gly Glu Lys Arg Lys Leu Val
100 105 110

Ile Pro Ser Asn Leu Ala Tyr Gly Asp Arg Gly Ala Gly Gly Lys Ile
115 120 125

Pro Gly Gly Ala Thr Leu Ile Phe Glu Val Glu Leu Leu Asp Ile Leu
130 135 140

Asn Arg Lys Ala Pro Ala Ser Glu Asp Gln Lys Glu His Lys Asp Glu
145 150 155 160

Leu

<210> SEQ ID NO 133
<211> LENGTH: 222
<212> TYPE: DNA
<213> ORGANISM: Phakopsora pachyrhizi
<220> FEATURE:
<221> NAME/KEY: misc_feature
<222> LOCATION: (1)..(222)
<223> OTHER INFORMATION: taa07765.01_phapa

<400> SEQUENCE: 133
atgcgctgct ttatctttgc tattgctttt attgctgctg ctcagtgtgt cctgggagca 60
ggagagtcta cttctaaaaa attgacccgc agagctcttg tcgacgttga aatccttaac 120
agaggtagac gtccatgcaa caccggcaat tcacttattg aagttgacat cctaaacagc 180
tatctgaaaa atgcttctaa agctgctaag aacgcccaat ag 222

<210> SEQ ID NO 134
<211> LENGTH: 73
<212> TYPE: PRT
<213> ORGANISM: Phakopsora pachyrhizi
<220> FEATURE:
<221> NAME/KEY: VARIANT
<222> LOCATION: (1)..(73)
<223> OTHER INFORMATION: taa07765.01_phapa

<400> SEQUENCE: 134

Met Arg Cys Phe Ile Phe Ala Ile Ala Phe Ile Ala Ala Ala Gln Cys
1 5 10 15

Val Leu Gly Ala Gly Glu Ser Thr Ser Lys Lys Leu Thr Arg Arg Ala
20 25 30

Leu Val Asp Val Glu Ile Leu Asn Arg Gly Arg Arg Pro Cys Asn Thr
35 40 45

Gly Asn Ser Leu Ile Glu Val Asp Ile Leu Asn Ser Tyr Leu Lys Asn
50 55 60

Ala Ser Lys Ala Ala Lys Asn Ala Gln
65 70

<210> SEQ ID NO 135
<211> LENGTH: 294
<212> TYPE: DNA
<213> ORGANISM: Phakopsora pachyrhizi
<220> FEATURE:
<221> NAME/KEY: misc_feature
<222> LOCATION: (1)..(294)
<223> OTHER INFORMATION: ta06712.01_phapa

<400> SEQUENCE: 135
atgcaagtat ttatctactc aatattcatt gttgccctgg ctcagctaat tggtgctgca 60
ccattcattg gcggcatcgg tggcatggga ggagtcggtg gcggattcgc aggaggagca 120
tctggattcc ataaacactc gttttcctcc gttcaccatt cccattcctc atcaggattc 180
accgcaggtc atggaggcgc tcacggcggt ttcggtcatg gtggtattgg aggtattggg 240
ggagtgggcc ctttccttaa ggatagcaaa cacaaaaaca aaaattcaca ataa 294

<210> SEQ ID NO 136
<211> LENGTH: 97
<212> TYPE: PRT
<213> ORGANISM: Phakopsora pachyrhizi
<220> FEATURE:
<221> NAME/KEY: VARIANT
<222> LOCATION: (1)..(97)
<223> OTHER INFORMATION: ta06712.01_phapa

<400> SEQUENCE: 136

Met Gln Val Phe Ile Tyr Ser Ile Phe Ile Val Ala Leu Ala Gln Leu
1 5 10 15

Ile Gly Ala Ala Pro Phe Ile Gly Gly Ile Gly Gly Met Gly Gly Val
20 25 30

Gly Gly Gly Phe Ala Gly Gly Ala Ser Gly Phe His Lys His Ser Phe
35 40 45

Ser Ser Val His His Ser His Ser Ser Ser Gly Phe Thr Ala Gly His
    50                  55                  60

Gly Gly Ala His Gly Gly Phe Gly His Gly Gly Ile Gly Gly Ile Gly
65                  70                  75                  80

Gly Val Gly Pro Phe Leu Lys Asp Ser Lys His Lys Asn Lys Asn Ser
                85                  90                  95

Gln

<210> SEQ ID NO 137
<211> LENGTH: 492
<212> TYPE: DNA
<213> ORGANISM: Phakopsora pachyrhizi
<220> FEATURE:
<221> NAME/KEY: misc_feature
<222> LOCATION: (1)..(492)
<223> OTHER INFORMATION: ta09985.01_phapa

<400> SEQUENCE: 137
atgatctaca ccggtctcgt tatttttgtg cttgccctct ccggcaaagt attttctact 60
ggcaccgctc aacaaggctc ctctaactca atgagctgga ctgctgacac taatacaacc 120
atgaaaccta ctgacgctgg cgccatgaac accacttcaa tccccaccat ggttcctggc 180
gacatgtcaa ccggaaagtg catgtgccct gccccagtta cttgcgatgc tggcccttca 240
aaagaaccaa acttacctac aataaatgtt ccaccacctt caacccatgt ccccgctggc 300
aacacaaact ccacccaggg ccatcagcca ggaaattacc caggcagtgg tgccactccc 360
cctgtcacaa accccccaac cccagatacc cctgttactg ataacaactc tacgagcggt 420
gttgccggac tgcctaactc ggtttccatt gccgggttca ttgctgtggc tgcctcagct 480
ttagtgatct ga 492

<210> SEQ ID NO 138
<211> LENGTH: 163
<212> TYPE: PRT
<213> ORGANISM: Phakopsora pachyrhizi
<220> FEATURE:
<221> NAME/KEY: VARIANT
<222> LOCATION: (1)..(163)
<223> OTHER INFORMATION: ta09985.01_phapa

<400> SEQUENCE: 138

Met Ile Tyr Thr Gly Leu Val Ile Phe Val Leu Ala Leu Ser Gly Lys
1               5                   10                  15

Val Phe Ser Thr Gly Thr Ala Gln Gln Gly Ser Ser Asn Ser Met Ser
            20                  25                  30

Trp Thr Ala Asp Thr Asn Thr Thr Met Lys Pro Thr Asp Ala Gly Ala
        35                  40                  45

Met Asn Thr Thr Ser Ile Pro Thr Met Val Pro Gly Asp Met Ser Thr
    50                  55                  60

Gly Lys Cys Met Cys Pro Ala Pro Val Thr Cys Asp Ala Gly Pro Ser
65                  70                  75                  80

Lys Glu Pro Asn Leu Pro Thr Ile Asn Val Pro Pro Pro Ser Thr His
                85                  90                  95

Val Pro Ala Gly Asn Thr Asn Ser Thr Gln Gly His Gln Pro Gly Asn
            100                 105                 110

Tyr Pro Gly Ser Gly Ala Thr Pro Pro Val Thr Asn Pro Pro Thr Pro
        115                 120                 125

Asp Thr Pro Val Thr Asp Asn Asn Ser Thr Ser Gly Val Ala Gly Leu

```
    130                 135                 140

Pro Asn Ser Val Ser Ile Ala Gly Phe Ile Ala Val Ala Ala Ser Ala
145                 150                 155                 160

Leu Val Ile
```

<210> SEQ ID NO 139
<211> LENGTH: 303
<212> TYPE: DNA
<213> ORGANISM: Phakopsora pachyrhizi
<220> FEATURE:
<221> NAME/KEY: misc_feature
<222> LOCATION: (1)..(303)
<223> OTHER INFORMATION: ta08989.02_phapa

<400> SEQUENCE: 139

```
atgaggttca cttatcaagc gttttttgct tttttttgg taatctcatt ggtcccagct      60

gttcccgaag aattgagccc taataatggg gaacttatcc aagctaaaga tgtttcaagt    120

gccaaaacaa aggatagctc aagcgagaaa tttatcgctc cccccggcta cggatggcga    180

ggtggaggac cttggagagg accatggggc catggcggac gatggggaaa tggtggacgt    240

tggggttggg gtccaggtgg tggctggcgc ggaccgggat ggcatggtca ctggcgcgag    300

tga                                                                  303
```

<210> SEQ ID NO 140
<211> LENGTH: 100
<212> TYPE: PRT
<213> ORGANISM: Phakopsora pachyrhizi
<220> FEATURE:
<221> NAME/KEY: VARIANT
<222> LOCATION: (1)..(100)
<223> OTHER INFORMATION: ta08989.02_phapa

<400> SEQUENCE: 140

```
Met Arg Phe Thr Tyr Gln Ala Phe Phe Ala Phe Phe Leu Val Ile Ser
1               5                   10                  15

Leu Val Pro Ala Val Pro Glu Glu Leu Ser Pro Asn Asn Gly Glu Leu
            20                  25                  30

Ile Gln Ala Lys Asp Val Ser Ser Ala Lys Thr Lys Asp Ser Ser Ser
        35                  40                  45

Glu Lys Phe Ile Ala Pro Pro Gly Tyr Gly Trp Arg Gly Gly Gly Pro
    50                  55                  60

Trp Arg Gly Pro Trp Gly His Gly Gly Arg Trp Gly Asn Gly Gly Arg
65                  70                  75                  80

Trp Gly Trp Gly Pro Gly Gly Gly Trp Arg Gly Pro Gly Trp His Gly
                85                  90                  95

His Trp Arg Glu
            100
```

<210> SEQ ID NO 141
<211> LENGTH: 375
<212> TYPE: DNA
<213> ORGANISM: Phakopsora pachyrhizi
<220> FEATURE:
<221> NAME/KEY: misc_feature
<222> LOCATION: (1)..(375)
<223> OTHER INFORMATION: ta10092.01_phapa

<400> SEQUENCE: 141

```
atgaaggtac ttatattctt cgcactaatt gctactatct gcttaccatt ggtagaaaat      60

agatgccgta ccactggagc ctcatttgga tcatctccga acagggcttt tgctactcag    120
```

```
ctattacctg acgtatgtag agaattccaa ggcacctatg ggcccaacca ggacaagacc    180

atatgtagaa acggtagaga cagagatacc agcttcagat actacataaa acacgtatct    240

ggtgggtata ggaacattga ctccactgag tgcacagacg gtctcaacaa agagattgta    300

aattgcgata gaggtggaaa aacagcttat ggtaactggg aatacagtgt ggacccgaat    360

aaaggaaatt gctaa                                                     375


<210> SEQ ID NO 142
<211> LENGTH: 124
<212> TYPE: PRT
<213> ORGANISM: Phakopsora pachyrhizi
<220> FEATURE:
<221> NAME/KEY: VARIANT
<222> LOCATION: (1)..(124)
<223> OTHER INFORMATION: ta10092.01_phapa

<400> SEQUENCE: 142

Met Lys Val Leu Ile Phe Phe Ala Leu Ile Ala Thr Ile Cys Leu Pro
1               5                   10                  15

Leu Val Glu Asn Arg Cys Arg Thr Thr Gly Ala Ser Phe Gly Ser Ser
            20                  25                  30

Pro Asn Arg Ala Phe Ala Thr Gln Leu Leu Pro Asp Val Cys Arg Glu
        35                  40                  45

Phe Gln Gly Thr Tyr Gly Pro Asn Gln Asp Lys Thr Ile Cys Arg Asn
    50                  55                  60

Gly Arg Asp Arg Asp Thr Ser Phe Arg Tyr Tyr Ile Lys His Val Ser
65                  70                  75                  80

Gly Gly Tyr Arg Asn Ile Asp Ser Thr Glu Cys Thr Asp Gly Leu Asn
                85                  90                  95

Lys Glu Ile Val Asn Cys Asp Arg Gly Gly Lys Thr Ala Tyr Gly Asn
            100                 105                 110

Trp Glu Tyr Ser Val Asp Pro Asn Lys Gly Asn Cys
        115                 120


<210> SEQ ID NO 143
<211> LENGTH: 366
<212> TYPE: DNA
<213> ORGANISM: Phakopsora pachyrhizi
<220> FEATURE:
<221> NAME/KEY: misc_feature
<222> LOCATION: (1)..(366)
<223> OTHER INFORMATION: ta03571.01_phapa

<400> SEQUENCE: 143

atgttccacg acttgaacta ctttgcacct gcccttattg ccttcgcctg tcttcttgag     60

cttagtgctg ctcaagaaca gaggtcctgt agtttctaca ctggtgccaa taccacttcc    120

gccacctgca acgagcaacc aaatgttgta tgcaccaagg gctgcactgg gcccttcgtc    180

actgcaactg aatgtacgcc ggttaatgag tcggaagaag ctattgcgag cactcaggtg    240

tgcagctttg gttttggtcg gaacacagct gctgcaaagg cctgcataaa tgaattaggt    300

acttttagat gcactggtca aaccacaggc tcagctacct gtgacggatg tcaagctagg    360

tcctaa                                                               366


<210> SEQ ID NO 144
<211> LENGTH: 121
<212> TYPE: PRT
<213> ORGANISM: Phakopsora pachyrhizi
<220> FEATURE:
```

<221> NAME/KEY: VARIANT
<222> LOCATION: (1)..(121)
<223> OTHER INFORMATION: ta03571.01_phapa

<400> SEQUENCE: 144

```
Met Phe His Asp Leu Asn Tyr Phe Ala Pro Ala Leu Ile Ala Phe Ala
1               5                   10                  15

Cys Leu Leu Glu Leu Ser Ala Ala Gln Glu Gln Arg Ser Cys Ser Phe
            20                  25                  30

Tyr Thr Gly Ala Asn Thr Thr Ser Ala Thr Cys Asn Glu Gln Pro Asn
        35                  40                  45

Val Val Cys Thr Lys Gly Cys Thr Gly Pro Phe Val Thr Ala Thr Glu
    50                  55                  60

Cys Thr Pro Val Asn Glu Ser Glu Glu Ala Ile Ala Ser Thr Gln Val
65                  70                  75                  80

Cys Ser Phe Gly Phe Gly Arg Asn Thr Ala Ala Ala Lys Ala Cys Ile
                85                  90                  95

Asn Glu Leu Gly Thr Phe Arg Cys Thr Gly Gln Thr Thr Gly Ser Ala
            100                 105                 110

Thr Cys Asp Gly Cys Gln Ala Arg Ser
        115                 120
```

<210> SEQ ID NO 145
<211> LENGTH: 567
<212> TYPE: DNA
<213> ORGANISM: Phakopsora pachyrhizi
<220> FEATURE:
<221> NAME/KEY: misc_feature
<222> LOCATION: (1)..(567)
<223> OTHER INFORMATION: ta05395.01_phapa

<400> SEQUENCE: 145

```
atgttcggtc ttaagactat catcgttgcc atcgctgcca tcctacaagt tgcggaggct      60

atcgacgact caggttgtgc ttccaagtgt atggctgtaa aattaaccga agccgctgtc     120

tggttcggtc aaggcaatct ctcaacctac tgccaacatc ctgaattcat caccgcatac     180

gattcgtgct taggcgataa ctgcaccagt cgcgatgagc tagaagtagc caagagaaat     240

ggccgcgctg cttgcgctgc tgctagtatc aattccgttg caaataatgt ttcatccatt     300

ggacgcaaca actctccagc agatatgcct gctggtgcag ggaaccgaag caccggttct     360

ccttcaccta cagtcccaac caacacaagc gttaacatca attctacctt actaacacct     420

aattctactg taaacgccac aaacagccga ttttccaacg caccattccc tgcgatttcg     480

gctgcggcaa acagcacggc ctcaacaata acttgttcat caatgataat tggtttaact     540

tctgctctgg ttttagcaag cctgtaa                                         567
```

<210> SEQ ID NO 146
<211> LENGTH: 188
<212> TYPE: PRT
<213> ORGANISM: Phakopsora pachyrhizi
<220> FEATURE:
<221> NAME/KEY: VARIANT
<222> LOCATION: (1)..(188)
<223> OTHER INFORMATION: ta05395.01_phapa

<400> SEQUENCE: 146

```
Met Phe Gly Leu Lys Thr Ile Ile Val Ala Ile Ala Ala Ile Leu Gln
1               5                   10                  15

Val Ala Glu Ala Ile Asp Asp Ser Gly Cys Ala Ser Lys Cys Met Ala
            20                  25                  30
```

```
Val Lys Leu Thr Glu Ala Ala Val Trp Phe Gly Gln Gly Asn Leu Ser
        35                  40                  45

Thr Tyr Cys Gln His Pro Glu Phe Ile Thr Ala Tyr Asp Ser Cys Leu
    50                  55                  60

Gly Asp Asn Cys Thr Ser Arg Asp Glu Leu Glu Val Ala Lys Arg Asn
65                  70                  75                  80

Gly Arg Ala Ala Cys Ala Ala Ala Ser Ile Asn Ser Val Ala Asn Asn
                85                  90                  95

Val Ser Ser Ile Gly Arg Asn Asn Ser Pro Ala Asp Met Pro Ala Gly
            100                 105                 110

Ala Gly Asn Arg Ser Thr Gly Ser Pro Ser Pro Thr Val Pro Thr Asn
        115                 120                 125

Thr Ser Val Asn Ile Asn Ser Thr Leu Leu Thr Pro Asn Ser Thr Val
    130                 135                 140

Asn Ala Thr Asn Ser Arg Phe Ser Asn Ala Pro Phe Pro Ala Ile Ser
145                 150                 155                 160

Ala Ala Ala Asn Ser Thr Ala Ser Thr Ile Thr Cys Ser Ser Met Ile
                165                 170                 175

Ile Gly Leu Thr Ser Ala Leu Val Leu Ala Ser Leu
            180                 185
```

<210> SEQ ID NO 147
<211> LENGTH: 192
<212> TYPE: DNA
<213> ORGANISM: Phakopsora pachyrhizi
<220> FEATURE:
<221> NAME/KEY: misc_feature
<222> LOCATION: (1)..(192)
<223> OTHER INFORMATION: ta01387.04_phapa

<400> SEQUENCE: 147

```
atgcattcat ttatttcgtc aaccctagtt ttaatcgtag cccagcttgt ctcagctgcc      60

ctcttgctga aagatcggag gtgcaatcat ctgtcggcca ctcagaacaa aaatttgcag     120

gactcggtgg ccttccgtgt cctcctgtcg gtggaatctt gcctcctgtt ggtggaatct     180

tgccccctgt ag                                                         192
```

<210> SEQ ID NO 148
<211> LENGTH: 63
<212> TYPE: PRT
<213> ORGANISM: Phakopsora pachyrhizi
<220> FEATURE:
<221> NAME/KEY: VARIANT
<222> LOCATION: (1)..(63)
<223> OTHER INFORMATION: ta01387.04_phapa

<400> SEQUENCE: 148

```
Met His Ser Phe Ile Ser Ser Thr Leu Val Leu Ile Val Ala Gln Leu
1               5                   10                  15

Val Ser Ala Ala Leu Leu Leu Lys Asp Arg Arg Cys Asn His Leu Ser
            20                  25                  30

Ala Thr Gln Asn Lys Asn Leu Gln Asp Ser Val Ala Phe Arg Val Leu
        35                  40                  45

Leu Ser Val Glu Ser Cys Leu Leu Leu Val Glu Ser Cys Pro Leu
    50                  55                  60
```

<210> SEQ ID NO 149
<211> LENGTH: 375
<212> TYPE: DNA

<213> ORGANISM: Phakopsora pachyrhizi
<220> FEATURE:
<221> NAME/KEY: misc_feature
<222> LOCATION: (1)..(375)
<223> OTHER INFORMATION: ta00470.01_phapa

<400> SEQUENCE: 149
atgaggataa ttgccttttt cgcactactt gctgccatct gcctcccatt tgtagagaac 60
agatgccata gaagtggagc cacattcgga tcgtctccca atagagctta tgctactcag 120
ttattgcctg gcgtatgcaa agaattccaa ggcacctatg gaccaaatca ggacaagtcc 180
gtttgtagaa acggcagaga tagagatacc agcttcagat actatatcaa acacgtctca 240
gatgggtata ggagcattgg cccaactgag tgtacagatg gcctcaacaa agagatagtc 300
aattgcgata gaggtggaaa aacggcttat ggcaactggg aatacaatgt tgaccctaac 360
aaaggaaggt gctag 375

<210> SEQ ID NO 150
<211> LENGTH: 124
<212> TYPE: PRT
<213> ORGANISM: Phakopsora pachyrhizi
<220> FEATURE:
<221> NAME/KEY: VARIANT
<222> LOCATION: (1)..(124)
<223> OTHER INFORMATION: ta00470.01_phapa

<400> SEQUENCE: 150

Met Arg Ile Ile Ala Phe Phe Ala Leu Leu Ala Ala Ile Cys Leu Pro
1 5 10 15

Phe Val Glu Asn Arg Cys His Arg Ser Gly Ala Thr Phe Gly Ser Ser
20 25 30

Pro Asn Arg Ala Tyr Ala Thr Gln Leu Leu Pro Gly Val Cys Lys Glu
35 40 45

Phe Gln Gly Thr Tyr Gly Pro Asn Gln Asp Lys Ser Val Cys Arg Asn
50 55 60

Gly Arg Asp Arg Asp Thr Ser Phe Arg Tyr Tyr Ile Lys His Val Ser
65 70 75 80

Asp Gly Tyr Arg Ser Ile Gly Pro Thr Glu Cys Thr Asp Gly Leu Asn
85 90 95

Lys Glu Ile Val Asn Cys Asp Arg Gly Gly Lys Thr Ala Tyr Gly Asn
100 105 110

Trp Glu Tyr Asn Val Asp Pro Asn Lys Gly Arg Cys
115 120

<210> SEQ ID NO 151
<211> LENGTH: 465
<212> TYPE: DNA
<213> ORGANISM: Phakopsora pachyrhizi
<220> FEATURE:
<221> NAME/KEY: misc_feature
<222> LOCATION: (1)..(465)
<223> OTHER INFORMATION: ta08619.01_phapa

<400> SEQUENCE: 151
atgcttaatc tatcattctc aggcctcttg atctttgcct gtgttctttt tcagtttacg 60
tctatatcag caaagaattt aactgctact gctgtaaaaa atgctctgta ttcttcttgt 120
gaaaagtctg ccttagccaa gccctgtggt ggggccctgg ataagctata tgacactgga 180
cgatttaaaa gtttcacgat cgagaaacaa gtacactttg ataaaacttc aaattgcaaa 240
ttcacctggt ggactgatac acaagttgct gctctaaatg tttccaaaac ttcagttcaa 300
aatgcactat tggagatcga aagcgaatgt gtagctaacg gcctttcacc aacccaacac 360
acgaacacct ccagtagcgc agatgtaccc actggaaaag gagtctatgt tggaactctt 420
gaagcgaagc aatacgtagt cttagagctg gagttgtttt cttag 465

<210> SEQ ID NO 152
<211> LENGTH: 154
<212> TYPE: PRT
<213> ORGANISM: Phakopsora pachyrhizi
<220> FEATURE:
<221> NAME/KEY: VARIANT
<222> LOCATION: (1)..(154)
<223> OTHER INFORMATION: ta08619.01_phapa

<400> SEQUENCE: 152

Met Leu Asn Leu Ser Phe Ser Gly Leu Leu Ile Phe Ala Cys Val Leu
1 5 10 15

Phe Gln Phe Thr Ser Ile Ser Ala Lys Asn Leu Thr Ala Thr Ala Val
20 25 30

Lys Asn Ala Leu Tyr Ser Ser Cys Glu Lys Ser Ala Leu Ala Lys Pro
35 40 45

Cys Gly Gly Ala Leu Asp Lys Leu Tyr Asp Thr Gly Arg Phe Lys Ser
50 55 60

Phe Thr Ile Glu Lys Gln Val His Phe Asp Lys Thr Ser Asn Cys Lys
65 70 75 80

Phe Thr Trp Trp Thr Asp Thr Gln Val Ala Ala Leu Asn Val Ser Lys
85 90 95

Thr Ser Val Gln Asn Ala Leu Leu Glu Ile Glu Ser Glu Cys Val Ala
100 105 110

Asn Gly Leu Ser Pro Thr Gln His Thr Asn Thr Ser Ser Ser Ala Asp
115 120 125

Val Pro Thr Gly Lys Gly Val Tyr Val Gly Thr Leu Glu Ala Lys Gln
130 135 140

Tyr Val Val Leu Glu Leu Glu Leu Phe Ser
145 150

<210> SEQ ID NO 153
<211> LENGTH: 432
<212> TYPE: DNA
<213> ORGANISM: Phakopsora pachyrhizi
<220> FEATURE:
<221> NAME/KEY: misc_feature
<222> LOCATION: (1)..(432)
<223> OTHER INFORMATION: ta10247.01_phapa

<400> SEQUENCE: 153
atgatgtcat tactatcttt ttccttggca ttcgttttat ttttaaatct tacggttact 60
atcgattgca taaaaatcaa taatggagta aaggttgact gcaatctgcg tgccgagcca 120
aaatattatg aaagaggcga tcctgattca ccgtatatga gatgcttcga tcaacaaaca 180
tccaatatgc acaaatgtga aattgaaagc tgctctgata atccagtctg cgataattgc 240
ttgatcacaa gcagtctacc accaaggcaa gtaactaacg gtctgacttg cctaaaatca 300
tatatcattc ctcaaagcaa tagcaatcta agaaatttga gagaatcagt tttctgtgac 360
actgattcag gaagttatac atgcgcagga ccctgcaggt cattcaaata ttgcagaaac 420
tgtgtccctt ga 432

<210> SEQ ID NO 154

<211> LENGTH: 120
<212> TYPE: PRT
<213> ORGANISM: Phakopsora pachyrhizi
<220> FEATURE:
<221> NAME/KEY: VARIANT
<222> LOCATION: (1)..(120)
<223> OTHER INFORMATION: ta10247.01_phapa

<400> SEQUENCE: 154

Met Met Ser Leu Leu Ser Phe Ser Leu Ala Phe Val Leu Phe Leu Asn
1 5 10 15

Leu Thr Val Thr Ile Asp Cys Ile Lys Ile Asn Asn Gly Val Lys Val
20 25 30

Asp Cys Asn Leu Arg Ala Glu Pro Lys Tyr Tyr Glu Arg Gly Asp Pro
35 40 45

Asp Ser Pro Tyr Met Arg Cys Phe Asp Gln Gln Thr Ser Asn Met His
50 55 60

Lys Cys Glu Ile Glu Ser Cys Ser Asp Asn Pro Val Cys Asp Asn Cys
65 70 75 80

Leu Ile Thr Ser Ser Leu Pro Pro Arg Gln Val Thr Asn Gly Leu Thr
85 90 95

Cys Leu Lys Ser Tyr Ile Ile Pro Gln Ser Asn Ser Asn Leu Arg Asn
100 105 110

Leu Arg Glu Ser Val Phe Cys Asp
115 120

<210> SEQ ID NO 155
<211> LENGTH: 276
<212> TYPE: DNA
<213> ORGANISM: Phakopsora pachyrhizi
<220> FEATURE:
<221> NAME/KEY: misc_feature
<222> LOCATION: (1)..(276)
<223> OTHER INFORMATION: ta03856.01_phapa

<400> SEQUENCE: 155
atgaggttta acaatttcca cagattctct tcgttcgaag cttcgaaggt taaattactt 60
ttcatcgtat gcgctttatc cattagcctg accagctctt tacaattaaa cattttgaag 120
ggtaccgaac ctggttgcgg ttcccttcct gagaataata tgattaatat gcaattatca 180
caatattcgg atgcgcgaga tcctggtaaa ggtagttctc ctaagaccaa taaggaatgg 240
ccatactctg atgataatca aaccgattta aagtga 276

<210> SEQ ID NO 156
<211> LENGTH: 91
<212> TYPE: PRT
<213> ORGANISM: Phakopsora pachyrhizi
<220> FEATURE:
<221> NAME/KEY: VARIANT
<222> LOCATION: (1)..(91)
<223> OTHER INFORMATION: ta03856.01_phapa

<400> SEQUENCE: 156

Met Arg Phe Asn Asn Phe His Arg Phe Ser Ser Phe Glu Ala Ser Lys
1 5 10 15

Val Lys Leu Leu Phe Ile Val Cys Ala Leu Ser Ile Ser Leu Thr Ser
20 25 30

Ser Leu Gln Leu Asn Ile Leu Lys Gly Thr Glu Pro Gly Cys Gly Ser
35 40 45

Leu Pro Glu Asn Asn Met Ile Asn Met Gln Leu Ser Gln Tyr Ser Asp
50 55 60

```
Ala Arg Asp Pro Gly Lys Gly Ser Ser Pro Lys Thr Asn Lys Glu Trp
65                  70                  75                  80

Pro Tyr Ser Asp Asp Asn Gln Thr Asp Leu Lys
                85                  90


<210> SEQ ID NO 157
<211> LENGTH: 462
<212> TYPE: DNA
<213> ORGANISM: Phakopsora pachyrhizi
<220> FEATURE:
<221> NAME/KEY: misc_feature
<222> LOCATION: (1)..(462)
<223> OTHER INFORMATION: ta10287.01_phapa

<400> SEQUENCE: 157

atgattgtga tgatttctag aacccttcca gttgttttct gtcttatttt attgatctca      60

aacattagta ctcgtacagc tcaaccaggt gacatggtaa agagagccaa cccagatgct     120

ttgtttaccg attgtaaaga cgccgttata aaagaaggct gtaacacggc tctggacgaa     180

ctttggaata acggaaaaat taaaaggttt acaaccgaac atcaatttgt cacccatcca     240

agcggttgca aaattacttg gtggtctgac ggtggcgtgg ttcgcgcagg ggataatcaa     300

aaaggttcat tgcagaatgc tttacagcaa attgatgatg cttgtacttc atccggcctt     360

tcatctgtct atgactcaaa taaaaaggga aacggtgctt acgttggtaa actgcttgga     420

aaccaatact tggtcatcat ggcagagact ggtgcacagt ag                        462


<210> SEQ ID NO 158
<211> LENGTH: 153
<212> TYPE: PRT
<213> ORGANISM: Phakopsora pachyrhizi
<220> FEATURE:
<221> NAME/KEY: VARIANT
<222> LOCATION: (1)..(153)
<223> OTHER INFORMATION: ta10287.01_phapa

<400> SEQUENCE: 158

Met Ile Val Met Ile Ser Arg Thr Leu Pro Val Val Phe Cys Leu Ile
1               5                   10                  15

Leu Leu Ile Ser Asn Ile Ser Thr Arg Thr Ala Gln Pro Gly Asp Met
            20                  25                  30

Val Lys Arg Ala Asn Pro Asp Ala Leu Phe Thr Asp Cys Lys Asp Ala
        35                  40                  45

Val Ile Lys Glu Gly Cys Asn Thr Ala Leu Asp Glu Leu Trp Asn Asn
    50                  55                  60

Gly Lys Ile Lys Arg Phe Thr Thr Glu His Gln Phe Val Thr His Pro
65                  70                  75                  80

Ser Gly Cys Lys Ile Thr Trp Trp Ser Asp Gly Gly Val Val Arg Ala
                85                  90                  95

Gly Asp Asn Gln Lys Gly Ser Leu Gln Asn Ala Leu Gln Gln Ile Asp
            100                 105                 110

Asp Ala Cys Thr Ser Ser Gly Leu Ser Ser Val Tyr Asp Ser Asn Lys
        115                 120                 125

Lys Gly Asn Gly Ala Tyr Val Gly Lys Leu Leu Gly Asn Gln Tyr Leu
    130                 135                 140

Val Ile Met Ala Glu Thr Gly Ala Gln
145                 150


<210> SEQ ID NO 159
```

<211> LENGTH: 315
<212> TYPE: DNA
<213> ORGANISM: Phakopsora pachyrhizi
<220> FEATURE:
<221> NAME/KEY: misc_feature
<222> LOCATION: (1)..(315)
<223> OTHER INFORMATION: ta08674.01_phapa

<400> SEQUENCE: 159
atgaacttct gcaagtttgc taccttaacc tttgcggcct ttctaggaat ctcactcttc 60
caactatctg ctgctgtagc tgtaccattt caaaaaagcg cgctggaaaa ctactcagat 120
acaatgaatg gagctgcaaa ccatcacgtc gacaaacgat cttcatcctc gttgctccca 180
caaactcaat caaaatcttc accaagctta cagaaacgat ttatatatac gagacctatt 240
gtacctttgg caccagtcag aagatgtata caatactctc ctatcactgg cctttgtgtt 300
ctttattcct tctag 315

<210> SEQ ID NO 160
<211> LENGTH: 104
<212> TYPE: PRT
<213> ORGANISM: Phakopsora pachyrhizi
<220> FEATURE:
<221> NAME/KEY: VARIANT
<222> LOCATION: (1)..(104)
<223> OTHER INFORMATION: ta08674.01_phapa

<400> SEQUENCE: 160

Met Asn Phe Cys Lys Phe Ala Thr Leu Thr Phe Ala Ala Phe Leu Gly
1 5 10 15

Ile Ser Leu Phe Gln Leu Ser Ala Ala Val Ala Val Pro Phe Gln Lys
20 25 30

Ser Ala Leu Glu Asn Tyr Ser Asp Thr Met Asn Gly Ala Ala Asn His
35 40 45

His Val Asp Lys Arg Ser Ser Ser Ser Leu Leu Pro Gln Thr Gln Ser
50 55 60

Lys Ser Ser Pro Ser Leu Gln Lys Arg Phe Ile Tyr Thr Arg Pro Ile
65 70 75 80

Val Pro Leu Ala Pro Val Arg Arg Cys Ile Gln Tyr Ser Pro Ile Thr
85 90 95

Gly Leu Cys Val Leu Tyr Ser Phe
100

<210> SEQ ID NO 161
<211> LENGTH: 249
<212> TYPE: DNA
<213> ORGANISM: Phakopsora pachyrhizi
<220> FEATURE:
<221> NAME/KEY: misc_feature
<222> LOCATION: (1)..(249)
<223> OTHER INFORMATION: ta08831.01_phapa

<400> SEQUENCE: 161
atgaacatca tcagctcaac ctacttagct gttgcagcta ttctgattgc caaaaacaat 60
tttgccggcg ccgccagcct aaaccctagg gatgaggttc cgaatttggc tcatatcaga 120
tatgaagcaa ggtcagttgg gaagtacaat caccttgagg cccgcaaaaa gaggccaaaa 180
aataaaactg gcgccaataa tgtaaactct gcaaacaaca aaaacaccag cgataatacg 240
ggaagataa 249

<210> SEQ ID NO 162

```
<211> LENGTH: 82
<212> TYPE: PRT
<213> ORGANISM: Phakopsora pachyrhizi
<220> FEATURE:
<221> NAME/KEY: VARIANT
<222> LOCATION: (1)..(82)
<223> OTHER INFORMATION: ta08831.01_phapa

<400> SEQUENCE: 162

Met Asn Ile Ile Ser Ser Thr Tyr Leu Ala Val Ala Ala Ile Leu Ile
1               5                   10                  15

Ala Lys Asn Asn Phe Ala Gly Ala Ala Ser Leu Asn Pro Arg Asp Glu
            20                  25                  30

Val Pro Asn Leu Ala His Ile Arg Tyr Glu Ala Arg Ser Val Gly Lys
        35                  40                  45

Tyr Asn His Leu Glu Ala Arg Lys Lys Arg Pro Lys Asn Lys Thr Gly
    50                  55                  60

Ala Asn Asn Val Asn Ser Ala Asn Asn Lys Asn Thr Ser Asp Asn Thr
65                  70                  75                  80

Gly Arg


<210> SEQ ID NO 163
<211> LENGTH: 366
<212> TYPE: DNA
<213> ORGANISM: Phakopsora pachyrhizi
<220> FEATURE:
<221> NAME/KEY: misc_feature
<222> LOCATION: (1)..(366)
<223> OTHER INFORMATION: ta10737.01_phapa

<400> SEQUENCE: 163

atgttcttcg caaagaaatt tttgctttca atttgcatga tgggccttat aagtatggcc      60

tgtgcacaaa cttcgccatt caaggtttca tgccaaggag attctggaat caaattagac     120

gattgcacaa ctgcaattgc caattttgac ggtaagctta ctgacgttgg attcaacact     180

caaggtgact ggagacagtt tggaagctgc agagtctata tcaggaaaaa ggttgctgct     240

tcaaataaat caaccataaa ccgaggctac tttatcaact ttgttaaggc agctttggaa     300

ggttgctctg gcggtactgg tgctgcggaa aattcagact actacgtttc gattataagc     360

aaatag                                                                366


<210> SEQ ID NO 164
<211> LENGTH: 121
<212> TYPE: PRT
<213> ORGANISM: Phakopsora pachyrhizi
<220> FEATURE:
<221> NAME/KEY: VARIANT
<222> LOCATION: (1)..(121)
<223> OTHER INFORMATION: ta10737.01_phapa

<400> SEQUENCE: 164

Met Phe Phe Ala Lys Lys Phe Leu Leu Ser Ile Cys Met Met Gly Leu
1               5                   10                  15

Ile Ser Met Ala Cys Ala Gln Thr Ser Pro Phe Lys Val Ser Cys Gln
            20                  25                  30

Gly Asp Ser Gly Ile Lys Leu Asp Asp Cys Thr Thr Ala Ile Ala Asn
        35                  40                  45

Phe Asp Gly Lys Leu Thr Asp Val Gly Phe Asn Thr Gln Gly Asp Trp
    50                  55                  60

Arg Gln Phe Gly Ser Cys Arg Val Tyr Ile Arg Lys Lys Val Ala Ala
65                  70                  75                  80
```

Ser Asn Lys Ser Thr Ile Asn Arg Gly Tyr Phe Ile Asn Phe Val Lys
85 90 95

Ala Ala Leu Glu Gly Cys Ser Gly Gly Thr Gly Ala Ala Glu Asn Ser
100 105 110

Asp Tyr Tyr Val Ser Ile Ile Ser Lys
115 120

<210> SEQ ID NO 165
<211> LENGTH: 486
<212> TYPE: DNA
<213> ORGANISM: Phakopsora pachyrhizi
<220> FEATURE:
<221> NAME/KEY: misc_feature
<222> LOCATION: (1)..(486)
<223> OTHER INFORMATION: ta02458.01_phapa

<400> SEQUENCE: 165
atgaactctt tgaaagcatt ttcgctcttt gctgtcctta tcctgacatt aggaagtcaa 60
aattcttcgc aaagagaatt gggaagctca aatcttttgg ccgtctgcgg agagaagtat 120
gaaaaggcga gctcagtgtt tgcctgcagc caaggaagat taagatgtaa cgcggagcct 180
ggagaaactg gaaaattttt ctgcacaggc gatggtaaat tgacgaaggt ggagggagaa 240
aaggcttcca agtgtggctt caacccagag tgtgaaaaac aagggaactc agaaagtgct 300
gagagtatgg attctgctaa caatttggcc aaaaggggga ataaaaagaa caagggtggt 360
gcaaccccac aacagaaaca gccacagcaa cagcagcaac aacaacaaca gcaacaacaa 420
aatcaattta taaacaagga ggattctgga gcgagcaaag cgcctgatcc aatcctagtt 480
gagtaa 486

<210> SEQ ID NO 166
<211> LENGTH: 161
<212> TYPE: PRT
<213> ORGANISM: Phakopsora pachyrhizi
<220> FEATURE:
<221> NAME/KEY: VARIANT
<222> LOCATION: (1)..(161)
<223> OTHER INFORMATION: ta02458.01_phapa

<400> SEQUENCE: 166

Met Asn Ser Leu Lys Ala Phe Ser Leu Phe Ala Val Leu Ile Leu Thr
1 5 10 15

Leu Gly Ser Gln Asn Ser Ser Gln Arg Glu Leu Gly Ser Ser Asn Leu
20 25 30

Leu Ala Val Cys Gly Glu Lys Tyr Glu Lys Ala Ser Ser Val Phe Ala
35 40 45

Cys Ser Gln Gly Arg Leu Arg Cys Asn Ala Glu Pro Gly Glu Thr Gly
50 55 60

Lys Phe Phe Cys Thr Gly Asp Gly Lys Leu Thr Lys Val Glu Gly Glu
65 70 75 80

Lys Ala Ser Lys Cys Gly Phe Asn Pro Glu Cys Glu Lys Gln Gly Asn
85 90 95

Ser Glu Ser Ala Glu Ser Met Asp Ser Ala Asn Asn Leu Ala Lys Arg
100 105 110

Gly Asn Lys Lys Asn Lys Gly Gly Ala Thr Pro Gln Gln Lys Gln Pro
115 120 125

Gln Gln Gln Gln Gln Gln Gln Gln Gln Gln Gln Gln Asn Gln Phe Ile
130 135 140

```
Asn Lys Glu Asp Ser Gly Ala Ser Lys Ala Pro Asp Pro Ile Leu Val
145                 150                 155                 160

Glu


<210> SEQ ID NO 167
<211> LENGTH: 366
<212> TYPE: DNA
<213> ORGANISM: Phakopsora pachyrhizi
<220> FEATURE:
<221> NAME/KEY: misc_feature
<222> LOCATION: (1)..(366)
<223> OTHER INFORMATION: ta09953.01_phapa

<400> SEQUENCE: 167

atgcataaac gtattatata tatatccttt ggtaatccaa atattatttt ggttcttctc      60

acaagttttc tatcttttta taattttaat gctgcacaat catcaaatct ggcggttcaa     120

caaactgagt ccacaaagaa atcaattgat tatgttaaac atagaggaca aattcctagt     180

gaggatgcta ctagactgca ggaaagattt tttccacgag ctgcagacgc aaccaaagtt     240

gaaaagctcg atagctccat aaaaataaaa gggaaacgga tagaaaaagg tacaaaagtc     300

aacggaagga aaaaaccggt agaaacaaat attaaacttg ctcatagttt ttcagtctca     360

aattaa                                                                366


<210> SEQ ID NO 168
<211> LENGTH: 121
<212> TYPE: PRT
<213> ORGANISM: Phakopsora pachyrhizi
<220> FEATURE:
<221> NAME/KEY: VARIANT
<222> LOCATION: (1)..(121)
<223> OTHER INFORMATION: ta09953.01_phapa

<400> SEQUENCE: 168

Met His Lys Arg Ile Ile Tyr Ile Ser Phe Gly Asn Pro Asn Ile Ile
1               5                   10                  15

Leu Val Leu Leu Thr Ser Phe Leu Ser Phe Tyr Asn Phe Asn Ala Ala
            20                  25                  30

Gln Ser Ser Asn Leu Ala Val Gln Gln Thr Glu Ser Thr Lys Lys Ser
        35                  40                  45

Ile Asp Tyr Val Lys His Arg Gly Gln Ile Pro Ser Glu Asp Ala Thr
    50                  55                  60

Arg Leu Gln Glu Arg Phe Phe Pro Arg Ala Ala Asp Ala Thr Lys Val
65                  70                  75                  80

Glu Lys Leu Asp Ser Ser Ile Lys Ile Lys Gly Lys Arg Ile Glu Lys
                85                  90                  95

Gly Thr Lys Val Asn Gly Arg Lys Lys Pro Val Glu Thr Asn Ile Lys
            100                 105                 110

Leu Ala His Ser Phe Ser Val Ser Asn
        115                 120


<210> SEQ ID NO 169
<211> LENGTH: 441
<212> TYPE: DNA
<213> ORGANISM: Phakopsora pachyrhizi
<220> FEATURE:
<221> NAME/KEY: misc_feature
<222> LOCATION: (1)..(441)
<223> OTHER INFORMATION: ta00392.02_phapa

<400> SEQUENCE: 169
```

atgttcagca ttaaaatctt cattgccctc gttttaatag cacagctgag ccaggcaagc 60
gtcatttcta gccatgactc aggagtgtca acggttaaaa atcattggaa aaagaagaaa 120
ccatgcacca agaggcccgt aaaagtaata cccccaccac cacctatagg tcgaccacca 180
atacctcacg ttggtgttgt ggctggcggt atacctcttg gaggcgttcc tggagtgcca 240
ccggttgggg gcttactacg ttgtgacggt ccgggatgtc cagcaggcgg tttttgtggt 300
ccaggagctt gcagtggatg tgttagaaca actttcggtt ttagttgtgg cagtgtatct 360
tcgtttacta ctacgttccc cggaggtttc atgacttcat cctcttctag tagttcttct 420
caatcatcct ttcctttta a 441

<210> SEQ ID NO 170
<211> LENGTH: 146
<212> TYPE: PRT
<213> ORGANISM: Phakopsora pachyrhizi
<220> FEATURE:
<221> NAME/KEY: VARIANT
<222> LOCATION: (1)..(146)
<223> OTHER INFORMATION: ta00392.02_phapa

<400> SEQUENCE: 170

Met Phe Ser Ile Lys Ile Phe Ile Ala Leu Val Leu Ile Ala Gln Leu
1               5                   10                  15

Ser Gln Ala Ser Val Ile Ser Ser His Asp Ser Gly Val Ser Thr Val
            20                  25                  30

Lys Asn His Trp Lys Lys Lys Lys Pro Cys Thr Lys Arg Pro Val Lys
        35                  40                  45

Val Ile Pro Pro Pro Pro Pro Ile Gly Arg Pro Pro Ile Pro His Val
    50                  55                  60

Gly Val Val Ala Gly Gly Ile Pro Leu Gly Gly Val Pro Gly Val Pro
65                  70                  75                  80

Pro Val Gly Gly Leu Leu Arg Cys Asp Gly Pro Gly Cys Pro Ala Gly
                85                  90                  95

Gly Phe Cys Gly Pro Gly Ala Cys Ser Gly Cys Val Arg Thr Thr Phe
            100                 105                 110

Gly Phe Ser Cys Gly Ser Val Ser Ser Phe Thr Thr Thr Phe Pro Gly
        115                 120                 125

Gly Phe Met Thr Ser Ser Ser Ser Ser Ser Ser Ser Gln Ser Ser Phe
    130                 135                 140

Pro Phe
145

<210> SEQ ID NO 171
<211> LENGTH: 492
<212> TYPE: DNA
<213> ORGANISM: Phakopsora pachyrhizi
<220> FEATURE:
<221> NAME/KEY: misc_feature
<222> LOCATION: (1)..(492)
<223> OTHER INFORMATION: ta09632.01_phapa

<400> SEQUENCE: 171
atggctaagc ggttattatc attctactac tttttaacct gttttgcgaa tattttgtcc 60
actccaaagc tgcagccttt ggtatgcccg aatgattggt cacttgatcc aatatcaagt 120
tcccaaaata ctaggcgtaa tgtttactgc tatgatcacc aattcttgtg cgaagaaagc 180
gattgttatg agtatccagt ttgcagctct tgcactagtg ataaagggaa attagccaag 240
acagttgcat gcaaaaatga ataccatgct tccgatccaa caactgacca acaagcaatc 300

```
tgtgtcagca gcgatgagac cttttggcaa tgctctggcc cttgcgaagg atacctaaaa    360

tgcataaatt tcagtcgtaa aggccctttc atcaaaagcc aactccgtaa aaggggcaat    420

ccgtttgcgg ttgcgatgaa tgggagtcca ggcggaacct cgagtaattt tgattctgtc    480

ttatcctttt ag                                                        492


<210> SEQ ID NO 172
<211> LENGTH: 163
<212> TYPE: PRT
<213> ORGANISM: Phakopsora pachyrhizi
<220> FEATURE:
<221> NAME/KEY: VARIANT
<222> LOCATION: (1)..(163)
<223> OTHER INFORMATION: ta09632.01_phapa

<400> SEQUENCE: 172

Met Ala Lys Arg Leu Leu Ser Phe Tyr Tyr Phe Leu Thr Cys Phe Ala
1               5                   10                  15

Asn Ile Leu Ser Thr Pro Lys Leu Gln Pro Leu Val Cys Pro Asn Asp
            20                  25                  30

Trp Ser Leu Asp Pro Ile Ser Ser Ser Gln Asn Thr Arg Arg Asn Val
        35                  40                  45

Tyr Cys Tyr Asp His Gln Phe Leu Cys Glu Glu Ser Asp Cys Tyr Glu
    50                  55                  60

Tyr Pro Val Cys Ser Ser Cys Thr Ser Asp Lys Gly Lys Leu Ala Lys
65                  70                  75                  80

Thr Val Ala Cys Lys Asn Glu Tyr His Ala Ser Asp Pro Thr Thr Asp
                85                  90                  95

Gln Gln Ala Ile Cys Val Ser Ser Asp Glu Thr Phe Trp Gln Cys Ser
            100                 105                 110

Gly Pro Cys Glu Gly Tyr Leu Lys Cys Ile Asn Phe Ser Arg Lys Gly
        115                 120                 125

Pro Phe Ile Lys Ser Gln Leu Arg Lys Arg Gly Asn Pro Phe Ala Val
    130                 135                 140

Ala Met Asn Gly Ser Pro Gly Gly Thr Ser Ser Asn Phe Asp Ser Val
145                 150                 155                 160

Leu Ser Phe


<210> SEQ ID NO 173
<211> LENGTH: 531
<212> TYPE: DNA
<213> ORGANISM: Phakopsora pachyrhizi
<220> FEATURE:
<221> NAME/KEY: misc_feature
<222> LOCATION: (1)..(531)
<223> OTHER INFORMATION: ta01929.01_phapa

<400> SEQUENCE: 173

atgtatattt cctcattgct agcagttcta tcttttgctt gctgtgttct tgcccaaacg     60

aatgtcaccg gcccaaacaa tcaaacaatg cctgctgttt ttgcaatgaa ttgtactaac    120

acctacttgc ctgtctcaga gcgccgatta gcgcaactgg cctctaacac ttccctaact    180

cccgaggaaa ctaacaaact ttccgataat ttcactcagg ccatttgtca aaacaccact    240

ttagatcttt gcttttgcga tatcacctct tgtggctctg gtgccattgg aaaaaattgc    300

gttaaactga attccacaac tggtgatcca ctcgaaaaaa atcaaacccc actgccaaca    360

gcgaattgct cagctagtct tgtttacaac cctaaagctc aatcggaagc tgacaaggcg    420
```

aacatgtgca tgaatgccga aggcgatttt tttgcttgtg aatcttacag tggcagtact 480
atgtgcagca tgtgtgtttc gtcttctgac cccactctta cgcaagttta g 531

<210> SEQ ID NO 174
<211> LENGTH: 176
<212> TYPE: PRT
<213> ORGANISM: Phakopsora pachyrhizi
<220> FEATURE:
<221> NAME/KEY: VARIANT
<222> LOCATION: (1)..(176)
<223> OTHER INFORMATION: ta01929.01_phapa

<400> SEQUENCE: 174

```
Met Tyr Ile Ser Ser Leu Leu Ala Val Leu Ser Phe Ala Cys Cys Val
1               5                   10                  15

Leu Ala Gln Thr Asn Val Thr Gly Pro Asn Asn Gln Thr Met Pro Ala
            20                  25                  30

Val Phe Ala Met Asn Cys Thr Asn Thr Tyr Leu Pro Val Ser Glu Arg
        35                  40                  45

Arg Leu Ala Gln Leu Ala Ser Asn Thr Ser Leu Thr Pro Glu Glu Thr
    50                  55                  60

Asn Lys Leu Ser Asp Asn Phe Thr Gln Ala Ile Cys Gln Asn Thr Thr
65                  70                  75                  80

Leu Asp Leu Cys Phe Cys Asp Ile Thr Ser Cys Gly Ser Gly Ala Ile
                85                  90                  95

Gly Lys Asn Cys Val Lys Leu Asn Ser Thr Thr Gly Asp Pro Leu Glu
            100                 105                 110

Lys Asn Gln Thr Pro Leu Pro Thr Ala Asn Cys Ser Ala Ser Leu Val
        115                 120                 125

Tyr Asn Pro Lys Ala Gln Ser Glu Ala Asp Lys Ala Asn Met Cys Met
    130                 135                 140

Asn Ala Glu Gly Asp Phe Phe Ala Cys Glu Ser Tyr Ser Gly Ser Thr
145                 150                 155                 160

Met Cys Ser Met Cys Val Ser Ser Ser Asp Pro Thr Leu Thr Gln Val
                165                 170                 175
```

<210> SEQ ID NO 175
<211> LENGTH: 423
<212> TYPE: DNA
<213> ORGANISM: Phakopsora pachyrhizi
<220> FEATURE:
<221> NAME/KEY: misc_feature
<222> LOCATION: (1)..(423)
<223> OTHER INFORMATION: ta00836.01_phapa

<400> SEQUENCE: 175
atggcgttta attttcagac tttgttcact gcactcatag taattgccat ggttttagct 60
ggttttgtgg ttgcagcata ctgcatctgg agcaaggtct tgcacaccga gaaaaatagt 120
atcacagcct accaaaaggc attagcaaaa gctacaagca cagaaatcaa gtataagaag 180
aagcatgaag acgtagctga aggtcataaa gatagcactt gccaatgttt taaaaaccag 240
tccacggccg tgaattcggg cgcaaaacta agattttcag gattctcacg tccacaatgc 300
aaccccaatt ttagccgcat taaccgtatt aatccgcaat ttcccacaac atcaaaaatc 360
atgacgaaac cacaaccgcg accgcaattt acaaccttga cacctgtgcc tgggagactt 420
tga 423

<210> SEQ ID NO 176

<211> LENGTH: 140
<212> TYPE: PRT
<213> ORGANISM: Phakopsora pachyrhizi
<220> FEATURE:
<221> NAME/KEY: VARIANT
<222> LOCATION: (1)..(140)
<223> OTHER INFORMATION: ta00836.01_phapa

<400> SEQUENCE: 176

Met Ala Phe Asn Phe Gln Thr Leu Phe Thr Ala Leu Ile Val Ile Ala
1 5 10 15

Met Val Leu Ala Gly Phe Val Val Ala Ala Tyr Cys Ile Trp Ser Lys
20 25 30

Val Leu His Thr Glu Lys Asn Ser Ile Thr Ala Tyr Gln Lys Ala Leu
35 40 45

Ala Lys Ala Thr Ser Thr Glu Ile Lys Tyr Lys Lys Lys His Glu Asp
50 55 60

Val Ala Glu Gly His Lys Asp Ser Thr Cys Gln Cys Phe Lys Asn Gln
65 70 75 80

Ser Thr Ala Val Asn Ser Gly Ala Lys Leu Arg Phe Ser Gly Phe Ser
85 90 95

Arg Pro Gln Cys Asn Pro Asn Phe Ser Arg Ile Asn Arg Ile Asn Pro
100 105 110

Gln Phe Pro Thr Thr Ser Lys Ile Met Thr Lys Pro Gln Pro Arg Pro
115 120 125

Gln Phe Thr Thr Leu Thr Pro Val Pro Gly Arg Leu
130 135 140

<210> SEQ ID NO 177
<211> LENGTH: 267
<212> TYPE: DNA
<213> ORGANISM: Phakopsora pachyrhizi
<220> FEATURE:
<221> NAME/KEY: misc_feature
<222> LOCATION: (1)..(267)
<223> OTHER INFORMATION: ta02276.02_phapa

<400> SEQUENCE: 177
atgagaggaa ccatcatttg ggtcgcggct attggtcttg ctatcataag tttggctgat 60
caagtaaaat ccgcgccttc agctcaggtc tctgagtttg gcaaagaccc aacaaaacta 120
ccatcatcac tccaaaaacg tagtccaaga ccagaaccaa agaataagga tggaaagact 180
aaaaagacta aaaagaccaa aaagaaaaag aaaaagggcc actcacacgg gggtgatgat 240
gatgatgatg atgatgatga tgattag 267

<210> SEQ ID NO 178
<211> LENGTH: 88
<212> TYPE: PRT
<213> ORGANISM: Phakopsora pachyrhizi
<220> FEATURE:
<221> NAME/KEY: VARIANT
<222> LOCATION: (1)..(88)
<223> OTHER INFORMATION: ta02276.02_phapa

<400> SEQUENCE: 178

Met Arg Gly Thr Ile Ile Trp Val Ala Ala Ile Gly Leu Ala Ile Ile
1 5 10 15

Ser Leu Ala Asp Gln Val Lys Ser Ala Pro Ser Ala Gln Val Ser Glu
20 25 30

Phe Gly Lys Asp Pro Thr Lys Leu Pro Ser Ser Leu Gln Lys Arg Ser
35 40 45

```
Pro Arg Pro Glu Pro Lys Asn Lys Asp Gly Lys Thr Lys Lys Thr Lys
    50                  55                  60

Lys Thr Lys Lys Lys Lys Lys Lys Gly His Ser His Gly Gly Asp Asp
65                  70                  75                  80

Asp Asp Asp Asp Asp Asp Asp Asp
                85


<210> SEQ ID NO 179
<211> LENGTH: 387
<212> TYPE: DNA
<213> ORGANISM: Phakopsora pachyrhizi
<220> FEATURE:
<221> NAME/KEY: misc_feature
<222> LOCATION: (1)..(387)
<223> OTHER INFORMATION: ta09592.01_phapa

<400> SEQUENCE: 179

atgaatcgtt tcatgatact agcttttgtg ctagttgaac ttttgctctt aacctcaaaa      60

gctcaagctt tatcatcaaa ctgtgaagaa gcttactttg agtctaacgt tccgaaagtt     120

gcaggagtcc cgcaggcagg ctgtaaatct agctcctcaa aggaaggatt cttatgctct     180

caaaatagct gcagcggcct taagtcctgc acccaatgta aacgctatat gccttcacca     240

acagctggaa agagcggtac tttcgttggg aacataattc ctatgagcat taactgcaag     300

accgactatg ttcttgtgaa caagatacaa atgtgctcaa acgctaacaa tgccggtacg     360

gatgcgttgg agcttgtacc ggtatga                                         387


<210> SEQ ID NO 180
<211> LENGTH: 128
<212> TYPE: PRT
<213> ORGANISM: Phakopsora pachyrhizi
<220> FEATURE:
<221> NAME/KEY: VARIANT
<222> LOCATION: (1)..(128)
<223> OTHER INFORMATION: ta09592.01_phapa

<400> SEQUENCE: 180

Met Asn Arg Phe Met Ile Leu Ala Phe Val Leu Val Glu Leu Leu Leu
1               5                   10                  15

Leu Thr Ser Lys Ala Gln Ala Leu Ser Ser Asn Cys Glu Glu Ala Tyr
            20                  25                  30

Phe Glu Ser Asn Val Pro Lys Val Ala Gly Val Pro Gln Ala Gly Cys
        35                  40                  45

Lys Ser Ser Ser Ser Lys Glu Gly Phe Leu Cys Ser Gln Asn Ser Cys
    50                  55                  60

Ser Gly Leu Lys Ser Cys Thr Gln Cys Lys Arg Tyr Met Pro Ser Pro
65                  70                  75                  80

Thr Ala Gly Lys Ser Gly Thr Phe Val Gly Asn Ile Ile Pro Met Ser
                85                  90                  95

Ile Asn Cys Lys Thr Asp Tyr Val Leu Val Asn Lys Ile Gln Met Cys
            100                 105                 110

Ser Asn Ala Asn Asn Ala Gly Thr Asp Ala Leu Glu Leu Val Pro Val
        115                 120                 125


<210> SEQ ID NO 181
<211> LENGTH: 201
<212> TYPE: DNA
<213> ORGANISM: Phakopsora pachyrhizi
<220> FEATURE:
<221> NAME/KEY: misc_feature
```

<222> LOCATION: (1)..(201)
<223> OTHER INFORMATION: ta01647.01_phapa

<400> SEQUENCE: 181
atgatgcatc tacgtcattt tttcattttg tttcgagtat ttatatttat atatatactc 60
tctgacttca ttctcccctc cattatattc ccatgttcaa gatttttaac gaaatggaaa 120
tatgtaagtc ccatgcgaag aaagcagaag attctaaaaa aaatggagga attgaggggg 180
atggagtacg ttgtagggta g 201

<210> SEQ ID NO 182
<211> LENGTH: 66
<212> TYPE: PRT
<213> ORGANISM: Phakopsora pachyrhizi
<220> FEATURE:
<221> NAME/KEY: VARIANT
<222> LOCATION: (1)..(66)
<223> OTHER INFORMATION: ta01647.01_phapa

<400> SEQUENCE: 182

Met Met His Leu Arg His Phe Phe Ile Leu Phe Arg Val Phe Ile Phe
1 5 10 15

Ile Tyr Ile Leu Ser Asp Phe Ile Leu Pro Ser Ile Ile Phe Pro Cys
20 25 30

Ser Arg Phe Leu Thr Lys Trp Lys Tyr Val Ser Pro Met Arg Arg Lys
35 40 45

Gln Lys Ile Leu Lys Lys Met Glu Glu Leu Arg Gly Met Glu Tyr Val
50 55 60

Val Gly
65

<210> SEQ ID NO 183
<211> LENGTH: 414
<212> TYPE: DNA
<213> ORGANISM: Phakopsora pachyrhizi
<220> FEATURE:
<221> NAME/KEY: misc_feature
<222> LOCATION: (1)..(414)
<223> OTHER INFORMATION: ta10088.01_phapa

<400> SEQUENCE: 183
atgattaaac attgcgcttt cattttaatg ggcctaatgg cgtttgtgtc cttatcattt 60
gcacagctac taccaagcgc ctacagctgt agcagggttg atctttacaa acctccacta 120
agacgtgaag attgcagaga ctccctaaat ttgtttccag ttccaaacgg cgataatgtt 180
atttaccttg gaagtggcaa ttggcgaggt tgtggaagct gcaaggtgac tatttacaat 240
aggggatcaa gagaatctcg tgtgactgcg ccaaaaggct gggcagctac ggcagtacac 300
caagctttcg accattgtga aggaaagccg ggatctgcta ctattggaga tgatgggaaa 360
attattgcaa aaatcgatta cggaaattct ggacaaggag attgtcctcc ctaa 414

<210> SEQ ID NO 184
<211> LENGTH: 137
<212> TYPE: PRT
<213> ORGANISM: Phakopsora pachyrhizi
<220> FEATURE:
<221> NAME/KEY: VARIANT
<222> LOCATION: (1)..(137)
<223> OTHER INFORMATION: ta10088.01_phapa

<400> SEQUENCE: 184

Met Ile Lys His Cys Ala Phe Ile Leu Met Gly Leu Met Ala Phe Val

```
1               5                   10                  15

Ser Leu Ser Phe Ala Gln Leu Leu Pro Ser Ala Tyr Ser Cys Ser Arg
            20                  25                  30

Val Asp Leu Tyr Lys Pro Pro Leu Arg Arg Glu Asp Cys Arg Asp Ser
        35                  40                  45

Leu Asn Leu Phe Pro Val Pro Asn Gly Asp Asn Val Ile Tyr Leu Gly
    50                  55                  60

Ser Gly Asn Trp Arg Gly Cys Gly Ser Cys Lys Val Thr Ile Tyr Asn
65                  70                  75                  80

Arg Gly Ser Arg Glu Ser Arg Val Thr Ala Pro Lys Gly Trp Ala Ala
                85                  90                  95

Thr Ala Val His Gln Ala Phe Asp His Cys Glu Gly Lys Pro Gly Ser
            100                 105                 110

Ala Thr Ile Gly Asp Asp Gly Lys Ile Ile Ala Lys Ile Asp Tyr Gly
        115                 120                 125

Asn Ser Gly Gln Gly Asp Cys Pro Pro
    130                 135
```

<210> SEQ ID NO 185
<211> LENGTH: 588
<212> TYPE: DNA
<213> ORGANISM: Phakopsora pachyrhizi
<220> FEATURE:
<221> NAME/KEY: misc_feature
<222> LOCATION: (1)..(588)
<223> OTHER INFORMATION: ta08848.01_phapa

<400> SEQUENCE: 185

```
atgataaaat cacccttgaa atttatttct tctttcactt taattttctt cctacataga     60

gcggttcatt cggctattat agaaacttct gcccagaggg agctgccaag gctggctcga    120

atctcgaacc ctacgaatgt agatgagggc tttaaaagca cgcggttatt tgctttagat    180

tcgtcatgct catttccaga aaagaataaa ataaataaaa atagagtcgg tatggtggtt    240

gagtcagaaa aaagttttaa gaaaaattta gctctagata aacttgaacc aaatagaatt    300

gagaatcaca ttcttgaaaa taatatcaag gctaaccccg gttccacgac tatgagtgat    360

aagagctccg aggtcttgag cccaggccca ggtaattcca aagtgaatcg tggccaaaat    420

tataagacac agtcggaaga aaccatagaa gatttaatcc cagtgaaaaa gcagagcgaa    480

caaggactag aaaattcttg ggatgcgccg aaaatacaga aatcatttag gagaagtaag    540

agtcgtcttg gtaaaaaacc ggaatttttg catgaaaaaa attcctga                 588
```

<210> SEQ ID NO 186
<211> LENGTH: 195
<212> TYPE: PRT
<213> ORGANISM: Phakopsora pachyrhizi
<220> FEATURE:
<221> NAME/KEY: VARIANT
<222> LOCATION: (1)..(195)
<223> OTHER INFORMATION: ta08848.01_phapa

<400> SEQUENCE: 186

```
Met Ile Lys Ser Pro Leu Lys Phe Ile Ser Ser Phe Thr Leu Ile Phe
1               5                   10                  15

Phe Leu His Arg Ala Val His Ser Ala Ile Ile Glu Thr Ser Ala Gln
            20                  25                  30

Arg Glu Leu Pro Arg Leu Ala Arg Ile Ser Asn Pro Thr Asn Val Asp
        35                  40                  45
```

```
Glu Gly Phe Lys Ser Thr Arg Leu Phe Ala Leu Asp Ser Ser Cys Ser
    50                  55                  60

Phe Pro Glu Lys Asn Lys Ile Asn Lys Asn Arg Val Gly Met Val Val
65                  70                  75                  80

Glu Ser Glu Lys Ser Phe Lys Lys Asn Leu Ala Leu Asp Lys Leu Glu
                85                  90                  95

Pro Asn Arg Ile Glu Asn His Ile Leu Glu Asn Asn Ile Lys Ala Asn
            100                 105                 110

Pro Gly Ser Thr Thr Met Ser Asp Lys Ser Ser Glu Val Leu Ser Pro
        115                 120                 125

Gly Pro Gly Asn Ser Lys Val Asn Arg Gly Gln Asn Tyr Lys Thr Gln
    130                 135                 140

Ser Glu Glu Thr Ile Glu Asp Leu Ile Pro Val Lys Lys Gln Ser Glu
145                 150                 155                 160

Gln Gly Leu Glu Asn Ser Trp Asp Ala Pro Lys Ile Gln Lys Ser Phe
                165                 170                 175

Arg Arg Ser Lys Ser Arg Leu Gly Lys Lys Pro Glu Phe Leu His Glu
            180                 185                 190

Lys Asn Ser
        195
```

<210> SEQ ID NO 187
<211> LENGTH: 435
<212> TYPE: DNA
<213> ORGANISM: Phakopsora pachyrhizi
<220> FEATURE:
<221> NAME/KEY: misc_feature
<222> LOCATION: (1)..(435)
<223> OTHER INFORMATION: ta06926.01_phapa

<400> SEQUENCE: 187

```
atgaaaaatt ttaagcaatt gaactggata attctgggat tattgatttc attatcctat      60

gaaatcagaa gctcagtcac gcaaaacatt tatgaaaccg aaattaatgt tctaagagcc     120

agacaggcag gccctcctac aattgacaca tcaactctgc gggaatgcaa aaacatgaag     180

atcgttggtg gcggtggttt caatggacga aaagcttctg actttacatt tagaccagag     240

gactctaaga ttttcaagca aaaagaagca cagaatctcg gaataatctg taatgccatg     300

tgcaatgatt tgaagaatgt ttgcaaattc aaagataagg acgaagtagt tgtaaattgt     360

aataagatca aaaattttat cggaactact aaagataaag gcaagatgga tctttggaac     420

tcgttgttcg tttga                                                      435
```

<210> SEQ ID NO 188
<211> LENGTH: 144
<212> TYPE: PRT
<213> ORGANISM: Phakopsora pachyrhizi
<220> FEATURE:
<221> NAME/KEY: VARIANT
<222> LOCATION: (1)..(144)
<223> OTHER INFORMATION: ta06926.01_phapa

<400> SEQUENCE: 188

```
Met Lys Asn Phe Lys Gln Leu Asn Trp Ile Ile Leu Gly Leu Leu Ile
1               5                   10                  15

Ser Leu Ser Tyr Glu Ile Arg Ser Ser Val Thr Gln Asn Ile Tyr Glu
            20                  25                  30

Thr Glu Ile Asn Val Leu Arg Ala Arg Gln Ala Gly Pro Pro Thr Ile
        35                  40                  45
```

-continued

Asp Thr Ser Thr Leu Arg Glu Cys Lys Asn Met Lys Ile Val Gly Gly
50 55 60

Gly Gly Phe Asn Gly Arg Lys Ala Ser Asp Phe Thr Phe Arg Pro Glu
65 70 75 80

Asp Ser Lys Ile Phe Lys Gln Lys Glu Ala Gln Asn Leu Gly Ile Ile
85 90 95

Cys Asn Ala Met Cys Asn Asp Leu Lys Asn Val Cys Lys Phe Lys Asp
100 105 110

Lys Asp Glu Val Val Val Asn Cys Asn Lys Ile Lys Asn Phe Ile Gly
115 120 125

Thr Thr Lys Asp Lys Gly Lys Met Asp Leu Trp Asn Ser Leu Phe Val
130 135 140

<210> SEQ ID NO 189
<211> LENGTH: 261
<212> TYPE: DNA
<213> ORGANISM: Phakopsora pachyrhizi
<220> FEATURE:
<221> NAME/KEY: misc_feature
<222> LOCATION: (1)..(261)
<223> OTHER INFORMATION: ta09197.01_phapa

<400> SEQUENCE: 189
atgtttatta aatcatattg ttttcttctt ggtctcacgc ttttcctttc atgtctttcg 60
actactataa ctggagagtt aaacaatatg gatgaccaaa tactagcagc taaatttcga 120
gcaaggcgtt ctattgaaac aatcaaagaa aatagtccta taaaacaaga acggaaaaaa 180
cttcgtaatg aaccagtaaa cacgctagtc gcttatccag tgagggatcc caattgcgtt 240
gatgatgatg ctccaagata g 261

<210> SEQ ID NO 190
<211> LENGTH: 86
<212> TYPE: PRT
<213> ORGANISM: Phakopsora pachyrhizi
<220> FEATURE:
<221> NAME/KEY: VARIANT
<222> LOCATION: (1)..(86)
<223> OTHER INFORMATION: ta09197.01_phapa

<400> SEQUENCE: 190

Met Phe Ile Lys Ser Tyr Cys Phe Leu Leu Gly Leu Thr Leu Phe Leu
1 5 10 15

Ser Cys Leu Ser Thr Thr Ile Thr Gly Glu Leu Asn Asn Met Asp Asp
20 25 30

Gln Ile Leu Ala Ala Lys Phe Arg Ala Arg Arg Ser Ile Glu Thr Ile
35 40 45

Lys Glu Asn Ser Pro Ile Lys Gln Glu Arg Lys Lys Leu Arg Asn Glu
50 55 60

Pro Val Asn Thr Leu Val Ala Tyr Pro Val Arg Asp Pro Asn Cys Val
65 70 75 80

Asp Asp Asp Ala Pro Arg
85

<210> SEQ ID NO 191
<211> LENGTH: 324
<212> TYPE: DNA
<213> ORGANISM: Phakopsora pachyrhizi
<220> FEATURE:
<221> NAME/KEY: misc_feature
<222> LOCATION: (1)..(324)
<223> OTHER INFORMATION: ta09320.01_phapa

<400> SEQUENCE: 191

```
atgtactcta aagtgcttat gatttatcta tttttcattg cgatcgcaat tcttgatttc      60
acaggtgctt tgaccacata cggtgaaaat gataagaaca tgcgcaaaag agcgatagag     120
gctagaagcg cagtacatgg aagcaattcg aaggaaacac cagaattttc attcccacca     180
cccgagttta tatataagaa agactgttgg aaataccaat ctgattgtaa ggcagtactt     240
aaagaacata aatgtccact gtactgttca gtaatttgtt cgtattgctc tggagatggt     300
acagaatatg atccaaaagt ataa                                            324
```

<210> SEQ ID NO 192
<211> LENGTH: 107
<212> TYPE: PRT
<213> ORGANISM: Phakopsora pachyrhizi
<220> FEATURE:
<221> NAME/KEY: VARIANT
<222> LOCATION: (1)..(107)
<223> OTHER INFORMATION: ta09320.01_phapa

<400> SEQUENCE: 192

```
Met Tyr Ser Lys Val Leu Met Ile Tyr Leu Phe Phe Ile Ala Ile Ala
1               5                   10                  15

Ile Leu Asp Phe Thr Gly Ala Leu Thr Thr Tyr Gly Glu Asn Asp Lys
            20                  25                  30

Asn Met Arg Lys Arg Ala Ile Glu Ala Arg Ser Ala Val His Gly Ser
        35                  40                  45

Asn Ser Lys Glu Thr Pro Glu Phe Ser Phe Pro Pro Pro Glu Phe Ile
    50                  55                  60

Tyr Lys Lys Asp Cys Trp Lys Tyr Gln Ser Asp Cys Lys Ala Val Leu
65                  70                  75                  80

Lys Glu His Lys Cys Pro Leu Tyr Cys Ser Val Ile Cys Ser Tyr Cys
                85                  90                  95

Ser Gly Asp Gly Thr Glu Tyr Asp Pro Lys Val
            100                 105
```

<210> SEQ ID NO 193
<211> LENGTH: 474
<212> TYPE: DNA
<213> ORGANISM: Phakopsora pachyrhizi
<220> FEATURE:
<221> NAME/KEY: misc_feature
<222> LOCATION: (1)..(474)
<223> OTHER INFORMATION: ta01319.01_phapa

<400> SEQUENCE: 193

```
atgtgttcca ttactaattc tgcatttata atctttgtcg tcgtgctctc tttttttct       60
actgaagcta gtccagccgg cattaatgtg ggggacaaaa gcgatcgagc caagtgcaag     120
ggaaatggtg ttcagaaagt ctgtcaacca attttagaaa aattgtggtc ctctggaaag     180
attaaagtct tcaaacccga gcagcaaaag gagaatgacg caagctgttc aatatcgtgg     240
aaaagtcttg acggcaataa agaaattaaa tcagaaaatt ccttgtttaa cgtcttcaag     300
aaaattgatg atgtttgtaa aaacaagacg gaatctgcaa gctctacttg gaatccaaat     360
attacccaat atggaaacct ttcagatggt aaaaactatt ccggaattgg ttacttctta     420
ggaaaagttg aacagaacac tgtttttatc acagccttgg ctgtaaaacc ataa           474
```

<210> SEQ ID NO 194
<211> LENGTH: 157

<212> TYPE: PRT
<213> ORGANISM: Phakopsora pachyrhizi
<220> FEATURE:
<221> NAME/KEY: VARIANT
<222> LOCATION: (1)..(157)
<223> OTHER INFORMATION: ta01319.01_phapa

<400> SEQUENCE: 194

Met Cys Ser Ile Thr Asn Ser Ala Phe Ile Ile Phe Val Val Val Leu
1 5 10 15

Ser Phe Phe Ser Thr Glu Ala Ser Pro Ala Gly Ile Asn Val Gly Asp
20 25 30

Lys Ser Asp Arg Ala Lys Cys Lys Gly Asn Gly Val Gln Lys Val Cys
35 40 45

Gln Pro Ile Leu Glu Lys Leu Trp Ser Ser Gly Lys Ile Lys Val Phe
50 55 60

Lys Pro Glu Gln Gln Lys Glu Asn Asp Ala Ser Cys Ser Ile Ser Trp
65 70 75 80

Lys Ser Leu Asp Gly Asn Lys Glu Ile Lys Ser Glu Asn Ser Leu Phe
85 90 95

Asn Val Phe Lys Lys Ile Asp Asp Val Cys Lys Asn Lys Thr Glu Ser
100 105 110

Ala Ser Ser Thr Trp Asn Pro Asn Ile Thr Gln Tyr Gly Asn Leu Ser
115 120 125

Asp Gly Lys Asn Tyr Ser Gly Ile Gly Tyr Phe Leu Gly Lys Val Glu
130 135 140

Gln Asn Thr Val Phe Ile Thr Ala Leu Ala Val Lys Pro
145 150 155

<210> SEQ ID NO 195
<211> LENGTH: 441
<212> TYPE: DNA
<213> ORGANISM: Phakopsora pachyrhizi
<220> FEATURE:
<221> NAME/KEY: misc_feature
<222> LOCATION: (1)..(441)
<223> OTHER INFORMATION: ta05216.01_phapa

<400> SEQUENCE: 195
atgaatttca ttgcccttaa atcttttgct cttgcgttgg ttctatttct attcaattca 60
catcaggcta aatgcttccc aaatccacgc tccccccact caagctctga gagaaagagc 120
gtcagcctta gaggatttcc tgaggaagaa tcggtttccg cctctaagag cggagtcttg 180
agaccaagca tcatccttaa aagtttaaat atggctcaga aaattagaac caggccaatt 240
aaagctcgag agttcccaag taccccgagg gtgcctgagg gagacacgga ggacgattcc 300
aaagctctat cgtctcacaa agtggcatat tcacccaaga ttgttttaaa gcaattcacc 360
aattcgattc cttacttagc agagccagtt gtagaatcag acccacgagt caaaccaaga 420
aaagctttac cacgcgaata a 441

<210> SEQ ID NO 196
<211> LENGTH: 146
<212> TYPE: PRT
<213> ORGANISM: Phakopsora pachyrhizi
<220> FEATURE:
<221> NAME/KEY: VARIANT
<222> LOCATION: (1)..(146)
<223> OTHER INFORMATION: ta05216.01_phapa

<400> SEQUENCE: 196

Met Asn Phe Ile Ala Leu Lys Ser Phe Ala Leu Ala Leu Val Leu Phe
1 5 10 15

Leu Phe Asn Ser His Gln Ala Lys Cys Phe Pro Asn Pro Arg Ser Pro
20 25 30

His Ser Ser Ser Glu Arg Lys Ser Val Ser Leu Arg Gly Phe Pro Glu
35 40 45

Glu Glu Ser Val Ser Ala Ser Lys Ser Gly Val Leu Arg Pro Ser Ile
50 55 60

Ile Leu Lys Ser Leu Asn Met Ala Gln Lys Ile Arg Thr Arg Pro Ile
65 70 75 80

Lys Ala Arg Glu Phe Pro Ser Thr Pro Arg Val Pro Glu Gly Asp Thr
85 90 95

Glu Asp Asp Ser Lys Ala Leu Ser Ser His Lys Val Ala Tyr Ser Pro
100 105 110

Lys Ile Val Leu Lys Gln Phe Thr Asn Ser Ile Pro Tyr Leu Ala Glu
115 120 125

Pro Val Val Glu Ser Asp Pro Arg Val Lys Pro Arg Lys Ala Leu Pro
130 135 140

Arg Glu
145

<210> SEQ ID NO 197
<211> LENGTH: 405
<212> TYPE: DNA
<213> ORGANISM: Phakopsora pachyrhizi
<220> FEATURE:
<221> NAME/KEY: misc_feature
<222> LOCATION: (1)..(405)
<223> OTHER INFORMATION: ta00624.01_phapa

<400> SEQUENCE: 197
atgatgttca cagttcttaa ggtagtacca tcgatgttcc tgatcctaca aactcttctg 60
gccttactag caacgagtct gaatatcggc atggcaaagg atataccacc ggcctcagtc 120
tgttatagtt attcgaattc ggataacgat cgtgccactt gtcacggtgc cacctgcccc 180
gatggttgtt cctggccctt tataactgcc caaaactgtg ttccaactgg accaacttca 240
tctaaatcta ccacccagac ctgtcatatt gggtattgga aagatggaac tgacggcata 300
tgcactaata ggttaagaga aatgtatcgc tgcagtggta aaactactgg agtggctttt 360
tgcacaggct gtaagaatta tactagcaag aaacgaatta attga 405

<210> SEQ ID NO 198
<211> LENGTH: 134
<212> TYPE: PRT
<213> ORGANISM: Phakopsora pachyrhizi
<220> FEATURE:
<221> NAME/KEY: VARIANT
<222> LOCATION: (1)..(134)
<223> OTHER INFORMATION: ta00624.01_phapa

<400> SEQUENCE: 198

Met Met Phe Thr Val Leu Lys Val Val Pro Ser Met Phe Leu Ile Leu
1 5 10 15

Gln Thr Leu Leu Ala Leu Leu Ala Thr Ser Leu Asn Ile Gly Met Ala
20 25 30

Lys Asp Ile Pro Pro Ala Ser Val Cys Tyr Ser Tyr Ser Asn Ser Asp
35 40 45

Asn Asp Arg Ala Thr Cys His Gly Ala Thr Cys Pro Asp Gly Cys Ser
50 55 60

```
Trp Pro Phe Ile Thr Ala Gln Asn Cys Val Pro Thr Gly Pro Thr Ser
65                  70                  75                  80

Ser Lys Ser Thr Thr Gln Thr Cys His Ile Gly Tyr Trp Lys Asp Gly
                85                  90                  95

Thr Asp Gly Ile Cys Thr Asn Arg Leu Arg Glu Met Tyr Arg Cys Ser
            100                 105                 110

Gly Lys Thr Thr Gly Val Ala Phe Cys Thr Gly Cys Lys Asn Tyr Thr
        115                 120                 125

Ser Lys Lys Arg Ile Asn
    130


<210> SEQ ID NO 199
<211> LENGTH: 471
<212> TYPE: DNA
<213> ORGANISM: Phakopsora pachyrhizi
<220> FEATURE:
<221> NAME/KEY: misc_feature
<222> LOCATION: (1)..(471)
<223> OTHER INFORMATION: ta00870.01_phapa

<400> SEQUENCE: 199

atgaggtact ctacttttct atcttgttct ttagccatat ttttttgct tgctgtcaat      60

gtttctcctc aaacacctgc gccaggcggt cctcccacta gcacaggagg ccctccgact    120

ggcactggaa gctctcctgc tggcccaggg ggtggctcga aggctccggg aggtgagggc    180

aaaagtcccg atgccaaagg tcccgatgct aagacctctg aaggcaaagg cccccaaggc    240

aaaagtcccg actcaaaagc cccgggagat gcaaaaagtc ccgggcttgg agactcgaag    300

tcaggttgta cttgtcctgg cgagcagcca cctccaacca cacagaagcc accagaggat    360

acttctcctt acccaaacgg cgctacaagc tatttgaagc cattctcaac ttcaacaaca    420

ctatgttttg ctacaaatct gtttgcaatt cttacagtct tatatactta g             471


<210> SEQ ID NO 200
<211> LENGTH: 156
<212> TYPE: PRT
<213> ORGANISM: Phakopsora pachyrhizi
<220> FEATURE:
<221> NAME/KEY: VARIANT
<222> LOCATION: (1)..(156)
<223> OTHER INFORMATION: ta00870.01_phapa

<400> SEQUENCE: 200

Met Arg Tyr Ser Thr Phe Leu Ser Cys Ser Leu Ala Ile Phe Phe Leu
1               5                   10                  15

Leu Ala Val Asn Val Ser Pro Gln Thr Pro Ala Pro Gly Gly Pro Pro
            20                  25                  30

Thr Ser Thr Gly Gly Pro Pro Thr Gly Thr Gly Ser Ser Pro Ala Gly
        35                  40                  45

Pro Gly Gly Gly Ser Lys Ala Pro Gly Gly Glu Gly Lys Ser Pro Asp
    50                  55                  60

Ala Lys Gly Pro Asp Ala Lys Thr Ser Glu Gly Lys Gly Pro Gln Gly
65                  70                  75                  80

Lys Ser Pro Asp Ser Lys Ala Pro Gly Asp Ala Lys Ser Pro Gly Leu
                85                  90                  95

Gly Asp Ser Lys Ser Gly Cys Thr Cys Pro Gly Glu Gln Pro Pro Pro
            100                 105                 110

Thr Thr Gln Lys Pro Pro Glu Asp Thr Ser Pro Tyr Pro Asn Gly Ala
        115                 120                 125
```

```
Thr Ser Tyr Leu Lys Pro Phe Ser Thr Ser Thr Thr Leu Cys Phe Ala
    130                 135                 140

Thr Asn Leu Phe Ala Ile Leu Thr Val Leu Tyr Thr
145                 150                 155
```

<210> SEQ ID NO 201
<211> LENGTH: 519
<212> TYPE: DNA
<213> ORGANISM: Phakopsora pachyrhizi
<220> FEATURE:
<221> NAME/KEY: misc_feature
<222> LOCATION: (1)..(519)
<223> OTHER INFORMATION: ta08469.01_phapa

<400> SEQUENCE: 201

```
atggcgaaat gttctttaag aatttggatt ttttttctag aaattttaac cctcttcctc     60

ttaactgcag agtctgagga tcgacaagcc aattctgctg cggttaataa tgtctgcgac    120

cgttcaatag cttgctctgt ttttgaagaa ggttggccta agaacaaatg gtttgaatgc    180

ggatctactc gggtttcccc tgcagcattc gcgacattgc gccagtcaat ttcgattgga    240

aatcctaaaa aaactcaagt ggacagcacg gatactactg aacatcatgt aaattgtgcc    300

accttggatg cgagctacag cagacattct tactacaatg gcagatttac agtaaattat    360

gccataaaag gagaatgtga ttgcaaagcg tccagatcag gtaaaagaag aaatcctatc    420

tgttccaatg cgttatctct gagcaattct gcctgtaatt tggctcactt taagttttgc    480

tcattgaaag aaaagaatac tctttgtgca acagtttaa                           519
```

<210> SEQ ID NO 202
<211> LENGTH: 172
<212> TYPE: PRT
<213> ORGANISM: Phakopsora pachyrhizi
<220> FEATURE:
<221> NAME/KEY: VARIANT
<222> LOCATION: (1)..(172)
<223> OTHER INFORMATION: ta08469.01_phapa

<400> SEQUENCE: 202

```
Met Ala Lys Cys Ser Leu Arg Ile Trp Ile Phe Phe Leu Glu Ile Leu
1               5                   10                  15

Thr Leu Phe Leu Leu Thr Ala Glu Ser Glu Asp Arg Gln Ala Asn Ser
            20                  25                  30

Ala Ala Val Asn Asn Val Cys Asp Arg Ser Ile Ala Cys Ser Val Phe
        35                  40                  45

Glu Glu Gly Trp Pro Lys Asn Lys Trp Phe Glu Cys Gly Ser Thr Arg
    50                  55                  60

Val Ser Pro Ala Ala Phe Ala Thr Leu Arg Gln Ser Ile Ser Ile Gly
65                  70                  75                  80

Asn Pro Lys Lys Thr Gln Val Asp Ser Thr Asp Thr Thr Glu His His
                85                  90                  95

Val Asn Cys Ala Thr Leu Asp Ala Ser Tyr Ser Arg His Ser Tyr Tyr
            100                 105                 110

Asn Gly Arg Phe Thr Val Asn Tyr Ala Ile Lys Gly Glu Cys Asp Cys
        115                 120                 125

Lys Ala Ser Arg Ser Gly Lys Arg Arg Asn Pro Ile Cys Ser Asn Ala
    130                 135                 140

Leu Ser Leu Ser Asn Ser Ala Cys Asn Leu Ala His Phe Lys Phe Cys
145                 150                 155                 160
```

Ser Leu Lys Glu Lys Asn Thr Leu Cys Ala Thr Val
165 170

<210> SEQ ID NO 203
<211> LENGTH: 381
<212> TYPE: DNA
<213> ORGANISM: Phakopsora pachyrhizi
<220> FEATURE:
<221> NAME/KEY: misc_feature
<222> LOCATION: (1)..(381)
<223> OTHER INFORMATION: ta10748.01_phapa

<400> SEQUENCE: 203
atgtcgttcg caaaacaggt tcttctctca atttgcttct tcgctgtttt cagcaagata 60
aacgctttga cggtagcaca accctcagtt cggtgcttgg gggataccaa tcctgctgcc 120
attaaagcgg aagattgtga taatgccatg tctcagttta gtgtggattc taacggctac 180
attcagtacg atccccaagg agaaaaaaga gattttggga gttgtagaat tcagattcaa 240
agtacttcag ctgcatcaaa cttagcaact attaatcctg aagtcttgaa gatatatata 300
tcaactggtt taacatcatg caacggagga acatcagcca ttgagccaca aggcctagtt 360
gtgaatgtta ttaagctcta a 381

<210> SEQ ID NO 204
<211> LENGTH: 126
<212> TYPE: PRT
<213> ORGANISM: Phakopsora pachyrhizi
<220> FEATURE:
<221> NAME/KEY: VARIANT
<222> LOCATION: (1)..(126)
<223> OTHER INFORMATION: ta10748.01_phapa

<400> SEQUENCE: 204

Met Ser Phe Ala Lys Gln Val Leu Leu Ser Ile Cys Phe Phe Ala Val
1 5 10 15

Phe Ser Lys Ile Asn Ala Leu Thr Val Ala Gln Pro Ser Val Arg Cys
20 25 30

Leu Gly Asp Thr Asn Pro Ala Ala Ile Lys Ala Glu Asp Cys Asp Asn
35 40 45

Ala Met Ser Gln Phe Ser Val Asp Ser Asn Gly Tyr Ile Gln Tyr Asp
50 55 60

Pro Gln Gly Glu Lys Arg Asp Phe Gly Ser Cys Arg Ile Gln Ile Gln
65 70 75 80

Ser Thr Ser Ala Ala Ser Asn Leu Ala Thr Ile Asn Pro Glu Val Leu
85 90 95

Lys Ile Tyr Ile Ser Thr Gly Leu Thr Ser Cys Asn Gly Gly Thr Ser
100 105 110

Ala Ile Glu Pro Gln Gly Leu Val Val Asn Val Ile Lys Leu
115 120 125

<210> SEQ ID NO 205
<211> LENGTH: 222
<212> TYPE: DNA
<213> ORGANISM: Phakopsora pachyrhizi
<220> FEATURE:
<221> NAME/KEY: misc_feature
<222> LOCATION: (1)..(222)
<223> OTHER INFORMATION: ta08283.01_phapa

<400> SEQUENCE: 205
atgaacatca tcagctcgat ctacctcgct gttgcagcta ttttgatttc tcaaaacaat 60
ttcaccagcg ccgcaaatct taatacccgg gacgaggttc cgaaacctgt tcatttcaga 120
tatgaagcca gatctgttga gcggtacaat caccttgagg ctcgtagaaa gaggcggaaa 180
ccacaaaact tcaatggaaa ctcagttaat actggtaatt ag 222

<210> SEQ ID NO 206
<211> LENGTH: 73
<212> TYPE: PRT
<213> ORGANISM: Phakopsora pachyrhizi
<220> FEATURE:
<221> NAME/KEY: VARIANT
<222> LOCATION: (1)..(73)
<223> OTHER INFORMATION: ta08283.01_phapa

<400> SEQUENCE: 206

Met Asn Ile Ile Ser Ser Ile Tyr Leu Ala Val Ala Ala Ile Leu Ile
1               5                   10                  15

Ser Gln Asn Asn Phe Thr Ser Ala Ala Asn Leu Asn Thr Arg Asp Glu
            20                  25                  30

Val Pro Lys Pro Val His Phe Arg Tyr Glu Ala Arg Ser Val Glu Arg
        35                  40                  45

Tyr Asn His Leu Glu Ala Arg Arg Lys Arg Arg Lys Pro Gln Asn Phe
    50                  55                  60

Asn Gly Asn Ser Val Asn Thr Gly Asn
65                  70

<210> SEQ ID NO 207
<211> LENGTH: 450
<212> TYPE: DNA
<213> ORGANISM: Phakopsora pachyrhizi
<220> FEATURE:
<221> NAME/KEY: misc_feature
<222> LOCATION: (1)..(450)
<223> OTHER INFORMATION: ta00466.01_phapa

<400> SEQUENCE: 207
atgttttcca gagctcttcc cgttgttctt tgccttatgt tcatgatttc aaacatcagt 60
gctcttgcaa ctcacacgag taaactagag aaaagaaaca ccccagacgg tttgtttacc 120
gattgtagaa acgctgttat taaacaaggc tgtaacgccg ctctggacga tctttggaac 180
aacggaagaa ttaaaaggtt tactaccgaa catcaatttg tcaaccatcc aagtggttgc 240
aaacttactt ggtggtctga cggtggcgta actcgccccg ctgatgacca aaaaggcaca 300
ttgcagaatg ctttacagca aatcgacgat gcttgtactt catccggtct atcatctgta 360
tatgactcaa atagaaaagg aaatggtgtt tacgtcggaa aactgtttaa caaccaatac 420
gtggttttga tggcacagac aggtgtatag 450

<210> SEQ ID NO 208
<211> LENGTH: 149
<212> TYPE: PRT
<213> ORGANISM: Phakopsora pachyrhizi
<220> FEATURE:
<221> NAME/KEY: VARIANT
<222> LOCATION: (1)..(149)
<223> OTHER INFORMATION: ta00466.01_phapa

<400> SEQUENCE: 208

Met Phe Ser Arg Ala Leu Pro Val Val Leu Cys Leu Met Phe Met Ile
1               5                   10                  15

Ser Asn Ile Ser Ala Leu Ala Thr His Thr Ser Lys Leu Glu Lys Arg
            20                  25                  30

```
Asn Thr Pro Asp Gly Leu Phe Thr Asp Cys Arg Asn Ala Val Ile Lys
        35                  40                  45

Gln Gly Cys Asn Ala Ala Leu Asp Asp Leu Trp Asn Asn Gly Arg Ile
    50                  55                  60

Lys Arg Phe Thr Thr Glu His Gln Phe Val Asn His Pro Ser Gly Cys
65                  70                  75                  80

Lys Leu Thr Trp Trp Ser Asp Gly Gly Val Thr Arg Pro Ala Asp Asp
                85                  90                  95

Gln Lys Gly Thr Leu Gln Asn Ala Leu Gln Gln Ile Asp Asp Ala Cys
            100                 105                 110

Thr Ser Ser Gly Leu Ser Ser Val Tyr Asp Ser Asn Arg Lys Gly Asn
        115                 120                 125

Gly Val Tyr Val Gly Lys Leu Phe Asn Asn Gln Tyr Val Val Leu Met
    130                 135                 140

Ala Gln Thr Gly Val
145


<210> SEQ ID NO 209
<211> LENGTH: 219
<212> TYPE: DNA
<213> ORGANISM: Phakopsora pachyrhizi
<220> FEATURE:
<221> NAME/KEY: misc_feature
<222> LOCATION: (1)..(219)
<223> OTHER INFORMATION: ta10007.01_phapa

<400> SEQUENCE: 209

atgcgcagct ttgtttcttg tgccttgctt atcgtatttt tccagctttc tataagtacg      60

cctattattg agagatctga ggttaggctt ccacagagca atcgacagag aaacttcttc     120

acgtcgtcgt tcccccgcca ccagctccct tacaccctca tccaccgccg ccaccaccac     180

cacctgttgc acatcaccct ccacgttctc ttgggatga                            219


<210> SEQ ID NO 210
<211> LENGTH: 72
<212> TYPE: PRT
<213> ORGANISM: Phakopsora pachyrhizi
<220> FEATURE:
<221> NAME/KEY: VARIANT
<222> LOCATION: (1)..(72)
<223> OTHER INFORMATION: ta10007.01_phapa

<400> SEQUENCE: 210

Met Arg Ser Phe Val Ser Cys Ala Leu Leu Ile Val Phe Phe Gln Leu
1               5                   10                  15

Ser Ile Ser Thr Pro Ile Ile Glu Arg Ser Glu Val Arg Leu Pro Gln
            20                  25                  30

Ser Asn Arg Gln Arg Asn Phe Phe Thr Ser Ser Phe Pro Arg His Gln
        35                  40                  45

Leu Pro Tyr Thr Leu Ile His Arg Arg His His His His Leu Leu His
    50                  55                  60

Ile Thr Leu His Val Leu Leu Gly
65                  70


<210> SEQ ID NO 211
<211> LENGTH: 510
<212> TYPE: DNA
<213> ORGANISM: Phakopsora pachyrhizi
<220> FEATURE:
<221> NAME/KEY: misc_feature
<222> LOCATION: (1)..(510)
```

<223> OTHER INFORMATION: ta07166.01_phapa

<400> SEQUENCE: 211

```
atgagttacc agaggatgtt tctgatgttt caactggtga ttctggcagt gatgatgaat      60
gatcagtcga actctgcacg agcaacgtta cttattcagg atgagccctt acatctgatc     120
aagactcagt ttgagatcaa acctcagaag ctcatcacag tgatcaggca gccaacccag     180
caggaagctt tggatctcag caggattggt caatcaactg gtactactac tactaccggt     240
gttgatggat ctatcataag ggtcagaccg tcatccagag ggatgatgtt caggttcgag     300
gatggtgttg gtggtggtgt tgagtcagac tctgggattg gtggaatgct gagtaagttt     360
ctcagtagga tcagtagacc gagtgtatca tctggtagta gtgttgaatc taaccttgga     420
gggtttgatc ttggttctat gttgaagagt gtaaagagct ctataagtga tgggatgact     480
actgtcagaa gattagtcgt agtctattaa                                      510
```

<210> SEQ ID NO 212
<211> LENGTH: 169
<212> TYPE: PRT
<213> ORGANISM: Phakopsora pachyrhizi
<220> FEATURE:
<221> NAME/KEY: VARIANT
<222> LOCATION: (1)..(169)
<223> OTHER INFORMATION: ta07166.01_phapa

<400> SEQUENCE: 212

```
Met Ser Tyr Gln Arg Met Phe Leu Met Phe Gln Leu Val Ile Leu Ala
1               5                   10                  15

Val Met Met Asn Asp Gln Ser Asn Ser Ala Arg Ala Thr Leu Leu Ile
            20                  25                  30

Gln Asp Glu Pro Leu His Leu Ile Lys Thr Gln Phe Glu Ile Lys Pro
        35                  40                  45

Gln Lys Leu Ile Thr Val Ile Arg Gln Pro Thr Gln Gln Glu Ala Leu
    50                  55                  60

Asp Leu Ser Arg Ile Gly Gln Ser Thr Gly Thr Thr Thr Thr Thr Gly
65                  70                  75                  80

Val Asp Gly Ser Ile Ile Arg Val Arg Pro Ser Ser Arg Gly Met Met
                85                  90                  95

Phe Arg Phe Glu Asp Gly Val Gly Gly Gly Val Glu Ser Asp Ser Gly
            100                 105                 110

Ile Gly Gly Met Leu Ser Lys Phe Leu Ser Arg Ile Ser Arg Pro Ser
        115                 120                 125

Val Ser Ser Gly Ser Ser Val Glu Ser Asn Leu Gly Gly Phe Asp Leu
    130                 135                 140

Gly Ser Met Leu Lys Ser Val Lys Ser Ser Ile Ser Asp Gly Met Thr
145                 150                 155                 160

Thr Val Arg Arg Leu Val Val Val Tyr
                165
```

<210> SEQ ID NO 213
<211> LENGTH: 402
<212> TYPE: DNA
<213> ORGANISM: Phakopsora pachyrhizi
<220> FEATURE:
<221> NAME/KEY: misc_feature
<222> LOCATION: (1)..(402)
<223> OTHER INFORMATION: ta05900.01_phapa

<400> SEQUENCE: 213
atgttcaaca aatcagcttt cgcagttact atcttctcac ttctctgtct cacgaatttt 60
tacaaagtga ctgtggcatc aatttcagaa acccaggtct gttcctatta cagcgattcg 120
tacggcaaca aatctacctg taacgagcaa cctaatgttg tttgtactgg gggatgccac 180
ggaccctacg ttgtggcgaa taactgcatg ttgcaagatg gcactgcgag tggcacttca 240
atcacctata acacaactca ggtatgcaca aagggctttg gacgaaacac ggcggcagcc 300
aaggcttgtc tcaatgagat cggacctttc acttgcactg gtcccacaaa cggtgcagca 360
gtgtgctacg gatgcaaaag caacacaatt caagatccat aa 402

<210> SEQ ID NO 214
<211> LENGTH: 133
<212> TYPE: PRT
<213> ORGANISM: Phakopsora pachyrhizi
<220> FEATURE:
<221> NAME/KEY: VARIANT
<222> LOCATION: (1)..(133)
<223> OTHER INFORMATION: ta05900.01_phapa

<400> SEQUENCE: 214

Met Phe Asn Lys Ser Ala Phe Ala Val Thr Ile Phe Ser Leu Leu Cys
1 5 10 15

Leu Thr Asn Phe Tyr Lys Val Thr Val Ala Ser Ile Ser Glu Thr Gln
20 25 30

Val Cys Ser Tyr Tyr Ser Asp Ser Tyr Gly Asn Lys Ser Thr Cys Asn
35 40 45

Glu Gln Pro Asn Val Val Cys Thr Gly Gly Cys His Gly Pro Tyr Val
50 55 60

Val Ala Asn Asn Cys Met Leu Gln Asp Gly Thr Ala Ser Gly Thr Ser
65 70 75 80

Ile Thr Tyr Asn Thr Thr Gln Val Cys Thr Lys Gly Phe Gly Arg Asn
85 90 95

Thr Ala Ala Ala Lys Ala Cys Leu Asn Glu Ile Gly Pro Phe Thr Cys
100 105 110

Thr Gly Pro Thr Asn Gly Ala Ala Val Cys Tyr Gly Cys Lys Ser Asn
115 120 125

Thr Ile Gln Asp Pro
130

<210> SEQ ID NO 215
<211> LENGTH: 456
<212> TYPE: DNA
<213> ORGANISM: Phakopsora pachyrhizi
<220> FEATURE:
<221> NAME/KEY: misc_feature
<222> LOCATION: (1)..(456)
<223> OTHER INFORMATION: ta00694.01_phapa

<400> SEQUENCE: 215
atgttttcca gagccctacc agccatcctc tgtgttcttt ttttaatttc aggaattagc 60
gcccttgcct cccagacaag taaattgata aaaaggaata ttgcagatgg tttgtatacc 120
acatgtcaaa acactgttgt aaaacatggc tgtaacaatc ttttggatca aatctggaat 180
agcgggcaga tcaaaaggtt tactacaaag catcaatttg ttgttgacag tgctgcaggg 240
tgcaaaatta cttggtgggc cgacagtggc gttgttcgcg ccaatgataa tcaaaaaagt 300
tcattgcaac aagctttaca acaaattgat gacgcctgta ccgcgtctgg catatccacc 360
gtttacgaca gaagcaagaa gggtgcaggt gtttatgttg gaagactgtt taacgaccag 420
tatgtggcaa ttatggcaga gactggagta cagtag 456

<210> SEQ ID NO 216
<211> LENGTH: 151
<212> TYPE: PRT
<213> ORGANISM: Phakopsora pachyrhizi
<220> FEATURE:
<221> NAME/KEY: VARIANT
<222> LOCATION: (1)..(151)
<223> OTHER INFORMATION: ta00694.01_phapa

<400> SEQUENCE: 216

Met Phe Ser Arg Ala Leu Pro Ala Ile Leu Cys Val Leu Phe Leu Ile
1 5 10 15

Ser Gly Ile Ser Ala Leu Ala Ser Gln Thr Ser Lys Leu Ile Lys Arg
20 25 30

Asn Ile Ala Asp Gly Leu Tyr Thr Thr Cys Gln Asn Thr Val Val Lys
35 40 45

His Gly Cys Asn Asn Leu Leu Asp Gln Ile Trp Asn Ser Gly Gln Ile
50 55 60

Lys Arg Phe Thr Thr Lys His Gln Phe Val Val Asp Ser Ala Ala Gly
65 70 75 80

Cys Lys Ile Thr Trp Trp Ala Asp Ser Gly Val Val Arg Ala Asn Asp
85 90 95

Asn Gln Lys Ser Ser Leu Gln Gln Ala Leu Gln Gln Ile Asp Asp Ala
100 105 110

Cys Thr Ala Ser Gly Ile Ser Thr Val Tyr Asp Arg Ser Lys Lys Gly
115 120 125

Ala Gly Val Tyr Val Gly Arg Leu Phe Asn Asp Gln Tyr Val Ala Ile
130 135 140

Met Ala Glu Thr Gly Val Gln
145 150

<210> SEQ ID NO 217
<211> LENGTH: 243
<212> TYPE: DNA
<213> ORGANISM: Phakopsora pachyrhizi
<220> FEATURE:
<221> NAME/KEY: misc_feature
<222> LOCATION: (1)..(243)
<223> OTHER INFORMATION: ta10860.01_phapa

<400> SEQUENCE: 217
atgttaggtc taacaaatct tattaacttt gccttaatct ctgctgtctt cttaggctta 60
gtatcatcaa taagcatacc gccaacggtt agtgaaagtt tagacagcgg ccttggagtc 120
cgatcgcttc ctcggaataa cgagggcccc aatcccagct atgacaaacg ccaggttagg 180
cctcttccgt tcatcaagtc tctccctcca acagagaacg tcgaacaaga agataccgcc 240
tag 243

<210> SEQ ID NO 218
<211> LENGTH: 80
<212> TYPE: PRT
<213> ORGANISM: Phakopsora pachyrhizi
<220> FEATURE:
<221> NAME/KEY: VARIANT
<222> LOCATION: (1)..(80)
<223> OTHER INFORMATION: ta10860.01_phapa

<400> SEQUENCE: 218

Met Leu Gly Leu Thr Asn Leu Ile Asn Phe Ala Leu Ile Ser Ala Val

```
1               5                   10                  15

Phe Leu Gly Leu Val Ser Ser Ile Ser Ile Pro Pro Thr Val Ser Glu
            20                  25                  30

Ser Leu Asp Ser Gly Leu Gly Val Arg Ser Leu Pro Arg Asn Asn Glu
        35                  40                  45

Gly Pro Asn Pro Ser Tyr Asp Lys Arg Gln Val Arg Pro Leu Pro Phe
    50                  55                  60

Ile Lys Ser Leu Pro Pro Thr Glu Asn Val Glu Gln Glu Asp Thr Ala
65                  70                  75                  80


<210> SEQ ID NO 219
<211> LENGTH: 480
<212> TYPE: DNA
<213> ORGANISM: Phakopsora pachyrhizi
<220> FEATURE:
<221> NAME/KEY: misc_feature
<222> LOCATION: (1)..(480)
<223> OTHER INFORMATION: ta09285.01_phapa

<400> SEQUENCE: 219

atgggttata ctcgggtttt gattttttg atcatctttc aagtctttta tcttgccttg      60

ggagattcat tcgacaaaaa tatctatact cgtcaaaact ctctctctac ttgcgcaaga     120

gactgctata caaatgcaac tgcaaacacc ggtgctttag gaacttgctc ccagacggat     180

aacctttgct tatgcaggag ggatgagttt ggcaatagcg taaaggactg ttgggataaa     240

tgtacggaca ttgaggaagc tgctgccaaa acttggttcg aaacagaatg cgctgcccat     300

ggggttgctg tgagatttaa caatgttaca agtgccgttt cagagacagc atcttctgtg     360

gcaaatacaa tcaacaacgc acgaaattcg cagcctaaga ctgtatcaat ttcagtggca     420

ttagcatttt gttctcttat gttatacatt ttatttcacc tctctgtaga tctttcctag     480


<210> SEQ ID NO 220
<211> LENGTH: 159
<212> TYPE: PRT
<213> ORGANISM: Phakopsora pachyrhizi
<220> FEATURE:
<221> NAME/KEY: VARIANT
<222> LOCATION: (1)..(159)
<223> OTHER INFORMATION: ta09285.01_phapa

<400> SEQUENCE: 220

Met Gly Tyr Thr Arg Val Leu Ile Phe Leu Ile Ile Phe Gln Val Phe
1               5                   10                  15

Tyr Leu Ala Leu Gly Asp Ser Phe Asp Lys Asn Ile Tyr Thr Arg Gln
            20                  25                  30

Asn Ser Leu Ser Thr Cys Ala Arg Asp Cys Tyr Thr Asn Ala Thr Ala
        35                  40                  45

Asn Thr Gly Ala Leu Gly Thr Cys Ser Gln Thr Asp Asn Leu Cys Leu
    50                  55                  60

Cys Arg Arg Asp Glu Phe Gly Asn Ser Val Lys Asp Cys Trp Asp Lys
65                  70                  75                  80

Cys Thr Asp Ile Glu Glu Ala Ala Ala Lys Thr Trp Phe Glu Thr Glu
                85                  90                  95

Cys Ala Ala His Gly Val Ala Val Arg Phe Asn Asn Val Thr Ser Ala
            100                 105                 110

Val Ser Glu Thr Ala Ser Ser Val Ala Asn Thr Ile Asn Asn Ala Arg
        115                 120                 125

Asn Ser Gln Pro Lys Thr Val Ser Ile Ser Val Ala Leu Ala Phe Cys
```

130 135 140

Ser Leu Met Leu Tyr Ile Leu Phe His Leu Ser Val Asp Leu Ser
145 150 155

<210> SEQ ID NO 221
<211> LENGTH: 204
<212> TYPE: DNA
<213> ORGANISM: Phakopsora pachyrhizi
<220> FEATURE:
<221> NAME/KEY: misc_feature
<222> LOCATION: (1)..(204)
<223> OTHER INFORMATION: ta06004.01_phapa

<400> SEQUENCE: 221
atgggaatct tgcttttgat ttatatttat aatggcagct gttgcatttc tgacttttgg 60
attcactcag gtttatatat catcatttta agtattatca gtagagaaag aaaggttgtt 120
ggcgctcctg atattttagc gggcaaaaat ccagtctaca gcgggttata ccgaaggcat 180
ggacttaatg tttcaaaggg ttaa 204

<210> SEQ ID NO 222
<211> LENGTH: 67
<212> TYPE: PRT
<213> ORGANISM: Phakopsora pachyrhizi
<220> FEATURE:
<221> NAME/KEY: VARIANT
<222> LOCATION: (1)..(67)
<223> OTHER INFORMATION: ta06004.01_phapa

<400> SEQUENCE: 222

Met Gly Ile Leu Leu Leu Ile Tyr Ile Tyr Asn Gly Ser Cys Cys Ile
1 5 10 15

Ser Asp Phe Trp Ile His Ser Gly Leu Tyr Ile Ile Ile Leu Ser Ile
20 25 30

Ile Ser Arg Glu Arg Lys Val Val Gly Ala Pro Asp Ile Leu Ala Gly
35 40 45

Lys Asn Pro Val Tyr Ser Gly Leu Tyr Arg Arg His Gly Leu Asn Val
50 55 60

Ser Lys Gly
65

<210> SEQ ID NO 223
<211> LENGTH: 315
<212> TYPE: DNA
<213> ORGANISM: Phakopsora pachyrhizi
<220> FEATURE:
<221> NAME/KEY: misc_feature
<222> LOCATION: (1)..(315)
<223> OTHER INFORMATION: ta00128.01_phapa

<400> SEQUENCE: 223
atgccttggt ttggacttgt tcccaccctg aagctcttag gtcttggtgg gggaggtggt 60
ggtggcggtt tcttgattga agtttttgca cctacagtct tgactgatgt cttactgcta 120
gtcttggatg atgatgagct gctaagaacg ttacgtttat ctagatcttc caagaagttt 180
gcagtttcta tgactttgga tgaacaatta gatttagaga tcggtcgggc aggtatggct 240
ggtttcctca ctccagtctt ctttggcggt atcggtggtg gtgatgatgg ggctgagatc 300
gttgatcttt tctga 315

<210> SEQ ID NO 224
<211> LENGTH: 104

<212> TYPE: PRT
<213> ORGANISM: Phakopsora pachyrhizi
<220> FEATURE:
<221> NAME/KEY: VARIANT
<222> LOCATION: (1)..(104)
<223> OTHER INFORMATION: ta00128.01_phapa

<400> SEQUENCE: 224

```
Met Pro Trp Phe Gly Leu Val Pro Thr Leu Lys Leu Leu Gly Leu Gly
1               5                   10                  15

Gly Gly Gly Gly Gly Gly Gly Phe Leu Ile Glu Val Phe Ala Pro Thr
            20                  25                  30

Val Leu Thr Asp Val Leu Leu Leu Val Leu Asp Asp Asp Glu Leu Leu
        35                  40                  45

Arg Thr Leu Arg Leu Ser Arg Ser Ser Lys Lys Phe Ala Val Ser Met
    50                  55                  60

Thr Leu Asp Glu Gln Leu Asp Leu Glu Ile Gly Arg Ala Gly Met Ala
65                  70                  75                  80

Gly Phe Leu Thr Pro Val Phe Phe Gly Gly Ile Gly Gly Gly Asp Asp
                85                  90                  95

Gly Ala Glu Ile Val Asp Leu Phe
            100
```

<210> SEQ ID NO 225
<211> LENGTH: 294
<212> TYPE: DNA
<213> ORGANISM: Phakopsora pachyrhizi
<220> FEATURE:
<221> NAME/KEY: misc_feature
<222> LOCATION: (1)..(294)
<223> OTHER INFORMATION: ta03398.01_phapa

<400> SEQUENCE: 225

```
atgaggttct cagcttcaat cccactcttc ctagcccttg ttttcggtat gcttgcgagt      60

gtgtccttag gtctgagtca gcaggacgaa gtaaggatgc tattgtcact tccaacgtgt     120

atgaagaatt gttatcttca gaacttgaat gctgccccat cgtgcaaggg cagagcaaat     180

tgtttgtgta gttcccaaat ttacacttat aaagttaagg cctgtgcaac gggttgtgac     240

ttgagcgaac aattgcaagg tctgagttat tcaagaactg tttgtaacca gtga           294
```

<210> SEQ ID NO 226
<211> LENGTH: 97
<212> TYPE: PRT
<213> ORGANISM: Phakopsora pachyrhizi
<220> FEATURE:
<221> NAME/KEY: VARIANT
<222> LOCATION: (1)..(97)
<223> OTHER INFORMATION: ta03398.01_phapa

<400> SEQUENCE: 226

```
Met Arg Phe Ser Ala Ser Ile Pro Leu Phe Leu Ala Leu Val Phe Gly
1               5                   10                  15

Met Leu Ala Ser Val Ser Leu Gly Leu Ser Gln Gln Asp Glu Val Arg
            20                  25                  30

Met Leu Leu Ser Leu Pro Thr Cys Met Lys Asn Cys Tyr Leu Gln Asn
        35                  40                  45

Leu Asn Ala Ala Pro Ser Cys Lys Gly Arg Ala Asn Cys Leu Cys Ser
    50                  55                  60

Ser Gln Ile Tyr Thr Tyr Lys Val Lys Ala Cys Ala Thr Gly Cys Asp
65                  70                  75                  80
```

Leu Ser Glu Gln Leu Gln Gly Leu Ser Tyr Ser Arg Thr Val Cys Asn
85 90 95

Gln

<210> SEQ ID NO 227
<211> LENGTH: 1077
<212> TYPE: DNA
<213> ORGANISM: Phakopsora pachyrhizi
<220> FEATURE:
<221> NAME/KEY: misc_feature
<222> LOCATION: (1)..(1077)
<223> OTHER INFORMATION: ta00591.01_phapa

<400> SEQUENCE: 227
atggtacttc ttcttgtagg ccagaggttt ctcttgctaa cactttacag catttctttc 60
acttgtattc aagcaaaaga aagttctttt atatctaata aaaggaacat tggtaccaca 120
aattttacaa atgggagaga aatttcttta aaaaactcaa ctgtaataca tgatccatgc 180
gctcgactgc cgctcactcc ggatctttgg aaatcactta atttaaacga ttatttgctt 240
aattatcctg atggaaataa gctcactcta gagaattatg ctgaaaaagt caatgccacc 300
aactttgatt gcggaatagg aaaacaatgc aacgccaacc agatctgcct ccctgttcgc 360
gctcctgatt ggtatatcct ggtggccgct cagaattgga atgctttcac caatgaaatg 420
tatcaagcaa cagcctttgc aatggaaatt gtacttggtc tatcttcttc aattgtgaat 480
gaggtagcat tccatgaatt ggattatctt gcgattgaag gtacacttct cggtctcttc 540
gctgggcttt gtggtgcaat acctggattt ctatatccac ctgcgtttgg attttttggt 600
cctaaaatat ggccgtttat tcaaggagga accggtctga ttgccggctt ggcgtggaca 660
tatcataata tttacgcaac gggccctgcg gatgaattct ctaagactac ggatgttcaa 720
aacttgctag ctaaagctca atcgcaagct caggccaaga tagcggaaga cgcaagaaaa 780
gttcttcaaa acggtattag ttcggaggat ggactttacg gtgttcttaa ggatggaatc 840
tttctcaaca accatagatc tatctcagag ttttcagaaa gggatataca ggacgctata 900
actatggttg ctcgagcaag gttgatagct gggatatgga aagctacgaa ctgttttgtt 960
gttcgtggaa atgcatcttg cactcaggat ggacctgatg gaacttttcc aggcaatgat 1020
gtcttatctt attgtgacga aaatggaata atgatgagta tcgtgcagtc caaaaaa 1077

<210> SEQ ID NO 228
<211> LENGTH: 359
<212> TYPE: PRT
<213> ORGANISM: Phakopsora pachyrhizi
<220> FEATURE:
<221> NAME/KEY: VARIANT
<222> LOCATION: (1)..(359)
<223> OTHER INFORMATION: ta00591.01_phapa

<400> SEQUENCE: 228

Met Val Leu Leu Leu Val Gly Gln Arg Phe Leu Leu Leu Thr Leu Tyr
1 5 10 15

Ser Ile Ser Phe Thr Cys Ile Gln Ala Lys Glu Ser Ser Phe Ile Ser
20 25 30

Asn Lys Arg Asn Ile Gly Thr Thr Asn Phe Thr Asn Gly Arg Glu Ile
35 40 45

Ser Leu Lys Asn Ser Thr Val Ile His Asp Pro Cys Ala Arg Leu Pro
50 55 60

Leu Thr Pro Asp Leu Trp Lys Ser Leu Asn Leu Asn Asp Tyr Leu Leu
65 70 75 80

```
Asn Tyr Pro Asp Gly Asn Lys Leu Thr Leu Glu Asn Tyr Ala Glu Lys
                85                  90                  95

Val Asn Ala Thr Asn Phe Asp Cys Gly Ile Gly Lys Gln Cys Asn Ala
            100                 105                 110

Asn Gln Ile Cys Leu Pro Val Arg Ala Pro Asp Trp Tyr Ile Leu Val
        115                 120                 125

Ala Ala Gln Asn Trp Asn Ala Phe Thr Asn Glu Met Tyr Gln Ala Thr
    130                 135                 140

Ala Phe Ala Met Glu Ile Val Leu Gly Leu Ser Ser Ser Ile Val Asn
145                 150                 155                 160

Glu Val Ala Phe His Glu Leu Asp Tyr Leu Ala Ile Glu Gly Thr Leu
                165                 170                 175

Leu Gly Leu Phe Ala Gly Leu Cys Gly Ala Ile Pro Gly Phe Leu Tyr
            180                 185                 190

Pro Pro Ala Phe Gly Phe Phe Gly Pro Lys Ile Trp Pro Phe Ile Gln
        195                 200                 205

Gly Gly Thr Gly Leu Ile Ala Gly Leu Ala Trp Thr Tyr His Asn Ile
    210                 215                 220

Tyr Ala Thr Gly Pro Ala Asp Glu Phe Ser Lys Thr Thr Asp Val Gln
225                 230                 235                 240

Asn Leu Leu Ala Lys Ala Gln Ser Gln Ala Gln Ala Lys Ile Ala Glu
                245                 250                 255

Asp Ala Arg Lys Val Leu Gln Asn Gly Ile Ser Ser Glu Asp Gly Leu
            260                 265                 270

Tyr Gly Val Leu Lys Asp Gly Ile Phe Leu Asn Asn His Arg Ser Ile
        275                 280                 285

Ser Glu Phe Ser Glu Arg Asp Ile Gln Asp Ala Ile Thr Met Val Ala
    290                 295                 300

Arg Ala Arg Leu Ile Ala Gly Ile Trp Lys Ala Thr Asn Cys Phe Val
305                 310                 315                 320

Val Arg Gly Asn Ala Ser Cys Thr Gln Asp Gly Pro Asp Gly Thr Phe
                325                 330                 335

Pro Gly Asn Asp Val Leu Ser Tyr Cys Asp Glu Asn Gly Ile Met Met
            340                 345                 350

Ser Ile Val Gln Ser Lys Lys
        355
```

<210> SEQ ID NO 229
<211> LENGTH: 1076
<212> TYPE: DNA
<213> ORGANISM: Phakopsora pachyrhizi
<220> FEATURE:
<221> NAME/KEY: misc_feature
<222> LOCATION: (1)..(1076)
<223> OTHER INFORMATION: ta11138.01

<400> SEQUENCE: 229

```
atgacaattg gtcatctcaa taaaggcttc attttctatt gggttgcgtt gatatttttg     60

ccaaagattg ttattggtag tttcacgcct aaatccaaag gtttcgaaac gatcattggt    120

gatgaaaaca aaattaaaaa tgttcccttg aaagatctga gcaaagaatc ctctagccaa    180

ttgaaagaat cccgagacga tgtttttggg cctggaagtt atgccatgag ctataatgct    240

aagtctcaag ctacaaaaca tgccccagga gatgatgtca gtaaatcaga ggctggagtg    300

tcatacaata ttgcaagaga tgtacaagat tccaagcgaa gcaagtcaga aggaaggtat    360
```

```
gacgaattgc atatcaagct tcgaaattca agcagaaaat ttcaaaaccc aaaagataaa    420

gaagtttatc gtagccttca gagcttgctt ttgcgcttaa aagattatct atccaaaaac    480

gttaatcaac taaatcccac tgataaagct agtttaatac ctcataagga atttgaagat    540

ttgatcttgg gagactttga cgaacttttt gggcgcatgt ttcaaaattt ttatcttaat    600

ttttatttta ataaatcttt acttcttgcg tttgatgtca tcgattggct cgctttgaat    660

gagtcagaca aaggaatcct tttaaataag ctattgataa gtgaaaaggt gattgaggga    720

ctagaccttt acatctcctc aaaaattatt cttgaaggag gttatatcga aatttttaag    780

gcggatgata ttcaacgcta tctgttaaaa catcaaaact tggaggaaat aagaaactta    840

ttaaattgtc tggaaaaaaa tcactggaaa agggttgaac ttggattcat tagggctcat    900

ctgactccat catttagtat aaatgtaaaa tattcaatca cagctacgaa cactgtgatt    960

ggctttgagg aaattcttaa ttcaatagaa aaagcccaca gctttaactc tggatggctc   1020

aaagttctaa gcatggataa agaaacagaa aatgctcttt tattttttgt agaaaa       1076
```

```
<210> SEQ ID NO 230
<211> LENGTH: 358
<212> TYPE: PRT
<213> ORGANISM: Phakopsora pachyrhizi
<220> FEATURE:
<221> NAME/KEY: VARIANT
<222> LOCATION: (1)..(358)
<223> OTHER INFORMATION: ta11138.01_phapa

<400> SEQUENCE: 230

Met Thr Ile Gly His Leu Asn Lys Gly Phe Ile Phe Tyr Trp Val Ala
1               5                   10                  15

Leu Ile Phe Leu Pro Lys Ile Val Ile Gly Ser Phe Thr Pro Lys Ser
            20                  25                  30

Lys Gly Phe Glu Thr Ile Ile Gly Asp Glu Asn Lys Ile Lys Asn Val
        35                  40                  45

Pro Leu Lys Asp Leu Ser Lys Glu Ser Ser Ser Gln Leu Lys Glu Ser
    50                  55                  60

Arg Asp Asp Val Phe Gly Pro Gly Ser Tyr Ala Met Ser Tyr Asn Ala
65                  70                  75                  80

Lys Ser Gln Ala Thr Lys His Ala Pro Gly Asp Asp Val Ser Lys Ser
                85                  90                  95

Glu Ala Gly Val Ser Tyr Asn Ile Ala Arg Asp Val Gln Asp Ser Lys
            100                 105                 110

Arg Ser Lys Ser Glu Gly Arg Tyr Asp Glu Leu His Ile Lys Leu Arg
        115                 120                 125

Asn Ser Ser Arg Lys Phe Gln Asn Pro Lys Asp Lys Glu Val Tyr Arg
    130                 135                 140

Ser Leu Gln Ser Leu Leu Leu Arg Leu Lys Asp Tyr Leu Ser Lys Asn
145                 150                 155                 160

Val Asn Gln Leu Asn Pro Thr Asp Lys Ala Ser Leu Ile Pro His Lys
                165                 170                 175

Glu Phe Glu Asp Leu Ile Leu Gly Asp Phe Asp Glu Leu Phe Gly Arg
            180                 185                 190

Met Phe Gln Asn Phe Tyr Leu Asn Phe Tyr Phe Asn Lys Ser Leu Leu
        195                 200                 205

Leu Ala Phe Asp Val Ile Asp Trp Leu Ala Leu Asn Glu Ser Asp Lys
    210                 215                 220

Gly Ile Leu Leu Asn Lys Leu Leu Ile Ser Glu Lys Val Ile Glu Gly
```

-continued

```
225                 230                 235                 240

Leu Asp Leu Tyr Ile Ser Ser Lys Ile Ile Leu Glu Gly Gly Tyr Ile
                245                 250                 255

Glu Ile Phe Lys Ala Asp Asp Ile Gln Arg Tyr Leu Leu Lys His Gln
            260                 265                 270

Asn Leu Glu Glu Ile Arg Asn Leu Leu Asn Cys Leu Glu Lys Asn His
        275                 280                 285

Trp Lys Arg Val Glu Leu Gly Phe Ile Arg Ala His Leu Thr Pro Ser
    290                 295                 300

Phe Ser Ile Asn Val Lys Tyr Ser Ile Thr Ala Thr Asn Thr Val Ile
305                 310                 315                 320

Gly Phe Glu Glu Ile Leu Asn Ser Ile Glu Lys Ala His Ser Phe Asn
                325                 330                 335

Ser Gly Trp Leu Lys Val Leu Ser Met Asp Lys Glu Thr Glu Asn Ala
            340                 345                 350

Leu Leu Phe Phe Val Glu
        355


<210> SEQ ID NO 231
<211> LENGTH: 1056
<212> TYPE: DNA
<213> ORGANISM: Phakopsora pachyrhizi
<220> FEATURE:
<221> NAME/KEY: misc_feature
<222> LOCATION: (1)..(1056)
<223> OTHER INFORMATION: ta07651.03_phapa

<400> SEQUENCE: 231

atgatgataa gttttaagta tagaattaaa tcatcagtcg tgattctctt tacgatcctc     60

ctatcctgct tgctcataga gataatcagt tctactcagt cgccctcgac aatacaagca    120

agaagcgctg tgaagaagat tgaaaaggat catcaacaga ggcggttgaa gataaggaag    180

agacaagtga cagatgcacc taatacaccc aacctggatc ttaacatcac tgatgccata    240

gccattcagg ctgatactat tccttggtac atgctggatc agtatcaaca ggaccatatt    300

agatttcatt gttacctatc aatggcttct tatggagatt acaagacatt atgccccagc    360

acgtttgcag tcgagggaaa agattttgag gtgattcagg agttccggac cgatctaggt    420

caaggggtgt ttgtagccag ggttccgttg atggacaaaa tcgtgatagt cttccaagga    480

tattccacag aaattcctct atcctgggaa cccgttcaga tcgacttcgg gcgacaaatc    540

gcaaattgta cggccaattg tactgcgggt agcggaatac tcgatctata caattcggct    600

aggatcgcta gtaacgattg ggagctggcc aaaaaggcag tcaatacgac tggtcacaag    660

tttagtgtca ctggtcatgg tattggggga gctgttgcta ctctggctgc actagatctg    720

ggatctagcg gatttgttca ttacgctcac tttcaagcct cgccgagagc agtctcacca    780

gcagcagcag cgatcttgca aaacatcttc caaggtgaat ctgcccagca ggttacggcc    840

aataacgatt tctttgtaca tgcgataccc cgttcaagct tttaccagag ggtaggtact    900

gccgtttgga tctttggtaa caagactgag tggatgagaa actgtaacta ttatcctgag    960

aatctcagct gcttgggaaa tggaactagc tttgctgatc acttttatta cttcacacct   1020

atgggacaat gtggatcagc tgataaagga ttttaa                             1056


<210> SEQ ID NO 232
<211> LENGTH: 351
<212> TYPE: PRT
<213> ORGANISM: Phakopsora pachyrhizi
```

<220> FEATURE:
<221> NAME/KEY: VARIANT
<222> LOCATION: (1)..(351)
<223> OTHER INFORMATION: ta07651.03_phapa

<400> SEQUENCE: 232

```
Met Met Ile Ser Phe Lys Tyr Arg Ile Lys Ser Ser Val Val Ile Leu
1               5                   10                  15

Phe Thr Ile Leu Leu Ser Cys Leu Leu Ile Glu Ile Ile Ser Ser Thr
            20                  25                  30

Gln Ser Pro Ser Thr Ile Gln Ala Arg Ser Ala Val Lys Lys Ile Glu
        35                  40                  45

Lys Asp His Gln Gln Arg Arg Leu Lys Ile Arg Lys Arg Gln Val Thr
    50                  55                  60

Asp Ala Pro Asn Thr Pro Asn Leu Asp Leu Asn Ile Thr Asp Ala Ile
65                  70                  75                  80

Ala Ile Gln Ala Asp Thr Ile Pro Trp Tyr Met Leu Asp Gln Tyr Gln
                85                  90                  95

Gln Asp His Ile Arg Phe His Cys Tyr Leu Ser Met Ala Ser Tyr Gly
            100                 105                 110

Asp Tyr Lys Thr Leu Cys Pro Ser Thr Phe Ala Val Glu Gly Lys Asp
        115                 120                 125

Phe Glu Val Ile Gln Glu Phe Arg Thr Asp Leu Gly Gln Gly Val Phe
    130                 135                 140

Val Ala Arg Val Pro Leu Met Asp Lys Ile Val Ile Val Phe Gln Gly
145                 150                 155                 160

Tyr Ser Thr Glu Ile Pro Leu Ser Trp Glu Pro Val Gln Ile Asp Phe
                165                 170                 175

Gly Arg Gln Ile Ala Asn Cys Thr Ala Asn Cys Thr Ala Gly Ser Gly
            180                 185                 190

Ile Leu Asp Leu Tyr Asn Ser Ala Arg Ile Ala Ser Asn Asp Trp Glu
        195                 200                 205

Leu Ala Lys Lys Ala Val Asn Thr Thr Gly His Lys Phe Ser Val Thr
    210                 215                 220

Gly His Gly Ile Gly Gly Ala Val Ala Thr Leu Ala Ala Leu Asp Leu
225                 230                 235                 240

Gly Ser Ser Gly Phe Val His Tyr Ala His Phe Gln Ala Ser Pro Arg
                245                 250                 255

Ala Val Ser Pro Ala Ala Ala Ala Ile Leu Gln Asn Ile Phe Gln Gly
            260                 265                 270

Glu Ser Ala Gln Gln Val Thr Ala Asn Asn Asp Phe Phe Val His Ala
        275                 280                 285

Ile Pro Arg Ser Ser Phe Tyr Gln Arg Val Gly Thr Ala Val Trp Ile
    290                 295                 300

Phe Gly Asn Lys Thr Glu Trp Met Arg Asn Cys Asn Tyr Tyr Pro Glu
305                 310                 315                 320

Asn Leu Ser Cys Leu Gly Asn Gly Thr Ser Phe Ala Asp His Phe Tyr
                325                 330                 335

Tyr Phe Thr Pro Met Gly Gln Cys Gly Ser Ala Asp Lys Gly Phe
            340                 345                 350
```

<210> SEQ ID NO 233
<211> LENGTH: 1056
<212> TYPE: DNA
<213> ORGANISM: Phakopsora pachyrhizi
<220> FEATURE:

<221> NAME/KEY: misc_feature
<222> LOCATION: (1)..(1056)
<223> OTHER INFORMATION: ta07651.02_phapa

<400> SEQUENCE: 233

```
atgatgataa gttttaagta tagaattaaa tcatcagtcg tgattctctt tacgatcctc     60

ctatcctgct tgctcataga gataatcagt tctactcagt cgccctcgac aatacaagca    120

agaagcgctg tgaagaagat tgaaaaggat catcaacaga ggcggttgaa gataaggaag    180

agacaagtga cagatgcacc taatacaccc aacctggatc ttaacatcac tgatgccata    240

gccattcagg ctgatactat tccttggtac atgctggatc agtatcaaca ggaccatatt    300

agatttcatt gttacctatc aatggcttct tatggagatt acaagacatt atgccccagc    360

acgtttgcag tcgagggaaa agattttgag gtgattcagg agttccggac cgatctaggt    420

caaggggtgt ttgtagccag ggttccgttg atggacaaaa tcgtgatagt cttccaagga    480

tattccacag aaattcctct atcctgggaa cccgttcaga tcgacttcgg gcgacaaatc    540

gcaaattgta cggccaattg tactgcgggt agcggaatac tcgatctata caattcggct    600

aggatcgcta gtaacgattg ggagctggcc aaaaaggcag tcaatacgac tggtcacaag    660

tttagtgtca ctggtcatgg tattggggga gctgttgcta ctctggctgc actagatctg    720

ggatctagcg gatttgttca ttacgctcac tttcaagcct cgccgagagc agtctcacca    780

gcagcagcag cgatcttgca aaacatcttc caaggtgaat ctgcccagca ggttacggcc    840

aataacgatt tctttgtaca tgcgataccc cgttcaagct tttaccagag ggtaggtact    900

gccgtttgga tctttggtaa caagactgag tggatgagaa actgtaacta ttatcctgag    960

aatctcagct gcttgggaaa tggaactagc tttgctgatc acttttatta cttcacacct   1020

atgggacaat gtggatcagc tgataaagga ttttaa                              1056
```

<210> SEQ ID NO 234
<211> LENGTH: 351
<212> TYPE: PRT
<213> ORGANISM: Phakopsora pachyrhizi
<220> FEATURE:
<221> NAME/KEY: VARIANT
<222> LOCATION: (1)..(351)
<223> OTHER INFORMATION: ta07651.02_phapa

<400> SEQUENCE: 234

```
Met Met Ile Ser Phe Lys Tyr Arg Ile Lys Ser Ser Val Val Ile Leu
1               5                   10                  15

Phe Thr Ile Leu Leu Ser Cys Leu Leu Ile Glu Ile Ile Ser Ser Thr
            20                  25                  30

Gln Ser Pro Ser Thr Ile Gln Ala Arg Ser Ala Val Lys Lys Ile Glu
        35                  40                  45

Lys Asp His Gln Gln Arg Arg Leu Lys Ile Arg Lys Arg Gln Val Thr
    50                  55                  60

Asp Ala Pro Asn Thr Pro Asn Leu Asp Leu Asn Ile Thr Asp Ala Ile
65                  70                  75                  80

Ala Ile Gln Ala Asp Thr Ile Pro Trp Tyr Met Leu Asp Gln Tyr Gln
                85                  90                  95

Gln Asp His Ile Arg Phe His Cys Tyr Leu Ser Met Ala Ser Tyr Gly
            100                 105                 110

Asp Tyr Lys Thr Leu Cys Pro Ser Thr Phe Ala Val Glu Gly Lys Asp
        115                 120                 125

Phe Glu Val Ile Gln Glu Phe Arg Thr Asp Leu Gly Gln Gly Val Phe
```

```
    130                 135                 140

Val Ala Arg Val Pro Leu Met Asp Lys Ile Val Ile Val Phe Gln Gly
145                 150                 155                 160

Tyr Ser Thr Glu Ile Pro Leu Ser Trp Glu Pro Val Gln Ile Asp Phe
                165                 170                 175

Gly Arg Gln Ile Ala Asn Cys Thr Ala Asn Cys Thr Ala Gly Ser Gly
            180                 185                 190

Ile Leu Asp Leu Tyr Asn Ser Ala Arg Ile Ala Ser Asn Asp Trp Glu
        195                 200                 205

Leu Ala Lys Lys Ala Val Asn Thr Thr Gly His Lys Phe Ser Val Thr
    210                 215                 220

Gly His Gly Ile Gly Gly Ala Val Ala Thr Leu Ala Ala Leu Asp Leu
225                 230                 235                 240

Gly Ser Ser Gly Phe Val His Tyr Ala His Phe Gln Ala Ser Pro Arg
                245                 250                 255

Ala Val Ser Pro Ala Ala Ala Ala Ile Leu Gln Asn Ile Phe Gln Gly
            260                 265                 270

Glu Ser Ala Gln Gln Val Thr Ala Asn Asn Asp Phe Phe Val His Ala
        275                 280                 285

Ile Pro Arg Ser Ser Phe Tyr Gln Arg Val Gly Thr Ala Val Trp Ile
    290                 295                 300

Phe Gly Asn Lys Thr Glu Trp Met Arg Asn Cys Asn Tyr Tyr Pro Glu
305                 310                 315                 320

Asn Leu Ser Cys Leu Gly Asn Gly Thr Ser Phe Ala Asp His Phe Tyr
                325                 330                 335

Tyr Phe Thr Pro Met Gly Gln Cys Gly Ser Ala Asp Lys Gly Phe
            340                 345                 350


<210> SEQ ID NO 235
<211> LENGTH: 1056
<212> TYPE: DNA
<213> ORGANISM: Phakopsora pachyrhizi
<220> FEATURE:
<221> NAME/KEY: misc_feature
<222> LOCATION: (1)..(1056)
<223> OTHER INFORMATION: ta07651.01_phapa

<400> SEQUENCE: 235

atgatgataa gttttaagta tagaattaaa tcatcagtcg tgattctctt tacgatcctc      60

ctatcctgct tgctcataga gataatcagt tctactcagt cgccctcgac aatacaagca     120

agaagcgctg tgaagaagat tgaaaaggat catcaacaga ggcggttgaa gataaggaag     180

agacaagtga cagatgcacc taatacaccc aacctggatc ttaacatcac tgatgccata     240

gccattcagg ctgatactat tccttggtac atgctggatc agtatcaaca ggaccatatt     300

agatttcatt gttacctatc aatggcttct tatggagatt acaagacatt atgccccagc     360

acgtttgcag tcgagggaaa agattttgag gtgattcagg agttccggac cgatctaggt     420

caaggggtgt ttgtagccag ggttccgttg atggacaaaa tcgtgatagt cttccaagga     480

tattccacag aaattcctct atcctgggaa cccgttcaga tcgacttcgg gcgacaaatc     540

gcaaattgta cggccaattg tactgcgggt agcggaatac tcgatctata caattcggct     600

aggatcgcta gtaacgattg ggagctggcc aaaaaggcag tcaatacgac tggtcacaag     660

tttagtgtca ctggtcatgg tattggggga gctgttgcta ctctggctgc actagatctg     720

ggatctagcg gatttgttca ttacgctcac tttcaagcct cgccgagagc agtctcacca     780
```

-continued

```
gcagcagcag cgatcttgca aaacatcttc caaggtgaat ctgcccagca ggttacggcc    840

aataacgatt tctttgtaca tgcgataccc cgttcaagct tttaccagag ggtaggtact    900

gccgtttgga tctttggtaa caagactgag tggatgagaa actgtaacta ttatcctgag    960

aatctcagct gcttgggaaa tggaactagc tttgctgatc acttttatta cttcacacct   1020

atgggacaat gtggatcagc tgataaagga ttttaa                              1056


<210> SEQ ID NO 236
<211> LENGTH: 351
<212> TYPE: PRT
<213> ORGANISM: Phakopsora pachyrhizi
<220> FEATURE:
<221> NAME/KEY: VARIANT
<222> LOCATION: (1)..(351)
<223> OTHER INFORMATION: ta07651.01_phapa

<400> SEQUENCE: 236

Met Met Ile Ser Phe Lys Tyr Arg Ile Lys Ser Ser Val Val Ile Leu
1               5                   10                  15

Phe Thr Ile Leu Leu Ser Cys Leu Leu Ile Glu Ile Ile Ser Ser Thr
            20                  25                  30

Gln Ser Pro Ser Thr Ile Gln Ala Arg Ser Ala Val Lys Lys Ile Glu
        35                  40                  45

Lys Asp His Gln Gln Arg Arg Leu Lys Ile Arg Lys Arg Gln Val Thr
    50                  55                  60

Asp Ala Pro Asn Thr Pro Asn Leu Asp Leu Asn Ile Thr Asp Ala Ile
65                  70                  75                  80

Ala Ile Gln Ala Asp Thr Ile Pro Trp Tyr Met Leu Asp Gln Tyr Gln
                85                  90                  95

Gln Asp His Ile Arg Phe His Cys Tyr Leu Ser Met Ala Ser Tyr Gly
            100                 105                 110

Asp Tyr Lys Thr Leu Cys Pro Ser Thr Phe Ala Val Glu Gly Lys Asp
        115                 120                 125

Phe Glu Val Ile Gln Glu Phe Arg Thr Asp Leu Gly Gln Gly Val Phe
    130                 135                 140

Val Ala Arg Val Pro Leu Met Asp Lys Ile Val Ile Val Phe Gln Gly
145                 150                 155                 160

Tyr Ser Thr Glu Ile Pro Leu Ser Trp Glu Pro Val Gln Ile Asp Phe
                165                 170                 175

Gly Arg Gln Ile Ala Asn Cys Thr Ala Asn Cys Thr Ala Gly Ser Gly
            180                 185                 190

Ile Leu Asp Leu Tyr Asn Ser Ala Arg Ile Ala Ser Asn Asp Trp Glu
        195                 200                 205

Leu Ala Lys Lys Ala Val Asn Thr Thr Gly His Lys Phe Ser Val Thr
    210                 215                 220

Gly His Gly Ile Gly Gly Ala Val Ala Thr Leu Ala Ala Leu Asp Leu
225                 230                 235                 240

Gly Ser Ser Gly Phe Val His Tyr Ala His Phe Gln Ala Ser Pro Arg
                245                 250                 255

Ala Val Ser Pro Ala Ala Ala Ala Ile Leu Gln Asn Ile Phe Gln Gly
            260                 265                 270

Glu Ser Ala Gln Gln Val Thr Ala Asn Asn Asp Phe Phe Val His Ala
        275                 280                 285

Ile Pro Arg Ser Ser Phe Tyr Gln Arg Val Gly Thr Ala Val Trp Ile
    290                 295                 300
```

```
Phe Gly Asn Lys Thr Glu Trp Met Arg Asn Cys Asn Tyr Tyr Pro Glu
305                 310                 315                 320

Asn Leu Ser Cys Leu Gly Asn Gly Thr Ser Phe Ala Asp His Phe Tyr
                325                 330                 335

Tyr Phe Thr Pro Met Gly Gln Cys Gly Ser Ala Asp Lys Gly Phe
            340                 345                 350


<210> SEQ ID NO 237
<211> LENGTH: 1029
<212> TYPE: DNA
<213> ORGANISM: Phakopsora pachyrhizi
<220> FEATURE:
<221> NAME/KEY: misc_feature
<222> LOCATION: (1)..(1029)
<223> OTHER INFORMATION: ta00414.01_phapa

<400> SEQUENCE: 237

atgatagcca tcaacattct attgatatat ctgctcgcta taggaagatt catcagggga     60

gatgaaggac aacaagctct agccagtgat caagaaccct acaaactctc aatattccat    120

agactttcat caaaattatc aaccggcgta gatcccaaca atcacagcaa cttctcgtcc    180

tccttctcaa atggccagac ctggaggaaa cgtggagacc tgaagataag gagagccaac    240

agtgattcca aaagtctgac aatctcatct tttaaaaggc ctaccatgga acacctgaag    300

atcgatgtga agagttggat ctcatcaaaa cacttaccag actatcagct cttgatttta    360

cctcatcaag aatctccttc gttgccattc gactatgatt ctcatggatc tatctcattc    420

tcattgtgta attttctctc tgacagggat cagcgattca aagagtattt aaacctatgg    480

gttgaagagg aggagattaa gagtggggcg gaaggatcga ataggatgga attaagaatt    540

ataggattga attggggtgt agaggaacgg tcaaggtcaa tctttgaatc tcaatcgatc    600

gataggagct gtaagataga tgatgaaatt tttaacgaca acaagattgg tgcgaagttt    660

gagaacgagg aggaagagaa gaggctgaaa agcgtcgaag gtcgtttgaa tgaggttttt    720

aaaagtgtag atagttggaa tacgaaagtt atgatcagaa gacctgaaac tttaccagaa    780

ccgtttctca ggccatttca aaaccaaggt ggagcagtag gaaatagacc gttagagtac    840

ttaccagatg gaaccattaa aaagacaaag caggagaggt tgagagagga agaggctaac    900

aagagttggt ttgccaagta ttggatgtat attttaccct ttgccatcct ggtcatgttt    960

ggtggaggtg gtaacagttt tgaagaagcc aaaactgaat caaagtcaac cccttcatcc   1020

tcttcataa                                                           1029


<210> SEQ ID NO 238
<211> LENGTH: 342
<212> TYPE: PRT
<213> ORGANISM: Phakopsora pachyrhizi
<220> FEATURE:
<221> NAME/KEY: VARIANT
<222> LOCATION: (1)..(342)
<223> OTHER INFORMATION: ta00414.01_phapa

<400> SEQUENCE: 238

Met Ile Ala Ile Asn Ile Leu Leu Ile Tyr Leu Leu Ala Ile Gly Arg
1               5                   10                  15

Phe Ile Arg Gly Asp Glu Gly Gln Gln Ala Leu Ala Ser Asp Gln Glu
            20                  25                  30

Pro Tyr Lys Leu Ser Ile Phe His Arg Leu Ser Ser Lys Leu Ser Thr
        35                  40                  45

Gly Val Asp Pro Asn Asn His Ser Asn Phe Ser Ser Ser Phe Ser Asn
```

```
    50                  55                  60

Gly Gln Thr Trp Arg Lys Arg Gly Asp Leu Lys Ile Arg Arg Ala Asn
65                  70                  75                  80

Ser Asp Ser Lys Ser Leu Thr Ile Ser Ser Phe Lys Arg Pro Thr Met
                85                  90                  95

Glu His Leu Lys Ile Asp Val Lys Ser Trp Ile Ser Ser Lys His Leu
            100                 105                 110

Pro Asp Tyr Gln Leu Leu Ile Leu Pro His Gln Glu Ser Pro Ser Leu
        115                 120                 125

Pro Phe Asp Tyr Asp Ser His Gly Ser Ile Ser Phe Ser Leu Cys Asn
    130                 135                 140

Phe Leu Ser Asp Arg Asp Gln Arg Phe Lys Glu Tyr Leu Asn Leu Trp
145                 150                 155                 160

Val Glu Glu Glu Glu Ile Lys Ser Gly Ala Glu Gly Ser Asn Arg Met
                165                 170                 175

Glu Leu Arg Ile Ile Gly Leu Asn Trp Gly Val Glu Glu Arg Ser Arg
            180                 185                 190

Ser Ile Phe Glu Ser Gln Ser Ile Asp Arg Ser Cys Lys Ile Asp Asp
        195                 200                 205

Glu Ile Phe Asn Asp Asn Lys Ile Gly Ala Lys Phe Glu Asn Glu Glu
    210                 215                 220

Glu Glu Lys Arg Leu Lys Ser Val Glu Gly Arg Leu Asn Glu Val Phe
225                 230                 235                 240

Lys Ser Val Asp Ser Trp Asn Thr Lys Val Met Ile Arg Arg Pro Glu
                245                 250                 255

Thr Leu Pro Glu Pro Phe Leu Arg Pro Phe Gln Asn Gln Gly Gly Ala
            260                 265                 270

Val Gly Asn Arg Pro Leu Glu Tyr Leu Pro Asp Gly Thr Ile Lys Lys
        275                 280                 285

Thr Lys Gln Glu Arg Leu Arg Glu Glu Glu Ala Asn Lys Ser Trp Phe
    290                 295                 300

Ala Lys Tyr Trp Met Tyr Ile Leu Pro Phe Ala Ile Leu Val Met Phe
305                 310                 315                 320

Gly Gly Gly Gly Asn Ser Phe Glu Glu Ala Lys Thr Glu Ser Lys Ser
                325                 330                 335

Thr Pro Ser Ser Ser Ser
            340


<210> SEQ ID NO 239
<211> LENGTH: 1011
<212> TYPE: DNA
<213> ORGANISM: Phakopsora pachyrhizi
<220> FEATURE:
<221> NAME/KEY: misc_feature
<222> LOCATION: (1)..(1011)
<223> OTHER INFORMATION: ta10160.01_phapa

<400> SEQUENCE: 239

atgaagagtc tcccgaggct ccttcagcct tactactgcc taaggctatt gagctgtttg      60

cctgccctgc tatacctctt caaactatca gagtctataa atcacttgag cgatagctca     120

gcctcttcaa acaaccgatc catccgtgga cagcaacaga ttcatctttc catgtcgttt     180

ctatctgatc agctgattgc aatcatgatc cccttggtcg gaataccgct attggtatct     240

ttgaggttga ggcagatcag aaagaccttt aaggttttgg acttaagcac tgaaacgttg     300

cttgaaagct ggtttgcaat tttgctggtg tataaccttg gtgtcttgat ctatgtcaga     360
```

```
caatggaatt accttacagg gtacttattt tggttatcta tatcgagctg tatgttttcg    420

aaaccaaagt atcaagggcc atcaaaactc aggacagtca ataccaagag cttttcaaat    480

gaggttttga atcgtagctt agaatcacta gttggttttt cagctgacga tatgttgagg    540

ataactcctg aagaactaga gagacggtca aaagcaaata agtctgcttc gtcatcaaat    600

cccgacaaac tttggattgt atggcccctg tttgattcaa cttatcggac cagagtcgga    660

tttatggatg ttgaagtgtt gttatctaga ctctctctta gctccagttc aaaagatttt    720

gagatattag ttctagatgt agaaggatcg agcgagttgt gttatgaact gaagttatgg    780

ggggaagacg attattcgaa tctaagctct aagcatcaat cggaagagaa agggatcatc    840

ctgctggtct ttagaggcgg aaaagaattg aggagaattc cacctcgccc taccgagcac    900

gattctgatt cttcagatgg cgattgtgaa gcgtcgaaga acttcaagag tttaggccaa    960

aaaccttttc tctggacact tgaagcaatc agatcggcaa tccaaatcta a            1011


<210> SEQ ID NO 240
<211> LENGTH: 336
<212> TYPE: PRT
<213> ORGANISM: Phakopsora pachyrhizi
<220> FEATURE:
<221> NAME/KEY: VARIANT
<222> LOCATION: (1)..(336)
<223> OTHER INFORMATION: >ta10160.01_phapa

<400> SEQUENCE: 240

Met Lys Ser Leu Pro Arg Leu Leu Gln Pro Tyr Tyr Cys Leu Arg Leu
1               5                   10                  15

Leu Ser Cys Leu Pro Ala Leu Leu Tyr Leu Phe Lys Leu Ser Glu Ser
            20                  25                  30

Ile Asn His Leu Ser Asp Ser Ser Ala Ser Ser Asn Asn Arg Ser Ile
        35                  40                  45

Arg Gly Gln Gln Gln Ile His Leu Ser Met Ser Phe Leu Ser Asp Gln
    50                  55                  60

Leu Ile Ala Ile Met Ile Pro Leu Val Gly Ile Pro Leu Leu Val Ser
65                  70                  75                  80

Leu Arg Leu Arg Gln Ile Arg Lys Thr Phe Lys Val Leu Asp Leu Ser
                85                  90                  95

Thr Glu Thr Leu Leu Glu Ser Trp Phe Ala Ile Leu Leu Val Tyr Asn
            100                 105                 110

Leu Gly Val Leu Ile Tyr Val Arg Gln Trp Asn Tyr Leu Thr Gly Tyr
        115                 120                 125

Leu Phe Trp Leu Ser Ile Ser Ser Cys Met Phe Ser Lys Pro Lys Tyr
    130                 135                 140

Gln Gly Pro Ser Lys Leu Arg Thr Val Asn Thr Lys Ser Phe Ser Asn
145                 150                 155                 160

Glu Val Leu Asn Arg Ser Leu Glu Ser Leu Val Gly Phe Ser Ala Asp
                165                 170                 175

Asp Met Leu Arg Ile Thr Pro Glu Glu Leu Glu Arg Arg Ser Lys Ala
            180                 185                 190

Asn Lys Ser Ala Ser Ser Ser Asn Pro Asp Lys Leu Trp Ile Val Trp
        195                 200                 205

Pro Leu Phe Asp Ser Thr Tyr Arg Thr Arg Val Gly Phe Met Asp Val
    210                 215                 220

Glu Val Leu Leu Ser Arg Leu Ser Leu Ser Ser Ser Ser Lys Asp Phe
225                 230                 235                 240
```

```
Glu Ile Leu Val Leu Asp Val Glu Gly Ser Ser Glu Leu Cys Tyr Glu
                245                 250                 255

Leu Lys Leu Trp Gly Glu Asp Asp Tyr Ser Asn Leu Ser Ser Lys His
            260                 265                 270

Gln Ser Glu Glu Lys Gly Ile Ile Leu Leu Val Phe Arg Gly Gly Lys
        275                 280                 285

Glu Leu Arg Arg Ile Pro Pro Arg Pro Thr Glu His Asp Ser Asp Ser
    290                 295                 300

Ser Asp Gly Asp Cys Glu Ala Ser Lys Asn Phe Lys Ser Leu Gly Gln
305                 310                 315                 320

Lys Pro Phe Leu Trp Thr Leu Glu Ala Ile Arg Ser Ala Ile Gln Ile
                325                 330                 335
```

<210> SEQ ID NO 241
<211> LENGTH: 993
<212> TYPE: DNA
<213> ORGANISM: Phakopsora pachyrhizi
<220> FEATURE:
<221> NAME/KEY: misc_feature
<222> LOCATION: (1)..(993)
<223> OTHER INFORMATION: ta09254.04_phapa

<400> SEQUENCE: 241

```
atgcctcacc ccctgtggat atcattcgtc ctctctgtac tgcttcaagt tatacctttg      60

gtttgggggc actgtaagat cgttactgct gccggaaatt taaatacttc aagtcaagtc     120

agctatggat ttggtgtgga tttacatagc aagtacccgt ggtttaagtc tcaagccggt     180

gatgccggag cggattctga agtttttact gaatcgaaag agtttgtcgc caatcctaat     240

ccccccttgtg gcatgcgtgc gaaaatgggt gccctagatt tcgactcatc ttttagtcaa     300

gccgaagcaa tgggcgtagg aaatacttta gaagatgggt cttttgaggc attgattttt     360

caggtcaacc gtgatggtgg aggacaatgc acttgtgaat acaacactgt aggacaacct     420

gacaaattta aattttgcaa gacactcatt aatccaccgg gacaaaatgg catttggcct     480

caagatcgtg taaatcatac ggccaaattt caactaccca gagatactac ttgccgtggt     540

ggaatgttca aagacaagtg cttgattaga atcagatgtg gagagtttct aagatttgga     600

ggatgtttgg caataaagac gcctgccagc ccacataaac ttcaattgaa ggttgtaatt     660

ggaggtaaaa catcaatgaa aaccaaaccg gacttaccaa gaaatgatgt ttccagcatc     720

gctcaaaagg ttttcaacac actgaaagcc aaaggggcct tcgtgccgat ttcttccggc     780

agatataaaa gaagtcctgc aatgcatatt catgccttgc agcatgtaag aacccttggc     840

gttacccctt taaaatcaaa ctttgactct atggcagatg aaatttcttt caaggtgatt     900

gaattgatgc gagccaacaa ggttttcctg gtagcgaaga aggccaaatc aatattgaag     960

gattataggg actctacatc tgcagaaaga taa                                  993
```

<210> SEQ ID NO 242
<211> LENGTH: 330
<212> TYPE: PRT
<213> ORGANISM: Phakopsora pachyrhizi
<220> FEATURE:
<221> NAME/KEY: VARIANT
<222> LOCATION: (1)..(330)
<223> OTHER INFORMATION: ta09254.04_phapa

<400> SEQUENCE: 242

```
Met Pro His Pro Leu Trp Ile Ser Phe Val Leu Ser Val Leu Leu Gln
1               5                   10                  15
```

```
Val Ile Pro Leu Val Trp Gly His Cys Lys Ile Val Thr Ala Ala Gly
            20                  25                  30

Asn Leu Asn Thr Ser Ser Gln Val Ser Tyr Gly Phe Gly Val Asp Leu
        35                  40                  45

His Ser Lys Tyr Pro Trp Phe Lys Ser Gln Ala Gly Asp Ala Gly Ala
    50                  55                  60

Asp Ser Glu Val Phe Thr Glu Ser Lys Glu Phe Val Ala Asn Pro Asn
65                  70                  75                  80

Pro Pro Cys Gly Met Arg Ala Lys Met Gly Ala Leu Asp Phe Asp Ser
                85                  90                  95

Ser Phe Ser Gln Ala Glu Ala Met Gly Val Gly Asn Thr Leu Glu Asp
            100                 105                 110

Gly Ser Phe Glu Ala Leu Ile Phe Gln Val Asn Arg Asp Gly Gly Gly
        115                 120                 125

Gln Cys Thr Cys Glu Tyr Asn Thr Val Gly Gln Pro Asp Lys Phe Lys
    130                 135                 140

Phe Cys Lys Thr Leu Ile Asn Pro Pro Gly Gln Asn Gly Ile Trp Pro
145                 150                 155                 160

Gln Asp Arg Val Asn His Thr Ala Lys Phe Gln Leu Pro Arg Asp Thr
                165                 170                 175

Thr Cys Arg Gly Gly Met Phe Lys Asp Lys Cys Leu Ile Arg Ile Arg
            180                 185                 190

Cys Gly Glu Phe Leu Arg Phe Gly Gly Cys Leu Ala Ile Lys Thr Pro
        195                 200                 205

Ala Ser Pro His Lys Leu Gln Leu Lys Val Val Ile Gly Gly Lys Thr
    210                 215                 220

Ser Met Lys Thr Lys Pro Asp Leu Pro Arg Asn Asp Val Ser Ser Ile
225                 230                 235                 240

Ala Gln Lys Val Phe Asn Thr Leu Lys Ala Lys Gly Ala Phe Val Pro
                245                 250                 255

Ile Ser Ser Gly Arg Tyr Lys Arg Ser Pro Ala Met His Ile His Ala
            260                 265                 270

Leu Gln His Val Arg Thr Leu Gly Val Thr Pro Leu Lys Ser Asn Phe
        275                 280                 285

Asp Ser Met Ala Asp Glu Ile Ser Phe Lys Val Ile Glu Leu Met Arg
    290                 295                 300

Ala Asn Lys Val Phe Leu Val Ala Lys Lys Ala Lys Ser Ile Leu Lys
305                 310                 315                 320

Asp Tyr Arg Asp Ser Thr Ser Ala Glu Arg
                325                 330


<210> SEQ ID NO 243
<211> LENGTH: 993
<212> TYPE: DNA
<213> ORGANISM: Phakopsora pachyrhizi
<220> FEATURE:
<221> NAME/KEY: misc_feature
<222> LOCATION: (1)..(993)
<223> OTHER INFORMATION: ta09254.03_phapa

<400> SEQUENCE: 243

atgcctcacc ccctgtggat atcattcgtc ctctctgtac tgcttcaagt tatacctttg      60

gtttgggggc actgtaagat cgttactgct gccggaaatt taaatacttc aagtcaagtc     120

agctatggat ttggtgtgga tttacatagc aagtacccgt ggtttaagtc tcaagccggt     180
```

-continued

```
gatgccggag cggattctga agtttttact gaatcgaaag agtttgtcgc caatcctaat    240

cccccttgtg gcatgcgtgc gaaaatgggt gccctagatt tcgactcatc ttttagtcaa    300

gccgaagcaa tgggcgtagg aaatacttta gaagatgggt cttttgaggc attgattttt    360

caggtcaacc gtgatggtgg aggacaatgc acttgtgaat acaacactgt aggacaacct    420

gacaaattta aattttgcaa gacactcatt aatccaccgg gacaaaatgg catttggcct    480

caagatcgtg taaatcatac ggccaaattt caactaccca gagatactac ttgccgtggt    540

ggaatgttca aagacaagtg cttgattaga atcagatgtg gagagtttct aagatttgga    600

ggatgtttgg caataaagac gcctgccagc ccacataaac ttcaattgaa ggttgtaatt    660

ggaggtaaaa catcaatgaa aaccaaaccg gacttaccaa gaaatgatgt ttccagcatc    720

gctcaaaagg ttttcaacac actgaaagcc aaaggggcct tcgtgccgat ttcttccggc    780

agatataaaa gaagtcctgc aatgcatatt catgccttgc agcatgtaag aacccttggc    840

gttacccctt taaaatcaaa ctttgactct atggcagatg aaatttcttt caaggtgatt    900

gaattgatgc gagccaacaa ggttttcctg gtagcgaaga aggccaaatc aatattgaag    960

gattataggg actctacatc tgcagaaaga taa                                 993
```

```
<210> SEQ ID NO 244
<211> LENGTH: 330
<212> TYPE: PRT
<213> ORGANISM: Phakopsora pachyrhizi
<220> FEATURE:
<221> NAME/KEY: VARIANT
<222> LOCATION: (1)..(330)
<223> OTHER INFORMATION: ta09254.03_phapa

<400> SEQUENCE: 244

Met Pro His Pro Leu Trp Ile Ser Phe Val Leu Ser Val Leu Leu Gln
1               5                   10                  15

Val Ile Pro Leu Val Trp Gly His Cys Lys Ile Val Thr Ala Ala Gly
            20                  25                  30

Asn Leu Asn Thr Ser Ser Gln Val Ser Tyr Gly Phe Gly Val Asp Leu
        35                  40                  45

His Ser Lys Tyr Pro Trp Phe Lys Ser Gln Ala Gly Asp Ala Gly Ala
    50                  55                  60

Asp Ser Glu Val Phe Thr Glu Ser Lys Glu Phe Val Ala Asn Pro Asn
65                  70                  75                  80

Pro Pro Cys Gly Met Arg Ala Lys Met Gly Ala Leu Asp Phe Asp Ser
                85                  90                  95

Ser Phe Ser Gln Ala Glu Ala Met Gly Val Gly Asn Thr Leu Glu Asp
            100                 105                 110

Gly Ser Phe Glu Ala Leu Ile Phe Gln Val Asn Arg Asp Gly Gly Gly
        115                 120                 125

Gln Cys Thr Cys Glu Tyr Asn Thr Val Gly Gln Pro Asp Lys Phe Lys
    130                 135                 140

Phe Cys Lys Thr Leu Ile Asn Pro Pro Gly Gln Asn Gly Ile Trp Pro
145                 150                 155                 160

Gln Asp Arg Val Asn His Thr Ala Lys Phe Gln Leu Pro Arg Asp Thr
                165                 170                 175

Thr Cys Arg Gly Gly Met Phe Lys Asp Lys Cys Leu Ile Arg Ile Arg
            180                 185                 190

Cys Gly Glu Phe Leu Arg Phe Gly Gly Cys Leu Ala Ile Lys Thr Pro
        195                 200                 205
```

```
Ala Ser Pro His Lys Leu Gln Leu Lys Val Val Ile Gly Gly Lys Thr
    210                 215                 220

Ser Met Lys Thr Lys Pro Asp Leu Pro Arg Asn Asp Val Ser Ser Ile
225                 230                 235                 240

Ala Gln Lys Val Phe Asn Thr Leu Lys Ala Lys Gly Ala Phe Val Pro
                245                 250                 255

Ile Ser Ser Gly Arg Tyr Lys Arg Ser Pro Ala Met His Ile His Ala
            260                 265                 270

Leu Gln His Val Arg Thr Leu Gly Val Thr Pro Leu Lys Ser Asn Phe
        275                 280                 285

Asp Ser Met Ala Asp Glu Ile Ser Phe Lys Val Ile Glu Leu Met Arg
    290                 295                 300

Ala Asn Lys Val Phe Leu Val Ala Lys Lys Ala Lys Ser Ile Leu Lys
305                 310                 315                 320

Asp Tyr Arg Asp Ser Thr Ser Ala Glu Arg
                325                 330
```

<210> SEQ ID NO 245
<211> LENGTH: 993
<212> TYPE: DNA
<213> ORGANISM: Phakopsora pachyrhizi
<220> FEATURE:
<221> NAME/KEY: misc_feature
<222> LOCATION: (1)..(993)
<223> OTHER INFORMATION: ta09254.05_phapa

<400> SEQUENCE: 245

```
atgcctcacc ccctgtggat atcattcgtc ctctctgtac tgcttcaagt tatacctttg      60

gtttgggggc actgtaagat cgttactgct gccggaaatt taaatacttc aagtcaagtc     120

agctatggat ttggtgtgga tttacatagc aagtacccgt ggtttaagtc tcaagccggt     180

gatgccggag cggattctga agtttttact gaatcgaaag agtttgtcgc caatcctaat     240

ccccccttgtg gcatgcgtgc gaaaatgggt gccctagatt tcgactcatc ttttagtcaa     300

gccgaagcaa tgggcgtagg aaatacttta gaagatgggt cttttgaggc attgattttt     360

caggtcaacc gtgatggtgg aggacaatgc acttgtgaat acaacactgt aggacaacct     420

gacaaattta aattttgcaa gacactcatt aatccaccgg gacaaaatgg catttggcct     480

caagatcgtg taaatcatac ggccaaattt caactaccca gagatactac ttgccgtggt     540

ggaatgttca aagacaagtg cttgattaga atcagatgtg gagagtttct aagatttgga     600

ggatgtttgg caataaagac gcctgccagc ccacataaac ttcaattgaa ggttgtaatt     660

ggaggtaaaa catcaatgaa aaccaaaccg gacttaccaa gaaatgatgt ttccagcatc     720

gctcaaaagg ttttcaacac actgaaagcc aaaggggcct tcgtgccgat ttcttccggc     780

agatataaaa gaagtcctgc aatgcatatt catgccttgc agcatgtaag aacccttggc     840

gttacccctt taaaatcaaa ctttgactct atggcagatg aaatttcttt caaggtgatt     900

gaattgatgc gagccaacaa ggttttcctg gtagcgaaga aggccaaatc aatattgaag     960

gattataggg actctacatc tgcagaaaga taa                                 993
```

<210> SEQ ID NO 246
<211> LENGTH: 330
<212> TYPE: PRT
<213> ORGANISM: Phakopsora pachyrhizi
<220> FEATURE:
<221> NAME/KEY: VARIANT
<222> LOCATION: (1)..(330)
<223> OTHER INFORMATION: ta09254.05_phapa

<400> SEQUENCE: 246

Met Pro His Pro Leu Trp Ile Ser Phe Val Leu Ser Val Leu Leu Gln
1 5 10 15

Val Ile Pro Leu Val Trp Gly His Cys Lys Ile Val Thr Ala Ala Gly
20 25 30

Asn Leu Asn Thr Ser Ser Gln Val Ser Tyr Gly Phe Gly Val Asp Leu
35 40 45

His Ser Lys Tyr Pro Trp Phe Lys Ser Gln Ala Gly Asp Ala Gly Ala
50 55 60

Asp Ser Glu Val Phe Thr Glu Ser Lys Glu Phe Val Ala Asn Pro Asn
65 70 75 80

Pro Pro Cys Gly Met Arg Ala Lys Met Gly Ala Leu Asp Phe Asp Ser
85 90 95

Ser Phe Ser Gln Ala Glu Ala Met Gly Val Gly Asn Thr Leu Glu Asp
100 105 110

Gly Ser Phe Glu Ala Leu Ile Phe Gln Val Asn Arg Asp Gly Gly Gly
115 120 125

Gln Cys Thr Cys Glu Tyr Asn Thr Val Gly Gln Pro Asp Lys Phe Lys
130 135 140

Phe Cys Lys Thr Leu Ile Asn Pro Pro Gly Gln Asn Gly Ile Trp Pro
145 150 155 160

Gln Asp Arg Val Asn His Thr Ala Lys Phe Gln Leu Pro Arg Asp Thr
165 170 175

Thr Cys Arg Gly Gly Met Phe Lys Asp Lys Cys Leu Ile Arg Ile Arg
180 185 190

Cys Gly Glu Phe Leu Arg Phe Gly Gly Cys Leu Ala Ile Lys Thr Pro
195 200 205

Ala Ser Pro His Lys Leu Gln Leu Lys Val Val Ile Gly Gly Lys Thr
210 215 220

Ser Met Lys Thr Lys Pro Asp Leu Pro Arg Asn Asp Val Ser Ser Ile
225 230 235 240

Ala Gln Lys Val Phe Asn Thr Leu Lys Ala Lys Gly Ala Phe Val Pro
245 250 255

Ile Ser Ser Gly Arg Tyr Lys Arg Ser Pro Ala Met His Ile His Ala
260 265 270

Leu Gln His Val Arg Thr Leu Gly Val Thr Pro Leu Lys Ser Asn Phe
275 280 285

Asp Ser Met Ala Asp Glu Ile Ser Phe Lys Val Ile Glu Leu Met Arg
290 295 300

Ala Asn Lys Val Phe Leu Val Ala Lys Lys Ala Lys Ser Ile Leu Lys
305 310 315 320

Asp Tyr Arg Asp Ser Thr Ser Ala Glu Arg
325 330

<210> SEQ ID NO 247
<211> LENGTH: 978
<212> TYPE: DNA
<213> ORGANISM: Phakopsora pachyrhizi
<220> FEATURE:
<221> NAME/KEY: misc_feature
<222> LOCATION: (1)..(978)
<223> OTHER INFORMATION: ta10705.02_phapa

<400> SEQUENCE: 247
atgcaaaagc tctacattct gcttcttttt tccattataa aactctgctc ttccgggctt 60

```
ataggttttg aagctgaaag atttaataat ccaaacacat ggaaaacagt tggcgaaatc    120

cacgaaataa ctccaacaga attaagcaga caaattaagg ccggaagtcc aattatcatc    180

agtgattttc ataaaacatt gataggcgat gaaaaggatc caaatcagtg gaaacggctt    240

aaaaaattaa tgactaaagt caccaagcac acaagatttg tgataatctc tcgtgggttc    300

agtgaaaaga tgattgaaaa ccttgcgcat ttgaatgggt tgtcaatttt ccaagggatg    360

gggtcaattt tttatcacga cggacaatat attgagttgt ttcctaatgt ttttggagag    420

ttcaatttta taaagagaaa aattattgaa cctgtactta caaaggtagg aaattcgcat    480

agcatggacg acgtaaagtg gtacaaaatc atcgaaaaat cactcaggtt tgactttaat    540

gaaaaatttg atgcaaacgt tccttcaaat agagcaaaac aaatcaagaa aaatatagct    600

gaagaaattc aacgaagaat tggagtagct agggagaaag aggaaccagt gattaagcta    660

gaatggaaag ttgatcacgt accgggtaaa ggcagtgtca gattactccc ttcaaattgt    720

aacaagctgg atctattaaa cttttactta gaaaaaattc aagcaggaaa tcctaatttg    780

atcagcttgg ggaatggtgc agaagatgaa gctttacatg gttttgtaaa caatcaaaaa    840

cattttgaaa acgatgtctt tgaatcagtg ttggtgcgta aacctgatga aaaggatcca    900

aaccgtatga gtgttgcaaa aaatcgcatg aacaactttg aagaagtaca caaattcttg    960

gaaatttata gctcttaa                                                   978
```

```
<210> SEQ ID NO 248
<211> LENGTH: 325
<212> TYPE: PRT
<213> ORGANISM: Phakopsora pachyrhizi
<220> FEATURE:
<221> NAME/KEY: VARIANT
<222> LOCATION: (1)..(325)
<223> OTHER INFORMATION: ta10705.02_phapa

<400> SEQUENCE: 248

Met Gln Lys Leu Tyr Ile Leu Leu Leu Phe Ser Ile Ile Lys Leu Cys
1               5                   10                  15

Ser Ser Gly Leu Ile Gly Phe Glu Ala Glu Arg Phe Asn Asn Pro Asn
            20                  25                  30

Thr Trp Lys Thr Val Gly Glu Ile His Glu Ile Thr Pro Thr Glu Leu
        35                  40                  45

Ser Arg Gln Ile Lys Ala Gly Ser Pro Ile Ile Ile Ser Asp Phe His
    50                  55                  60

Lys Thr Leu Ile Gly Asp Glu Lys Asp Pro Asn Gln Trp Lys Arg Leu
65                  70                  75                  80

Lys Lys Leu Met Thr Lys Val Thr Lys His Thr Arg Phe Val Ile Ile
                85                  90                  95

Ser Arg Gly Phe Ser Glu Lys Met Ile Glu Asn Leu Ala His Leu Asn
            100                 105                 110

Gly Leu Ser Ile Phe Gln Gly Met Gly Ser Ile Phe Tyr His Asp Gly
        115                 120                 125

Gln Tyr Ile Glu Leu Phe Pro Asn Val Phe Gly Glu Phe Asn Phe Ile
    130                 135                 140

Lys Arg Lys Ile Ile Glu Pro Val Leu Thr Lys Val Gly Asn Ser His
145                 150                 155                 160

Ser Met Asp Asp Val Lys Trp Tyr Lys Ile Ile Glu Lys Ser Leu Arg
                165                 170                 175

Phe Asp Phe Asn Glu Lys Phe Asp Ala Asn Val Pro Ser Asn Arg Ala
```

```
            180                 185                 190

Lys Gln Ile Lys Lys Asn Ile Ala Glu Glu Ile Gln Arg Arg Ile Gly
        195                 200                 205

Val Ala Arg Glu Lys Glu Glu Pro Val Ile Lys Leu Glu Trp Lys Val
    210                 215                 220

Asp His Val Pro Gly Lys Gly Ser Val Arg Leu Leu Pro Ser Asn Cys
225                 230                 235                 240

Asn Lys Leu Asp Leu Leu Asn Phe Tyr Leu Glu Lys Ile Gln Ala Gly
                245                 250                 255

Asn Pro Asn Leu Ile Ser Leu Gly Asn Gly Ala Glu Asp Glu Ala Leu
            260                 265                 270

His Gly Phe Val Asn Asn Gln Lys His Phe Glu Asn Asp Val Phe Glu
        275                 280                 285

Ser Val Leu Val Arg Lys Pro Asp Glu Lys Asp Pro Asn Arg Met Ser
    290                 295                 300

Val Ala Lys Asn Arg Met Asn Asn Phe Glu Glu Val His Lys Phe Leu
305                 310                 315                 320

Glu Ile Tyr Ser Ser
                325
```

<210> SEQ ID NO 249
<211> LENGTH: 963
<212> TYPE: DNA
<213> ORGANISM: Phakopsora pachyrhizi
<220> FEATURE:
<221> NAME/KEY: misc_feature
<222> LOCATION: (1)..(963)
<223> OTHER INFORMATION: ta10430.01_phapa

<400> SEQUENCE: 249

```
atgcagtcct gctggatttt ttttcaccat ttattattcc tgcctcggat ttggggccgt      60

tgttatggtg caataaaatt caatgatatg aatcaatttg ggctagctgt tgaaatctgt     120

ggtcaggtct taaattcttt aggcgcaatt tttggattgg gtctgttgcc tagccgcttg     180

ggcaacttca aaagtatcct gattatggcg ggatattcca taaaaatccg gtcatctcga     240

gctgcgtttc tactaaaagc aaatcctagt acagacctta agaagattga taagaacgac     300

ctactagaag ttttaagcgc ctactatgaa tttaaaattg agagattgga ggcgggtatt     360

gaccaagatg aaatcaacat cgaagatcaa gtaatgattc tgaatgaaat agaactcttt     420

agagtaaaaa aggcaataga agctttgact agaaggttgt cttggtataa atctcagcct     480

agtgaaactc atcacgcgtt tccaattttc ggggctttat ttattataat tttatctttg     540

ataaacagca ttgctaattg tgtactttgc tactttatgt ggacatactc tgcttcgaaa     600

aggccaatga ttgcgctttt gatctgtggc gcaatattag ttcttactgg aatttcatct     660

gcggcattaa tttggttttt gggtgtaaag actaaaaaga aggtagagaa aattcaaggc     720

ggattgatac caacaataga agaagacgta gaagaggaag agaacgacga tgataaatat     780

gaagatgttg atgttgatgt aagaagagat attcaccagg gtggaaatta tgttccagga     840

gaagagagcc aacaatttat gaataacttt gaaaacgaag aaacgcaagt tgagcaaagg     900

gagcaacatg aagccgaaaa cgatgacggc aattgccgat caaagagcga tcgctatatg     960

tag                                                                   963
```

<210> SEQ ID NO 250
<211> LENGTH: 320
<212> TYPE: PRT

<213> ORGANISM: Phakopsora pachyrhizi
<220> FEATURE:
<221> NAME/KEY: VARIANT
<222> LOCATION: (1)..(320)
<223> OTHER INFORMATION: ta10430.01_phapa

<400> SEQUENCE: 250

```
Met Gln Ser Cys Trp Ile Phe Phe His His Leu Leu Phe Leu Pro Arg
1               5                   10                  15

Ile Trp Gly Arg Cys Tyr Gly Ala Ile Lys Phe Asn Asp Met Asn Gln
            20                  25                  30

Phe Gly Leu Ala Val Glu Ile Cys Gly Gln Val Leu Asn Ser Leu Gly
        35                  40                  45

Ala Ile Phe Gly Leu Gly Leu Leu Pro Ser Arg Leu Gly Asn Phe Lys
    50                  55                  60

Ser Ile Leu Ile Met Ala Gly Tyr Ser Ile Lys Ile Arg Ser Ser Arg
65                  70                  75                  80

Ala Ala Phe Leu Leu Lys Ala Asn Pro Ser Thr Asp Leu Lys Lys Ile
                85                  90                  95

Asp Lys Asn Asp Leu Leu Glu Val Leu Ser Ala Tyr Tyr Glu Phe Lys
            100                 105                 110

Ile Glu Arg Leu Glu Ala Gly Ile Asp Gln Asp Glu Ile Asn Ile Glu
        115                 120                 125

Asp Gln Val Met Ile Leu Asn Glu Ile Glu Leu Phe Arg Val Lys Lys
    130                 135                 140

Ala Ile Glu Ala Leu Thr Arg Arg Leu Ser Trp Tyr Lys Ser Gln Pro
145                 150                 155                 160

Ser Glu Thr His His Ala Phe Pro Ile Phe Gly Ala Leu Phe Ile Ile
                165                 170                 175

Ile Leu Ser Leu Ile Asn Ser Ile Ala Asn Cys Val Leu Cys Tyr Phe
            180                 185                 190

Met Trp Thr Tyr Ser Ala Ser Lys Arg Pro Met Ile Ala Leu Leu Ile
        195                 200                 205

Cys Gly Ala Ile Leu Val Leu Thr Gly Ile Ser Ser Ala Ala Leu Ile
    210                 215                 220

Trp Phe Leu Gly Val Lys Thr Lys Lys Lys Val Glu Lys Ile Gln Gly
225                 230                 235                 240

Gly Leu Ile Pro Thr Ile Glu Glu Asp Val Glu Glu Glu Glu Asn Asp
                245                 250                 255

Asp Asp Lys Tyr Glu Asp Val Asp Val Asp Val Arg Arg Asp Ile His
            260                 265                 270

Gln Gly Gly Asn Tyr Val Pro Gly Glu Glu Ser Gln Gln Phe Met Asn
        275                 280                 285

Asn Phe Glu Asn Glu Glu Thr Gln Val Glu Gln Arg Glu Gln His Glu
    290                 295                 300

Ala Glu Asn Asp Asp Gly Asn Cys Arg Ser Lys Ser Asp Arg Tyr Met
305                 310                 315                 320
```

<210> SEQ ID NO 251
<211> LENGTH: 954
<212> TYPE: DNA
<213> ORGANISM: Phakopsora pachyrhizi
<220> FEATURE:
<221> NAME/KEY: misc_feature
<222> LOCATION: (1)..(954)
<223> OTHER INFORMATION: ta08910.01_phapa

<400> SEQUENCE: 251

```
atgccaaaaa acctgtctgt gataatatgc ctcttagtaa gccttaatgt ttttcaagga      60

gctggggcaa gctttttgac aaagactgta ggaagtgttg atggtgagcc cagcttcagc     120

tcttggagcg ctgcttggat gtctaatgct aggaatgcta aggccaatat tgttaaatcg     180

aatggtgtgc tggaaaaagc ggcatacacc ttccctaagc aattatcctt gtctgataag     240

gagatgaaaa acctcaaaga atttaatttt catggtgaac cacaaattgc cgcccagtac     300

agagacctta ttaatagtta ctcatcgcca gagcagataa tccttcacaa ggaaaataaa     360

gaaagcttag ctttattaaa cagaaattta aaagagctta ccactgagga caaagaagca     420

ctagaaaaat gggcaagcaa aaactttcgc cctgatatct tagtagaaaa tgaacgccca     480

aacgaatttc aaaatgctaa ggctgcttta gattggaacc tcaagagagc ttctgctaaa     540

caagatgtat ggtggaccga aaaagatctt caacattggg gtgaaaaaaa ttctgatgaa     600

acggttatca ttaaatttgg tgatctcttt aagtttgatg aaaagagcaa agattattta     660

tttaaagaaa accctgtcca attaggtatg aagcttttca aagcccttga aaaaccatca     720

gatgatgtta ttttcaaaaa gcgagtagtt tggcccgtta aagaagtgca attattggga     780

ttaatcaagg ccgaagactc agataaatct ttacttcata tgcgattgga tcaaatgttt     840

aagagctcaa acaacttaaa aggccaaaca aattctgaaa ctggaaacat tcgtaatatt     900

attcgttctt caatctctgg taaaactgaa actgaaaaaa atttgcacca atag          954
```

<210> SEQ ID NO 252
<211> LENGTH: 317
<212> TYPE: PRT
<213> ORGANISM: Phakopsora pachyrhizi
<220> FEATURE:
<221> NAME/KEY: VARIANT
<222> LOCATION: (1)..(317)
<223> OTHER INFORMATION: ta08910.01_phapa

<400> SEQUENCE: 252

```
Met Pro Lys Asn Leu Ser Val Ile Ile Cys Leu Leu Val Ser Leu Asn
1               5                   10                  15

Val Phe Gln Gly Ala Gly Ala Ser Phe Leu Thr Lys Thr Val Gly Ser
            20                  25                  30

Val Asp Gly Glu Pro Ser Phe Ser Ser Trp Ser Ala Ala Trp Met Ser
        35                  40                  45

Asn Ala Arg Asn Ala Lys Ala Asn Ile Val Lys Ser Asn Gly Val Leu
    50                  55                  60

Glu Lys Ala Ala Tyr Thr Phe Pro Lys Gln Leu Ser Leu Ser Asp Lys
65                  70                  75                  80

Glu Met Lys Asn Leu Lys Glu Phe Asn Phe His Gly Glu Pro Gln Ile
                85                  90                  95

Ala Ala Gln Tyr Arg Asp Leu Ile Asn Ser Tyr Ser Ser Pro Glu Gln
            100                 105                 110

Ile Ile Leu His Lys Glu Asn Lys Glu Ser Leu Ala Leu Leu Asn Arg
        115                 120                 125

Asn Leu Lys Glu Leu Thr Thr Glu Asp Lys Glu Ala Leu Glu Lys Trp
    130                 135                 140

Ala Ser Lys Asn Phe Arg Pro Asp Ile Leu Val Glu Asn Glu Arg Pro
145                 150                 155                 160

Asn Glu Phe Gln Asn Ala Lys Ala Ala Leu Asp Trp Asn Leu Lys Arg
                165                 170                 175

Ala Ser Ala Lys Gln Asp Val Trp Trp Thr Glu Lys Asp Leu Gln His
```

```
            180                 185                 190

Trp Gly Glu Lys Asn Ser Asp Glu Thr Val Ile Ile Lys Phe Gly Asp
        195                 200                 205

Leu Phe Lys Phe Asp Glu Lys Ser Lys Asp Tyr Leu Phe Lys Glu Asn
    210                 215                 220

Pro Val Gln Leu Gly Met Lys Leu Phe Lys Ala Leu Glu Lys Pro Ser
225                 230                 235                 240

Asp Asp Val Ile Phe Lys Lys Arg Val Val Trp Pro Val Lys Glu Val
                245                 250                 255

Gln Leu Leu Gly Leu Ile Lys Ala Glu Asp Ser Asp Lys Ser Leu Leu
            260                 265                 270

His Met Arg Leu Asp Gln Met Phe Lys Ser Ser Asn Asn Leu Lys Gly
        275                 280                 285

Gln Thr Asn Ser Glu Thr Gly Asn Ile Arg Asn Ile Ile Arg Ser Ser
    290                 295                 300

Ile Ser Gly Lys Thr Glu Thr Glu Lys Asn Leu His Gln
305                 310                 315
```

<210> SEQ ID NO 253
<211> LENGTH: 948
<212> TYPE: DNA
<213> ORGANISM: Phakopsora pachyrhizi
<220> FEATURE:
<221> NAME/KEY: misc_feature
<222> LOCATION: (1)..(948)
<223> OTHER INFORMATION: ta00023.01_phapa

<400> SEQUENCE: 253

```
atgccaacct tcagcttcac ctggacagac gctgcactgt tcgggctgac tgcaggattg      60

atcgccacga tcgccctgat cggtcgcagc tcatcatcac aatctaaaaa gagcgtctta     120

gattcatcca gaacaaacca gtcccagagc tccaagaaga gtaagaagaa gaataaacct     180

aagaagtctc ctccccaacc cagctctcag acaacaatcg gctctaatca gaaatccgaa     240

ccaaggcata ccgatgagag gaaggcttca ccccctaaat cttctaaccc atcacccaaa     300

ccgatctctg agccgaagaa gaaaaagatt caacagcccc aaattcctaa actcgatgac     360

aatgagtttc ctacccttgc aaattcgact ggaatgtcag ctgttagagc taaagaatct     420

aaagatgtac cgattgctga gaggagacgc gcaaatgcgc caaagacagc agttgatgat     480

atgattgatg aagaggtaga aaaacctgtt cagatggcac gagtgatggc aattgtcgag     540

ccagaaccaa agattatact gaatcaagag agtgacccag aagatggctg ggagaaagtt     600

cccaattcta aaaaaccgcg aggggcagga agtgctatgt ctactacatc ctcatcagta     660

tctcgaagtg ctgtgccaaa gcaaagcaac gcagactcat ccagcgctgc ctccactaag     720

cgacagcgac agaacgctaa gaaaaaggaa gctgcaaagt caatcaaaga ggcagaagag     780

gcagaacgac tcagtaggct tgcatcttac aagcgtcagc aggagaatga gaggatccga     840

agtcaagcca ctggtagtac taaacctacc ggccagaact caaacaaccc ctcaggtgct     900

aaacaggact caaagcttgc cccgaatggg caacttattt gggaatga                 948
```

<210> SEQ ID NO 254
<211> LENGTH: 315
<212> TYPE: PRT
<213> ORGANISM: Phakopsora pachyrhizi
<220> FEATURE:
<221> NAME/KEY: VARIANT
<222> LOCATION: (1)..(315)
<223> OTHER INFORMATION: ta00023.01_phapa

<400> SEQUENCE: 254

```
Met Pro Thr Phe Ser Phe Thr Trp Thr Asp Ala Ala Leu Phe Gly Leu
1               5                   10                  15

Thr Ala Gly Leu Ile Ala Thr Ile Ala Leu Ile Gly Arg Ser Ser Ser
            20                  25                  30

Ser Gln Ser Lys Lys Ser Val Leu Asp Ser Ser Arg Thr Asn Gln Ser
        35                  40                  45

Gln Ser Ser Lys Lys Ser Lys Lys Lys Asn Lys Pro Lys Lys Ser Pro
    50                  55                  60

Pro Gln Pro Ser Ser Gln Thr Thr Ile Gly Ser Asn Gln Lys Ser Glu
65                  70                  75                  80

Pro Arg His Thr Asp Glu Arg Lys Ala Ser Pro Pro Lys Ser Ser Asn
                85                  90                  95

Pro Ser Pro Lys Pro Ile Ser Glu Pro Lys Lys Lys Lys Ile Gln Gln
            100                 105                 110

Pro Gln Ile Pro Lys Leu Asp Asp Asn Glu Phe Pro Thr Leu Ala Asn
        115                 120                 125

Ser Thr Gly Met Ser Ala Val Arg Ala Lys Glu Ser Lys Asp Val Pro
    130                 135                 140

Ile Ala Glu Arg Arg Arg Ala Asn Ala Pro Lys Thr Ala Val Asp Asp
145                 150                 155                 160

Met Ile Asp Glu Glu Val Glu Lys Pro Val Gln Met Ala Arg Val Met
                165                 170                 175

Ala Ile Val Glu Pro Glu Pro Lys Ile Ile Leu Asn Gln Glu Ser Asp
            180                 185                 190

Pro Glu Asp Gly Trp Glu Lys Val Pro Asn Ser Lys Lys Pro Arg Gly
        195                 200                 205

Ala Gly Ser Ala Met Ser Thr Thr Ser Ser Ser Val Ser Arg Ser Ala
    210                 215                 220

Val Pro Lys Gln Ser Asn Ala Asp Ser Ser Ser Ala Ala Ser Thr Lys
225                 230                 235                 240

Arg Gln Arg Gln Asn Ala Lys Lys Lys Glu Ala Ala Lys Ser Ile Lys
                245                 250                 255

Glu Ala Glu Glu Ala Glu Arg Leu Ser Arg Leu Ala Ser Tyr Lys Arg
            260                 265                 270

Gln Gln Glu Asn Glu Arg Ile Arg Ser Gln Ala Thr Gly Ser Thr Lys
        275                 280                 285

Pro Thr Gly Gln Asn Ser Asn Asn Pro Ser Gly Ala Lys Gln Asp Ser
    290                 295                 300

Lys Leu Ala Pro Asn Gly Gln Leu Ile Trp Glu
305                 310                 315
```

<210> SEQ ID NO 255
<211> LENGTH: 924
<212> TYPE: DNA
<213> ORGANISM: Phakopsora pachyrhizi
<220> FEATURE:
<221> NAME/KEY: misc_feature
<222> LOCATION: (1)..(924)
<223> OTHER INFORMATION: ta04133.01_phapa

<400> SEQUENCE: 255

```
atgaaccgaa ttaggatagc catcgtctta gcttctttaa gcttggcgaa ctgccaattt      60

ttatttgggg atcctgcagc agatgctcag aacagctcaa caaatcaggc taattcaaca     120
```

-continued

```
ggctctaaac tttcacccac tcaaagcagt gaccaaactg ttcctttgac ttattcctca    180

aattccagtg atacaaactc attgaactca gctaatggca cagctactaa tagctctatc    240

ctaacaggcg gcacgaacgc ttttgacaat actggttcta atagctccat caaaacaaac    300

ggcagcagcc tttttaacgg tactgctacc aacagctcta ttcaatccac agggctcatt    360

ggtagctata atgggacaat ctcaccctcc aaaaacactt caatgttttc agaagtctac    420

actttagact acagtattaa atgggatgaa agtgatttca atgtctatgg ccaaaatggt    480

aaagttgaat ataccattag taacaaagtg gagggagtca acatgtcaaa gaaagaattt    540

gttgtgaaag aagccaccga tggacaagca aaagttagaa ttgacgccaa taataaattc    600

tgtggatttg gtaaaactta cacatcagat gatggggcaa gctttacaat cgacccacgc    660

atgtttttac ctgatcgctg gtttatcagg caaagcaatg ttacgtacgt tttaaaacgc    720

ttcgccatga gtcttaatgg agatatcttg gatgtcgaaa acaagcgcct tgtagcgcag    780

gtcaaagtcg acaaagctaa tactacgagt gaagaaaaga agaaaaagat gatcatttta    840

aattcagatg gttctatctc aggttgggat ttggttgcct tcatcgctgt ggttagaaat    900

cgcatccgcc aatgcggtta ctaa                                            924
```

<210> SEQ ID NO 256
<211> LENGTH: 307
<212> TYPE: PRT
<213> ORGANISM: Phakopsora pachyrhizi
<220> FEATURE:
<221> NAME/KEY: VARIANT
<222> LOCATION: (1)..(307)
<223> OTHER INFORMATION: ta04133.01_phapa

<400> SEQUENCE: 256

```
Met Asn Arg Ile Arg Ile Ala Ile Val Leu Ala Ser Leu Ser Leu Ala
1               5                   10                  15

Asn Cys Gln Phe Leu Phe Gly Asp Pro Ala Ala Asp Ala Gln Asn Ser
            20                  25                  30

Ser Thr Asn Gln Ala Asn Ser Thr Gly Ser Lys Leu Ser Pro Thr Gln
        35                  40                  45

Ser Ser Asp Gln Thr Val Pro Leu Thr Tyr Ser Ser Asn Ser Ser Asp
    50                  55                  60

Thr Asn Ser Leu Asn Ser Ala Asn Gly Thr Ala Thr Asn Ser Ser Ile
65                  70                  75                  80

Leu Thr Gly Gly Thr Asn Ala Phe Asp Asn Thr Gly Ser Asn Ser Ser
                85                  90                  95

Ile Lys Thr Asn Gly Ser Ser Leu Phe Asn Gly Thr Ala Thr Asn Ser
            100                 105                 110

Ser Ile Gln Ser Thr Gly Leu Ile Gly Ser Tyr Asn Gly Thr Ile Ser
        115                 120                 125

Pro Ser Lys Asn Thr Ser Met Phe Ser Glu Val Tyr Thr Leu Asp Tyr
    130                 135                 140

Ser Ile Lys Trp Asp Glu Ser Asp Phe Asn Val Tyr Gly Gln Asn Gly
145                 150                 155                 160

Lys Val Glu Tyr Thr Ile Ser Asn Lys Val Glu Gly Val Asn Met Ser
                165                 170                 175

Lys Lys Glu Phe Val Val Lys Glu Ala Thr Asp Gly Gln Ala Lys Val
            180                 185                 190

Arg Ile Asp Ala Asn Asn Lys Phe Cys Gly Phe Gly Lys Thr Tyr Thr
        195                 200                 205
```

```
Ser Asp Asp Gly Ala Ser Phe Thr Ile Asp Pro Arg Met Phe Leu Pro
    210                 215                 220

Asp Arg Trp Phe Ile Arg Gln Ser Asn Val Thr Tyr Val Phe Lys Arg
225                 230                 235                 240

Phe Ala Met Ser Leu Asn Gly Asp Ile Leu Asp Val Glu Asn Lys Arg
                245                 250                 255

Leu Val Ala Gln Val Lys Val Asp Lys Ala Asn Thr Thr Ser Glu Glu
            260                 265                 270

Lys Lys Lys Lys Met Ile Ile Leu Asn Ser Asp Gly Ser Ile Ser Gly
        275                 280                 285

Trp Asp Leu Val Ala Phe Ile Ala Val Val Arg Asn Arg Ile Arg Gln
    290                 295                 300

Cys Gly Tyr
305
```

<210> SEQ ID NO 257
<211> LENGTH: 906
<212> TYPE: DNA
<213> ORGANISM: Phakopsora pachyrhizi
<220> FEATURE:
<221> NAME/KEY: misc_feature
<222> LOCATION: (1)..(906)
<223> OTHER INFORMATION: ta10945.01_phapa

<400> SEQUENCE: 257

```
atgtactcaa aaatctcaaa cctttctatt ctcttagtga cttcaagttt tattttctta      60

aattgtgcag attgctttac cacaaatttt caatcaagga ctagtgagta caagcctgct     120

tcaaactcag tgcagaacgt aacgataaaa gattctggag ataaaaaata ttttcctgtt     180

cgttttgtca ctgtctacgc accggcctct caacatcaag caacgtcctc tgatcaaaac     240

attagtcaag taaccaaagg tgaaaatgta acaagtaccc cttcaaatga gaagccgaga     300

gatactgttt acgtcaacga atcagaagtt ggtaacttga ttccgatggc aacccaagga     360

attcttgatg aagtctatgt gatgaataga gaattggatt ggaccaataa cgagtttccg     420

atctacaact caacaggggg aatcgcttat acgattacca ataagataaa cggctctcag     480

ttggcagagt cacagttcgc aatcatcggt cctgaccgtt ggttagttct aacttctgat     540

acgaaatctg gtctctgtgg tttttcaaat gagtactctt cctccgacca cgttttatac     600

agcttaagac caagactttt catgccagat cgttggtacc tatctggtga cttggtcagt     660

ccactgaaag atcatgctta cgaatttcgc cggggtgctc taagttttga gggtgatata     720

ctcactttgg gaactcatac cagacatgct aagatcagca atggtaaatt ggctcaaggg     780

tggatcgata agaagattcc gggtggccgc acaatttccg tctttactga tggtactatt     840

cctttgccaa acttaatttc tctgatagtg ataagcgtga caagaattaa aaaatgcggt     900

ttttag                                                                906
```

<210> SEQ ID NO 258
<211> LENGTH: 301
<212> TYPE: PRT
<213> ORGANISM: Phakopsora pachyrhizi
<220> FEATURE:
<221> NAME/KEY: VARIANT
<222> LOCATION: (1)..(301)
<223> OTHER INFORMATION: ta10945.01_phapa

<400> SEQUENCE: 258

```
Met Tyr Ser Lys Ile Ser Asn Leu Ser Ile Leu Leu Val Thr Ser Ser
1               5                   10                  15
```

```
Phe Ile Phe Leu Asn Cys Ala Asp Cys Phe Thr Thr Asn Phe Gln Ser
            20                  25                  30

Arg Thr Ser Glu Tyr Lys Pro Ala Ser Asn Ser Val Gln Asn Val Thr
        35                  40                  45

Ile Lys Asp Ser Gly Asp Lys Lys Tyr Phe Pro Val Arg Phe Val Thr
    50                  55                  60

Val Tyr Ala Pro Ala Ser Gln His Gln Ala Thr Ser Ser Asp Gln Asn
65                  70                  75                  80

Ile Ser Gln Val Thr Lys Gly Glu Asn Val Thr Ser Thr Pro Ser Asn
                85                  90                  95

Glu Lys Pro Arg Asp Thr Val Tyr Val Asn Glu Ser Glu Val Gly Asn
            100                 105                 110

Leu Ile Pro Met Ala Thr Gln Gly Ile Leu Asp Glu Val Tyr Val Met
        115                 120                 125

Asn Arg Glu Leu Asp Trp Thr Asn Asn Glu Phe Pro Ile Tyr Asn Ser
    130                 135                 140

Thr Gly Gly Ile Ala Tyr Thr Ile Thr Asn Lys Ile Asn Gly Ser Gln
145                 150                 155                 160

Leu Ala Glu Ser Gln Phe Ala Ile Ile Gly Pro Asp Arg Trp Leu Val
                165                 170                 175

Leu Thr Ser Asp Thr Lys Ser Gly Leu Cys Gly Phe Ser Asn Glu Tyr
            180                 185                 190

Ser Ser Ser Asp His Val Leu Tyr Ser Leu Arg Pro Arg Leu Phe Met
        195                 200                 205

Pro Asp Arg Trp Tyr Leu Ser Gly Asp Leu Val Ser Pro Leu Lys Asp
    210                 215                 220

His Ala Tyr Glu Phe Arg Arg Gly Ala Leu Ser Phe Glu Gly Asp Ile
225                 230                 235                 240

Leu Thr Leu Gly Thr His Thr Arg His Ala Lys Ile Ser Asn Gly Lys
                245                 250                 255

Leu Ala Gln Gly Trp Ile Asp Lys Lys Ile Pro Gly Gly Arg Thr Ile
            260                 265                 270

Ser Val Phe Thr Asp Gly Thr Ile Pro Leu Pro Asn Leu Ile Ser Leu
        275                 280                 285

Ile Val Ile Ser Val Thr Arg Ile Lys Lys Cys Gly Phe
    290                 295                 300
```

```
<210> SEQ ID NO 259
<211> LENGTH: 892
<212> TYPE: DNA
<213> ORGANISM: Phakopsora pachyrhizi
<220> FEATURE:
<221> NAME/KEY: misc_feature
<222> LOCATION: (1)..(892)
<223> OTHER INFORMATION: ta00652.01

<400> SEQUENCE: 259

atgccaactc ttagatcaat ccgctaccga aggaccttgc tagcatgcat tggtattatg      60

tcctcaatct cagctcagaa cattaccagt gactttccag ccagcgacac tctttcaaca     120

gcctgtaggg attcaataaa taatttaatt aacggagaat ttgggaagtg ttcaaaaatt     180

tcagatttaa ttcaatttgc ctactcgaat aattccaacc cgttatctag gtacagcaac     240

tatgttaaaa atttttgtga ggctgaggtg tgctcgagtg aaattttatc caagacggtc     300

aagtctttaa gatctacatg cctctctgac ctaaaaactg ggaatattga tgtcatcaga     360
```

```
acttatgcca cgagctctca atactcactt ctacgtaatt ccctctgcct aagacgtgtt    420

tccgactcta ccctgtgcct cacctcaatg ctggatgaat tacaagtgtt tgggaaggtc    480

ccttttagtg tttctcagat tgaaaacgtt gtaataggag gattcccatc cattatatct    540

tcacttgata acctaccaga aaaattttgt aatgactgca ttcatggtct cattacagtg    600

ctacctagca caacagctaa cggtgacgca gccctaccac cggtcgctaa aggccttcct    660

gatggtgtca agattcaagc ccatccaatc ttacaaaatg cgcaacctgc cacaatgacc    720

attgctgcat tgtgtggtgc ttctgtgatt gatggaaaaa ttcctccaag tctggtcaca    780

ggcttgggta gtcgtccagc tgcaaacgct agcttcgttt caaagacatc ggacgcttct    840

cgcaccactt tttacacctc aaactgcaaa cgactggctt gctcagctgc at            892


<210> SEQ ID NO 260
<211> LENGTH: 297
<212> TYPE: PRT
<213> ORGANISM: Phakopsora pachyrhizi
<220> FEATURE:
<221> NAME/KEY: VARIANT
<222> LOCATION: (1)..(297)
<223> OTHER INFORMATION: ta00652.01_phapa

<400> SEQUENCE: 260

Met Pro Thr Leu Arg Ser Ile Arg Tyr Arg Arg Thr Leu Leu Ala Cys
1               5                   10                  15

Ile Gly Ile Met Ser Ser Ile Ser Ala Gln Asn Ile Thr Ser Asp Phe
            20                  25                  30

Pro Ala Ser Asp Thr Leu Ser Thr Ala Cys Arg Asp Ser Ile Asn Asn
        35                  40                  45

Leu Ile Asn Gly Glu Phe Gly Lys Cys Ser Lys Ile Ser Asp Leu Ile
    50                  55                  60

Gln Phe Ala Tyr Ser Asn Asn Ser Asn Pro Leu Ser Arg Tyr Ser Asn
65                  70                  75                  80

Tyr Val Lys Asn Phe Cys Glu Ala Glu Val Cys Ser Ser Glu Ile Leu
                85                  90                  95

Ser Lys Thr Val Lys Ser Leu Arg Ser Thr Cys Leu Ser Asp Leu Lys
            100                 105                 110

Thr Gly Asn Ile Asp Val Ile Arg Thr Tyr Ala Thr Ser Ser Gln Tyr
        115                 120                 125

Ser Leu Leu Arg Asn Ser Leu Cys Leu Arg Arg Val Ser Asp Ser Thr
    130                 135                 140

Leu Cys Leu Thr Ser Met Leu Asp Glu Leu Gln Val Phe Gly Lys Val
145                 150                 155                 160

Pro Phe Ser Val Ser Gln Ile Glu Asn Val Val Ile Gly Gly Phe Pro
                165                 170                 175

Ser Ile Ile Ser Ser Leu Asp Asn Leu Pro Glu Lys Phe Cys Asn Asp
            180                 185                 190

Cys Ile His Gly Leu Ile Thr Val Leu Pro Ser Thr Thr Ala Asn Gly
        195                 200                 205

Asp Ala Ala Leu Pro Pro Val Ala Lys Gly Leu Pro Asp Gly Val Lys
    210                 215                 220

Ile Gln Ala His Pro Ile Leu Gln Asn Ala Gln Pro Ala Thr Met Thr
225                 230                 235                 240

Ile Ala Ala Leu Cys Gly Ala Ser Val Ile Asp Gly Lys Ile Pro Pro
                245                 250                 255

Ser Leu Val Thr Gly Leu Gly Ser Arg Pro Ala Ala Asn Ala Ser Phe
```

```
            260                 265                 270

Val Ser Lys Thr Ser Asp Ala Ser Arg Thr Thr Phe Tyr Thr Ser Asn
        275                 280                 285

Cys Lys Arg Leu Ala Cys Ser Ala Ala
    290                 295


<210> SEQ ID NO 261
<211> LENGTH: 886
<212> TYPE: DNA
<213> ORGANISM: Phakopsora pachyrhizi
<220> FEATURE:
<221> NAME/KEY: misc_feature
<222> LOCATION: (1)..(886)
<223> OTHER INFORMATION: ta03308.01

<400> SEQUENCE: 261

atgcgattgc ttttgaaact ttgttgtttt ttgacttttt tttgcaactg ggggtctacc      60

aggcaatgct taagactatt tcagaaaata gatagcccca atgaaatttg catagtcgag     120

aacgccaacg atttaagttt caacccaact aatgagtcgg gaagttttgc gaaattatta     180

aaatcaccaa aacaaatgtc ctgtatccca acttcaagca ccaggtccaa aaaagtaaaa     240

aaaagctctg ctaaaaaaaa ccccgatatt ataaattatt ttgaatctca aggagagtgg     300

ctagagagcc aaaaagaaat agataatctc aattcacgaa agccaaaaac taaagcaaaa     360

gacttaagat caaaatcaga gaaaagcaag gaaaaaatct ccgacatttc taaaaattta     420

gttgttgatc gaaattctag atccttgccg ccaaaaaaat ctccaccttt gggagccaaa     480

gctataaaat caaagtcgtt gccgcactta agcaaatata gttttgcgga agcttatgag     540

gctttatatt taaccgattc accacggcgt cctaaaatac tcccccttaaa cagccacatc    600

gcacaaccaa aaagtaaaat atctatttca ccttccccag ctattgataa aaaccctacc     660

gagcataatt cttatgaagt cttacaaaat ttccttcggc gaaaaagcaa aagtctttcc     720

ccatcagtaa cttctggctc cagctcaaag cattttgaat ccaagcaggt tgacttaaat     780

atacccgtta cacctcacaa ggcacctaaa agtgaaattg aagagggtcg tatgattagt     840

aaattaactg atgataaaag cattggagaa ttgtccttta gattta                   886


<210> SEQ ID NO 262
<211> LENGTH: 295
<212> TYPE: PRT
<213> ORGANISM: Phakopsora pachyrhizi
<220> FEATURE:
<221> NAME/KEY: VARIANT
<222> LOCATION: (1)..(295)
<223> OTHER INFORMATION: ta03308.01_phapa

<400> SEQUENCE: 262

Met Arg Leu Leu Leu Lys Leu Cys Cys Phe Leu Thr Phe Phe Cys Asn
1               5                   10                  15

Trp Gly Ser Thr Arg Gln Cys Leu Arg Leu Phe Gln Lys Ile Asp Ser
            20                  25                  30

Pro Asn Glu Ile Cys Ile Val Glu Asn Ala Asn Asp Leu Ser Phe Asn
        35                  40                  45

Pro Thr Asn Glu Ser Gly Ser Phe Ala Lys Leu Leu Lys Ser Pro Lys
    50                  55                  60

Gln Met Ser Cys Ile Pro Thr Ser Ser Thr Arg Ser Lys Lys Val Lys
65                  70                  75                  80

Lys Ser Ser Ala Lys Lys Asn Pro Asp Ile Ile Asn Tyr Phe Glu Ser
                85                  90                  95
```

```
Gln Gly Glu Trp Leu Glu Ser Gln Lys Glu Ile Asp Asn Leu Asn Ser
            100                 105                 110

Arg Lys Pro Lys Thr Lys Ala Lys Asp Leu Arg Ser Lys Ser Glu Lys
        115                 120                 125

Ser Lys Glu Lys Ile Ser Asp Ile Ser Lys Asn Leu Val Val Asp Arg
    130                 135                 140

Asn Ser Arg Ser Leu Pro Pro Lys Lys Ser Pro Pro Leu Gly Ala Lys
145                 150                 155                 160

Ala Ile Lys Ser Lys Ser Leu Pro His Leu Ser Lys Tyr Ser Phe Ala
                165                 170                 175

Glu Ala Tyr Glu Ala Leu Tyr Leu Thr Asp Ser Pro Arg Arg Pro Lys
            180                 185                 190

Ile Leu Pro Leu Asn Ser His Ile Ala Gln Pro Lys Ser Lys Ile Ser
        195                 200                 205

Ile Ser Pro Ser Pro Ala Ile Asp Lys Asn Pro Thr Glu His Asn Ser
    210                 215                 220

Tyr Glu Val Leu Gln Asn Phe Leu Arg Arg Lys Ser Lys Ser Leu Ser
225                 230                 235                 240

Pro Ser Val Thr Ser Gly Ser Ser Ser Lys His Phe Glu Ser Lys Gln
                245                 250                 255

Val Asp Leu Asn Ile Pro Val Thr Pro His Lys Ala Pro Lys Ser Glu
            260                 265                 270

Ile Glu Glu Gly Arg Met Ile Ser Lys Leu Thr Asp Asp Lys Ser Ile
        275                 280                 285

Gly Glu Leu Ser Phe Arg Phe
    290                 295
```

<210> SEQ ID NO 263
<211> LENGTH: 882
<212> TYPE: DNA
<213> ORGANISM: Phakopsora pachyrhizi
<220> FEATURE:
<221> NAME/KEY: misc_feature
<222> LOCATION: (1)..(882)
<223> OTHER INFORMATION: ta01346.01_phapa

<400> SEQUENCE: 263

```
atggaaagaa gacaaaatta tgcatttcta tttgtccttc tggctacatt tagtctgttt     60

gggcttacct tatctattcc gatgaatacg atgttgattg cgacagatac agcaaaagct    120

acacactcag cctctgaggc tggcacagcg gcaaagatag cggaaggggt aaaatttagc    180

gatgcttcag atgtggcatt tattgacaga aatggggata gtgtgaaagg agtattagaa    240

actgctaccg atggagggaa aactgctgag agtttaaact ttggatccaa ggcgaacatg    300

ctcccaccac atgttatagt tgagcctatc cctcaaccca agcccagctt gtatgccaag    360

acaaaagcat tttttgtcag gatttggcgg aaaatgatgg ggggttttag gaaaagccca    420

ttaggtaaat taagccggaa ggtatcaaat tcaaaaccgg caaaacaaac caataattac    480

tttcaaaagg ggaggggttg gatcaatgaa aaatggagta aatcaaaatc aatccccaag    540

acgtctgaat ctgtgaatgt ttccccaggg gctgagcaca atattccaga actgaattcg    600

gtgaaacccg aagcatcagc gaagcaaaat atgctggagg tcaattccgt acaaccagag    660

gcagctgcta aacccgtaaa tactaaggtc gaggaacctg ctactattaa gactaaatcg    720

actgcttctg tggagtcaca acctgagtca accctttctg gtaaaactga gccaaaagta    780

aatggtgaac ctgaaaaagc cccggaaaaa gcagaaccaa aaccagaaaa ctcagatccc    840
```

gtatcgaaac ctccaccgcc accaactaac caagcccaat ga 882

<210> SEQ ID NO 264
<211> LENGTH: 293
<212> TYPE: PRT
<213> ORGANISM: Phakopsora pachyrhizi
<220> FEATURE:
<221> NAME/KEY: VARIANT
<222> LOCATION: (1)..(293)
<223> OTHER INFORMATION: ta01346.01_phapa

<400> SEQUENCE: 264

Met Glu Arg Arg Gln Asn Tyr Ala Phe Leu Phe Val Leu Leu Ala Thr
1 5 10 15

Phe Ser Leu Phe Gly Leu Thr Leu Ser Ile Pro Met Asn Thr Met Leu
20 25 30

Ile Ala Thr Asp Thr Ala Lys Ala Thr His Ser Ala Ser Glu Ala Gly
35 40 45

Thr Ala Ala Lys Ile Ala Glu Gly Val Lys Phe Ser Asp Ala Ser Asp
50 55 60

Val Ala Phe Ile Asp Arg Asn Gly Asp Ser Val Lys Gly Val Leu Glu
65 70 75 80

Thr Ala Thr Asp Gly Gly Lys Thr Ala Glu Ser Leu Asn Phe Gly Ser
85 90 95

Lys Ala Asn Met Leu Pro Pro His Val Ile Val Glu Pro Ile Pro Gln
100 105 110

Pro Lys Pro Ser Leu Tyr Ala Lys Thr Lys Ala Phe Phe Val Arg Ile
115 120 125

Trp Arg Lys Met Met Gly Gly Phe Arg Lys Ser Pro Leu Gly Lys Leu
130 135 140

Ser Arg Lys Val Ser Asn Ser Lys Pro Ala Lys Gln Thr Asn Asn Tyr
145 150 155 160

Phe Gln Lys Gly Arg Gly Trp Ile Asn Glu Lys Trp Ser Lys Ser Lys
165 170 175

Ser Ile Pro Lys Thr Ser Glu Ser Val Asn Val Ser Pro Gly Ala Glu
180 185 190

His Asn Ile Pro Glu Leu Asn Ser Val Lys Pro Glu Ala Ser Ala Lys
195 200 205

Gln Asn Met Leu Glu Val Asn Ser Val Gln Pro Glu Ala Ala Ala Lys
210 215 220

Pro Val Asn Thr Lys Val Glu Glu Pro Ala Thr Ile Lys Thr Lys Ser
225 230 235 240

Thr Ala Ser Val Glu Ser Gln Pro Glu Ser Thr Leu Ser Gly Lys Thr
245 250 255

Glu Pro Lys Val Asn Gly Glu Pro Glu Lys Ala Pro Glu Lys Ala Glu
260 265 270

Pro Lys Pro Glu Asn Ser Asp Pro Val Ser Lys Pro Pro Pro Pro Pro
275 280 285

Thr Asn Gln Ala Gln
290

<210> SEQ ID NO 265
<211> LENGTH: 876
<212> TYPE: DNA
<213> ORGANISM: Phakopsora pachyrhizi
<220> FEATURE:
<221> NAME/KEY: misc_feature
<222> LOCATION: (1)..(876)
<223> OTHER INFORMATION: ta03255.01_phapa

<400> SEQUENCE: 265

```
atgttgcact tttctagttt aacttctcta ggaatttttg cgtgccaaac tgcttggctc     60

gttgcagttt caaacgcctt cgtagcggaa catgcagtta tccaggacat aaccaatctt    120

gcttttagtc ctaataagat tgtagataga acacttggac aaaaaaaccc aaattttgcc    180

aagttcgtca atgcagaacc attactttat cgtgaaatgg ctcgcaaagc tggacgatct    240

gttggaacag tcttaactga ctctcgagga accaatcttc ctctactcat ccgtgacctt    300

cgagtcaccg actggattca tagcgatccg gtaattaagg gaatgccacc aaacaatcta    360

cctcaaaatg ctattgaact tgcccagaac tccttcgcat ctcgtctagt ggacattcgg    420

aacgcaaatg ataaagccaa gttcgaccag cacgcattaa tagcacgtaa ccacttagct    480

aaggtactgt tttacatcat aagtgagatg catatatcta tgcttccgaa acttgatgta    540

gtcaatgtag ctgcgtggca gaaagaaagg gcaggccgcg tcgctctttt gatgacacaa    600

aatcctttcc tcaagcggct ttattccgtc caccaacaaa tcggaaatcc ggatcaatac    660

attactcctg agactgcgga tgcagctttt atgaaacttt ttcctcatca aaattcaaac    720

aaacagggtc atccttcaca atcggcaaca tctgaaaaaa tgaaaactca ccctgagggc    780

gaaggaaact ttcctgccca tcgccctgtg gatgaaaata aagagggcat tgtccctgga    840

actcacccta atgctgcaac tgtttcttct tcttaa                              876
```

<210> SEQ ID NO 266
<211> LENGTH: 291
<212> TYPE: PRT
<213> ORGANISM: Phakopsora pachyrhizi
<220> FEATURE:
<221> NAME/KEY: VARIANT
<222> LOCATION: (1)..(291)
<223> OTHER INFORMATION: ta03255.01_phapa

<400> SEQUENCE: 266

```
Met Leu His Phe Ser Ser Leu Thr Ser Leu Gly Ile Phe Ala Cys Gln
1               5                   10                  15

Thr Ala Trp Leu Val Ala Val Ser Asn Ala Phe Val Ala Glu His Ala
            20                  25                  30

Val Ile Gln Asp Ile Thr Asn Leu Ala Phe Ser Pro Asn Lys Ile Val
        35                  40                  45

Asp Arg Thr Leu Gly Gln Lys Asn Pro Asn Phe Ala Lys Phe Val Asn
    50                  55                  60

Ala Glu Pro Leu Leu Tyr Arg Glu Met Ala Arg Lys Ala Gly Arg Ser
65                  70                  75                  80

Val Gly Thr Val Leu Thr Asp Ser Arg Gly Thr Asn Leu Pro Leu Leu
                85                  90                  95

Ile Arg Asp Leu Arg Val Thr Asp Trp Ile His Ser Asp Pro Val Ile
            100                 105                 110

Lys Gly Met Pro Pro Asn Asn Leu Pro Gln Asn Ala Ile Glu Leu Ala
        115                 120                 125

Gln Asn Ser Phe Ala Ser Arg Leu Val Asp Ile Arg Asn Ala Asn Asp
    130                 135                 140

Lys Ala Lys Phe Asp Gln His Ala Leu Ile Ala Arg Asn His Leu Ala
145                 150                 155                 160

Lys Val Leu Phe Tyr Ile Ile Ser Glu Met His Ile Ser Met Leu Pro
                165                 170                 175
```

```
Lys Leu Asp Val Val Asn Val Ala Ala Trp Gln Lys Glu Arg Ala Gly
            180                 185                 190

Arg Val Ala Leu Leu Met Thr Gln Asn Pro Phe Leu Lys Arg Leu Tyr
        195                 200                 205

Ser Val His Gln Gln Ile Gly Asn Pro Asp Gln Tyr Ile Thr Pro Glu
    210                 215                 220

Thr Ala Asp Ala Ala Phe Met Lys Leu Phe Pro His Gln Asn Ser Asn
225                 230                 235                 240

Lys Gln Gly His Pro Ser Gln Ser Ala Thr Ser Glu Lys Met Lys Thr
                245                 250                 255

His Pro Glu Gly Glu Gly Asn Phe Pro Ala His Arg Pro Val Asp Glu
            260                 265                 270

Asn Lys Glu Gly Ile Val Pro Gly Thr His Pro Asn Ala Ala Thr Val
        275                 280                 285

Ser Ser Ser
    290
```

<210> SEQ ID NO 267
<211> LENGTH: 858
<212> TYPE: DNA
<213> ORGANISM: Phakopsora pachyrhizi
<220> FEATURE:
<221> NAME/KEY: misc_feature
<222> LOCATION: (1)..(858)
<223> OTHER INFORMATION: ta10969.01_phapa

<400> SEQUENCE: 267

```
atgttttgga aagatttttt tttgcttgct tttgggttta ctaccctact ttacaaatct     60

ctagctcaaa gtcaaaatta ctctggggat gtcatgcttc agattccgga cttttatccc    120

gagaatgggg ctggtcttcc tagcaatggc aaagtatact tcagcagcct ctacaaagca    180

agtgttatag agtatgaccc gttaaataac acttatcgag agttcaaaat ccctggcatt    240

agtggcaatc ctatggccca cgtctctgga attgaagcaa gcaagtggtc cagtgatacg    300

atatgggcga taatcgaccc ggcttttgtt ttcgcgacaa atggagccaa tatgaccggg    360

ccggatgggt tagtttccat caatattact gatcagtcaa tggacatcat atacttgaaa    420

ccagtactag aaagagctca atccattaat ggcggaactc gggtagttgg cgcacaagat    480

ttggtgcaag ctcccgatgg aagcgtttac ctaataataa gcttcgggca ggcaataatc    540

aagattgtgc cacaaactag ggcgctctca gttttttata gcccaaagcc agcaatctca    600

aagatttcct atacgggaat agagctcgta tcaaatcaca cattagtagt ctggaatact    660

gctgaaggaa gattcgagac gtttgaaatc aattcgccag agccaaaggc gaaattcgtt    720

aaaattttaa attctaaatc gttggacagt cgaaaaattt atggagatgc actctttggt    780

ccgagctttg ctcaaggacg ctgtctgctt ctcagcaacc ctggtgcaaa aaccatagaa    840

gttttcacat cgaacaac                                                  858
```

<210> SEQ ID NO 268
<211> LENGTH: 286
<212> TYPE: PRT
<213> ORGANISM: Phakopsora pachyrhizi
<220> FEATURE:
<221> NAME/KEY: VARIANT
<222> LOCATION: (1)..(286)
<223> OTHER INFORMATION: ta10969.01_phapa

<400> SEQUENCE: 268

```
Met Phe Trp Lys Asp Phe Phe Leu Leu Ala Phe Gly Phe Thr Thr Leu
1               5                   10                  15

Leu Tyr Lys Ser Leu Ala Gln Ser Gln Asn Tyr Ser Gly Asp Val Met
            20                  25                  30

Leu Gln Ile Pro Asp Phe Tyr Pro Glu Asn Gly Ala Gly Leu Pro Ser
        35                  40                  45

Asn Gly Lys Val Tyr Phe Ser Ser Leu Tyr Lys Ala Ser Val Ile Glu
    50                  55                  60

Tyr Asp Pro Leu Asn Asn Thr Tyr Arg Glu Phe Lys Ile Pro Gly Ile
65                  70                  75                  80

Ser Gly Asn Pro Met Ala His Val Ser Gly Ile Glu Ala Ser Lys Trp
                85                  90                  95

Ser Ser Asp Thr Ile Trp Ala Ile Ile Asp Pro Ala Phe Val Phe Ala
            100                 105                 110

Thr Asn Gly Ala Asn Met Thr Gly Pro Asp Gly Leu Val Ser Ile Asn
        115                 120                 125

Ile Thr Asp Gln Ser Met Asp Ile Ile Tyr Leu Lys Pro Val Leu Glu
    130                 135                 140

Arg Ala Gln Ser Ile Asn Gly Gly Thr Arg Val Val Gly Ala Gln Asp
145                 150                 155                 160

Leu Val Gln Ala Pro Asp Gly Ser Val Tyr Leu Ile Ile Ser Phe Gly
                165                 170                 175

Gln Ala Ile Ile Lys Ile Val Pro Gln Thr Arg Ala Leu Ser Val Phe
            180                 185                 190

Tyr Ser Pro Lys Pro Ala Ile Ser Lys Ile Ser Tyr Thr Gly Ile Glu
        195                 200                 205

Leu Val Ser Asn His Thr Leu Val Val Trp Asn Thr Ala Glu Gly Arg
    210                 215                 220

Phe Glu Thr Phe Glu Ile Asn Ser Pro Glu Pro Lys Ala Lys Phe Val
225                 230                 235                 240

Lys Ile Leu Asn Ser Lys Ser Leu Asp Ser Arg Lys Ile Tyr Gly Asp
                245                 250                 255

Ala Leu Phe Gly Pro Ser Phe Ala Gln Gly Arg Cys Leu Leu Leu Ser
            260                 265                 270

Asn Pro Gly Ala Lys Thr Ile Glu Val Phe Thr Ser Asn Asn
        275                 280                 285
```

```
<210> SEQ ID NO 269
<211> LENGTH: 846
<212> TYPE: DNA
<213> ORGANISM: Phakopsora pachyrhizi
<220> FEATURE:
<221> NAME/KEY: misc_feature
<222> LOCATION: (1)..(846)
<223> OTHER INFORMATION: ta10991.01_phapa

<400> SEQUENCE: 269

atgtttgctc ggtacttgtc atttattctg ctacttttaa tattctctaa tgattccaag      60

tgcagcttca aagagggcct ttctggactc aagaggcgat tatcgtttcc agatatcaaa     120

gatcccagtt ttgaaattcc ggctcttaat gaacccaatc cacatgcact tgattctagt     180

gaaggatacc ctatcacctc ttatggcgta agcgaaggtg gaatcaaaag agataaggat     240

atttcaatgc aatcacatat aaaaatagat caattggcgg aaaagaagaa agcacaaagt     300

gattccctgg ttgatcacca acatcaaaac ttacacagaa ccaaaaagtt aaaaaccgat     360

cagagcgaga tggaggcggg ttatgaagat cttaaaaact gtattcaaga aactaaaaaa     420
```

```
caaatatggt ggccaagaca tatcgaaggt ttaaaaaaaa tcgaaaaaac tttagagaat    480

gacttatcta gtattatgtt tgaagggata gatgataact gttttaaaac cttgtccgaa    540

gttctaagca gctatgaaaa tgtattaaaa cctggtcgcc caataagcag tgtgccagta    600

atcccactaa tatttaaaat actcgactac atcgaaaaat ttgaattgca agcgaataga    660

atggaaagca ataaatcact aatcaaaaaa ttctttaatg aaaaggaact actcaaacag    720

cttatctggt acatatcaac agtcttaatt cagaaatggg ggtttattgg ggttttttg     780

accagtgatt ttaaagaata catccgggat cataatgatt tgaatcatat aagattttg     840

ttaaat                                                                846
```

<210> SEQ ID NO 270
<211> LENGTH: 282
<212> TYPE: PRT
<213> ORGANISM: Phakopsora pachyrhizi
<220> FEATURE:
<221> NAME/KEY: VARIANT
<222> LOCATION: (1)..(282)
<223> OTHER INFORMATION: ta10991.01_phapa

<400> SEQUENCE: 270

```
Met Phe Ala Arg Tyr Leu Ser Phe Ile Leu Leu Leu Leu Ile Phe Ser
1               5                   10                  15

Asn Asp Ser Lys Cys Ser Phe Lys Glu Gly Leu Ser Gly Leu Lys Arg
            20                  25                  30

Arg Leu Ser Phe Pro Asp Ile Lys Asp Pro Ser Phe Glu Ile Pro Ala
        35                  40                  45

Leu Asn Glu Pro Asn Pro His Ala Leu Asp Ser Ser Glu Gly Tyr Pro
    50                  55                  60

Ile Thr Ser Tyr Gly Val Ser Glu Gly Gly Ile Lys Arg Asp Lys Asp
65                  70                  75                  80

Ile Ser Met Gln Ser His Ile Lys Ile Asp Gln Leu Ala Glu Lys Lys
                85                  90                  95

Lys Ala Gln Ser Asp Ser Leu Val Asp His Gln His Gln Asn Leu His
            100                 105                 110

Arg Thr Lys Lys Leu Lys Thr Asp Gln Ser Glu Met Glu Ala Gly Tyr
        115                 120                 125

Glu Asp Leu Lys Asn Cys Ile Gln Glu Thr Lys Lys Gln Ile Trp Trp
    130                 135                 140

Pro Arg His Ile Glu Gly Leu Lys Lys Ile Glu Lys Thr Leu Glu Asn
145                 150                 155                 160

Asp Leu Ser Ser Ile Met Phe Glu Gly Ile Asp Asp Asn Cys Phe Lys
                165                 170                 175

Thr Leu Ser Glu Val Leu Ser Ser Tyr Glu Asn Val Leu Lys Pro Gly
            180                 185                 190

Arg Pro Ile Ser Ser Val Pro Val Ile Pro Leu Ile Phe Lys Ile Leu
        195                 200                 205

Asp Tyr Ile Glu Lys Phe Glu Leu Gln Ala Asn Arg Met Glu Ser Asn
    210                 215                 220

Lys Ser Leu Ile Lys Lys Phe Phe Asn Glu Lys Glu Leu Leu Lys Gln
225                 230                 235                 240

Leu Ile Trp Tyr Ile Ser Thr Val Leu Ile Gln Lys Trp Gly Phe Ile
                245                 250                 255

Gly Val Phe Leu Thr Ser Asp Phe Lys Glu Tyr Ile Arg Asp His Asn
            260                 265                 270
```

```
Asp Leu Asn His Ile Arg Phe Leu Leu Asn
        275                 280


<210> SEQ ID NO 271
<211> LENGTH: 846
<212> TYPE: DNA
<213> ORGANISM: Phakopsora pachyrhizi
<220> FEATURE:
<221> NAME/KEY: misc_feature
<222> LOCATION: (1)..(846)
<223> OTHER INFORMATION: ta02873.01_phapa

<400> SEQUENCE: 271

atgatttctc taactactct catctcgact attttactat actctatggt tatttccatc      60

accaactctg tcgttctcga cagaggctct tatcaatctg acaactatca tcatcatcaa     120

agcaagagat ggttgaattc tccctttgcg ccctactaca tcagtggtag ttcggtctat     180

gggggttact acgatccgag atataacttt tcaccaagct atccgatcgg ctctgcaaag     240

ttctacactc agggattaac taactatctg acctggtgtc caagtgggat ctacggcttt     300

ggtgcaagct acgaattctc gaaccagaac tataggacag tacccaatcc gagcagctac     360

tcattcttta agaaattctc acagtctgat aagagctcta agaggagcta tgtcagtcat     420

gaacacagta acgacgagga agattatgag atcagaaagg ttagccgtaa cagccataac     480

tttatcaagc ggggcgacca ggttcaatgt agaaatcaga agggtgaaac tatctctttc     540

gtaaaatcgg attgtgatgc ggctgcaatt aagatggtaa accagaaaag tgcagtctca     600

aacgttggaa gctgtggact ggttctcatt ggacctcaag gccaactgtc tagttcaaat     660

ctacctattg agaagattca gaatgatgtt cagaacattt taaatacgtg cacgatgggt     720

gggccttcaa ataattttaa caaccaattc acaaataaca gaaactcttt tatcaattta     780

cccaggggtg cgaatccaaa ctacgtgatt ctattaacaa aaggagacgg aagtccagat     840

tattag                                                                846


<210> SEQ ID NO 272
<211> LENGTH: 281
<212> TYPE: PRT
<213> ORGANISM: Phakopsora pachyrhizi
<220> FEATURE:
<221> NAME/KEY: VARIANT
<222> LOCATION: (1)..(281)
<223> OTHER INFORMATION: ta02873.01_phapa

<400> SEQUENCE: 272

Met Ile Ser Leu Thr Thr Leu Ile Ser Thr Ile Leu Leu Tyr Ser Met
1               5                   10                  15

Val Ile Ser Ile Thr Asn Ser Val Val Leu Asp Arg Gly Ser Tyr Gln
            20                  25                  30

Ser Asp Asn Tyr His His His Gln Ser Lys Arg Trp Leu Asn Ser Pro
        35                  40                  45

Phe Ala Pro Tyr Tyr Ile Ser Gly Ser Ser Val Tyr Gly Gly Tyr Tyr
    50                  55                  60

Asp Pro Arg Tyr Asn Phe Ser Pro Ser Tyr Pro Ile Gly Ser Ala Lys
65                  70                  75                  80

Phe Tyr Thr Gln Gly Leu Thr Asn Tyr Leu Thr Trp Cys Pro Ser Gly
                85                  90                  95

Ile Tyr Gly Phe Gly Ala Ser Tyr Glu Phe Ser Asn Gln Asn Tyr Arg
            100                 105                 110
```

```
Thr Val Pro Asn Pro Ser Ser Tyr Ser Phe Phe Lys Lys Phe Ser Gln
        115                 120                 125

Ser Asp Lys Ser Ser Lys Arg Ser Tyr Val Ser His Glu His Ser Asn
    130                 135                 140

Asp Glu Glu Asp Tyr Glu Ile Arg Lys Val Ser Arg Asn Ser His Asn
145                 150                 155                 160

Phe Ile Lys Arg Gly Asp Gln Val Gln Cys Arg Asn Gln Lys Gly Glu
                165                 170                 175

Thr Ile Ser Phe Val Lys Ser Asp Cys Asp Ala Ala Ala Ile Lys Met
            180                 185                 190

Val Asn Gln Lys Ser Ala Val Ser Asn Val Gly Ser Cys Gly Leu Val
        195                 200                 205

Leu Ile Gly Pro Gln Gly Gln Leu Ser Ser Ser Asn Leu Pro Ile Glu
    210                 215                 220

Lys Ile Gln Asn Asp Val Gln Asn Ile Leu Asn Thr Cys Thr Met Gly
225                 230                 235                 240

Gly Pro Ser Asn Asn Phe Asn Asn Gln Phe Thr Asn Asn Arg Asn Ser
                245                 250                 255

Phe Ile Asn Leu Pro Arg Gly Ala Asn Pro Asn Tyr Val Ile Leu Leu
            260                 265                 270

Thr Lys Gly Asp Gly Ser Pro Asp Tyr
        275                 280
```

<210> SEQ ID NO 273
<211> LENGTH: 843
<212> TYPE: DNA
<213> ORGANISM: Phakopsora pachyrhizi
<220> FEATURE:
<221> NAME/KEY: misc_feature
<222> LOCATION: (1)..(843)
<223> OTHER INFORMATION: ta04966.01_phapa

<400> SEQUENCE: 273

```
atgaagtctt ttgttttggc ctcaggcatt acaattacaa tttttacggc tcttgaaatt     60

gggatgttaa tttttggtgg ttccgcattt gcatcaattg tggcattgat ggccttgggc    120

gctacggcgg ttactatggg tggtgcaggt ggtgtaggaa ctaaactggc acttatgcat    180

ccggaggaaa ctccatttga aaggtggtcc agatatgcgt tttatctctc tgaatggcag    240

caacacgttc aaaaacgagt tgcaaatgaa gccaggacag taatcaacgc tggtattagc    300

tcaccgaagg gattggctaa tattgttaag aatggtgtat tcttccgaga ggttccccaa    360

ttcagtgaag cagatttgat ttcaggcctc aaaaatacga ctacggctag aatagcagtc    420

gatatcttga ggactcaggg cgctttcgtt acaattgcaa gtgacaagtg cacaggtaaa    480

ggtccgggtg gggcatggga aggtaatgac aaactgtctt actgctctaa gaatgggact    540

atgatgaaca ttattcatgg ctacaagaaa aaagttaaga atacctggtt caatgcccaa    600

ctcctagaaa agaagtacgg tatcactgtt cagtatcttg cggagcaatc gtttcactgt    660

cagcaaaatc acaaaagctt tggattcgac ccttacaagt ctggaacctt tcctagttca    720

ttagatgcag agtgtattgg aaatcttcct gtctgcgatt tcaggattca agaacttgcg    780

gaggcgaaat ctgagaaagg caccatgcga gcttgtcgga gcgttggaag gttgccgatt    840

tga                                                                  843
```

<210> SEQ ID NO 274
<211> LENGTH: 280
<212> TYPE: PRT

<213> ORGANISM: Phakopsora pachyrhizi
<220> FEATURE:
<221> NAME/KEY: VARIANT
<222> LOCATION: (1)..(280)
<223> OTHER INFORMATION: ta04966.01_phapa

<400> SEQUENCE: 274

```
Met Lys Ser Phe Val Leu Ala Ser Gly Ile Thr Ile Thr Ile Phe Thr
1               5                   10                  15

Ala Leu Glu Ile Gly Met Leu Ile Phe Gly Gly Ser Ala Phe Ala Ser
            20                  25                  30

Ile Val Ala Leu Met Ala Leu Gly Ala Thr Ala Val Thr Met Gly Gly
        35                  40                  45

Ala Gly Gly Val Gly Thr Lys Leu Ala Leu Met His Pro Glu Glu Thr
    50                  55                  60

Pro Phe Glu Arg Trp Ser Arg Tyr Ala Phe Tyr Leu Ser Glu Trp Gln
65                  70                  75                  80

Gln His Val Gln Lys Arg Val Ala Asn Glu Ala Arg Thr Val Ile Asn
                85                  90                  95

Ala Gly Ile Ser Ser Pro Lys Gly Leu Ala Asn Ile Val Lys Asn Gly
            100                 105                 110

Val Phe Phe Arg Glu Val Pro Gln Phe Ser Glu Ala Asp Leu Ile Ser
        115                 120                 125

Gly Leu Lys Asn Thr Thr Thr Ala Arg Ile Ala Val Asp Ile Leu Arg
    130                 135                 140

Thr Gln Gly Ala Phe Val Thr Ile Ala Ser Asp Lys Cys Thr Gly Lys
145                 150                 155                 160

Gly Pro Gly Gly Ala Trp Glu Gly Asn Asp Lys Leu Ser Tyr Cys Ser
                165                 170                 175

Lys Asn Gly Thr Met Met Asn Ile Ile His Gly Tyr Lys Lys Lys Val
            180                 185                 190

Lys Asn Thr Trp Phe Asn Ala Gln Leu Leu Glu Lys Lys Tyr Gly Ile
        195                 200                 205

Thr Val Gln Tyr Leu Ala Glu Gln Ser Phe His Cys Gln Gln Asn His
    210                 215                 220

Lys Ser Phe Gly Phe Asp Pro Tyr Lys Ser Gly Thr Phe Pro Ser Ser
225                 230                 235                 240

Leu Asp Ala Glu Cys Ile Gly Asn Leu Pro Val Cys Asp Phe Arg Ile
                245                 250                 255

Gln Glu Leu Ala Glu Ala Lys Ser Glu Lys Gly Thr Met Arg Ala Cys
            260                 265                 270

Arg Ser Val Gly Arg Leu Pro Ile
        275                 280
```

<210> SEQ ID NO 275
<211> LENGTH: 825
<212> TYPE: DNA
<213> ORGANISM: Phakopsora pachyrhizi
<220> FEATURE:
<221> NAME/KEY: misc_feature
<222> LOCATION: (1)..(825)
<223> OTHER INFORMATION: ta07858.01_phapa

<400> SEQUENCE: 275

```
atgaattctc acattggctc aaagaccatt ccccacattc ttttacttcc ctatttccta      60

atccttctta cttcgattta ccattcggtt attggtacat caatagaatc acttgtcaca     120

gcagttgatc aaaaagatgt acatgaaggt ataaatttta tgcttgatgg ctcaacacat     180
```

```
ggtgcacggc atgaattgaa agttggtgaa gaagataaaa atgttacatt gaaggatcat    240

ggtcaaagtc atctacttga aattgttaga aaattagaaa agaggtattc ttctcacacc    300

acgacgattg aaaaaacgga aaattttcca aaaagttctg ctcggtccca tcattttaaa    360

aggagtactc catcatctgg agaaatcaga agatggctta gaagtcacaa taaatttaga    420

gcccaatact ctgcctctcc gttggtgtgg gatcagaact tggctgacaa agccaattca    480

gagactaata cctgcgtttg gagacactct tacaacgata tatatggcga aaacattgca    540

gccggccagg aatcgattga agaggttgtg gatgagtggg tcacaggttc agaagagaga    600

agagtttatt caccaaataa ccctacatat tcacatttta cccaagttgt ttggggagac    660

acaaggcgtt taggatgtgc aatgacctct tgtagaaata ttcgaggctc tggtttacca    720

caatctcctg taaagttttg ggcttgtgaa tattatccgc ctggaaatgt agatggccag    780

tatcgtcaaa acgtcaaagc tagatatggt ggctctcctc tataa                    825
```

```
<210> SEQ ID NO 276
<211> LENGTH: 274
<212> TYPE: PRT
<213> ORGANISM: Phakopsora pachyrhizi
<220> FEATURE:
<221> NAME/KEY: VARIANT
<222> LOCATION: (1)..(274)
<223> OTHER INFORMATION: ta07858.01_phapa

<400> SEQUENCE: 276

Met Asn Ser His Ile Gly Ser Lys Thr Ile Pro His Ile Leu Leu Leu
1               5                   10                  15

Pro Tyr Phe Leu Ile Leu Leu Thr Ser Ile Tyr His Ser Val Ile Gly
            20                  25                  30

Thr Ser Ile Glu Ser Leu Val Thr Ala Val Asp Gln Lys Asp Val His
        35                  40                  45

Glu Gly Ile Asn Phe Met Leu Asp Gly Ser Thr His Gly Ala Arg His
    50                  55                  60

Glu Leu Lys Val Gly Glu Glu Asp Lys Asn Val Thr Leu Lys Asp His
65                  70                  75                  80

Gly Gln Ser His Leu Leu Glu Ile Val Arg Lys Leu Glu Lys Arg Tyr
                85                  90                  95

Ser Ser His Thr Thr Thr Ile Glu Lys Thr Glu Asn Phe Pro Lys Ser
            100                 105                 110

Ser Ala Arg Ser His His Phe Lys Arg Ser Thr Pro Ser Ser Gly Glu
        115                 120                 125

Ile Arg Arg Trp Leu Arg Ser His Asn Lys Phe Arg Ala Gln Tyr Ser
    130                 135                 140

Ala Ser Pro Leu Val Trp Asp Gln Asn Leu Ala Asp Lys Ala Asn Ser
145                 150                 155                 160

Glu Thr Asn Thr Cys Val Trp Arg His Ser Tyr Asn Asp Ile Tyr Gly
                165                 170                 175

Glu Asn Ile Ala Ala Gly Gln Glu Ser Ile Glu Glu Val Val Asp Glu
            180                 185                 190

Trp Val Thr Gly Ser Glu Glu Arg Arg Val Tyr Ser Pro Asn Asn Pro
        195                 200                 205

Thr Tyr Ser His Phe Thr Gln Val Val Trp Gly Asp Thr Arg Arg Leu
    210                 215                 220

Gly Cys Ala Met Thr Ser Cys Arg Asn Ile Arg Gly Ser Gly Leu Pro
225                 230                 235                 240
```

```
Gln Ser Pro Val Lys Phe Trp Ala Cys Glu Tyr Tyr Pro Pro Gly Asn
                245                 250                 255

Val Asp Gly Gln Tyr Arg Gln Asn Val Lys Ala Arg Tyr Gly Gly Ser
            260                 265                 270

Pro Leu


<210> SEQ ID NO 277
<211> LENGTH: 813
<212> TYPE: DNA
<213> ORGANISM: Phakopsora pachyrhizi
<220> FEATURE:
<221> NAME/KEY: misc_feature
<222> LOCATION: (1)..(813)
<223> OTHER INFORMATION: ta09549.01_phapa

<400> SEQUENCE: 277

atgttaatgt acccgattgc atttatcttt atgatattgc ccctttcaac ttttagatta      60

gcggcattgg cgggtcatga ttggggagtc actgcagcct cagtttgtgg ttcaatatat     120

tgtctaagtg gctttattga tgtgctcctt tttgggacta cgcgaagcat aatttctgtt     180

ccaatatttt cattcaagtc acatcaaaga gttcatcctc agggtgctac ggcaattatt     240

ggcaccaatg gtatcggaat gagttctagt gggttgggca ctcgatcagt cggatttaga     300

gttgaagtta tacaagaaac ggtgattgac ttggacgaac caaacgaggg ggatttacat     360

gaattaaaga agaacccaaa tcccaaacat gaccatcatc gccgaatgag tgaattaaac     420

gatgtgctcc cttcagattc aattataaaa ccggttgaag ctactcatgg tgaaaggtat     480

gattctatgg actcacagac ggcgggtgaa aacataaatc aaacttcgaa cacaaatatt     540

ccagagaata ccaaccttac aagcttctta aatctggaca caacctcatc agatcttaag     600

tctgagactt cgaaaccgat gagtagatat atgtttgggg ttgccgataa ttcaagctgt     660

gcatcaacta attcaaatag accgatgttt tgttttgaac ctgataataa tcaatctaac     720

tatcctcaaa ttcttcatca tgagtctcaa aacttttctt ctcatcgatc tgaatttaca     780

gaccccatac cgtggcagaa gtcaagctca taa                                  813


<210> SEQ ID NO 278
<211> LENGTH: 270
<212> TYPE: PRT
<213> ORGANISM: Phakopsora pachyrhizi
<220> FEATURE:
<221> NAME/KEY: VARIANT
<222> LOCATION: (1)..(270)
<223> OTHER INFORMATION: ta09549.01_phapa

<400> SEQUENCE: 278

Met Leu Met Tyr Pro Ile Ala Phe Ile Phe Met Ile Leu Pro Leu Ser
1               5                   10                  15

Thr Phe Arg Leu Ala Ala Leu Ala Gly His Asp Trp Gly Val Thr Ala
            20                  25                  30

Ala Ser Val Cys Gly Ser Ile Tyr Cys Leu Ser Gly Phe Ile Asp Val
        35                  40                  45

Leu Leu Phe Gly Thr Thr Arg Ser Ile Ile Ser Val Pro Ile Phe Ser
    50                  55                  60

Phe Lys Ser His Gln Arg Val His Pro Gln Gly Ala Thr Ala Ile Ile
65                  70                  75                  80

Gly Thr Asn Gly Ile Gly Met Ser Ser Ser Gly Leu Gly Thr Arg Ser
                85                  90                  95
```

```
Val Gly Phe Arg Val Glu Val Ile Gln Glu Thr Val Ile Asp Leu Asp
            100                 105                 110

Glu Pro Asn Glu Gly Asp Leu His Glu Leu Lys Lys Asn Pro Asn Pro
        115                 120                 125

Lys His Asp His His Arg Arg Met Ser Glu Leu Asn Asp Val Leu Pro
    130                 135                 140

Ser Asp Ser Ile Ile Lys Pro Val Glu Ala Thr His Gly Glu Arg Tyr
145                 150                 155                 160

Asp Ser Met Asp Ser Gln Thr Ala Gly Glu Asn Ile Asn Gln Thr Ser
                165                 170                 175

Asn Thr Asn Ile Pro Glu Asn Thr Asn Leu Thr Ser Phe Leu Asn Leu
            180                 185                 190

Asp Thr Thr Ser Ser Asp Leu Lys Ser Glu Thr Ser Lys Pro Met Ser
        195                 200                 205

Arg Tyr Met Phe Gly Val Ala Asp Asn Ser Ser Cys Ala Ser Thr Asn
    210                 215                 220

Ser Asn Arg Pro Met Phe Cys Phe Glu Pro Asp Asn Asn Gln Ser Asn
225                 230                 235                 240

Tyr Pro Gln Ile Leu His His Glu Ser Gln Asn Phe Ser Ser His Arg
                245                 250                 255

Ser Glu Phe Thr Asp Pro Ile Pro Trp Gln Lys Ser Ser Ser
            260                 265                 270
```

<210> SEQ ID NO 279
<211> LENGTH: 813
<212> TYPE: DNA
<213> ORGANISM: Phakopsora pachyrhizi
<220> FEATURE:
<221> NAME/KEY: misc_feature
<222> LOCATION: (1)..(813)
<223> OTHER INFORMATION: ta08378.02_phapa

<400> SEQUENCE: 279

```
atggttaaga gtttcgaact tctgctggtc cttttgatct ttcaaacttt ttctctgaac      60

ttctatgttt ctggatccta cgagtatcaa ctcaatggag ttaacaatca attcgcagta     120

ctggattcta agatctcgaa gattcagtcc ctagctcaac aacaaggaca ttccgatgtt     180

aaagaattgt gcttggaagc taaggatcac ttgtcggctg caatcgatgg gtgggaaaga     240

atctcaaagg tttacaaaga taagatttgg ttagcttcag agtcaaagta taaggacaat     300

gtgcaagata gcttggataa gtgtggtgaa tcaatcatga agattctaga caatgatcac     360

gtgaagagcg tttctggacg ttacggatct caggttgaag attgtaaacg atactatgaa     420

acttgtcaac actcttgcaa gaatatttgg gactggggac ccccgagtcc aacaccgagt     480

ggatcttaca cttcgtacaa caagcgacaa aatgttaatt ctctgagacg tagaagcttg     540

gaaggcgatg aaagtgatca gattcagaaa tgccccaaag gggagactgc ttgtccgatc     600

tcagagaatt ctattggatt tgagtgcctt gatactaagc tggaactgac taactgtggt     660

ggatgtcgta ctaagaatga aggtgaaaac tgcttggaga ttgaaggctc agttggtgtc     720

ggttgtatga agggtaaatg tgtcgttttt tctgttcaac ctgggtatta tttaagtaag     780

aggatcaacc ggccggtcct caagagaaaa taa                                  813
```

<210> SEQ ID NO 280
<211> LENGTH: 270
<212> TYPE: PRT
<213> ORGANISM: Phakopsora pachyrhizi
<220> FEATURE:

<221> NAME/KEY: VARIANT
<222> LOCATION: (1)..(270)
<223> OTHER INFORMATION: ta08378.02_phapa

<400> SEQUENCE: 280

Met Val Lys Ser Phe Glu Leu Leu Leu Val Leu Leu Ile Phe Gln Thr
1 5 10 15

Phe Ser Leu Asn Phe Tyr Val Ser Gly Ser Tyr Glu Tyr Gln Leu Asn
20 25 30

Gly Val Asn Asn Gln Phe Ala Val Leu Asp Ser Lys Ile Ser Lys Ile
35 40 45

Gln Ser Leu Ala Gln Gln Gln Gly His Ser Asp Val Lys Glu Leu Cys
50 55 60

Leu Glu Ala Lys Asp His Leu Ser Ala Ala Ile Asp Gly Trp Glu Arg
65 70 75 80

Ile Ser Lys Val Tyr Lys Asp Lys Ile Trp Leu Ala Ser Glu Ser Lys
85 90 95

Tyr Lys Asp Asn Val Gln Asp Ser Leu Asp Lys Cys Gly Glu Ser Ile
100 105 110

Met Lys Ile Leu Asp Asn Asp His Val Lys Ser Val Ser Gly Arg Tyr
115 120 125

Gly Ser Gln Val Glu Asp Cys Lys Arg Tyr Tyr Glu Thr Cys Gln His
130 135 140

Ser Cys Lys Asn Ile Trp Asp Trp Gly Pro Pro Ser Pro Thr Pro Ser
145 150 155 160

Gly Ser Tyr Thr Ser Tyr Asn Lys Arg Gln Asn Val Asn Ser Leu Arg
165 170 175

Arg Arg Ser Leu Glu Gly Asp Glu Ser Asp Gln Ile Gln Lys Cys Pro
180 185 190

Lys Gly Glu Thr Ala Cys Pro Ile Ser Glu Asn Ser Ile Gly Phe Glu
195 200 205

Cys Leu Asp Thr Lys Leu Glu Leu Thr Asn Cys Gly Gly Cys Arg Thr
210 215 220

Lys Asn Glu Gly Glu Asn Cys Leu Glu Ile Glu Gly Ser Val Gly Val
225 230 235 240

Gly Cys Met Lys Gly Lys Cys Val Val Phe Ser Val Gln Pro Gly Tyr
245 250 255

Tyr Leu Ser Lys Arg Ile Asn Arg Pro Val Leu Lys Arg Lys
260 265 270

<210> SEQ ID NO 281
<211> LENGTH: 813
<212> TYPE: DNA
<213> ORGANISM: Phakopsora pachyrhizi
<220> FEATURE:
<221> NAME/KEY: misc_feature
<222> LOCATION: (1)..(813)
<223> OTHER INFORMATION: ta08378.03_phapa

<400> SEQUENCE: 281
atggttaaga gtttcgaact tctgctggtc cttttgatct ttcaaacttt ttctctgaac 60
ttctatgttt ctggatccta cgagtatcaa ctcaatggag ttaacaatca attcgcagta 120
ctggattcta agatctcgaa gattcagtcc ctagctcaac aacaaggaca ttccgatgtt 180
aaagaattgt gcttggaagc taaggatcac ttgtcggctg caatcgatgg gtgggaaaga 240
atctcaaagg tttacaaaga taagatttgg ttagcttcag agtcaaagta taaggacaat 300

```
gtgcaagata gcttggataa gtgtggtgaa tcaatcatga agattctaga caatgatcac    360
gtgaagagcg tttctggacg ttacggatct caggttgaag attgtaaacg atactatgaa    420
acttgtcaac actcttgcaa gaatatttgg gactggggac ccccgagtcc aacaccgagt    480
ggatcttaca cttcgtacaa caagcgacaa aatgttaatt ctctgagacg tagaagcttg    540
gaaggcgatg aaagtgatca gattcagaaa tgccccaaag gggagactgc ttgtccgatc    600
tcagagaatt ctattggatt tgagtgcctt gatactaagc tggaactgac taactgtggt    660
ggatgtcgta ctaagaatga aggtgaaaac tgcttggaga ttgaaggctc agttggtgtc    720
ggttgtatga agggtaaatg tgtcgttttt tctgttcaac ctgggtatta tttaagtaag    780
aggatcaacc ggccggtcct caagagaaaa taa                                 813
```

```
<210> SEQ ID NO 282
<211> LENGTH: 270
<212> TYPE: PRT
<213> ORGANISM: Phakopsora pachyrhizi
<220> FEATURE:
<221> NAME/KEY: VARIANT
<222> LOCATION: (1)..(270)
<223> OTHER INFORMATION: ta08378.03_phapa

<400> SEQUENCE: 282

Met Val Lys Ser Phe Glu Leu Leu Leu Val Leu Leu Ile Phe Gln Thr
1               5                   10                  15

Phe Ser Leu Asn Phe Tyr Val Ser Gly Ser Tyr Glu Tyr Gln Leu Asn
            20                  25                  30

Gly Val Asn Asn Gln Phe Ala Val Leu Asp Ser Lys Ile Ser Lys Ile
        35                  40                  45

Gln Ser Leu Ala Gln Gln Gln Gly His Ser Asp Val Lys Glu Leu Cys
    50                  55                  60

Leu Glu Ala Lys Asp His Leu Ser Ala Ala Ile Asp Gly Trp Glu Arg
65                  70                  75                  80

Ile Ser Lys Val Tyr Lys Asp Lys Ile Trp Leu Ala Ser Glu Ser Lys
                85                  90                  95

Tyr Lys Asp Asn Val Gln Asp Ser Leu Asp Lys Cys Gly Glu Ser Ile
            100                 105                 110

Met Lys Ile Leu Asp Asn Asp His Val Lys Ser Val Ser Gly Arg Tyr
        115                 120                 125

Gly Ser Gln Val Glu Asp Cys Lys Arg Tyr Tyr Glu Thr Cys Gln His
    130                 135                 140

Ser Cys Lys Asn Ile Trp Asp Trp Gly Pro Pro Ser Pro Thr Pro Ser
145                 150                 155                 160

Gly Ser Tyr Thr Ser Tyr Asn Lys Arg Gln Asn Val Asn Ser Leu Arg
                165                 170                 175

Arg Arg Ser Leu Glu Gly Asp Glu Ser Asp Gln Ile Gln Lys Cys Pro
            180                 185                 190

Lys Gly Glu Thr Ala Cys Pro Ile Ser Glu Asn Ser Ile Gly Phe Glu
        195                 200                 205

Cys Leu Asp Thr Lys Leu Glu Leu Thr Asn Cys Gly Gly Cys Arg Thr
    210                 215                 220

Lys Asn Glu Gly Glu Asn Cys Leu Glu Ile Glu Gly Ser Val Gly Val
225                 230                 235                 240

Gly Cys Met Lys Gly Lys Cys Val Val Phe Ser Val Gln Pro Gly Tyr
                245                 250                 255

Tyr Leu Ser Lys Arg Ile Asn Arg Pro Val Leu Lys Arg Lys
```

260 265 270

<210> SEQ ID NO 283
<211> LENGTH: 813
<212> TYPE: DNA
<213> ORGANISM: Phakopsora pachyrhizi
<220> FEATURE:
<221> NAME/KEY: misc_feature
<222> LOCATION: (1)..(813)
<223> OTHER INFORMATION: ta03276.01_phapa

<400> SEQUENCE: 283
atgaactgtt ttcggcttct tttattcact gtctctatct acattcttta ccttgagtca 60
gtaaccacgc acttctacat caagcaatgg aagtctagta acgacaacag gcttagacca 120
gctcaaaagg cagatttatc acattcagcg tatcgcagtt cctccgataa tattggttgg 180
ataggcagta agtttctgac atcaaatcat gctattgttt gtggagcttc aaacactccc 240
aaaggaaaag tggccccagc tggtggaaga tttttctcag atgcgtctca tgctgctggc 300
caaacgctcg aagtgaatgc aggcggtcac attacattag ttataacaaa tgggggagga 360
acaggatatc cccactacga aggtcacatt caggcatatc taggatactg tggtgcctcg 420
ccaattgctt gtcaatcttt cgacgcttca aaggcttatt tcttcaaaat tcaagagtca 480
ataaatggtg ttaagagact acgacgccaa atgtcccatt ctctaggggg agatgtatgg 540
gaggttccaa tccccgcggg agttcctagg ggcagctata tacttcggtt tgaaataata 600
acgccccatg aatctgttgc ctccgaagga tttcaagatc aatactaccc ctcttgtggc 660
cagatttatg ttaaatcaaa caggaactct gttcacctga accaacttcc tctcctccga 720
cttcctgggg gctacgaaaa taggaatatg aaagcttctc aagctccggg gcctcggctt 780
gcaagcttta attctcttcg tttacgaaac tag 813

<210> SEQ ID NO 284
<211> LENGTH: 270
<212> TYPE: PRT
<213> ORGANISM: Phakopsora pachyrhizi
<220> FEATURE:
<221> NAME/KEY: VARIANT
<222> LOCATION: (1)..(270)
<223> OTHER INFORMATION: ta03276.01_phapa

<400> SEQUENCE: 284

Met Asn Cys Phe Arg Leu Leu Leu Phe Thr Val Ser Ile Tyr Ile Leu
1 5 10 15

Tyr Leu Glu Ser Val Thr Thr His Phe Tyr Ile Lys Gln Trp Lys Ser
20 25 30

Ser Asn Asp Asn Arg Leu Arg Pro Ala Gln Lys Ala Asp Leu Ser His
35 40 45

Ser Ala Tyr Arg Ser Ser Ser Asp Asn Ile Gly Trp Ile Gly Ser Lys
50 55 60

Phe Leu Thr Ser Asn His Ala Ile Val Cys Gly Ala Ser Asn Thr Pro
65 70 75 80

Lys Gly Lys Val Ala Pro Ala Gly Gly Arg Phe Phe Ser Asp Ala Ser
85 90 95

His Ala Ala Gly Gln Thr Leu Glu Val Asn Ala Gly Gly His Ile Thr
100 105 110

Leu Val Ile Thr Asn Gly Gly Gly Thr Gly Tyr Pro His Tyr Glu Gly
115 120 125

His Ile Gln Ala Tyr Leu Gly Tyr Cys Gly Ala Ser Pro Ile Ala Cys

```
    130                 135                 140

Gln Ser Phe Asp Ala Ser Lys Ala Tyr Phe Phe Lys Ile Gln Glu Ser
145                 150                 155                 160

Ile Asn Gly Val Lys Arg Leu Arg Arg Gln Met Ser His Ser Leu Gly
                165                 170                 175

Gly Asp Val Trp Glu Val Pro Ile Pro Ala Gly Val Pro Arg Gly Ser
            180                 185                 190

Tyr Ile Leu Arg Phe Glu Ile Ile Thr Pro His Glu Ser Val Ala Ser
        195                 200                 205

Glu Gly Phe Gln Asp Gln Tyr Tyr Pro Ser Cys Gly Gln Ile Tyr Val
    210                 215                 220

Lys Ser Asn Arg Asn Ser Val His Leu Asn Gln Leu Pro Leu Leu Arg
225                 230                 235                 240

Leu Pro Gly Gly Tyr Glu Asn Arg Asn Met Lys Ala Ser Gln Ala Pro
                245                 250                 255

Gly Pro Arg Leu Ala Ser Phe Asn Ser Leu Arg Leu Arg Asn
            260                 265                 270


<210> SEQ ID NO 285
<211> LENGTH: 807
<212> TYPE: DNA
<213> ORGANISM: Phakopsora pachyrhizi
<220> FEATURE:
<221> NAME/KEY: misc_feature
<222> LOCATION: (1)..(807)
<223> OTHER INFORMATION: ta07479.01_phapa

<400> SEQUENCE: 285

atgcaacatt tagtctattc ttcttcatta ctggcttcaa tcaccacact ggttctttcg      60

atatactcat tgaatgcacc agcttggatc agatttgaca ccccatcatc atcaccactt     120

cagtattcag aaagttatgg attaaaattc aaatgtggca gatcgaacat tgccccagat     180

tttgtctgta gaccttttcc agatcgatca agagactgtg gtgcatcctc taactctatc     240

cttgaagatc cattttttga gaaactctta tcagcagatg atcgacaact gcccttaaat     300

agatctatcc atcagtttct acatcgtaaa aactcatcgt caagcatcaa aacggcccca     360

atgggtagtg gatctatcga gctgcttgaa tcagcctcat ctgttttgga tcgattaggt     420

gctcaaagat tcgggttctg tgagaagtgg aactcggctg gattttgtgc tgagatgagt     480

attgtcattg gagcaatttc aatcttttgt gtctcgatcg tccttctggg taatcgtcac     540

cgtcagaaac acggatggaa gatctgtgct ggtttgatag ctattcatgc cgtttctcag     600

ataaccacat gggttttcgt attgcagatc ttcaacactg ataacagatt ttatatagga     660

tcaaaacttt cgacaagttt ttacatctca gtcgcctcta gcatgatcga tttgatctgt     720

ttgactggac tagttgcagc tggaattgtc gagaacgatg atgatgatga tagtaatgac     780

gaatcaaact atcagccaat cccttga                                         807


<210> SEQ ID NO 286
<211> LENGTH: 268
<212> TYPE: PRT
<213> ORGANISM: Phakopsora pachyrhizi
<220> FEATURE:
<221> NAME/KEY: VARIANT
<222> LOCATION: (1)..(268)
<223> OTHER INFORMATION: ta07479.01_phapa

<400> SEQUENCE: 286

Met Gln His Leu Val Tyr Ser Ser Ser Leu Leu Ala Ser Ile Thr Thr
```

-continued

```
1               5                   10                  15

Leu Val Leu Ser Ile Tyr Ser Leu Asn Ala Pro Ala Trp Ile Arg Phe
            20                  25                  30

Asp Thr Pro Ser Ser Ser Pro Leu Gln Tyr Ser Glu Ser Tyr Gly Leu
        35                  40                  45

Lys Phe Lys Cys Gly Arg Ser Asn Ile Ala Pro Asp Phe Val Cys Arg
    50                  55                  60

Pro Phe Pro Asp Arg Ser Arg Asp Cys Gly Ala Ser Ser Asn Ser Ile
65                  70                  75                  80

Leu Glu Asp Pro Phe Phe Glu Lys Leu Leu Ser Ala Asp Asp Arg Gln
                85                  90                  95

Leu Pro Leu Asn Arg Ser Ile His Gln Phe Leu His Arg Lys Asn Ser
            100                 105                 110

Ser Ser Ser Ile Lys Thr Ala Pro Met Gly Ser Gly Ser Ile Glu Leu
        115                 120                 125

Leu Glu Ser Ala Ser Ser Val Leu Asp Arg Leu Gly Ala Gln Arg Phe
    130                 135                 140

Gly Phe Cys Glu Lys Trp Asn Ser Ala Gly Phe Cys Ala Glu Met Ser
145                 150                 155                 160

Ile Val Ile Gly Ala Ile Ser Ile Phe Cys Val Ser Ile Val Leu Leu
                165                 170                 175

Gly Asn Arg His Arg Gln Lys His Gly Trp Lys Ile Cys Ala Gly Leu
            180                 185                 190

Ile Ala Ile His Ala Val Ser Gln Ile Thr Thr Trp Val Phe Val Leu
        195                 200                 205

Gln Ile Phe Asn Thr Asp Asn Arg Phe Tyr Ile Gly Ser Lys Leu Ser
    210                 215                 220

Thr Ser Phe Tyr Ile Ser Val Ala Ser Ser Met Ile Asp Leu Ile Cys
225                 230                 235                 240

Leu Thr Gly Leu Val Ala Ala Gly Ile Val Glu Asn Asp Asp Asp Asp
                245                 250                 255

Asp Ser Asn Asp Glu Ser Asn Tyr Gln Pro Ile Pro
            260                 265
```

<210> SEQ ID NO 287
<211> LENGTH: 801
<212> TYPE: DNA
<213> ORGANISM: Phakopsora pachyrhizi
<220> FEATURE:
<221> NAME/KEY: misc_feature
<222> LOCATION: (1)..(801)
<223> OTHER INFORMATION: ta09035.01_phapa

<400> SEQUENCE: 287

```
atgaggttga atttattcat ttacagtaaa atgcgcttcg tactgttggt ttttttatta     60

tcattcgctc ttcaggcgag tgttaatggt gaggacgtgg taagactgcc acaagaaagc    120

aatctcatca actcagtttc gcgagatcaa agatcagata aattagaccc caaagtaatt    180

caactggctt cttcacagaa tggttctccg gatggaaacc aatctgcttc aatgacttct    240

ttaaataatt ttattaactt ttgctcttcg aaagaagcgc tcagcgcaaa attgacaaat    300

ggaactcaat ctcctgatga aatcacttgt aatccaattc caatgggaat gattgtaccg    360

cttaaaaacg cgccaagttg cagattccag cagccaaaaa actttgacaa acttaaagct    420

gacactgctt ttaaaatgat tttaaaaatt aaaaaccttg agactggtag ttttgttaac    480

ccaaagacaa attatttctc agcacctcaa gtattatcaa aaaaaactca caacgtgatt    540
```

```
ggacatgctc acgtcgtggc gcaaaaaatt aaaagcttaa catctacgga ggtattgaga    600

ccagataaat ttgaattttt caaaggcata gacgtttcaa ccgatgagga tggatacagc    660

tctgtgattt tagaaaaagg tttaccggct ggggcctatc gtgtttcaac tttattatca    720

gccgctaatc atcaaccaat cctagctggg gttgctcaaa gaggtgcttt tgatgatgta    780

atatatttta ccgtggaata a                                              801


<210> SEQ ID NO 288
<211> LENGTH: 266
<212> TYPE: PRT
<213> ORGANISM: Phakopsora pachyrhizi
<220> FEATURE:
<221> NAME/KEY: VARIANT
<222> LOCATION: (1)..(266)
<223> OTHER INFORMATION: ta09035.01_phapa

<400> SEQUENCE: 288

Met Arg Leu Asn Leu Phe Ile Tyr Ser Lys Met Arg Phe Val Leu Leu
1               5                   10                  15

Val Phe Leu Leu Ser Phe Ala Leu Gln Ala Ser Val Asn Gly Glu Asp
            20                  25                  30

Val Val Arg Leu Pro Gln Glu Ser Asn Leu Ile Asn Ser Val Ser Arg
        35                  40                  45

Asp Gln Arg Ser Asp Lys Leu Asp Pro Lys Val Ile Gln Leu Ala Ser
    50                  55                  60

Ser Gln Asn Gly Ser Pro Asp Gly Asn Gln Ser Ala Ser Met Thr Ser
65                  70                  75                  80

Leu Asn Asn Phe Ile Asn Phe Cys Ser Ser Lys Glu Ala Leu Ser Ala
                85                  90                  95

Lys Leu Thr Asn Gly Thr Gln Ser Pro Asp Glu Ile Thr Cys Asn Pro
            100                 105                 110

Ile Pro Met Gly Met Ile Val Pro Leu Lys Asn Ala Pro Ser Cys Arg
        115                 120                 125

Phe Gln Gln Pro Lys Asn Phe Asp Lys Leu Lys Ala Asp Thr Ala Phe
    130                 135                 140

Lys Met Ile Leu Lys Ile Lys Asn Leu Glu Thr Gly Ser Phe Val Asn
145                 150                 155                 160

Pro Lys Thr Asn Tyr Phe Ser Ala Pro Gln Val Leu Ser Lys Lys Thr
                165                 170                 175

His Asn Val Ile Gly His Ala His Val Val Ala Gln Lys Ile Lys Ser
            180                 185                 190

Leu Thr Ser Thr Glu Val Leu Arg Pro Asp Lys Phe Glu Phe Phe Lys
        195                 200                 205

Gly Ile Asp Val Ser Thr Asp Glu Asp Gly Tyr Ser Ser Val Ile Leu
    210                 215                 220

Glu Lys Gly Leu Pro Ala Gly Ala Tyr Arg Val Ser Thr Leu Leu Ser
225                 230                 235                 240

Ala Ala Asn His Gln Pro Ile Leu Ala Gly Val Ala Gln Arg Gly Ala
                245                 250                 255

Phe Asp Asp Val Ile Tyr Phe Thr Val Glu
            260                 265


<210> SEQ ID NO 289
<211> LENGTH: 801
<212> TYPE: DNA
<213> ORGANISM: Phakopsora pachyrhizi
```

<220> FEATURE:
<221> NAME/KEY: misc_feature
<222> LOCATION: (1)..(801)
<223> OTHER INFORMATION: ta09976.04_phapa

<400> SEQUENCE: 289

```
atgctctctt acgctaccat tctttgcctt ttgagcgttt ctggcttggt tcggtctggt     60

gtcgtaccga cgaagcctgg tcccggggaa acctacaacg aggggggca atgccaaatt    120

gcatgggcct tagataccac agggacttgg aactcatttt caattgattt gatgtctggc    180

tccaattttg ctatgcagca agtagttaat gtgttaaaaa atcaagacgg taccaaaggg    240

ccaggaacct acagttttcc atgccctgaa gtcactccca actcagcaat atacttttat    300

caattttctc aacataatgc tgaaactacc tggactacgc gattcactat agcttctgct    360

gatggccaaa cgactccccc tgctaatcca aatcagccaa acggtcagcc gattccatgg    420

ggaattggag cacttgcctc agccaatact caaaactctt ccagtgctac acctgttgtg    480

aatactactg cgaccgtgac tccgcccctt aatggtaacc tgactgcctt gaccacaccg    540

gcaaacacta ccagcagcag taacaatatt accaactcta atgtaaacac caccactagt    600

gttacataca gtaatccccc ttcatctact cttggaaaat ccggtgcttc aaactcctct    660

tcaggtacca ccccttctgc accaaaggca actggcaccg gcaaatcttc aggatctaaa    720

actttttcta caagcggctt ttatttcttt tcatcatcat tagggcttat gctcattgga    780

tctatttcat tactattgta a                                               801
```

<210> SEQ ID NO 290
<211> LENGTH: 266
<212> TYPE: PRT
<213> ORGANISM: Phakopsora pachyrhizi
<220> FEATURE:
<221> NAME/KEY: VARIANT
<222> LOCATION: (1)..(266)
<223> OTHER INFORMATION: ta09976.04_phapa

<400> SEQUENCE: 290

```
Met Leu Ser Tyr Ala Thr Ile Leu Cys Leu Leu Ser Val Ser Gly Leu
1               5                   10                  15

Val Arg Ser Gly Val Val Pro Thr Lys Pro Gly Pro Gly Glu Thr Tyr
            20                  25                  30

Asn Glu Gly Gly Gln Cys Gln Ile Ala Trp Ala Leu Asp Thr Thr Gly
        35                  40                  45

Thr Trp Asn Ser Phe Ser Ile Asp Leu Met Ser Gly Ser Asn Phe Ala
    50                  55                  60

Met Gln Gln Val Val Asn Val Leu Lys Asn Gln Asp Gly Thr Lys Gly
65                  70                  75                  80

Pro Gly Thr Tyr Ser Phe Pro Cys Pro Glu Val Thr Pro Asn Ser Ala
                85                  90                  95

Ile Tyr Phe Tyr Gln Phe Ser Gln His Asn Ala Glu Thr Thr Trp Thr
            100                 105                 110

Thr Arg Phe Thr Ile Ala Ser Ala Asp Gly Gln Thr Thr Pro Pro Ala
        115                 120                 125

Asn Pro Asn Gln Pro Asn Gly Gln Pro Ile Pro Trp Gly Ile Gly Ala
    130                 135                 140

Leu Ala Ser Ala Asn Thr Gln Asn Ser Ser Ser Ala Thr Pro Val Val
145                 150                 155                 160

Asn Thr Thr Ala Thr Val Thr Pro Pro Leu Asn Gly Asn Leu Thr Ala
                165                 170                 175
```

```
Leu Thr Thr Pro Ala Asn Thr Thr Ser Ser Ser Asn Asn Ile Thr Asn
            180                 185                 190

Ser Asn Val Asn Thr Thr Thr Ser Val Thr Tyr Ser Asn Pro Pro Ser
        195                 200                 205

Ser Thr Leu Gly Lys Ser Gly Ala Ser Asn Ser Ser Ser Gly Thr Thr
    210                 215                 220

Pro Ser Ala Pro Lys Ala Thr Gly Thr Gly Lys Ser Ser Gly Ser Lys
225                 230                 235                 240

Thr Phe Ser Thr Ser Gly Phe Tyr Phe Phe Ser Ser Ser Leu Gly Leu
                245                 250                 255

Met Leu Ile Gly Ser Ile Ser Leu Leu Leu
            260                 265
```

<210> SEQ ID NO 291
<211> LENGTH: 801
<212> TYPE: DNA
<213> ORGANISM: Phakopsora pachyrhizi
<220> FEATURE:
<221> NAME/KEY: misc_feature
<222> LOCATION: (1)..(801)
<223> OTHER INFORMATION: ta09976.03_phapa

<400> SEQUENCE: 291

```
atgctctctt acgctaccat tctttgcctt ttgagcgttt ctggcttggt tcggtctggt      60

gtcgtaccga cgaagcctgg tcccggggaa acctacaacg aggggggca atgccaaatt      120

gcatgggcct tagataccac agggacttgg aactcatttt caattgattt gatgtctggc     180

tccaattttg ctatgcagca agtagttaat gtgttaaaaa atcaagacgg taccaaaggg     240

ccaggaacct acagttttcc atgccctgaa gtcactccca actcagcaat atacttttat     300

caattttctc aacataatgc tgaaactacc tggactacgc gattcactat agcttctgct     360

gatggccaaa cgactccccc tgctaatcca aatcagccaa acggtcagcc gattccatgg     420

ggaattggag cacttgcctc agccaatact caaaactctt ccagtgctac acctgttgtg     480

aatactactg cgaccgtgac tccgcccctt aatggtaacc tgactgcctt gaccacaccg     540

gcaaacacta ccagcagcag taacaatatt accaactcta atgtaaacac caccactagt     600

gttacataca gtaatccccc ttcatctact cttggaaaat ccggtgcttc aaactcctct     660

tcaggtacca cccccttctgc accaaaggca actggcaccg gcaaatcttc aggatctaaa    720

actttttcta caagcggctt ttatttcttt tcatcatcat tagggcttat gctcattgga     780

tctatttcat tactattgta a                                               801
```

<210> SEQ ID NO 292
<211> LENGTH: 266
<212> TYPE: PRT
<213> ORGANISM: Phakopsora pachyrhizi
<220> FEATURE:
<221> NAME/KEY: VARIANT
<222> LOCATION: (1)..(266)
<223> OTHER INFORMATION: ta09976.03_phapa

<400> SEQUENCE: 292

```
Met Leu Ser Tyr Ala Thr Ile Leu Cys Leu Leu Ser Val Ser Gly Leu
1               5                   10                  15

Val Arg Ser Gly Val Val Pro Thr Lys Pro Gly Pro Gly Glu Thr Tyr
            20                  25                  30

Asn Glu Gly Gly Gln Cys Gln Ile Ala Trp Ala Leu Asp Thr Thr Gly
        35                  40                  45
```

```
Thr Trp Asn Ser Phe Ser Ile Asp Leu Met Ser Gly Ser Asn Phe Ala
    50                  55                  60

Met Gln Gln Val Val Asn Val Leu Lys Asn Gln Asp Gly Thr Lys Gly
65                  70                  75                  80

Pro Gly Thr Tyr Ser Phe Pro Cys Pro Glu Val Thr Pro Asn Ser Ala
                85                  90                  95

Ile Tyr Phe Tyr Gln Phe Ser Gln His Asn Ala Glu Thr Thr Trp Thr
            100                 105                 110

Thr Arg Phe Thr Ile Ala Ser Ala Asp Gly Gln Thr Thr Pro Pro Ala
        115                 120                 125

Asn Pro Asn Gln Pro Asn Gly Gln Pro Ile Pro Trp Gly Ile Gly Ala
    130                 135                 140

Leu Ala Ser Ala Asn Thr Gln Asn Ser Ser Ser Ala Thr Pro Val Val
145                 150                 155                 160

Asn Thr Thr Ala Thr Val Thr Pro Pro Leu Asn Gly Asn Leu Thr Ala
                165                 170                 175

Leu Thr Thr Pro Ala Asn Thr Thr Ser Ser Ser Asn Asn Ile Thr Asn
            180                 185                 190

Ser Asn Val Asn Thr Thr Thr Ser Val Thr Tyr Ser Asn Pro Pro Ser
        195                 200                 205

Ser Thr Leu Gly Lys Ser Gly Ala Ser Asn Ser Ser Ser Gly Thr Thr
    210                 215                 220

Pro Ser Ala Pro Lys Ala Thr Gly Thr Gly Lys Ser Ser Gly Ser Lys
225                 230                 235                 240

Thr Phe Ser Thr Ser Gly Phe Tyr Phe Phe Ser Ser Ser Leu Gly Leu
                245                 250                 255

Met Leu Ile Gly Ser Ile Ser Leu Leu Leu
            260                 265
```

<210> SEQ ID NO 293
<211> LENGTH: 801
<212> TYPE: DNA
<213> ORGANISM: Phakopsora pachyrhizi
<220> FEATURE:
<221> NAME/KEY: misc_feature
<222> LOCATION: (1)..(801)
<223> OTHER INFORMATION: ta09976.01_phapa

<400> SEQUENCE: 293

```
atgctctctt acgctaccat tctttgcctt ttgagcgttt ctggcttggt tcggtctggt     60

gtcgtaccga cgaagcctgg tcccggggaa acctacaacg agggggggca atgccaaatt    120

gcatgggcct tagataccac agggacttgg aactcatttt caattgattt gatgtctggc    180

tccaattttg ctatgcagca agtagttaat gtgttaaaaa atcaagacgg taccaaaggg    240

ccaggaacct acagttttcc atgccctgaa gtcactccca actcagcaat atacttttat    300

caattttctc aacataatgc tgaaactacc tggactacgc gattcactat agcttctgct    360

gatggccaaa cgactccccc tgctaatcca aatcagccaa acggtcagcc gattccatgg    420

ggaattggag cacttgcctc agccaatact caaaactctt ccagtgctac acctgttgtg    480

aatactactg cgaccgtgac tccgcccctt aatggtaacc tgactgcctt gaccacaccg    540

gcaaacacta ccagcagcag taacaatatt accaactcta atgtaaacac caccactagt    600

gttacataca gtaatccccc ttcatctact cttggaaaat ccggtgcttc aaactcctct    660

tcaggtacca ccccttctgc accaaaggca actggcaccg gcaaatcttc aggatctaaa    720
```

```
actttttcta caagcggctt ttatttcttt tcatcatcat tagggcttat gctcattgga    780

tctatttcat tactattgta a                                              801


<210> SEQ ID NO 294
<211> LENGTH: 266
<212> TYPE: PRT
<213> ORGANISM: Phakopsora pachyrhizi
<220> FEATURE:
<221> NAME/KEY: VARIANT
<222> LOCATION: (1)..(266)
<223> OTHER INFORMATION: ta09976.01_phapa

<400> SEQUENCE: 294

Met Leu Ser Tyr Ala Thr Ile Leu Cys Leu Leu Ser Val Ser Gly Leu
1               5                   10                  15

Val Arg Ser Gly Val Val Pro Thr Lys Pro Gly Pro Gly Glu Thr Tyr
            20                  25                  30

Asn Glu Gly Gly Gln Cys Gln Ile Ala Trp Ala Leu Asp Thr Thr Gly
        35                  40                  45

Thr Trp Asn Ser Phe Ser Ile Asp Leu Met Ser Gly Ser Asn Phe Ala
    50                  55                  60

Met Gln Gln Val Val Asn Val Leu Lys Asn Gln Asp Gly Thr Lys Gly
65                  70                  75                  80

Pro Gly Thr Tyr Ser Phe Pro Cys Pro Glu Val Thr Pro Asn Ser Ala
                85                  90                  95

Ile Tyr Phe Tyr Gln Phe Ser Gln His Asn Ala Glu Thr Thr Trp Thr
            100                 105                 110

Thr Arg Phe Thr Ile Ala Ser Ala Asp Gly Gln Thr Thr Pro Pro Ala
        115                 120                 125

Asn Pro Asn Gln Pro Asn Gly Gln Pro Ile Pro Trp Gly Ile Gly Ala
    130                 135                 140

Leu Ala Ser Ala Asn Thr Gln Asn Ser Ser Ser Ala Thr Pro Val Val
145                 150                 155                 160

Asn Thr Thr Ala Thr Val Thr Pro Pro Leu Asn Gly Asn Leu Thr Ala
                165                 170                 175

Leu Thr Thr Pro Ala Asn Thr Thr Ser Ser Ser Asn Asn Ile Thr Asn
            180                 185                 190

Ser Asn Val Asn Thr Thr Thr Ser Val Thr Tyr Ser Asn Pro Pro Ser
        195                 200                 205

Ser Thr Leu Gly Lys Ser Gly Ala Ser Asn Ser Ser Ser Gly Thr Thr
    210                 215                 220

Pro Ser Ala Pro Lys Ala Thr Gly Thr Gly Lys Ser Ser Gly Ser Lys
225                 230                 235                 240

Thr Phe Ser Thr Ser Gly Phe Tyr Phe Phe Ser Ser Ser Leu Gly Leu
                245                 250                 255

Met Leu Ile Gly Ser Ile Ser Leu Leu Leu
            260                 265


<210> SEQ ID NO 295
<211> LENGTH: 795
<212> TYPE: DNA
<213> ORGANISM: Phakopsora pachyrhizi
<220> FEATURE:
<221> NAME/KEY: misc_feature
<222> LOCATION: (1)..(795)
<223> OTHER INFORMATION: ta07155.01_phapa

<400> SEQUENCE: 295
```

```
atgaactcca agtctaccct cgcgatactt gtcgtggtca ccgccagttt gttaccatac     60

agctggggat ttaatcagga tagctcagaa actcaaacat ttgagcatcc ttcctccgcg    120

aaggaatcac aatcttcatt cagttatgag agtaatgaaa gcaagtcatc ttactcaagc    180

aatcaaatat cgacaaaaaa tcaatatggg cctagtagta gcttaggagg aagcactgaa    240

gacggctttg atcctgaatt cgatccaaca gaggaagaca caattacagc agagactcca    300

actaaaacaa tcttttgtcc aggaccaatt aataccggaa cgggagaggg tgtatggata    360

gatggacatt gtgaaattat gtgcttcaac aatctcgtac tggatggaga tcgatgtacc    420

tgccccccaa cctatcactt tgaccacaaa aatgtgaaat gcgtttgcag acctccactc    480

tgtgaacaag gcggtaagtg tatcttgaag ccatcgcaat atcctggcgt ccacaactct    540

gcccatagaa agaggtcaat gcctgcgcag cttcgattaa ccccacaagt ttataatgga    600

aatcatgctc gaacatcttt cgatgataag cactgcattt caaatgagat cgcctgtcgc    660

attggtagta tgactggtgg agttcaatgc gttgatccca caagtgacct ggaacactgt    720

ggggggtgct ccaacaccac agaaggcata aactgcaatc aaattcccgg ggtagaaaac    780

gctggatgca atcag                                                     795
```

```
<210> SEQ ID NO 296
<211> LENGTH: 265
<212> TYPE: PRT
<213> ORGANISM: Phakopsora pachyrhizi
<220> FEATURE:
<221> NAME/KEY: VARIANT
<222> LOCATION: (1)..(265)
<223> OTHER INFORMATION: ta07155.01_phapa

<400> SEQUENCE: 296

Met Asn Ser Lys Ser Thr Leu Ala Ile Leu Val Val Val Thr Ala Ser
1               5                   10                  15

Leu Leu Pro Tyr Ser Trp Gly Phe Asn Gln Asp Ser Ser Glu Thr Gln
            20                  25                  30

Thr Phe Glu His Pro Ser Ser Ala Lys Glu Ser Gln Ser Ser Phe Ser
        35                  40                  45

Tyr Glu Ser Asn Glu Ser Lys Ser Ser Tyr Ser Ser Asn Gln Ile Ser
    50                  55                  60

Thr Lys Asn Gln Tyr Gly Pro Ser Ser Ser Leu Gly Gly Ser Thr Glu
65                  70                  75                  80

Asp Gly Phe Asp Pro Glu Phe Asp Pro Thr Glu Glu Asp Thr Ile Thr
                85                  90                  95

Ala Glu Thr Pro Thr Lys Thr Ile Phe Cys Pro Gly Pro Ile Asn Thr
            100                 105                 110

Gly Thr Gly Glu Gly Val Trp Ile Asp Gly His Cys Glu Ile Met Cys
        115                 120                 125

Phe Asn Asn Leu Val Leu Asp Gly Asp Arg Cys Thr Cys Pro Pro Thr
    130                 135                 140

Tyr His Phe Asp His Lys Asn Val Lys Cys Val Cys Arg Pro Pro Leu
145                 150                 155                 160

Cys Glu Gln Gly Gly Lys Cys Ile Leu Lys Pro Ser Gln Tyr Pro Gly
                165                 170                 175

Val His Asn Ser Ala His Arg Lys Arg Ser Met Pro Ala Gln Leu Arg
            180                 185                 190

Leu Thr Pro Gln Val Tyr Asn Gly Asn His Ala Arg Thr Ser Phe Asp
        195                 200                 205
```

```
Asp Lys His Cys Ile Ser Asn Glu Ile Ala Cys Arg Ile Gly Ser Met
    210                 215                 220

Thr Gly Gly Val Gln Cys Val Asp Pro Thr Ser Asp Leu Glu His Cys
225                 230                 235                 240

Gly Gly Cys Ser Asn Thr Thr Glu Gly Ile Asn Cys Asn Gln Ile Pro
                245                 250                 255

Gly Val Glu Asn Ala Gly Cys Asn Gln
            260                 265
```

```
<210> SEQ ID NO 297
<211> LENGTH: 786
<212> TYPE: DNA
<213> ORGANISM: Phakopsora pachyrhizi
<220> FEATURE:
<221> NAME/KEY: misc_feature
<222> LOCATION: (1)..(786)
<223> OTHER INFORMATION: ta02824.01_phapa

<400> SEQUENCE: 297

atgaagtttt ttctggctct ctcaatttcg gttggattac tctcagccgc cctcgtttca      60

gctgatgtag ttgaagaagg tatctggcaa cgccgaccaa acgctgaatt aaaatcgagt     120

cgcggtaatt caattaaagc aagaaaccca gtatcagcta aagccttgag tcgagatgaa     180

tctagtgcgg attatggttt ggccgatgac gatgagagtg attacgtctc aggagtttat     240

gagaaactga gttcgatgct agaaaagatt cagccttcgg ttgaccaaat cgcagcttta     300

tctagtaacg ccaatgataa gaacgcggac gaatattctg aaaaaatatc taagcacttg     360

gacttcatcg ttgctgctgg agattctgtt gttaatgaaa tacaaactga agaaacttct     420

ccaattgaga ccgaagttaa taatggtatt gagccccagt ggtgtcaccg ttgccacaag     480

aaaaaacatc acaaacaccg acactgccat gagtgcaaaa agcgcgacca cgatgaatgt     540

ggccatcttt tgaagaagtg ggtttatgcc tgcaaagtta gcacttctgc agtcctgact     600

tgcaagacca aaaaggtgaa agacaagtgc gaagaacacg tccctaaggt aactaaatgt     660

gctacccaag ttgtcaacag ctgtggaaaa tacggaattt ctcaagcgtt ccgctcagtt     720

gcacaatctg agattgatgc gttttcaaaa attgggtatg gctcctcggc catttctgag     780

gcatag                                                                786

<210> SEQ ID NO 298
<211> LENGTH: 261
<212> TYPE: PRT
<213> ORGANISM: Phakopsora pachyrhizi
<220> FEATURE:
<221> NAME/KEY: VARIANT
<222> LOCATION: (1)..(261)
<223> OTHER INFORMATION: ta02824.01_phapa

<400> SEQUENCE: 298

Met Lys Phe Phe Leu Ala Leu Ser Ile Ser Val Gly Leu Leu Ser Ala
1               5                   10                  15

Ala Leu Val Ser Ala Asp Val Val Glu Glu Gly Ile Trp Gln Arg Arg
            20                  25                  30

Pro Asn Ala Glu Leu Lys Ser Ser Arg Gly Asn Ser Ile Lys Ala Arg
        35                  40                  45

Asn Pro Val Ser Ala Lys Ala Leu Ser Arg Asp Glu Ser Ser Ala Asp
    50                  55                  60

Tyr Gly Leu Ala Asp Asp Asp Glu Ser Asp Tyr Val Ser Gly Val Tyr
65                  70                  75                  80
```

```
Glu Lys Leu Ser Ser Met Leu Glu Lys Ile Gln Pro Ser Val Asp Gln
                85                  90                  95

Ile Ala Ala Leu Ser Ser Asn Ala Asn Asp Lys Asn Ala Asp Glu Tyr
            100                 105                 110

Ser Glu Lys Ile Ser Lys His Leu Asp Phe Ile Val Ala Ala Gly Asp
        115                 120                 125

Ser Val Val Asn Glu Ile Gln Thr Glu Glu Thr Ser Pro Ile Glu Thr
    130                 135                 140

Glu Val Asn Asn Gly Ile Glu Pro Gln Trp Cys His Arg Cys His Lys
145                 150                 155                 160

Lys Lys His His Lys His Arg His Cys His Glu Cys Lys Lys Arg Asp
                165                 170                 175

His Asp Glu Cys Gly His Leu Leu Lys Lys Trp Val Tyr Ala Cys Lys
            180                 185                 190

Val Ser Thr Ser Ala Val Leu Thr Cys Lys Thr Lys Lys Val Lys Asp
        195                 200                 205

Lys Cys Glu Glu His Val Pro Lys Val Thr Lys Cys Ala Thr Gln Val
    210                 215                 220

Val Asn Ser Cys Gly Lys Tyr Gly Ile Ser Gln Ala Phe Arg Ser Val
225                 230                 235                 240

Ala Gln Ser Glu Ile Asp Ala Phe Ser Lys Ile Gly Tyr Gly Ser Ser
                245                 250                 255

Ala Ile Ser Glu Ala
            260
```

<210> SEQ ID NO 299
<211> LENGTH: 777
<212> TYPE: DNA
<213> ORGANISM: Phakopsora pachyrhizi
<220> FEATURE:
<221> NAME/KEY: misc_feature
<222> LOCATION: (1)..(777)
<223> OTHER INFORMATION: ta09817.01_phapa

<400> SEQUENCE: 299

```
atgtttaaga agagtactat gattcttact tttctctttt tggctttaca cgggactctg     60

tcttcaccag tgccagattc tttgacctct aatgataata acgatataaa ctttagctca    120

gaaatatttg cgcgagctgt ccaggatgaa tatccacaag agcaggagaa ctcaaggagt    180

ggcataccag ggaacgaatt tgaaaatagc aacgtagtca ataatgcaag agacccagca    240

gagttgaacg agcagaatga acaaattcgc ggtgataatc aacctactac taactctaat    300

attcaactca atcttaaatc aagcaccgag gacaagacgg caaaagattc accaagaaaa    360

aggtctccag aatcctttga tacaactagc agcgtacaac cttctcccag agaatcaaat    420

ggggaaatca caaatcctca agtcaatgat gtttctcaca gcgatcagat taactcaggt    480

aactctccga ctgagggctt tcatccagga gatttgaaca cgagcggaga tcaagggttg    540

tctaaaatct ggccaaacaa ggatgaaccc caagtgaact atgatcctca caaagatcaa    600

acaacctcag aaagttttcc gacacagggc tctactcaag gtaattttca acctcagcca    660

tctagggata ccactcagat taacgaaaat ccttcgattg atcaaacaaa ctcaggtaca    720

actactccaa atccagtcaa ttctcaagat ggtaataagc cacatggtga taaatga       777
```

<210> SEQ ID NO 300
<211> LENGTH: 258
<212> TYPE: PRT
<213> ORGANISM: Phakopsora pachyrhizi
<220> FEATURE:
<221> NAME/KEY: VARIANT
<222> LOCATION: (1)..(258)
<223> OTHER INFORMATION: ta09817.01_phapa

<400> SEQUENCE: 300

```
Met Phe Lys Lys Ser Thr Met Ile Leu Thr Phe Leu Phe Leu Ala Leu
1               5                   10                  15

His Gly Thr Leu Ser Ser Pro Val Pro Asp Ser Leu Thr Ser Asn Asp
            20                  25                  30

Asn Asn Asp Ile Asn Phe Ser Ser Glu Ile Phe Ala Arg Ala Val Gln
        35                  40                  45

Asp Glu Tyr Pro Gln Glu Gln Glu Asn Ser Arg Ser Gly Ile Pro Gly
    50                  55                  60

Asn Glu Phe Glu Asn Ser Asn Val Val Asn Asn Ala Arg Asp Pro Ala
65                  70                  75                  80

Glu Leu Asn Glu Gln Asn Glu Gln Ile Arg Gly Asp Asn Gln Pro Thr
                85                  90                  95

Thr Asn Ser Asn Ile Gln Leu Asn Leu Lys Ser Ser Thr Glu Asp Lys
            100                 105                 110

Thr Ala Lys Asp Ser Pro Arg Lys Arg Ser Pro Glu Ser Phe Asp Thr
        115                 120                 125

Thr Ser Ser Val Gln Pro Ser Pro Arg Glu Ser Asn Gly Glu Ile Thr
    130                 135                 140

Asn Pro Gln Val Asn Asp Val Ser His Ser Asp Gln Ile Asn Ser Gly
145                 150                 155                 160

Asn Ser Pro Thr Glu Gly Phe His Pro Gly Asp Leu Asn Thr Ser Gly
                165                 170                 175

Asp Gln Gly Leu Ser Lys Ile Trp Pro Asn Lys Asp Glu Pro Gln Val
            180                 185                 190

Asn Tyr Asp Pro His Lys Asp Gln Thr Thr Ser Glu Ser Phe Pro Thr
        195                 200                 205

Gln Gly Ser Thr Gln Gly Asn Phe Gln Pro Gln Pro Ser Arg Asp Thr
    210                 215                 220

Thr Gln Ile Asn Glu Asn Pro Ser Ile Asp Gln Thr Asn Ser Gly Thr
225                 230                 235                 240

Thr Thr Pro Asn Pro Val Asn Ser Gln Asp Gly Asn Lys Pro His Gly
                245                 250                 255

Asp Lys
```

<210> SEQ ID NO 301
<211> LENGTH: 771
<212> TYPE: DNA
<213> ORGANISM: Phakopsora pachyrhizi
<220> FEATURE:
<221> NAME/KEY: misc_feature
<222> LOCATION: (1)..(771)
<223> OTHER INFORMATION: ta08887.01_phapa

<400> SEQUENCE: 301

```
atgtcttttc gtctcatatc tacgagaagg cttcacgtac tatactcaac ccctcttttg      60

ctcagcctag catgtataat acttatacta tcatcgctgt gcgggcttgt tccatggcat     120

cacacctctg gttcaatttt aattgttaaa aaaacctctc aaaatagtac tcttgtcgaa     180

aaatcaaatg aaacggcatc attttatttc ggattgcttg gttcttgtta tcgaccttca     240

aaggcagaaa aactacagtg cacctcttca gcattcccac ctgatctatt agctactatc     300
```

-continued

```
gagaaggggg gtagtgggat caacgctcct catctacaac tagctttgcc tgagctgccc    360

ccagttttca tgtcctgggc agcagtttcg cttttggcac tcgtatgcga aatcctaggt    420

agccttccat tttacattcc taggagattc ggtcattgta gtcgtttttg ctatggattt    480

tttactgctg cactatggat tcttgggttg ggctgggctc ttggattctc ggccgttcta    540

gccctagcgt gctttgctca gagctttggg gaagagtaca atgcattttc tgcagacttc    600

ttttacaata cagccacgcc aggatcaata ttcgttccgc aagtaattgc gctagtcgtt    660

caaatattaa ttggaatagc tacaattgtc aaaatcgaaa attcttcaaa aaaagactca    720

ttcattaatt catcaacgtg gtctaacaat ctaagagtaa ctggtccata a             771
```

<210> SEQ ID NO 302
<211> LENGTH: 256
<212> TYPE: PRT
<213> ORGANISM: Phakopsora pachyrhizi
<220> FEATURE:
<221> NAME/KEY: VARIANT
<222> LOCATION: (1)..(256)
<223> OTHER INFORMATION: ta08887.01_phapa

<400> SEQUENCE: 302

```
Met Ser Phe Arg Leu Ile Ser Thr Arg Arg Leu His Val Leu Tyr Ser
1               5                   10                  15

Thr Pro Leu Leu Leu Ser Leu Ala Cys Ile Ile Leu Ile Leu Ser Ser
            20                  25                  30

Leu Cys Gly Leu Val Pro Trp His His Thr Ser Gly Ser Ile Leu Ile
        35                  40                  45

Val Lys Lys Thr Ser Gln Asn Ser Thr Leu Val Glu Lys Ser Asn Glu
    50                  55                  60

Thr Ala Ser Phe Tyr Phe Gly Leu Leu Gly Ser Cys Tyr Arg Pro Ser
65                  70                  75                  80

Lys Ala Glu Lys Leu Gln Cys Thr Ser Ser Ala Phe Pro Pro Asp Leu
                85                  90                  95

Leu Ala Thr Ile Glu Lys Gly Gly Ser Gly Ile Asn Ala Pro His Leu
            100                 105                 110

Gln Leu Ala Leu Pro Glu Leu Pro Pro Val Phe Met Ser Trp Ala Ala
        115                 120                 125

Val Ser Leu Leu Ala Leu Val Cys Glu Ile Leu Gly Ser Leu Pro Phe
    130                 135                 140

Tyr Ile Pro Arg Arg Phe Gly His Cys Ser Arg Phe Cys Tyr Gly Phe
145                 150                 155                 160

Phe Thr Ala Ala Leu Trp Ile Leu Gly Leu Gly Trp Ala Leu Gly Phe
                165                 170                 175

Ser Ala Val Leu Ala Leu Ala Cys Phe Ala Gln Ser Phe Gly Glu Glu
            180                 185                 190

Tyr Asn Ala Phe Ser Ala Asp Phe Phe Tyr Asn Thr Ala Thr Pro Gly
        195                 200                 205

Ser Ile Phe Val Pro Gln Val Ile Ala Leu Val Val Gln Ile Leu Ile
    210                 215                 220

Gly Ile Ala Thr Ile Val Lys Ile Glu Asn Ser Ser Lys Lys Asp Ser
225                 230                 235                 240

Phe Ile Asn Ser Ser Thr Trp Ser Asn Asn Leu Arg Val Thr Gly Pro
                245                 250                 255
```

<210> SEQ ID NO 303
<211> LENGTH: 768

<212> TYPE: DNA
<213> ORGANISM: Phakopsora pachyrhizi
<220> FEATURE:
<221> NAME/KEY: misc_feature
<222> LOCATION: (1)..(768)
<223> OTHER INFORMATION: ta03435.01_phapa

<400> SEQUENCE: 303
atgttttcta aatcatttca aggattgagc ctactcgtag ttctgatggc ctctattatc 60
tttaactgtg atgaatcaaa cgcccagagt aactttaact cttttcaaca accaggcacg 120
aactgttacg aacagtcaaa atcctatgga atcaatttcg aacattgtga aaaagctcta 180
aggaaaattt catacgattc taatggtaac ttggataatt catccaagac ggtttttgtc 240
tggcataaat cttgtgtggt caaagttcaa aaggcaacat acgctcaacc atcgagacaa 300
caagtagaat atggtgttag aaacttacta cagacttgtc ctacgagggg agggatttat 360
atcccttcaa atgactttag gacctatgtt tactcttcaa atcgtgaaaa cgtttacaat 420
ttgaacagcc cagtgtgcat taagcaccaa tgtcatatca accctaatga ctgtttgatg 480
gcctttaaca acattcctct tagtactaaa ggtttttct taccatctgg ttcaacctct 540
tctaatgtta taaagacttc tagtggtaac tgcactgtta aacttgtcac tactgatggt 600
gcaggattca gaattaacca tcctgaaatt aactctggta tcaaaactct actctcaaaa 660
tgtggtagca gacctggtta caactatttc ggtggtggca gtctaggaat gaatggtgat 720
attaaaatca tcactcaaaa cagttacaac aacggtcaat gtaattaa 768

<210> SEQ ID NO 304
<211> LENGTH: 255
<212> TYPE: PRT
<213> ORGANISM: Phakopsora pachyrhizi
<220> FEATURE:
<221> NAME/KEY: VARIANT
<222> LOCATION: (1)..(255)
<223> OTHER INFORMATION: ta03435.01_phapa

<400> SEQUENCE: 304

Met Phe Ser Lys Ser Phe Gln Gly Leu Ser Leu Leu Val Val Leu Met
1 5 10 15

Ala Ser Ile Ile Phe Asn Cys Asp Glu Ser Asn Ala Gln Ser Asn Phe
20 25 30

Asn Ser Phe Gln Gln Pro Gly Thr Asn Cys Tyr Glu Gln Ser Lys Ser
35 40 45

Tyr Gly Ile Asn Phe Glu His Cys Glu Lys Ala Leu Arg Lys Ile Ser
50 55 60

Tyr Asp Ser Asn Gly Asn Leu Asp Asn Ser Ser Lys Thr Val Phe Val
65 70 75 80

Trp His Lys Ser Cys Val Val Lys Val Gln Lys Ala Thr Tyr Ala Gln
85 90 95

Pro Ser Arg Gln Gln Val Glu Tyr Gly Val Arg Asn Leu Leu Gln Thr
100 105 110

Cys Pro Thr Arg Gly Gly Ile Tyr Ile Pro Ser Asn Asp Phe Arg Thr
115 120 125

Tyr Val Tyr Ser Ser Asn Arg Glu Asn Val Tyr Asn Leu Asn Ser Pro
130 135 140

Val Cys Ile Lys His Gln Cys His Ile Asn Pro Asn Asp Cys Leu Met
145 150 155 160

Ala Phe Asn Asn Ile Pro Leu Ser Thr Lys Gly Phe Phe Leu Pro Ser
165 170 175

```
Gly Ser Thr Ser Ser Asn Val Ile Lys Thr Ser Ser Gly Asn Cys Thr
            180                 185                 190

Val Lys Leu Val Thr Thr Asp Gly Ala Gly Phe Arg Ile Asn His Pro
        195                 200                 205

Glu Ile Asn Ser Gly Ile Lys Thr Leu Leu Ser Lys Cys Gly Ser Arg
    210                 215                 220

Pro Gly Tyr Asn Tyr Phe Gly Gly Gly Ser Leu Gly Met Asn Gly Asp
225                 230                 235                 240

Ile Lys Ile Ile Thr Gln Asn Ser Tyr Asn Asn Gly Gln Cys Asn
                245                 250                 255
```

<210> SEQ ID NO 305
<211> LENGTH: 765
<212> TYPE: DNA
<213> ORGANISM: Phakopsora pachyrhizi
<220> FEATURE:
<221> NAME/KEY: misc_feature
<222> LOCATION: (1)..(765)
<223> OTHER INFORMATION: ta05344.01_phapa

<400> SEQUENCE: 305

```
atgaacatga aacttagagt attcatttcc ttaactgttg cgctttcttt gattgctcaa      60

tccccaagcc tagctgtaac tttaaataga gatcggcctt caaatgccca tgcgctccag     120

gctagacagg aacaagctgc agagctagct gctgtcacgg taccggaaga acaagctgcc     180

gctagtgctc ccgagcagaa ggctgctgct gctgcctccg ctccagagca cgctgctgct     240

tcctccgctc ccgagcacgc tgcttctgct gccgctcctc aaagtgacct agacaaagct     300

gccaatagat tgtacgactt aatggtaaac cttggaaatg gattggagat cgtcacaaat     360

cttgaggcca gtccacagga tatcaaggcc cagactcaaa aagtcaaaca atattttggt     420

gaaatgaatg agctaagaaa caagttgctc cagatgagcc ccatacattc tggaaacctc     480

cccaaatctg ttcaagatgc caatgaagct caggaaacat tacagaaagc gttgattgct     540

attagtgatt cggcagaaga cgcaaatgtt ctaaaaaaga actacccagt cctttcgaag     600

acttttaaat ccgtaactac tgctggagaa gatctgttct caactttgta ccctggctat     660

ggtgagaaaa ctcaggaagg acaagatgct caacaacaca gccagcccca agcaacgcaa     720

gagggtgctg ctcctgtagc tgctgctgaa gcccctcaag cttaa                      765
```

<210> SEQ ID NO 306
<211> LENGTH: 254
<212> TYPE: PRT
<213> ORGANISM: Phakopsora pachyrhizi
<220> FEATURE:
<221> NAME/KEY: VARIANT
<222> LOCATION: (1)..(254)
<223> OTHER INFORMATION: ta05344.01_phapa

<400> SEQUENCE: 306

```
Met Asn Met Lys Leu Arg Val Phe Ile Ser Leu Thr Val Ala Leu Ser
1               5                   10                  15

Leu Ile Ala Gln Ser Pro Ser Leu Ala Val Thr Leu Asn Arg Asp Arg
            20                  25                  30

Pro Ser Asn Ala His Ala Leu Gln Ala Arg Gln Glu Gln Ala Ala Glu
        35                  40                  45

Leu Ala Ala Val Thr Val Pro Glu Glu Gln Ala Ala Ala Ser Ala Pro
    50                  55                  60

Glu Gln Lys Ala Ala Ala Ala Ala Ser Ala Pro Glu His Ala Ala Ala
```

```
65                  70                  75                  80

Ser Ser Ala Pro Glu His Ala Ala Ser Ala Ala Ala Pro Gln Ser Asp
                85                  90                  95

Leu Asp Lys Ala Ala Asn Arg Leu Tyr Asp Leu Met Val Asn Leu Gly
            100                 105                 110

Asn Gly Leu Glu Ile Val Thr Asn Leu Glu Ala Ser Pro Gln Asp Ile
        115                 120                 125

Lys Ala Gln Thr Gln Lys Val Lys Gln Tyr Phe Gly Glu Met Asn Glu
    130                 135                 140

Leu Arg Asn Lys Leu Leu Gln Met Ser Pro Ile His Ser Gly Asn Leu
145                 150                 155                 160

Pro Lys Ser Val Gln Asp Ala Asn Glu Ala Gln Glu Thr Leu Gln Lys
                165                 170                 175

Ala Leu Ile Ala Ile Ser Asp Ser Ala Glu Asp Ala Asn Val Leu Lys
            180                 185                 190

Lys Asn Tyr Pro Val Leu Ser Lys Thr Phe Lys Ser Val Thr Thr Ala
        195                 200                 205

Gly Glu Asp Leu Phe Ser Thr Leu Tyr Pro Gly Tyr Gly Glu Lys Thr
    210                 215                 220

Gln Glu Gly Gln Asp Ala Gln Gln His Ser Gln Pro Gln Ala Thr Gln
225                 230                 235                 240

Glu Gly Ala Ala Pro Val Ala Ala Ala Glu Ala Pro Gln Ala
                245                 250
```

```
<210> SEQ ID NO 307
<211> LENGTH: 762
<212> TYPE: DNA
<213> ORGANISM: Phakopsora pachyrhizi
<220> FEATURE:
<221> NAME/KEY: misc_feature
<222> LOCATION: (1)..(762)
<223> OTHER INFORMATION: ta01958.01_phapa

<400> SEQUENCE: 307

atgaatcgat tggtcaggct gatactactg ctatcatcat ctctgacgct ctggatgata      60

aacctctttg gttcacaggt tatggcttca tccagactgt tgggtagagt gactctaaac     120

gataaactaa cagatatcaa tctgattcct actgattcaa gagtctcgat cagtaacggt     180

gatttaacca ctagggttca tatcagatca gatggtacat tcgtatttca agatctaaag     240

ccaggaagat acatcctcag ggtacagtgt cgaaggttca gcttcccaat gctaaaggtc     300

agactgtcgg atgatgacca gggctcgatt ccgatcgtca gcccatactc catctcacag     360

gcagaacctg accctagggc aaaccacttc gaacataagc tccaacaccc gattcagata     420

tctccaatct ctatcctcga gtactacgag attccagtag gcttcaatcc actctcgatc     480

ttactcggaa accccatgta cctgttgatg ggaggaatgg tcatcttcat gatcctgatg     540

cctaaactct taaacctgtt ggatcctgat gcattggccg aactccagga gaaccagtca     600

aacatgcaca aacagatgag tctgattcaa aacatggacc taacctctgg catatctaac     660

attctatcgc aacagtcaga ggaagatgaa aagaggacta gtactcaggg gagaatcagt     720

agtgataaac aaaaggatgc ctcaatcaaa aggagaagat ga                        762

<210> SEQ ID NO 308
<211> LENGTH: 253
<212> TYPE: PRT
<213> ORGANISM: Phakopsora pachyrhizi
<220> FEATURE:
```

<221> NAME/KEY: VARIANT
<222> LOCATION: (1)..(253)
<223> OTHER INFORMATION: ta01958.01_phapa

<400> SEQUENCE: 308

```
Met Asn Arg Leu Val Arg Leu Ile Leu Leu Leu Ser Ser Ser Leu Thr
1               5                   10                  15

Leu Trp Met Ile Asn Leu Phe Gly Ser Gln Val Met Ala Ser Ser Arg
            20                  25                  30

Leu Leu Gly Arg Val Thr Leu Asn Asp Lys Leu Thr Asp Ile Asn Leu
        35                  40                  45

Ile Pro Thr Asp Ser Arg Val Ser Ile Ser Asn Gly Asp Leu Thr Thr
    50                  55                  60

Arg Val His Ile Arg Ser Asp Gly Thr Phe Val Phe Gln Asp Leu Lys
65                  70                  75                  80

Pro Gly Arg Tyr Ile Leu Arg Val Gln Cys Arg Arg Phe Ser Phe Pro
                85                  90                  95

Met Leu Lys Val Arg Leu Ser Asp Asp Asp Gln Gly Ser Ile Pro Ile
            100                 105                 110

Val Ser Pro Tyr Ser Ile Ser Gln Ala Glu Pro Asp Pro Arg Ala Asn
        115                 120                 125

His Phe Glu His Lys Leu Gln His Pro Ile Gln Ile Ser Pro Ile Ser
    130                 135                 140

Ile Leu Glu Tyr Tyr Glu Ile Pro Val Gly Phe Asn Pro Leu Ser Ile
145                 150                 155                 160

Leu Leu Gly Asn Pro Met Tyr Leu Leu Met Gly Gly Met Val Ile Phe
                165                 170                 175

Met Ile Leu Met Pro Lys Leu Leu Asn Leu Leu Asp Pro Asp Ala Leu
            180                 185                 190

Ala Glu Leu Gln Glu Asn Gln Ser Asn Met His Lys Gln Met Ser Leu
        195                 200                 205

Ile Gln Asn Met Asp Leu Thr Ser Gly Ile Ser Asn Ile Leu Ser Gln
    210                 215                 220

Gln Ser Glu Glu Asp Glu Lys Arg Thr Ser Thr Gln Gly Arg Ile Ser
225                 230                 235                 240

Ser Asp Lys Gln Lys Asp Ala Ser Ile Lys Arg Arg Arg
                245                 250
```

<210> SEQ ID NO 309
<211> LENGTH: 750
<212> TYPE: DNA
<213> ORGANISM: Phakopsora pachyrhizi
<220> FEATURE:
<221> NAME/KEY: misc_feature
<222> LOCATION: (1)..(750)
<223> OTHER INFORMATION: ta10330.02_phapa

<400> SEQUENCE: 309

```
atgaagtgca ctcttagctc tgtaatattt ataggattta tattgtttac agcgactgga      60

tgtgcacaca ctgcggtaca aaattctcat ttcgataaat ttagagacgc attcagcgcc     120

agtgggttgg ttcctaattt gattccaagt tttgatccca aggcaataat gattcttcga     180

ttcgaagatg gaactaatgt ccgtcatcct gatagcagaa tcaaaacact ctcagcccac     240

acgccacctg ttattgaagt tcatccgtac gatttcggaa ggctaagaga tgatcaaaaa     300

tttaccctct taattgtcag cacaaattac tcggtccgcc caagctcatt gggggtcaag     360

ctacatcttc tggggactaa ttttgccctt cgacgaatag aatcaccgga ggagatttac     420
```

```
aacttagtga acgagactaa atttgctgtt gaatatcgag ctcctgattc aacagaatca    480

aggcaataca atgttctttt gtacgatggg gttgcatctt cctcacctct tcaggaagtt    540

caggaccata aagtagatca taacaatttt aatgtgacac atttcacatc taatgcgggc    600

ctatcaccct cgccgtattc tggggcaatc tttggactaa gtgaaaatgc tcagaactct    660

gccaatgaag catcaagagc tcaaggactc gcaaaatcaa gtataatctt ggttttatca    720

ttcataaatc tcttcatgtt tggaaattga                                    750


<210> SEQ ID NO 310
<211> LENGTH: 249
<212> TYPE: PRT
<213> ORGANISM: Phakopsora pachyrhizi
<220> FEATURE:
<221> NAME/KEY: VARIANT
<222> LOCATION: (1)..(249)
<223> OTHER INFORMATION: ta10330.02_phapa

<400> SEQUENCE: 310

Met Lys Cys Thr Leu Ser Ser Val Ile Phe Ile Gly Phe Ile Leu Phe
1               5                   10                  15

Thr Ala Thr Gly Cys Ala His Thr Ala Val Gln Asn Ser His Phe Asp
            20                  25                  30

Lys Phe Arg Asp Ala Phe Ser Ala Ser Gly Leu Val Pro Asn Leu Ile
        35                  40                  45

Pro Ser Phe Asp Pro Lys Ala Ile Met Ile Leu Arg Phe Glu Asp Gly
    50                  55                  60

Thr Asn Val Arg His Pro Asp Ser Arg Ile Lys Thr Leu Ser Ala His
65                  70                  75                  80

Thr Pro Pro Val Ile Glu Val His Pro Tyr Asp Phe Gly Arg Leu Arg
                85                  90                  95

Asp Asp Gln Lys Phe Thr Leu Leu Ile Val Ser Thr Asn Tyr Ser Val
            100                 105                 110

Arg Pro Ser Ser Leu Gly Val Lys Leu His Leu Leu Gly Thr Asn Phe
        115                 120                 125

Ala Leu Arg Arg Ile Glu Ser Pro Glu Glu Ile Tyr Asn Leu Val Asn
    130                 135                 140

Glu Thr Lys Phe Ala Val Glu Tyr Arg Ala Pro Asp Ser Thr Glu Ser
145                 150                 155                 160

Arg Gln Tyr Asn Val Leu Leu Tyr Asp Gly Val Ala Ser Ser Ser Pro
                165                 170                 175

Leu Gln Glu Val Gln Asp His Lys Val Asp His Asn Asn Phe Asn Val
            180                 185                 190

Thr His Phe Thr Ser Asn Ala Gly Leu Ser Pro Ser Pro Tyr Ser Gly
        195                 200                 205

Ala Ile Phe Gly Leu Ser Glu Asn Ala Gln Asn Ser Ala Asn Glu Ala
    210                 215                 220

Ser Arg Ala Gln Gly Leu Ala Lys Ser Ser Ile Ile Leu Val Leu Ser
225                 230                 235                 240

Phe Ile Asn Leu Phe Met Phe Gly Asn
                245


<210> SEQ ID NO 311
<211> LENGTH: 726
<212> TYPE: DNA
<213> ORGANISM: Phakopsora pachyrhizi
<220> FEATURE:
```

<221> NAME/KEY: misc_feature
<222> LOCATION: (1)..(726)
<223> OTHER INFORMATION: ta00415.01_phapa

<400> SEQUENCE: 311
atgcaattcc tcatcgctgc ttctcttgtg ttcctcgctc tccagggggt ttctgcctct 60
gatgaaaaag ctaccgtccc aaccgtctca agaaagccga atacgttacc tcacacgttt 120
tgttataatt tttttttaca aaaagactcg tgtgtcattg gttctccaat taaagaagac 180
cgatgtgatc cagataaaaa ggacccaaag aaatctgaga aatgtaacaa agttgaacac 240
ccaaacaagc gtcatgctaa acagcgtgtg ctaacgaaaa gatacgatga cgaaggtagt 300 tctttttca taaacagtgg aagtgggatc tgtggtgttt atgacagtaa ccaacctgga 360
gcttgcctat ttagtggtta cgatgatagc ggagcaaact cagctctagc aggatggttg 420
aacggaaatc aaacctccaa ctgcggaaag caaatctata taatgaggca gtcggatgcc 480
aatttagcta aagaaaagag gaatgttcaa tacgcgcccg ttgttgatgg ctgtagtttt 540
aaccttggcg ggaattcggc taagaagaat ggagacggct gtttcagaat tggtgtcaca 600
aatcatactt tctttgccct taaccccact gcgggagaga ttcaaaacgg aacaatctcc 660
caactccttt gggattttga tgctgaatcc agcgacgata aggcaaagga gaacggacct 720
ttttaa 726

<210> SEQ ID NO 312
<211> LENGTH: 241
<212> TYPE: PRT
<213> ORGANISM: Phakopsora pachyrhizi
<220> FEATURE:
<221> NAME/KEY: VARIANT
<222> LOCATION: (1)..(241)
<223> OTHER INFORMATION: ta00415.01_phapa

<400> SEQUENCE: 312

Met Gln Phe Leu Ile Ala Ala Ser Leu Val Phe Leu Ala Leu Gln Gly
1 5 10 15

Val Ser Ala Ser Asp Glu Lys Ala Thr Val Pro Thr Val Ser Arg Lys
20 25 30

Pro Asn Thr Leu Pro His Thr Phe Cys Tyr Asn Phe Phe Leu Gln Lys
35 40 45

Asp Ser Cys Val Ile Gly Ser Pro Ile Lys Glu Asp Arg Cys Asp Pro
50 55 60

Asp Lys Lys Asp Pro Lys Lys Ser Glu Lys Cys Asn Lys Val Glu His
65 70 75 80

Pro Asn Lys Arg His Ala Lys Gln Arg Val Leu Thr Lys Arg Tyr Asp
85 90 95

Asp Glu Gly Ser Ser Phe Phe Ile Asn Ser Gly Ser Gly Ile Cys Gly
100 105 110

Val Tyr Asp Ser Asn Gln Pro Gly Ala Cys Leu Phe Ser Gly Tyr Asp
115 120 125

Asp Ser Gly Ala Asn Ser Ala Leu Ala Gly Trp Leu Asn Gly Asn Gln
130 135 140

Thr Ser Asn Cys Gly Lys Gln Ile Tyr Ile Met Arg Gln Ser Asp Ala
145 150 155 160

Asn Leu Ala Lys Glu Lys Arg Asn Val Gln Tyr Ala Pro Val Val Asp
165 170 175

Gly Cys Ser Phe Asn Leu Gly Gly Asn Ser Ala Lys Lys Asn Gly Asp
180 185 190

```
Gly Cys Phe Arg Ile Gly Val Thr Asn His Thr Phe Phe Ala Leu Asn
        195                 200                 205

Pro Thr Ala Gly Glu Ile Gln Asn Gly Thr Ile Ser Gln Leu Leu Trp
    210                 215                 220

Asp Phe Asp Ala Glu Ser Ser Asp Asp Lys Ala Lys Glu Asn Gly Pro
225                 230                 235                 240

Phe


<210> SEQ ID NO 313
<211> LENGTH: 717
<212> TYPE: DNA
<213> ORGANISM: Phakopsora pachyrhizi
<220> FEATURE:
<221> NAME/KEY: misc_feature
<222> LOCATION: (1)..(717)
<223> OTHER INFORMATION: ta04712.01_phapa

<400> SEQUENCE: 313

atggctaata atctcacagt ttctaccttc ttactgctag ccctttcacc atttgtttct      60

tacgctgccg ttcaccctca gctcgtcgcc ttcaaaacct tttctttccc caagggtact     120

tcgccaagct cagaaaatgg taaaaatctt caatttttta aagcagctga ctctccagca     180

gccactgagg tgcccagtca gggcaacaat ctggttaata gtggcctaac ttcaaccgtc     240

tgcaaatctt ccgagggcaa ggaatttact ttcactaatc aagactgtct agatgctgct     300

agagtcatcg ccaatgaatc cacttcatct gcacagtgcg gtaactgcgt tatcggcttg     360

ttcgatgtca ataagaagaa agcttttaca ccacctggcc cggtgtcacc ctcagttcta     420

gagaatcaag ttaataaggt tttatcggaa tgtagcaaca gagctagcag taccaaccca     480

ccagtgaata ataagcgcag tcttttacct tcacaatctg gagttgaaag tgtcagcgga     540

agtgatagta tagctaatca ccctgcagtt gcaaacgctg gtgggcataa taacttggcc     600

actcaacctg gaactacaag ccccggtggg tcgcaacctg ggagtggaag tggaaactca     660

gattcagcta cagttcaaat ggtcatggga tacaacccca cttcaaaagc ttgctga        717


<210> SEQ ID NO 314
<211> LENGTH: 238
<212> TYPE: PRT
<213> ORGANISM: Phakopsora pachyrhizi
<220> FEATURE:
<221> NAME/KEY: VARIANT
<222> LOCATION: (1)..(238)
<223> OTHER INFORMATION: ta04712.01_phapa

<400> SEQUENCE: 314

Met Ala Asn Asn Leu Thr Val Ser Thr Phe Leu Leu Leu Ala Leu Ser
1               5                   10                  15

Pro Phe Val Ser Tyr Ala Ala Val His Pro Gln Leu Val Ala Phe Lys
            20                  25                  30

Thr Phe Ser Phe Pro Lys Gly Thr Ser Pro Ser Ser Glu Asn Gly Lys
        35                  40                  45

Asn Leu Gln Phe Phe Lys Ala Ala Asp Ser Pro Ala Ala Thr Glu Val
    50                  55                  60

Pro Ser Gln Gly Asn Asn Leu Val Asn Ser Gly Leu Thr Ser Thr Val
65                  70                  75                  80

Cys Lys Ser Ser Glu Gly Lys Glu Phe Thr Phe Thr Asn Gln Asp Cys
                85                  90                  95

Leu Asp Ala Ala Arg Val Ile Ala Asn Glu Ser Thr Ser Ser Ala Gln
```

```
            100                 105                 110

Cys Gly Asn Cys Val Ile Gly Leu Phe Asp Val Asn Lys Lys Lys Ala
        115                 120                 125

Phe Thr Pro Pro Gly Pro Val Ser Pro Ser Val Leu Glu Asn Gln Val
    130                 135                 140

Asn Lys Val Leu Ser Glu Cys Ser Asn Arg Ala Ser Ser Thr Asn Pro
145                 150                 155                 160

Pro Val Asn Asn Lys Arg Ser Leu Leu Pro Ser Gln Ser Gly Val Glu
                165                 170                 175

Ser Val Ser Gly Ser Asp Ser Ile Ala Asn His Pro Ala Val Ala Asn
            180                 185                 190

Ala Gly Gly His Asn Asn Leu Ala Thr Gln Pro Gly Thr Thr Ser Pro
        195                 200                 205

Gly Gly Ser Gln Pro Gly Ser Gly Ser Gly Asn Ser Asp Ser Ala Thr
    210                 215                 220

Val Gln Met Val Met Gly Tyr Asn Pro Thr Ser Lys Ala Cys
225                 230                 235


<210> SEQ ID NO 315
<211> LENGTH: 711
<212> TYPE: DNA
<213> ORGANISM: Phakopsora pachyrhizi
<220> FEATURE:
<221> NAME/KEY: misc_feature
<222> LOCATION: (1)..(711)
<223> OTHER INFORMATION: ta10589.01_phapa

<400> SEQUENCE: 315

atgaagttct cttactccca attgattgtt ctgctgtctg tgatttctct gagctttgtt      60

gcatctgaag aaactaaaag tcagagggca gaatcttccg atgagaaatg gttcggacta     120

ggttacaaca gcttgaggtg gaactactgg aacggccttg ccggatgggg tggtatagga     180

tcattatacc cttggctggg tgcttacagc ggtgcctatg ggattggtct atgctcagga     240

aactacctca acagctggtt caagtctgcc caaggcgaaa agcagcgccg ctctttcgag     300

ttcaattcag gagctcaact ccaaacccgt ggtgagccag acttattgga gactgtgacg     360

tgcaagaaca ccaagggtga atctcagcag ttcctcacaa gcagttgttt gaaggcagca     420

gagcagttgg tcgagaaaca aacttcatct gccacttgtg gtagctgcac tctccaactc     480

catggtccat caggagatct atcagcaaag agcattcctg cctcagagct aaccaccgca     540

gcctctaaca tcctgaaggc ctgctccaag gctgagaaca agattcttag cacctcagag     600

ctccagagac gtggaaacga agctgagaac agctcttcgg acaacaatgc taaggattcg     660

aagaactcct ttgccgttgt gctcctcaaa ggcaatggtc cagagtgcta g              711


<210> SEQ ID NO 316
<211> LENGTH: 236
<212> TYPE: PRT
<213> ORGANISM: Phakopsora pachyrhizi
<220> FEATURE:
<221> NAME/KEY: VARIANT
<222> LOCATION: (1)..(236)
<223> OTHER INFORMATION: ta10589.01_phapa

<400> SEQUENCE: 316

Met Lys Phe Ser Tyr Ser Gln Leu Ile Val Leu Leu Ser Val Ile Ser
1               5                   10                  15

Leu Ser Phe Val Ala Ser Glu Glu Thr Lys Ser Gln Arg Ala Glu Ser
            20                  25                  30
```

```
Ser Asp Glu Lys Trp Phe Gly Leu Gly Tyr Asn Ser Leu Arg Trp Asn
        35                  40                  45

Tyr Trp Asn Gly Leu Ala Gly Trp Gly Gly Ile Gly Ser Leu Tyr Pro
    50                  55                  60

Trp Leu Gly Ala Tyr Ser Gly Ala Tyr Gly Ile Gly Leu Cys Ser Gly
65                  70                  75                  80

Asn Tyr Leu Asn Ser Trp Phe Lys Ser Ala Gln Gly Glu Lys Gln Arg
                85                  90                  95

Arg Ser Phe Glu Phe Asn Ser Gly Ala Gln Leu Gln Thr Arg Gly Glu
            100                 105                 110

Pro Asp Leu Leu Glu Thr Val Thr Cys Lys Asn Thr Lys Gly Glu Ser
        115                 120                 125

Gln Gln Phe Leu Thr Ser Ser Cys Leu Lys Ala Ala Glu Gln Leu Val
    130                 135                 140

Glu Lys Gln Thr Ser Ser Ala Thr Cys Gly Ser Cys Thr Leu Gln Leu
145                 150                 155                 160

His Gly Pro Ser Gly Asp Leu Ser Ala Lys Ser Ile Pro Ala Ser Glu
                165                 170                 175

Leu Thr Thr Ala Ala Ser Asn Ile Leu Lys Ala Cys Ser Lys Ala Glu
            180                 185                 190

Asn Lys Ile Leu Ser Thr Ser Glu Leu Gln Arg Arg Gly Asn Glu Ala
        195                 200                 205

Glu Asn Ser Ser Ser Asp Asn Asn Ala Lys Asp Ser Lys Asn Ser Phe
    210                 215                 220

Ala Val Val Leu Leu Lys Gly Asn Gly Pro Glu Cys
225                 230                 235
```

<210> SEQ ID NO 317
<211> LENGTH: 705
<212> TYPE: DNA
<213> ORGANISM: Phakopsora pachyrhizi
<220> FEATURE:
<221> NAME/KEY: misc_feature
<222> LOCATION: (1)..(705)
<223> OTHER INFORMATION: ta00721.05_phapa

<400> SEQUENCE: 317

```
atgaaattat cgtttgcaaa cttgattgct ctcctctctg ttatctcatt aactttggtg     60

gtagctgagg atgtaagtga caagagtggc gatgtctctg acagtaagtt ctttggttat    120

ggcctaggcg cttatggagg tagttggggc tactggggag gaggtagctg gggaggtctt    180

ggtggatact cgtggttgaa cccatggatg ggaaatgcct acgggtttgg tctctaccgc    240

ggattttatg gtggatggct caaatcggct gatggtcacc aagagcgtcg atcaatccag    300

gaattgcaca acctcatgtc acgggctgat cacaccgtat catgcaagaa caagaacggt    360

gaagttgctc atttcgaaac caagagctgc ttgagtgctg caaacaagtt agctaatcaa    420

cacgcttcga gcgctacctg tggcgcgtgc tctctgagca tccaaggtcc caacggtgct    480

ctatctgcta agtctattcc atcatctgag ttgacaaagg cgactcttaa cattttgaag    540

gcttgcgcca aaggtgaaag caagatgctt gctgcttcag aacttgagcg ccgctctcca    600

ttaccagagg aaattccatc ccaatcctcg tctagcaacg aaaagagcat caaggatgca    660

tttgcagttg tgctactgaa aggcaacggg ccggcctgtg cttag                    705
```

<210> SEQ ID NO 318
<211> LENGTH: 234

<212> TYPE: PRT
<213> ORGANISM: Phakopsora pachyrhizi
<220> FEATURE:
<221> NAME/KEY: VARIANT
<222> LOCATION: (1)..(234)
<223> OTHER INFORMATION: ta00721.05_phapa

<400> SEQUENCE: 318

```
Met Lys Leu Ser Phe Ala Asn Leu Ile Ala Leu Leu Ser Val Ile Ser
1               5                   10                  15

Leu Thr Leu Val Val Ala Glu Asp Val Ser Asp Lys Ser Gly Asp Val
            20                  25                  30

Ser Asp Ser Lys Phe Phe Gly Tyr Gly Leu Gly Ala Tyr Gly Gly Ser
        35                  40                  45

Trp Gly Tyr Trp Gly Gly Gly Ser Trp Gly Gly Leu Gly Gly Tyr Ser
    50                  55                  60

Trp Leu Asn Pro Trp Met Gly Asn Ala Tyr Gly Phe Gly Leu Tyr Arg
65                  70                  75                  80

Gly Phe Tyr Gly Gly Trp Leu Lys Ser Ala Asp Gly His Gln Glu Arg
                85                  90                  95

Arg Ser Ile Gln Glu Leu His Asn Leu Met Ser Arg Ala Asp His Thr
            100                 105                 110

Val Ser Cys Lys Asn Lys Asn Gly Glu Val Ala His Phe Glu Thr Lys
        115                 120                 125

Ser Cys Leu Ser Ala Ala Asn Lys Leu Ala Asn Gln His Ala Ser Ser
    130                 135                 140

Ala Thr Cys Gly Ala Cys Ser Leu Ser Ile Gln Gly Pro Asn Gly Ala
145                 150                 155                 160

Leu Ser Ala Lys Ser Ile Pro Ser Ser Glu Leu Thr Lys Ala Thr Leu
                165                 170                 175

Asn Ile Leu Lys Ala Cys Ala Lys Gly Glu Ser Lys Met Leu Ala Ala
            180                 185                 190

Ser Glu Leu Glu Arg Arg Ser Pro Leu Pro Glu Glu Ile Pro Ser Gln
        195                 200                 205

Ser Ser Ser Ser Asn Glu Lys Ser Ile Lys Asp Ala Phe Ala Val Val
    210                 215                 220

Leu Leu Lys Gly Asn Gly Pro Ala Cys Ala
225                 230
```

<210> SEQ ID NO 319
<211> LENGTH: 702
<212> TYPE: DNA
<213> ORGANISM: Phakopsora pachyrhizi
<220> FEATURE:
<221> NAME/KEY: misc_feature
<222> LOCATION: (1)..(702)
<223> OTHER INFORMATION: ta09817.02_phapa

<400> SEQUENCE: 319

```
atgtttaaga agagtactat gattcttact tttctctttt tggctttaca cgggactctg      60

tcttcaccag tgccagattc tttgacctct aatgataata acgatataaa ctttagctca     120

gaaatatttg cgcgagctgt ccaggatgaa tatccacaag agcaggagaa ctcaaggagt     180

ggcataccag ggaacgaatt tgaaaatagc aacgtagtca ataatgcaag agacccagca     240

gagttgaacg agcagaatga acaaattcgc ggtgataatc aacctactac taactctaat     300

attcaactca atcttaaatc aagcaccgag gacaagacgg caaaagattc accaagaaaa     360

aggtctccag aatcctttga tacaactagc agcgtacaac cttctcccag agaatcaaat     420
```

```
ggggaaatca caaatcctca agtcaatgat gtttctcaca gcgatcagat taactcaggt    480

aactctccga ctgagggctt tcatccagga gatttgaaca cgagcggaga tcaagggttg    540

tctaaaatct ggccaaacaa ggatgaaccc caagtgaact atgatcctca caaagatcaa    600

acaacctcag aaagttttcc gacacagggc tctactcaag gtacaactac tccaaatcca    660

gtcaattctc aagatggtaa taagccacat ggtgataaat ga                       702
```

<210> SEQ ID NO 320
<211> LENGTH: 233
<212> TYPE: PRT
<213> ORGANISM: Phakopsora pachyrhizi
<220> FEATURE:
<221> NAME/KEY: VARIANT
<222> LOCATION: (1)..(233)
<223> OTHER INFORMATION: ta09817.02_phapa

<400> SEQUENCE: 320

```
Met Phe Lys Lys Ser Thr Met Ile Leu Thr Phe Leu Phe Leu Ala Leu
1               5                   10                  15

His Gly Thr Leu Ser Ser Pro Val Pro Asp Ser Leu Thr Ser Asn Asp
            20                  25                  30

Asn Asn Asp Ile Asn Phe Ser Ser Glu Ile Phe Ala Arg Ala Val Gln
        35                  40                  45

Asp Glu Tyr Pro Gln Glu Gln Glu Asn Ser Arg Ser Gly Ile Pro Gly
    50                  55                  60

Asn Glu Phe Glu Asn Ser Asn Val Val Asn Asn Ala Arg Asp Pro Ala
65                  70                  75                  80

Glu Leu Asn Glu Gln Asn Glu Gln Ile Arg Gly Asp Asn Gln Pro Thr
                85                  90                  95

Thr Asn Ser Asn Ile Gln Leu Asn Leu Lys Ser Ser Thr Glu Asp Lys
            100                 105                 110

Thr Ala Lys Asp Ser Pro Arg Lys Arg Ser Pro Glu Ser Phe Asp Thr
        115                 120                 125

Thr Ser Ser Val Gln Pro Ser Pro Arg Glu Ser Asn Gly Glu Ile Thr
    130                 135                 140

Asn Pro Gln Val Asn Asp Val Ser His Ser Asp Gln Ile Asn Ser Gly
145                 150                 155                 160

Asn Ser Pro Thr Glu Gly Phe His Pro Gly Asp Leu Asn Thr Ser Gly
                165                 170                 175

Asp Gln Gly Leu Ser Lys Ile Trp Pro Asn Lys Asp Glu Pro Gln Val
            180                 185                 190

Asn Tyr Asp Pro His Lys Asp Gln Thr Thr Ser Glu Ser Phe Pro Thr
        195                 200                 205

Gln Gly Ser Thr Gln Gly Thr Thr Thr Pro Asn Pro Val Asn Ser Gln
    210                 215                 220

Asp Gly Asn Lys Pro His Gly Asp Lys
225                 230
```

<210> SEQ ID NO 321
<211> LENGTH: 699
<212> TYPE: DNA
<213> ORGANISM: Phakopsora pachyrhizi
<220> FEATURE:
<221> NAME/KEY: misc_feature
<222> LOCATION: (1)..(699)
<223> OTHER INFORMATION: ta01937.01_phapa

<400> SEQUENCE: 321

```
atgggtgttt caaagctgtt tttcatatgg attggccttt tcaccatctc aaagctcagc     60

acaactcttt ctgttagctt tggcaaggga ataaatccat tgtcactagc agacgagggc    120

gagagtgtgc tgaagcagtt tcaaatcttt ggtaaaaata atgaggtcgt gaatgtcaag    180

attgtttcaa agtttaactc tgattctaac tcattaagat tcacaaagag agacctcctg    240

ggaattgagg atgagaagag taatgagaag ggaaacgata aggtgaagaa tcaggcccag    300

aatagaaatt acactagagt cgatcttaca cctgctcgtc ctacttcaga aacctgttac    360

tctggttcat tccaaggacc aaaccagagt gattgcgatg tgatattcta tgcccagaag    420

tataactctt atggtagttt aactgctttc ccaggaacgt ttgtttatgt ttactactct    480

tcgtgtgtgg tggcttttca aaaccccaat catagtaact attcattaga ctacaattgg    540

gcaatgctag gtgctaaagc agagcagatt aagaacagat gcctcagaga tgaggagcag    600

tcgattggtg gatcttttct atttgaaaac tatttgggct acacttttca aaatgtgctt    660

ataagtcttc aaaggtatgc tggcaatata acggcgtaa                           699


<210> SEQ ID NO 322
<211> LENGTH: 232
<212> TYPE: PRT
<213> ORGANISM: Phakopsora pachyrhizi
<220> FEATURE:
<221> NAME/KEY: VARIANT
<222> LOCATION: (1)..(232)
<223> OTHER INFORMATION: ta01937.01_phapa

<400> SEQUENCE: 322

Met Gly Val Ser Lys Leu Phe Phe Ile Trp Ile Gly Leu Phe Thr Ile
1               5                   10                  15

Ser Lys Leu Ser Thr Thr Leu Ser Val Ser Phe Gly Lys Gly Ile Asn
            20                  25                  30

Pro Leu Ser Leu Ala Asp Glu Gly Glu Ser Val Leu Lys Gln Phe Gln
        35                  40                  45

Ile Phe Gly Lys Asn Asn Glu Val Val Asn Val Lys Ile Val Ser Lys
    50                  55                  60

Phe Asn Ser Asp Ser Asn Ser Leu Arg Phe Thr Lys Arg Asp Leu Leu
65                  70                  75                  80

Gly Ile Glu Asp Glu Lys Ser Asn Glu Lys Gly Asn Asp Lys Val Lys
                85                  90                  95

Asn Gln Ala Gln Asn Arg Asn Tyr Thr Arg Val Asp Leu Thr Pro Ala
            100                 105                 110

Arg Pro Thr Ser Glu Thr Cys Tyr Ser Gly Ser Phe Gln Gly Pro Asn
        115                 120                 125

Gln Ser Asp Cys Asp Val Ile Phe Tyr Ala Gln Lys Tyr Asn Ser Tyr
    130                 135                 140

Gly Ser Leu Thr Ala Phe Pro Gly Thr Phe Val Tyr Val Tyr Tyr Ser
145                 150                 155                 160

Ser Cys Val Val Ala Phe Gln Asn Pro Asn His Ser Asn Tyr Ser Leu
                165                 170                 175

Asp Tyr Asn Trp Ala Met Leu Gly Ala Lys Ala Glu Gln Ile Lys Asn
            180                 185                 190

Arg Cys Leu Arg Asp Glu Glu Gln Ser Ile Gly Gly Ser Phe Leu Phe
        195                 200                 205

Glu Asn Tyr Leu Gly Tyr Thr Phe Gln Asn Val Leu Ile Ser Leu Gln
    210                 215                 220
```

Arg Tyr Ala Gly Asn Ile Thr Ala
225 230

<210> SEQ ID NO 323
<211> LENGTH: 699
<212> TYPE: DNA
<213> ORGANISM: Phakopsora pachyrhizi
<220> FEATURE:
<221> NAME/KEY: misc_feature
<222> LOCATION: (1)..(699)
<223> OTHER INFORMATION: ta01937.02_phapa

<400> SEQUENCE: 323
atgggtgttt caaagctgtt tttcatatgg attggccttt tcaccatctc aaagctcagc 60
acaactcttt ctgttagctt tggcaaggga ataaatccat tgtcactagc agacgagggc 120
gagagtgtgc tgaagcagtt tcaaatcttt ggtaaaaata atgaggtcgt gaatgtcaag 180
attgtttcaa agtttaactc tgattctaac tcattaagat tcacaaagag agacctcctg 240
ggaattgagg atgagaagag taatgagaag ggaaacgata aggtgaagaa tcaggcccag 300
aatagaaatt acactagagt cgatcttaca cctgctcgtc ctacttcaga aacctgttac 360
tctggttcat tccaaggacc aaaccagagt gattgcgatg tgatattcta tgcccagaag 420
tataactctt atggtagttt aactgctttc ccaggaacgt ttgtttatgt ttactactct 480
tcgtgtgtgg tggcttttca aaaccccaat catagtaact attcattaga ctacaattgg 540
gcaatgctag gtgctaaagc agagcagatt aagaacagat gcctcagaga tgaggagcag 600
tcgattggtg gatcttttct atttgaaaac tatttgggct acacttttca aaatgtgctt 660
ataagtcttc aaaggtatgc tggcaatata acggcgtaa 699

<210> SEQ ID NO 324
<211> LENGTH: 232
<212> TYPE: PRT
<213> ORGANISM: Phakopsora pachyrhizi
<220> FEATURE:
<221> NAME/KEY: VARIANT
<222> LOCATION: (1)..(232)
<223> OTHER INFORMATION: ta01937.02_phapa

<400> SEQUENCE: 324

Met Gly Val Ser Lys Leu Phe Phe Ile Trp Ile Gly Leu Phe Thr Ile
1 5 10 15

Ser Lys Leu Ser Thr Thr Leu Ser Val Ser Phe Gly Lys Gly Ile Asn
20 25 30

Pro Leu Ser Leu Ala Asp Glu Gly Glu Ser Val Leu Lys Gln Phe Gln
35 40 45

Ile Phe Gly Lys Asn Asn Glu Val Val Asn Val Lys Ile Val Ser Lys
50 55 60

Phe Asn Ser Asp Ser Asn Ser Leu Arg Phe Thr Lys Arg Asp Leu Leu
65 70 75 80

Gly Ile Glu Asp Glu Lys Ser Asn Glu Lys Gly Asn Asp Lys Val Lys
85 90 95

Asn Gln Ala Gln Asn Arg Asn Tyr Thr Arg Val Asp Leu Thr Pro Ala
100 105 110

Arg Pro Thr Ser Glu Thr Cys Tyr Ser Gly Ser Phe Gln Gly Pro Asn
115 120 125

Gln Ser Asp Cys Asp Val Ile Phe Tyr Ala Gln Lys Tyr Asn Ser Tyr
130 135 140

Gly Ser Leu Thr Ala Phe Pro Gly Thr Phe Val Tyr Val Tyr Tyr Ser

```
145                 150                 155                 160

Ser Cys Val Val Ala Phe Gln Asn Pro Asn His Ser Asn Tyr Ser Leu
                165                 170                 175

Asp Tyr Asn Trp Ala Met Leu Gly Ala Lys Ala Glu Gln Ile Lys Asn
            180                 185                 190

Arg Cys Leu Arg Asp Glu Glu Gln Ser Ile Gly Gly Ser Phe Leu Phe
        195                 200                 205

Glu Asn Tyr Leu Gly Tyr Thr Phe Gln Asn Val Leu Ile Ser Leu Gln
    210                 215                 220

Arg Tyr Ala Gly Asn Ile Thr Ala
225                 230


<210> SEQ ID NO 325
<211> LENGTH: 696
<212> TYPE: DNA
<213> ORGANISM: Phakopsora pachyrhizi
<220> FEATURE:
<221> NAME/KEY: misc_feature
<222> LOCATION: (1)..(696)
<223> OTHER INFORMATION: ta00721.07_phapa

<400> SEQUENCE: 325

atgaaattgt catacgccta cttgattgtt ctcatctctg tcctgtcttc aacttttgtg      60

gtagctgagg atgttagcga caaaaacgct gaggtttctg acagcaagtt ctttggacta     120

ggtggacttg gggttgggg ttactgggga ggtggtagat ttgctggtct tggtggatac     180

tcgtggttga acccatggat gggaaatgcc tacgggtttg gtctctaccg cggattttat     240

ggtggatggc tcaaatcggc tgatggtcac caagagcgtc gatcaatcca ggaattgcac     300

aacctcatgt cacgggctga tcacacagtt tcatgcaaga ataagaacgg tgaagttgct     360

caattcaaca ccaagagctg cttaagtgcc gctaacaagc tagctaatca acactcctca     420

agtgctacct gtggggcgtg ctctctcagc attcagggtc caaatggcgc actttctgcc     480

aagtctatcc catcatctga gttgaccaaa gcaactgtca atatcttgaa ggcttgcgcc     540

aaaggtgaga gcaagatgct ctcagcttca gagctcgagc gccgttctcc cttaccagag     600

gaaatccaat ctcaatcatc atctagcaac gagaagggta ataaggatgc ttttgcagtt     660

gtgctcctca aaggtaacgg ccccgagtgc tcttaa                              696


<210> SEQ ID NO 326
<211> LENGTH: 231
<212> TYPE: PRT
<213> ORGANISM: Phakopsora pachyrhizi
<220> FEATURE:
<221> NAME/KEY: VARIANT
<222> LOCATION: (1)..(231)
<223> OTHER INFORMATION: ta00721.07_phapa

<400> SEQUENCE: 326

Met Lys Leu Ser Tyr Ala Tyr Leu Ile Val Leu Ile Ser Val Leu Ser
1               5                   10                  15

Ser Thr Phe Val Val Ala Glu Asp Val Ser Asp Lys Asn Ala Glu Val
            20                  25                  30

Ser Asp Ser Lys Phe Phe Gly Leu Gly Gly Leu Gly Gly Trp Gly Tyr
        35                  40                  45

Trp Gly Gly Gly Arg Phe Ala Gly Leu Gly Gly Tyr Ser Trp Leu Asn
    50                  55                  60

Pro Trp Met Gly Asn Ala Tyr Gly Phe Gly Leu Tyr Arg Gly Phe Tyr
65                  70                  75                  80
```

```
Gly Gly Trp Leu Lys Ser Ala Asp Gly His Gln Glu Arg Arg Ser Ile
                85                  90                  95

Gln Glu Leu His Asn Leu Met Ser Arg Ala Asp His Thr Val Ser Cys
            100                 105                 110

Lys Asn Lys Asn Gly Glu Val Ala Gln Phe Asn Thr Lys Ser Cys Leu
        115                 120                 125

Ser Ala Ala Asn Lys Leu Ala Asn Gln His Ser Ser Ser Ala Thr Cys
    130                 135                 140

Gly Ala Cys Ser Leu Ser Ile Gln Gly Pro Asn Gly Ala Leu Ser Ala
145                 150                 155                 160

Lys Ser Ile Pro Ser Ser Glu Leu Thr Lys Ala Thr Val Asn Ile Leu
                165                 170                 175

Lys Ala Cys Ala Lys Gly Glu Ser Lys Met Leu Ser Ala Ser Glu Leu
            180                 185                 190

Glu Arg Arg Ser Pro Leu Pro Glu Glu Ile Gln Ser Gln Ser Ser Ser
        195                 200                 205

Ser Asn Glu Lys Gly Asn Lys Asp Ala Phe Ala Val Val Leu Leu Lys
    210                 215                 220

Gly Asn Gly Pro Glu Cys Ser
225                 230
```

<210> SEQ ID NO 327
<211> LENGTH: 696
<212> TYPE: DNA
<213> ORGANISM: Phakopsora pachyrhizi
<220> FEATURE:
<221> NAME/KEY: misc_feature
<222> LOCATION: (1)..(696)
<223> OTHER INFORMATION: ta10435.01_phapa

<400> SEQUENCE: 327

```
atgaatatct ctttaaaaaa ctttgtgcaa gtttcaatct tgctaattct cgtgtctgga      60

gtcatcagtc ttgatgcttc tactccaaac agccatcacc tatcaagaag acagaataag     120

gatcaggtca aggatcagac aaagaagact caacaacagg tacaagaaat caaagatgga     180

aaaggtggag cagcccaggg cggtactcct acagagaaag ctgcaaacca gatgatgcag     240

atgcttatgc agattggtca aagtttagat gcagtcacca gcctggggtc cacccctgag     300

accgtaaagt cgacagcaga ggcaatcata aaaatggttc ctgatgtcgg caaggcaaca     360

aagtctttga tagacactat gccgaacaaa gcacaacttg agggcgtcgc tgataaagcc     420

actcaatcag cggaacagct aggaaaagtc ctcaaaacca ttgagcaaag tccagaagat     480

gccaacttta tcaaaaaaca ttataaagcc ctgggtgacg cctttacagg aatctttggt     540

gctgtggatc ccgtcttcag ctctgcattt cctgatgata aaaatggtgg acaacaacaa     600

gccggtaaaa ccgacgggag acaactaaac actcagactg aaggggccca aaaggatcaa     660

aaagatacaa aggaaaaaaa caaaaagaaa acctag                               696
```

<210> SEQ ID NO 328
<211> LENGTH: 231
<212> TYPE: PRT
<213> ORGANISM: Phakopsora pachyrhizi
<220> FEATURE:
<221> NAME/KEY: VARIANT
<222> LOCATION: (1)..(231)
<223> OTHER INFORMATION: ta10435.01_phapa

<400> SEQUENCE: 328

-continued

```
Met Asn Ile Ser Leu Lys Asn Phe Val Gln Val Ser Ile Leu Leu Ile
1               5                   10                  15

Leu Val Ser Gly Val Ile Ser Leu Asp Ala Ser Thr Pro Asn Ser His
            20                  25                  30

His Leu Ser Arg Arg Gln Asn Lys Asp Gln Val Lys Asp Gln Thr Lys
        35                  40                  45

Lys Thr Gln Gln Gln Val Gln Glu Ile Lys Asp Gly Lys Gly Gly Ala
    50                  55                  60

Ala Gln Gly Gly Thr Pro Thr Glu Lys Ala Ala Asn Gln Met Met Gln
65                  70                  75                  80

Met Leu Met Gln Ile Gly Gln Ser Leu Asp Ala Val Thr Ser Leu Gly
                85                  90                  95

Ser Thr Pro Glu Thr Val Lys Ser Thr Ala Glu Ala Ile Ile Lys Met
            100                 105                 110

Val Pro Asp Val Gly Lys Ala Thr Lys Ser Leu Ile Asp Thr Met Pro
        115                 120                 125

Asn Lys Ala Gln Leu Glu Gly Val Ala Asp Lys Ala Thr Gln Ser Ala
    130                 135                 140

Glu Gln Leu Gly Lys Val Leu Lys Thr Ile Glu Gln Ser Pro Glu Asp
145                 150                 155                 160

Ala Asn Phe Ile Lys Lys His Tyr Lys Ala Leu Gly Asp Ala Phe Thr
                165                 170                 175

Gly Ile Phe Gly Ala Val Asp Pro Val Phe Ser Ser Ala Phe Pro Asp
            180                 185                 190

Asp Lys Asn Gly Gly Gln Gln Gln Ala Gly Lys Thr Asp Gly Arg Gln
        195                 200                 205

Leu Asn Thr Gln Thr Glu Gly Ala Gln Lys Asp Gln Lys Asp Thr Lys
    210                 215                 220

Glu Lys Asn Lys Lys Lys Thr
225                 230
```

<210> SEQ ID NO 329
<211> LENGTH: 696
<212> TYPE: DNA
<213> ORGANISM: Phakopsora pachyrhizi
<220> FEATURE:
<221> NAME/KEY: misc_feature
<222> LOCATION: (1)..(696)
<223> OTHER INFORMATION: ta00721.03_phapa

<400> SEQUENCE: 329

```
atgaaattgt catacgccta cttgattgtt ctcatctctg tcctgtcttc aacttttgtg     60

gtagctgagg atgttagcga caaaaacgct gaggtttctg acagcaagtt ctttggacta    120

ggtggacttg gggttgggg ttactgggga ggtggtagat ttgctggtct tggtggatac    180

tcgtggttga acccatggat gggaaatgcc tacgggtttg gtctctaccg cggattttat    240

ggtggatggc tcaaatcggc tgatggtcac caagagcgtc gatcaatcca ggaattgcac    300

aacctcatgt cacgggctga tcacaccgta tcatgcaaga acaagaacgg tgaagttgct    360

catttcgaaa ccaagagctg cttgagtgct gcaaacaagt tagctaatca acacgcttcg    420

agcgctacct gtggcgcgtg ctctctgagc atccaaggtc ccaacggtgc tctatctgct    480

aagtctattc catcatctga gttgacaaag gcgactctta acattttgaa ggcttgcgcc    540

aaaggtgaaa gcaagatgct tgctgcttca gaacttgagc gccgctctcc attaccagag    600

gaaattccat ctcaatcttc gtctagcaac gacaagagca ccaaggatgc gtttgcagtc    660
```

gtgctactga aaggcaacgg gccagcctgt gcttaa 696

<210> SEQ ID NO 330
<211> LENGTH: 231
<212> TYPE: PRT
<213> ORGANISM: Phakopsora pachyrhizi
<220> FEATURE:
<221> NAME/KEY: VARIANT
<222> LOCATION: (1)..(231)
<223> OTHER INFORMATION: ta00721.03_phapa

<400> SEQUENCE: 330

Met Lys Leu Ser Tyr Ala Tyr Leu Ile Val Leu Ile Ser Val Leu Ser
1 5 10 15

Ser Thr Phe Val Val Ala Glu Asp Val Ser Asp Lys Asn Ala Glu Val
20 25 30

Ser Asp Ser Lys Phe Phe Gly Leu Gly Gly Leu Gly Gly Trp Gly Tyr
35 40 45

Trp Gly Gly Gly Arg Phe Ala Gly Leu Gly Gly Tyr Ser Trp Leu Asn
50 55 60

Pro Trp Met Gly Asn Ala Tyr Gly Phe Gly Leu Tyr Arg Gly Phe Tyr
65 70 75 80

Gly Gly Trp Leu Lys Ser Ala Asp Gly His Gln Glu Arg Arg Ser Ile
85 90 95

Gln Glu Leu His Asn Leu Met Ser Arg Ala Asp His Thr Val Ser Cys
100 105 110

Lys Asn Lys Asn Gly Glu Val Ala His Phe Glu Thr Lys Ser Cys Leu
115 120 125

Ser Ala Ala Asn Lys Leu Ala Asn Gln His Ala Ser Ser Ala Thr Cys
130 135 140

Gly Ala Cys Ser Leu Ser Ile Gln Gly Pro Asn Gly Ala Leu Ser Ala
145 150 155 160

Lys Ser Ile Pro Ser Ser Glu Leu Thr Lys Ala Thr Leu Asn Ile Leu
165 170 175

Lys Ala Cys Ala Lys Gly Glu Ser Lys Met Leu Ala Ala Ser Glu Leu
180 185 190

Glu Arg Arg Ser Pro Leu Pro Glu Glu Ile Pro Ser Gln Ser Ser Ser
195 200 205

Ser Asn Asp Lys Ser Thr Lys Asp Ala Phe Ala Val Val Leu Leu Lys
210 215 220

Gly Asn Gly Pro Ala Cys Ala
225 230

<210> SEQ ID NO 331
<211> LENGTH: 696
<212> TYPE: DNA
<213> ORGANISM: Phakopsora pachyrhizi
<220> FEATURE:
<221> NAME/KEY: misc_feature
<222> LOCATION: (1)..(696)
<223> OTHER INFORMATION: ta00721.04_phapa

<400> SEQUENCE: 331
atgaaattgt catacgccta cttgattgtt ctcatctctg tcctgtcttc aacttttgtg 60
gtagctgagg atgttagcga caaaaacgct gaggtttctg acagcaagtt ctttggacta 120
ggtggacttg gggttgggg ttactgggga ggtggtagat ttgctggtct tggtggatac 180
tcgtggttga acccatggat gggaaatgcc tacgggtttg gtctataccg cggcttatat 240

```
ggcggatggc taaaatctgc tgatggccac caagagcgtc gatcaatcca agagttacaa    300

aaactcatgg cacgggctga tcacaccgta tcatgcaaga acaagaacgg tgaagttgct    360

catttcgaaa ccaagagctg cttgagtgct gcaaacaagt tagctaatca acacgcttcg    420

agcgctacct gtggcgcgtg ctctctgagc atccaaggtc ccaacggtgc tctatctgct    480

aagtctattc catcatctga gttgacaaag gcgactctta acattttgaa ggcttgcgcc    540

aaaggtgaaa gcaagatgct tgctgcttca gaacttgagc gccgctctcc attaccagag    600

gaaattccat cccaatcctc gtctagcaac gaaaagagca tcaaggatgc atttgcagtt    660

gtgctactga aaggcaacgg gccggcctgt gcttag                              696
```

<210> SEQ ID NO 332
<211> LENGTH: 231
<212> TYPE: PRT
<213> ORGANISM: Phakopsora pachyrhizi
<220> FEATURE:
<221> NAME/KEY: VARIANT
<222> LOCATION: (1)..(231)
<223> OTHER INFORMATION: ta00721.04_phapa

<400> SEQUENCE: 332

```
Met Lys Leu Ser Tyr Ala Tyr Leu Ile Val Leu Ile Ser Val Leu Ser
1               5                   10                  15

Ser Thr Phe Val Val Ala Glu Asp Val Ser Asp Lys Asn Ala Glu Val
            20                  25                  30

Ser Asp Ser Lys Phe Phe Gly Leu Gly Gly Leu Gly Gly Trp Gly Tyr
        35                  40                  45

Trp Gly Gly Gly Arg Phe Ala Gly Leu Gly Gly Tyr Ser Trp Leu Asn
    50                  55                  60

Pro Trp Met Gly Asn Ala Tyr Gly Phe Gly Leu Tyr Arg Gly Leu Tyr
65                  70                  75                  80

Gly Gly Trp Leu Lys Ser Ala Asp Gly His Gln Glu Arg Arg Ser Ile
                85                  90                  95

Gln Glu Leu Gln Lys Leu Met Ala Arg Ala Asp His Thr Val Ser Cys
            100                 105                 110

Lys Asn Lys Asn Gly Glu Val Ala His Phe Glu Thr Lys Ser Cys Leu
        115                 120                 125

Ser Ala Ala Asn Lys Leu Ala Asn Gln His Ala Ser Ser Ala Thr Cys
    130                 135                 140

Gly Ala Cys Ser Leu Ser Ile Gln Gly Pro Asn Gly Ala Leu Ser Ala
145                 150                 155                 160

Lys Ser Ile Pro Ser Ser Glu Leu Thr Lys Ala Thr Leu Asn Ile Leu
                165                 170                 175

Lys Ala Cys Ala Lys Gly Glu Ser Lys Met Leu Ala Ala Ser Glu Leu
            180                 185                 190

Glu Arg Arg Ser Pro Leu Pro Glu Glu Ile Pro Ser Gln Ser Ser Ser
        195                 200                 205

Ser Asn Glu Lys Ser Ile Lys Asp Ala Phe Ala Val Val Leu Leu Lys
    210                 215                 220

Gly Asn Gly Pro Ala Cys Ala
225                 230
```

<210> SEQ ID NO 333
<211> LENGTH: 693
<212> TYPE: DNA
<213> ORGANISM: Phakopsora pachyrhizi
<220> FEATURE:

<221> NAME/KEY: misc_feature
<222> LOCATION: (1)..(693)
<223> OTHER INFORMATION: ta09424.01_phapa

<400> SEQUENCE: 333
atgaagatct gtagatctgg actatcgctc gtttctatcc ttttcttcag ccttatccta 60
actgtcgaga tcacaagctc gaccgatcaa tctaatgata atattaaact ccaaagaagg 120
tatccctcag atagccacac cagtaataac gataatgata accccaataa taaccctcaa 180
aaacctttaa ctgaagctgg gaatgttcat ggtggaggaa aaaagatgaa ttgcagtggt 240
actccaaaca actgtcatcc ctcatcatca gcattaatac agaaccgcac cgatgctcga 300
aagccaactc cgttctctca accatgtcaa gagtactaca gtgcaaacac cgatcatgcc 360
gtttgcagag gagatcgatc aattatgtgc cactctggct gtactggagc agtagtttct 420
caaaactgtc aagttgatga aaattctata aagacgaatc agacttgtaa tgtagcattt 480
tcaaagacgt cgatgaattc atttctttgt actacgagtg aaggagcatt tacttgtgca 540
ggtccattcg aaggtcaagc tatttgtaat aattgtttac cgacgaatga taatgaagaa 600
aacgatggcg atcatagttc tgctaatcat catttcaata aaaatattat ccaaaaatta 660
actctaatca gcttaatcat aagtcttctt taa 693

<210> SEQ ID NO 334
<211> LENGTH: 230
<212> TYPE: PRT
<213> ORGANISM: Phakopsora pachyrhizi
<220> FEATURE:
<221> NAME/KEY: VARIANT
<222> LOCATION: (1)..(230)
<223> OTHER INFORMATION: ta09424.01_phapa

<400> SEQUENCE: 334

Met Lys Ile Cys Arg Ser Gly Leu Ser Leu Val Ser Ile Leu Phe Phe
1 5 10 15

Ser Leu Ile Leu Thr Val Glu Ile Thr Ser Ser Thr Asp Gln Ser Asn
20 25 30

Asp Asn Ile Lys Leu Gln Arg Arg Tyr Pro Ser Asp Ser His Thr Ser
35 40 45

Asn Asn Asp Asn Asp Asn Pro Asn Asn Asn Pro Gln Lys Pro Leu Thr
50 55 60

Glu Ala Gly Asn Val His Gly Gly Gly Lys Lys Met Asn Cys Ser Gly
65 70 75 80

Thr Pro Asn Asn Cys His Pro Ser Ser Ser Ala Leu Ile Gln Asn Arg
85 90 95

Thr Asp Ala Arg Lys Pro Thr Pro Phe Ser Gln Pro Cys Gln Glu Tyr
100 105 110

Tyr Ser Ala Asn Thr Asp His Ala Val Cys Arg Gly Asp Arg Ser Ile
115 120 125

Met Cys His Ser Gly Cys Thr Gly Ala Val Val Ser Gln Asn Cys Gln
130 135 140

Val Asp Glu Asn Ser Ile Lys Thr Asn Gln Thr Cys Asn Val Ala Phe
145 150 155 160

Ser Lys Thr Ser Met Asn Ser Phe Leu Cys Thr Thr Ser Glu Gly Ala
165 170 175

Phe Thr Cys Ala Gly Pro Phe Glu Gly Gln Ala Ile Cys Asn Asn Cys
180 185 190

Leu Pro Thr Asn Asp Asn Glu Glu Asn Asp Gly Asp His Ser Ser Ala

```
        195                 200                 205

Asn His His Phe Asn Lys Asn Ile Ile Gln Lys Leu Thr Leu Ile Ser
    210                 215                 220

Leu Ile Ile Ser Leu Leu
225                 230


<210> SEQ ID NO 335
<211> LENGTH: 681
<212> TYPE: DNA
<213> ORGANISM: Phakopsora pachyrhizi
<220> FEATURE:
<221> NAME/KEY: misc_feature
<222> LOCATION: (1)..(681)
<223> OTHER INFORMATION: ta10800.02_phapa

<400> SEQUENCE: 335

atggttcact tgatcccctt ctttgcatta gtcctcgccg gtgctattgc tgctgaaaac      60

gacaagtcaa gtagcaaggc atttggaggc ggggccgttg gaggtggagc cttcgggggc     120

gctgcttcag gctttagctc aagttcatct tctgctagtg tctcccacca ctccaaaagc     180

ggctttgttg caggtggtgg gggtggattc aacttcggtg gtcttggact acccatggcc     240

ttcagcccctt ttggtggcct tattaatcag ataggagcat gtcgttcttc tttggtatct    300

gggatctctg cacaagtggc atttagtcaa gttagccgca ttgcttcaat gtttcaacaa     360

gcaataggtt ccttacaagg ttgtggtact tgcggccttg ttggtcctgg attgagcgct     420

tttggcggcg ttatccaacg aattaccggc ggtataatat cgttagtcgg gagacttcag     480

ggtatcttcc cttctatgtg gcaagggatc ctaacttccg ctttccaacc acttggtggt     540

tctctcccag gactgtttaa cttttgcaac ggtgtcggcc ttcccgttaa caaatttttt     600

ggtggaggat tttctcagtg ccttgctcct ctcaagattg gctctctgaa ccaatctctc     660

tctcgtttcg gcctactttg a                                               681


<210> SEQ ID NO 336
<211> LENGTH: 226
<212> TYPE: PRT
<213> ORGANISM: Phakopsora pachyrhizi
<220> FEATURE:
<221> NAME/KEY: VARIANT
<222> LOCATION: (1)..(226)
<223> OTHER INFORMATION: ta10800.02_phapa

<400> SEQUENCE: 336

Met Val His Leu Ile Pro Phe Phe Ala Leu Val Leu Ala Gly Ala Ile
1               5                   10                  15

Ala Ala Glu Asn Asp Lys Ser Ser Ser Lys Ala Phe Gly Gly Gly Ala
            20                  25                  30

Val Gly Gly Gly Ala Phe Gly Gly Ala Ala Ser Gly Phe Ser Ser Ser
        35                  40                  45

Ser Ser Ser Ala Ser Val Ser His His Ser Lys Ser Gly Phe Val Ala
    50                  55                  60

Gly Gly Gly Gly Gly Phe Asn Phe Gly Gly Leu Gly Leu Pro Met Ala
65                  70                  75                  80

Phe Ser Pro Phe Gly Gly Leu Ile Asn Gln Ile Gly Ala Cys Arg Ser
                85                  90                  95

Ser Leu Val Ser Gly Ile Ser Ala Gln Val Ala Phe Ser Gln Val Ser
            100                 105                 110

Arg Ile Ala Ser Met Phe Gln Gln Ala Ile Gly Ser Leu Gln Gly Cys
        115                 120                 125
```

```
Gly Thr Cys Gly Leu Val Gly Pro Gly Leu Ser Ala Phe Gly Gly Val
    130                 135                 140

Ile Gln Arg Ile Thr Gly Gly Ile Ile Ser Leu Val Gly Arg Leu Gln
145                 150                 155                 160

Gly Ile Phe Pro Ser Met Trp Gln Gly Ile Leu Thr Ser Ala Phe Gln
                165                 170                 175

Pro Leu Gly Gly Ser Leu Pro Gly Leu Phe Asn Phe Cys Asn Gly Val
            180                 185                 190

Gly Leu Pro Val Asn Lys Phe Phe Gly Gly Gly Phe Ser Gln Cys Leu
        195                 200                 205

Ala Pro Leu Lys Ile Gly Ser Leu Asn Gln Ser Leu Ser Arg Phe Gly
    210                 215                 220

Leu Leu
225


<210> SEQ ID NO 337
<211> LENGTH: 678
<212> TYPE: DNA
<213> ORGANISM: Phakopsora pachyrhizi
<220> FEATURE:
<221> NAME/KEY: misc_feature
<222> LOCATION: (1)..(678)
<223> OTHER INFORMATION: ta00012.04_phapa

<400> SEQUENCE: 337

atgtttagat ctttattttt aggaatttta gcttgttctg cagttaaact taccatttgt      60

agtccaagtg atgaggtagt tgtcaaacct cgacagatag gttatggagc tggtcttggt     120

gctggaggag cttcctcaag ctctttcagt agtagtacca gcgtttcttc cttcagttcg     180

ttcgttcaag gttggagtgt aattccaact gctttcggta cctgtgcagc tgtctttcag     240

agacaggtaa cagttgaggt ggccattcaa tctgttcagg agttacatag tacagtatct     300

ggtgttctgg gtaattatgg aagttgttct agctgtggtg gtgcttcggc agctagctct     360

tactcgtctc actaccaaag tataattgta aagaccttta cctcatggca atctatcatg     420

tcagtcggtc attcactata tgacaatgtc tgggaacctc agtttgctcc tctctttcga     480

caattcaacc cattccttac agccgttcaa cagaactcag gtttctttgg tatcaacctt     540

ggaaacattc ttggtggtct tcatctaaac ttaaacctat tctcatcttg tggtcttaac     600

attggtggat tacttggagg tgttttgagt acggttggtg gattgttagg tggtcttaaa     660

gatcatgaag aagcttga                                                   678


<210> SEQ ID NO 338
<211> LENGTH: 225
<212> TYPE: PRT
<213> ORGANISM: Phakopsora pachyrhizi
<220> FEATURE:
<221> NAME/KEY: VARIANT
<222> LOCATION: (1)..(225)
<223> OTHER INFORMATION: ta00012.04_phapa

<400> SEQUENCE: 338

Met Phe Arg Ser Leu Phe Leu Gly Ile Leu Ala Cys Ser Ala Val Lys
1               5                   10                  15

Leu Thr Ile Cys Ser Pro Ser Asp Glu Val Val Val Lys Pro Arg Gln
            20                  25                  30

Ile Gly Tyr Gly Ala Gly Leu Gly Ala Gly Gly Ala Ser Ser Ser Ser
        35                  40                  45
```

-continued

Phe Ser Ser Ser Thr Ser Val Ser Ser Phe Ser Ser Phe Val Gln Gly
    50                  55                  60

Trp Ser Val Ile Pro Thr Ala Phe Gly Thr Cys Ala Ala Val Phe Gln
65                  70                  75                  80

Arg Gln Val Thr Val Glu Val Ala Ile Gln Ser Val Gln Glu Leu His
                85                  90                  95

Ser Thr Val Ser Gly Val Leu Gly Asn Tyr Gly Ser Cys Ser Ser Cys
            100                 105                 110

Gly Gly Ala Ser Ala Ala Ser Ser Tyr Ser Ser His Tyr Gln Ser Ile
        115                 120                 125

Ile Val Lys Thr Phe Thr Ser Trp Gln Ser Ile Met Ser Val Gly His
    130                 135                 140

Ser Leu Tyr Asp Asn Val Trp Glu Pro Gln Phe Ala Pro Leu Phe Arg
145                 150                 155                 160

Gln Phe Asn Pro Phe Leu Thr Ala Val Gln Gln Asn Ser Gly Phe Phe
                165                 170                 175

Gly Ile Asn Leu Gly Asn Ile Leu Gly Gly Leu His Leu Asn Leu Asn
            180                 185                 190

Leu Phe Ser Ser Cys Gly Leu Asn Ile Gly Gly Leu Leu Gly Gly Val
        195                 200                 205

Leu Ser Thr Val Gly Gly Leu Leu Gly Gly Leu Lys Asp His Glu Glu
    210                 215                 220

Ala
225

<210> SEQ ID NO 339
<211> LENGTH: 663
<212> TYPE: DNA
<213> ORGANISM: Phakopsora pachyrhizi
<220> FEATURE:
<221> NAME/KEY: misc_feature
<222> LOCATION: (1)..(663)
<223> OTHER INFORMATION: ta04963.01_phapa

<400> SEQUENCE: 339
atggtttact caaaggcaac cttcaccctg gtctcactcc tacctatgat cctggcccag 60
cagagcatca acaacagtga taccacaacc acggctgcta ccccggccag tcccaccata 120
ggctcaactg gtactaccaa cagcagcagc tctaccacta cttccactac cacctctaac 180
actgccagtg gagctgctca gtccttccct gcgccaacag tctcaggaac atcctgtggt 240
acagcccagc agaactttaa ccagtgtgtt accaaagtat caaaggatat ctcctcatgt 300
ccctctaccg ataacacctg tctttgccaa acgtatgcaa acctagccta ctgttacaac 360
gcctgtccag atctggcatc atcaggggcc ggatacctgc agcagtccac agtgaactgt 420
gatgcagcag gtatcaagcc aaacgctact tccaacgtca ccaccacccc tgtcacctcc 480
accactaaca ggaacaccac caacacctca cccatctcta acacaaacaa gaacaattct 540
acctcgggca acactgctgc tacatttgct gctggaaact ccaaggcaag tgggattgag 600
gccccgttac tgagcgttgc tgttgttggg ctgtgtggta tcattgctag cctatttgca 660
tga 663

<210> SEQ ID NO 340
<211> LENGTH: 220
<212> TYPE: PRT
<213> ORGANISM: Phakopsora pachyrhizi
<220> FEATURE:
<221> NAME/KEY: VARIANT
<222> LOCATION: (1)..(220)
<223> OTHER INFORMATION: ta04963.01_phapa

<400> SEQUENCE: 340

Met Val Tyr Ser Lys Ala Thr Phe Thr Leu Val Ser Leu Leu Pro Met
1               5                   10                  15

Ile Leu Ala Gln Gln Ser Ile Asn Asn Ser Asp Thr Thr Thr Thr Ala
            20                  25                  30

Ala Thr Pro Ala Ser Pro Thr Ile Gly Ser Thr Gly Thr Thr Asn Ser
        35                  40                  45

Ser Ser Ser Thr Thr Thr Ser Thr Thr Thr Ser Asn Thr Ala Ser Gly
    50                  55                  60

Ala Ala Gln Ser Phe Pro Ala Pro Thr Val Ser Gly Thr Ser Cys Gly
65                  70                  75                  80

Thr Ala Gln Gln Asn Phe Asn Gln Cys Val Thr Lys Val Ser Lys Asp
                85                  90                  95

Ile Ser Ser Cys Pro Ser Thr Asp Asn Thr Cys Leu Cys Gln Thr Tyr
            100                 105                 110

Ala Asn Leu Ala Tyr Cys Tyr Asn Ala Cys Pro Asp Leu Ala Ser Ser
        115                 120                 125

Gly Ala Gly Tyr Leu Gln Gln Ser Thr Val Asn Cys Asp Ala Ala Gly
    130                 135                 140

Ile Lys Pro Asn Ala Thr Ser Asn Val Thr Thr Thr Pro Val Thr Ser
145                 150                 155                 160

Thr Thr Asn Arg Asn Thr Thr Asn Thr Ser Pro Ile Ser Asn Thr Asn
                165                 170                 175

Lys Asn Asn Ser Thr Ser Gly Asn Thr Ala Ala Thr Phe Ala Ala Gly
            180                 185                 190

Asn Ser Lys Ala Ser Gly Ile Glu Ala Pro Leu Leu Ser Val Ala Val
        195                 200                 205

Val Gly Leu Cys Gly Ile Ile Ala Ser Leu Phe Ala
    210                 215                 220

<210> SEQ ID NO 341
<211> LENGTH: 660
<212> TYPE: DNA
<213> ORGANISM: Phakopsora pachyrhizi
<220> FEATURE:
<221> NAME/KEY: misc_feature
<222> LOCATION: (1)..(660)
<223> OTHER INFORMATION: ta01860.01_phapa

<400> SEQUENCE: 341
atgaagattt cttttgcaaa cttatttgtt cttttctccg cactctctgt ggccttagtt 60
gctaccgagg atgttcaagg tgtaaaaggc gataactcgg aagctaaatg gctatactgg 120
ggtggtggta taggttatgg tggattagga agctattatg gtaattggtt gagcccatac 180
tacaacaatg ccttcgggtt tggggtatac aattacttgc ctagacgctg gtaccgtcgt 240
gctctacaaa ccagagggga tgagtcgaat gccaaagctt cggttagctc aactgttcag 300
tgctccaacg cgcagggggt caagcaagag ttctcaactg ctagttgttt aaaggccgct 360
accaagattt ccaaagagca aatcaccact gctacctgtg gcacatgcac catccagctt 420
cacaataaag agggaccaat tcaatttaat gcgatccccc ctcaatctga attaaactcg 480
gcagtaaaca acatgctaaa ggcctgcagt aaaagccagg acaaacttct cagcgcttca 540
gagctctcga gacgctcccc agctgaaaat ggtaatggtg tggattctaa ggatacttcg 600

-continued agcaacaaga acgccttggc gattatatta cttaaaggca acgggccaga gtgtaactaa 660

<210> SEQ ID NO 342
<211> LENGTH: 219
<212> TYPE: PRT
<213> ORGANISM: Phakopsora pachyrhizi
<220> FEATURE:
<221> NAME/KEY: VARIANT
<222> LOCATION: (1)..(219)
<223> OTHER INFORMATION: ta01860.01_phapa

<400> SEQUENCE: 342

Met Lys Ile Ser Phe Ala Asn Leu Phe Val Leu Phe Ser Ala Leu Ser
1 5 10 15

Val Ala Leu Val Ala Thr Glu Asp Val Gln Gly Val Lys Gly Asp Asn
20 25 30

Ser Glu Ala Lys Trp Leu Tyr Trp Gly Gly Gly Ile Gly Tyr Gly Gly
35 40 45

Leu Gly Ser Tyr Tyr Gly Asn Trp Leu Ser Pro Tyr Tyr Asn Asn Ala
50 55 60

Phe Gly Phe Gly Val Tyr Asn Tyr Leu Pro Arg Arg Trp Tyr Arg Arg
65 70 75 80

Ala Leu Gln Thr Arg Gly Asp Glu Ser Asn Ala Lys Ala Ser Val Ser
85 90 95

Ser Thr Val Gln Cys Ser Asn Ala Gln Gly Val Lys Gln Glu Phe Ser
100 105 110

Thr Ala Ser Cys Leu Lys Ala Ala Thr Lys Ile Ser Lys Glu Gln Ile
115 120 125

Thr Thr Ala Thr Cys Gly Thr Cys Thr Ile Gln Leu His Asn Lys Glu
130 135 140

Gly Pro Ile Gln Phe Asn Ala Ile Pro Pro Gln Ser Glu Leu Asn Ser
145 150 155 160

Ala Val Asn Asn Met Leu Lys Ala Cys Ser Lys Ser Gln Asp Lys Leu
165 170 175

Leu Ser Ala Ser Glu Leu Ser Arg Arg Ser Pro Ala Glu Asn Gly Asn
180 185 190

Gly Val Asp Ser Lys Asp Thr Ser Ser Asn Lys Asn Ala Leu Ala Ile
195 200 205

Ile Leu Leu Lys Gly Asn Gly Pro Glu Cys Asn
210 215

<210> SEQ ID NO 343
<211> LENGTH: 657
<212> TYPE: DNA
<213> ORGANISM: Phakopsora pachyrhizi
<220> FEATURE:
<221> NAME/KEY: misc_feature
<222> LOCATION: (1)..(657)
<223> OTHER INFORMATION: ta09379.01_phapa

<400> SEQUENCE: 343
atgctttttg ctacactaat agccgtttgc ttacttgctc tgggaggcaa agctgagagt 60
gatgtccaaa gtgataccgc atctaaactt cagcgacgag gacatgatga ctctctacct 120
cctgtgacat ttattatgag agatagcaac gagcatgtag gcggaaagct gttgatctac 180
aattctgatg gaacactagc tttcaccttt cgcagagcag ttttgaactc tgatggcctt 240
tccaacgttg aagtcagaga tgtgcgaaat aatttttcga taaacttaga atctaacgat 300
gacacctgct ttaaaaagtc tcactatgtt gaaagagaaa aaaatctggg tcaattcaaa 360
attgatccac gaggtgcaaa agcagacaga tggcatttca ctaggaaaac tccacacgga 420
gatttcaagt atgactttca tcgcaagtat ttttcgaagg acggtaatat ttacataaaa 480
gacacccatg tgcgagtggc ttccctgaca tccgaaattc gacatgaagc ttggctccaa 540
ccggggaaac atggtgttcc aacattctca ttgcatcttc aatataacac tgagcctatc 600
ttttttgtag ctttgatggg cttagatctc accagagtag acacatgtgg actttga 657

<210> SEQ ID NO 344
<211> LENGTH: 218
<212> TYPE: PRT
<213> ORGANISM: Phakopsora pachyrhizi
<220> FEATURE:
<221> NAME/KEY: VARIANT
<222> LOCATION: (1)..(218)
<223> OTHER INFORMATION: ta09379.01_phapa

<400> SEQUENCE: 344

Met Leu Phe Ala Thr Leu Ile Ala Val Cys Leu Leu Ala Leu Gly Gly
1 5 10 15

Lys Ala Glu Ser Asp Val Gln Ser Asp Thr Ala Ser Lys Leu Gln Arg
20 25 30

Arg Gly His Asp Asp Ser Leu Pro Pro Val Thr Phe Ile Met Arg Asp
35 40 45

Ser Asn Glu His Val Gly Gly Lys Leu Leu Ile Tyr Asn Ser Asp Gly
50 55 60

Thr Leu Ala Phe Thr Phe Arg Arg Ala Val Leu Asn Ser Asp Gly Leu
65 70 75 80

Ser Asn Val Glu Val Arg Asp Val Arg Asn Asn Phe Ser Ile Asn Leu
85 90 95

Glu Ser Asn Asp Asp Thr Cys Phe Lys Lys Ser His Tyr Val Glu Arg
100 105 110

Glu Lys Asn Leu Gly Gln Phe Lys Ile Asp Pro Arg Gly Ala Lys Ala
115 120 125

Asp Arg Trp His Phe Thr Arg Lys Thr Pro His Gly Asp Phe Lys Tyr
130 135 140

Asp Phe His Arg Lys Tyr Phe Ser Lys Asp Gly Asn Ile Tyr Ile Lys
145 150 155 160

Asp Thr His Val Arg Val Ala Ser Leu Thr Ser Glu Ile Arg His Glu
165 170 175

Ala Trp Leu Gln Pro Gly Lys His Gly Val Pro Thr Phe Ser Leu His
180 185 190

Leu Gln Tyr Asn Thr Glu Pro Ile Phe Phe Val Ala Leu Met Gly Leu
195 200 205

Asp Leu Thr Arg Val Asp Thr Cys Gly Leu
210 215

<210> SEQ ID NO 345
<211> LENGTH: 657
<212> TYPE: DNA
<213> ORGANISM: Phakopsora pachyrhizi
<220> FEATURE:
<221> NAME/KEY: misc_feature
<222> LOCATION: (1)..(657)
<223> OTHER INFORMATION: ta07208.01_phapa

<400> SEQUENCE: 345
atgagtctaa gttttaaggc tttactagtc tttctaccag tgatcttctt ctacctggtg 60

```
ttggctgtaa aacaaccatc agatcaaaca actcattcta cccaaccaca gaagcataac    120

actcatcaaa catctatcaa ctcaaagcga gaactacaac agcaactcag tcagttcaat    180

ccacatcatc aatctttagc ttcatcaacc aggatgtcat cagtcaatga tagaacagct    240

tcaccaatca cagatattga ctcaaacaca aacgttccaa cagctgccaa gggtgaggag    300

gagtccacaa aacagaagct tgaagatcaa ccagcaggcg atggtacaaa ggcatcatta    360

tcagctaacc ctggtgaatc gcaacagagt gacgagaaga atcttaaatc tcagaatgtt    420

tccccgagtc aagaacacat gagtagatac attgtcactt tctcgcgtga gactacttct    480

gcccagttga aggaatacgc tgataaaatc attcagagag gtggaaagat taaccatacg    540

tatgattcag cgattcttaa aggatttgct gtttctataa gtgatagtct ggttacaacc    600

ctggatgatg atccaaatgt aaagagtgtt gaacctgatg gtgaagtaca catctga       657
```

<210> SEQ ID NO 346
<211> LENGTH: 218
<212> TYPE: PRT
<213> ORGANISM: Phakopsora pachyrhizi
<220> FEATURE:
<221> NAME/KEY: VARIANT
<222> LOCATION: (1)..(218)
<223> OTHER INFORMATION: ta07208.01_phapa

<400> SEQUENCE: 346

```
Met Ser Leu Ser Phe Lys Ala Leu Leu Val Phe Leu Pro Val Ile Phe
1               5                   10                  15

Phe Tyr Leu Val Leu Ala Val Lys Gln Pro Ser Asp Gln Thr Thr His
            20                  25                  30

Ser Thr Gln Pro Gln Lys His Asn Thr His Gln Thr Ser Ile Asn Ser
        35                  40                  45

Lys Arg Glu Leu Gln Gln Gln Leu Ser Gln Phe Asn Pro His His Gln
    50                  55                  60

Ser Leu Ala Ser Ser Thr Arg Met Ser Ser Val Asn Asp Arg Thr Ala
65                  70                  75                  80

Ser Pro Ile Thr Asp Ile Asp Ser Asn Thr Asn Val Pro Thr Ala Ala
                85                  90                  95

Lys Gly Glu Glu Glu Ser Thr Lys Gln Lys Leu Glu Asp Gln Pro Ala
            100                 105                 110

Gly Asp Gly Thr Lys Ala Ser Leu Ser Ala Asn Pro Gly Glu Ser Gln
        115                 120                 125

Gln Ser Asp Glu Lys Asn Leu Lys Ser Gln Asn Val Ser Pro Ser Gln
    130                 135                 140

Glu His Met Ser Arg Tyr Ile Val Thr Phe Ser Arg Glu Thr Thr Ser
145                 150                 155                 160

Ala Gln Leu Lys Glu Tyr Ala Asp Lys Ile Ile Gln Arg Gly Gly Lys
                165                 170                 175

Ile Asn His Thr Tyr Asp Ser Ala Ile Leu Lys Gly Phe Ala Val Ser
            180                 185                 190

Ile Ser Asp Ser Leu Val Thr Thr Leu Asp Asp Asp Pro Asn Val Lys
        195                 200                 205

Ser Val Glu Pro Asp Gly Glu Val His Ile
    210                 215
```

<210> SEQ ID NO 347
<211> LENGTH: 651
<212> TYPE: DNA
<213> ORGANISM: Phakopsora pachyrhizi
<220> FEATURE:
<221> NAME/KEY: misc_feature
<222> LOCATION: (1)..(651)
<223> OTHER INFORMATION: ta05865.01_phapa

<400> SEQUENCE: 347

```
atgtttggtt taaaggctat cataatcgcc actggcttga tctatcaggt cactgcggct     60

gccaatacct ctgccaccac tgctcccgga caggatcagg gccaaggtca aggtcctgaa    120

tctggtggtt gtgcagccaa gtgtatggcc gcaaagctgg atgacgctgc caagtggttt    180

ggtccaggta accttgcatc ctactgtcaa catgccgagt tcatcactgc atacgacaca    240

tgtttgggcg ataactgtgc caaccatgaa gagctagatg ccggtaagaa aagcggtcgt    300

gaggcttgcg ctgctgctgg agtcacctca ccgggatcga ttgccccacc cacaggacat    360

acccctccta ccagtgggaa taactctcta gcagatttgc ctgccggtgc tactaatcat    420

agcatgagca ctaattctac tccaagtgca actaccacca actctaccct tggtggtacc    480

ctcaataaca cccttcatac ccctaacacc acctccaccg ctactaacag tagattttcc    540

agtgcggtta actctgctgc ttctgctgct gccaacagta cagcttcaac actcactagc    600

tcttctatct tgcttggtat ctcttctgta ctggtgattg ccaacctcta a             651
```

<210> SEQ ID NO 348
<211> LENGTH: 216
<212> TYPE: PRT
<213> ORGANISM: Phakopsora pachyrhizi
<220> FEATURE:
<221> NAME/KEY: VARIANT
<222> LOCATION: (1)..(216)
<223> OTHER INFORMATION: ta05865.01_phapa

<400> SEQUENCE: 348

```
Met Phe Gly Leu Lys Ala Ile Ile Ile Ala Thr Gly Leu Ile Tyr Gln
1               5                   10                  15

Val Thr Ala Ala Ala Asn Thr Ser Ala Thr Thr Ala Pro Gly Gln Asp
            20                  25                  30

Gln Gly Gln Gly Gln Gly Pro Glu Ser Gly Gly Cys Ala Ala Lys Cys
        35                  40                  45

Met Ala Ala Lys Leu Asp Asp Ala Ala Lys Trp Phe Gly Pro Gly Asn
    50                  55                  60

Leu Ala Ser Tyr Cys Gln His Ala Glu Phe Ile Thr Ala Tyr Asp Thr
65                  70                  75                  80

Cys Leu Gly Asp Asn Cys Ala Asn His Glu Glu Leu Asp Ala Gly Lys
                85                  90                  95

Lys Ser Gly Arg Glu Ala Cys Ala Ala Ala Gly Val Thr Ser Pro Gly
            100                 105                 110

Ser Ile Ala Pro Pro Thr Gly His Thr Pro Pro Thr Ser Gly Asn Asn
        115                 120                 125

Ser Leu Ala Asp Leu Pro Ala Gly Ala Thr Asn His Ser Met Ser Thr
    130                 135                 140

Asn Ser Thr Pro Ser Ala Thr Thr Thr Asn Ser Thr Leu Gly Gly Thr
145                 150                 155                 160

Leu Asn Asn Thr Leu His Thr Pro Asn Thr Thr Ser Thr Ala Thr Asn
                165                 170                 175

Ser Arg Phe Ser Ser Ala Val Asn Ser Ala Ala Ser Ala Ala Ala Asn
            180                 185                 190

Ser Thr Ala Ser Thr Leu Thr Ser Ser Ser Ile Leu Leu Gly Ile Ser
        195                 200                 205
```

Ser Val Leu Val Ile Ala Asn Leu
    210                 215

<210> SEQ ID NO 349
<211> LENGTH: 651
<212> TYPE: DNA
<213> ORGANISM: Phakopsora pachyrhizi
<220> FEATURE:
<221> NAME/KEY: misc_feature
<222> LOCATION: (1)..(651)
<223> OTHER INFORMATION: ta05865.02_phapa

<400> SEQUENCE: 349
atgtttggtt taaaggctat cataatcgcc actggcttga tctatcaggt cactgcggct 60
gccaatacct ctgccaccac tgctcccgga caggatcagg gccaaggtca aggtcctgaa 120
tctggtggtt gtgcagccaa gtgtatggcc gcaaagctgg atgacgctgc caagtggttt 180
ggtccaggta accttgcatc ctactgtcaa catgccgagt tcatcactgc atacgacaca 240
tgtttgggcg ataactgtgc caaccatgaa gagctagatg ccggtaagaa aagcggtcgt 300
gaggcttgcg ctgctgctgg agtcacctca ccgggatcga ttgccccacc cacaggacat 360
acccctccta ccagtgggaa taactctcta gcagatttgc ctgccggtgc tactaatcat 420
agcatgagca ctaattctac tccaagtgca actaccacca actctaccct tggtggtacc 480
ctcaataaca cccttcatac ccctaacacc acctccaccg ctactaacag tagattttcc 540
agtgcggtta actctgctgc ttctgctgct gccaacagta cagcttcaac actcactagc 600
tcttctatct tgcttggtat ctcttctgta ctggtgattg ccaacctcta a 651

<210> SEQ ID NO 350
<211> LENGTH: 216
<212> TYPE: PRT
<213> ORGANISM: Phakopsora pachyrhizi
<220> FEATURE:
<221> NAME/KEY: VARIANT
<222> LOCATION: (1)..(216)
<223> OTHER INFORMATION: ta05865.02_phapa

<400> SEQUENCE: 350

Met Phe Gly Leu Lys Ala Ile Ile Ile Ala Thr Gly Leu Ile Tyr Gln
1               5                   10                  15

Val Thr Ala Ala Ala Asn Thr Ser Ala Thr Thr Ala Pro Gly Gln Asp
            20                  25                  30

Gln Gly Gln Gly Gln Gly Pro Glu Ser Gly Gly Cys Ala Ala Lys Cys
        35                  40                  45

Met Ala Ala Lys Leu Asp Asp Ala Ala Lys Trp Phe Gly Pro Gly Asn
    50                  55                  60

Leu Ala Ser Tyr Cys Gln His Ala Glu Phe Ile Thr Ala Tyr Asp Thr
65                  70                  75                  80

Cys Leu Gly Asp Asn Cys Ala Asn His Glu Glu Leu Asp Ala Gly Lys
                85                  90                  95

Lys Ser Gly Arg Glu Ala Cys Ala Ala Ala Gly Val Thr Ser Pro Gly
            100                 105                 110

Ser Ile Ala Pro Pro Thr Gly His Thr Pro Pro Thr Ser Gly Asn Asn
        115                 120                 125

Ser Leu Ala Asp Leu Pro Ala Gly Ala Thr Asn His Ser Met Ser Thr
    130                 135                 140

Asn Ser Thr Pro Ser Ala Thr Thr Thr Asn Ser Thr Leu Gly Gly Thr
145                 150                 155                 160

```
Leu Asn Asn Thr Leu His Thr Pro Asn Thr Thr Ser Thr Ala Thr Asn
                165                 170                 175

Ser Arg Phe Ser Ser Ala Val Asn Ser Ala Ala Ser Ala Ala Ala Asn
            180                 185                 190

Ser Thr Ala Ser Thr Leu Thr Ser Ser Ser Ile Leu Leu Gly Ile Ser
        195                 200                 205

Ser Val Leu Val Ile Ala Asn Leu
    210                 215


<210> SEQ ID NO 351
<211> LENGTH: 651
<212> TYPE: DNA
<213> ORGANISM: Phakopsora pachyrhizi
<220> FEATURE:
<221> NAME/KEY: misc_feature
<222> LOCATION: (1)..(651)
<223> OTHER INFORMATION: ta00656.02_phapa

<400> SEQUENCE: 351

atgattgcca accccgtcaa ttttgttttc ttgttgagcg tatttctgag ctttcaaatt      60

cagaatgcct caacaaaaag aggtagaggg ggaccgattg cagctctctg ccaaggaaag     120

gagcaaaatg tgaaagttat cgctacttgc agtgaaggaa aaattttatg cgagggtttg     180

gatgaaagtg gtactggaac aatgtcttgt tcagatggag gaaaactttt agaggtaaaa     240

agtgaagaag ccgctcagtg tggcgccaat ccccgttgca agaagttggc gaagggaagt     300

aaagttattg aattaggaaa ggttgtgggt gcagctctag ctgatggcaa gtccctcgca     360

cctggaagca gagcagcagt ccaaacaggg ggtaaagaag gtaaagaagg taaagagggt     420

aaagagggta aagagggtaa agatgataaa ggtggtaaag ctgttgattt ggctctgggc     480

aagggtgatg caaaagctgc tgattcagca aacggggtta aagtagatgt aaaaggcaaa     540

gagttggcaa atgcgggcaa ggaaaacaat aaagagaatg aggcacagaa agctacagaa     600

cctactctca atactcaggc tgcttcaggt ggagaagagg taaaagcata g              651


<210> SEQ ID NO 352
<211> LENGTH: 216
<212> TYPE: PRT
<213> ORGANISM: Phakopsora pachyrhizi
<220> FEATURE:
<221> NAME/KEY: VARIANT
<222> LOCATION: (1)..(216)
<223> OTHER INFORMATION: ta00656.02_phapa

<400> SEQUENCE: 352

Met Ile Ala Asn Pro Val Asn Phe Val Phe Leu Leu Ser Val Phe Leu
1               5                   10                  15

Ser Phe Gln Ile Gln Asn Ala Ser Thr Lys Arg Gly Arg Gly Gly Pro
            20                  25                  30

Ile Ala Ala Leu Cys Gln Gly Lys Glu Gln Asn Val Lys Val Ile Ala
        35                  40                  45

Thr Cys Ser Glu Gly Lys Ile Leu Cys Glu Gly Leu Asp Glu Ser Gly
    50                  55                  60

Thr Gly Thr Met Ser Cys Ser Asp Gly Gly Lys Leu Leu Glu Val Lys
65                  70                  75                  80

Ser Glu Glu Ala Ala Gln Cys Gly Ala Asn Pro Arg Cys Lys Lys Leu
                85                  90                  95

Ala Lys Gly Ser Lys Val Ile Glu Leu Gly Lys Val Val Gly Ala Ala
            100                 105                 110
```

```
Leu Ala Asp Gly Lys Ser Leu Ala Pro Gly Ser Arg Ala Ala Val Gln
        115                 120                 125

Thr Gly Gly Lys Glu Gly Lys Glu Gly Lys Glu Gly Lys Glu Gly Lys
    130                 135                 140

Glu Gly Lys Asp Asp Lys Gly Gly Lys Ala Val Asp Leu Ala Leu Gly
145                 150                 155                 160

Lys Gly Asp Ala Lys Ala Ala Asp Ser Ala Asn Gly Val Lys Val Asp
                165                 170                 175

Val Lys Gly Lys Glu Leu Ala Asn Ala Gly Lys Glu Asn Asn Lys Glu
            180                 185                 190

Asn Glu Ala Gln Lys Ala Thr Glu Pro Thr Leu Asn Thr Gln Ala Ala
        195                 200                 205

Ser Gly Gly Glu Glu Val Lys Ala
    210                 215


<210> SEQ ID NO 353
<211> LENGTH: 645
<212> TYPE: DNA
<213> ORGANISM: Phakopsora pachyrhizi
<220> FEATURE:
<221> NAME/KEY: misc_feature
<222> LOCATION: (1)..(645)
<223> OTHER INFORMATION: ta09778.01_phapa

<400> SEQUENCE: 353

atgcttcgct taatttcgct aggacttttg gtatgctctg ccgcaagatt gaccgtgagc      60

agtccaagcg atctctcact aagacctcgt cagcttggct taggtgccgg cggagcagcc     120

gcaggttcct tcagcagtag taccagcgta tcgacattta gctccttcgt tcaaggttgg     180

agcgtcattc caactgcttt cggaacttgc gcggccacct tccaacaaag agttactgtt     240

caagttgctg ttcagtcggt acagcagtta tacagtactg tgaatggagt tctaggacat     300

tacggtggtt gtggtggttg cggtggtgct tctgctgctg gtgcttacgc ttctaaatat     360

caatccatca tcacccagag tttcacttcc tggcaaacta tacttcaagt tgggcaatcc     420

tcatacgcca atgcttggga ctctcaattt attcctctct tccgacaatt caaccctttc     480

cttacagcgg tacaacagaa ttccggactt tttggcatca atctcggtaa ccttcttggt     540

ggtctccacc ttaacatcaa cctcttctct tcatgtggtc ttaacgttgg tggactgcta     600

gggggtgttt tgaatgtagt cggtggatta ttgggcggtc attga                      645


<210> SEQ ID NO 354
<211> LENGTH: 214
<212> TYPE: PRT
<213> ORGANISM: Phakopsora pachyrhizi
<220> FEATURE:
<221> NAME/KEY: VARIANT
<222> LOCATION: (1)..(214)
<223> OTHER INFORMATION: ta09778.01_phapa

<400> SEQUENCE: 354

Met Leu Arg Leu Ile Ser Leu Gly Leu Leu Val Cys Ser Ala Ala Arg
1               5                   10                  15

Leu Thr Val Ser Ser Pro Ser Asp Leu Ser Leu Arg Pro Arg Gln Leu
            20                  25                  30

Gly Leu Gly Ala Gly Gly Ala Ala Ala Gly Ser Phe Ser Ser Ser Thr
        35                  40                  45

Ser Val Ser Thr Phe Ser Ser Phe Val Gln Gly Trp Ser Val Ile Pro
    50                  55                  60
```

```
Thr Ala Phe Gly Thr Cys Ala Ala Thr Phe Gln Gln Arg Val Thr Val
65                  70                  75                  80

Gln Val Ala Val Gln Ser Val Gln Gln Leu Tyr Ser Thr Val Asn Gly
                85                  90                  95

Val Leu Gly His Tyr Gly Gly Cys Gly Gly Cys Gly Gly Ala Ser Ala
            100                 105                 110

Ala Gly Ala Tyr Ala Ser Lys Tyr Gln Ser Ile Ile Thr Gln Ser Phe
        115                 120                 125

Thr Ser Trp Gln Thr Ile Leu Gln Val Gly Gln Ser Ser Tyr Ala Asn
    130                 135                 140

Ala Trp Asp Ser Gln Phe Ile Pro Leu Phe Arg Gln Phe Asn Pro Phe
145                 150                 155                 160

Leu Thr Ala Val Gln Gln Asn Ser Gly Leu Phe Gly Ile Asn Leu Gly
                165                 170                 175

Asn Leu Leu Gly Gly Leu His Leu Asn Ile Asn Leu Phe Ser Ser Cys
            180                 185                 190

Gly Leu Asn Val Gly Gly Leu Leu Gly Gly Val Leu Asn Val Val Gly
        195                 200                 205

Gly Leu Leu Gly Gly His
    210
```

```
<210> SEQ ID NO 355
<211> LENGTH: 645
<212> TYPE: DNA
<213> ORGANISM: Phakopsora pachyrhizi
<220> FEATURE:
<221> NAME/KEY: misc_feature
<222> LOCATION: (1)..(645)
<223> OTHER INFORMATION: ta00721.08_phapa

<400> SEQUENCE: 355

atgaaattgt catacgccta cttgattgtt ctcatctctg tcctgtcttc aacttttgtg      60

gtagctgagg atgttagcga caaaaacgct gaggtttctg acagcaagtt ctttggacta     120

ggtggacttg gggttgggg ttactgggga ggtggtagat ttgctggtct tggtggatac     180

tcgtggttga acccatggat gggaaatgcc tacgggtttg gtctctaccg cggattttat     240

ggtggatggc tcaaatcggc tgatggtcac caagagcgtc gatcaatcca ggaattgcac     300

aacctcatgt cacgggctga tcacaccgta tcatgcaaga acaagaacgg tgaagttgct     360

catttcgaaa ccaagagctg cttgagtgct gcaaacaagt tagctaatca acacgcttcg     420

agcgctacct gtggcgcgtg ctctctgagc atccaaggtc ccaacggtgc tctatctgct     480

aagtctattc catcatctga gttgacaaag gcgactctta acattttgaa ggcttgcgcc     540

aaaggtgaaa gcaagatgct tgctgcttca gagcttgagc gccgctctcc attgcccgag     600

gaaatttcca tctcaatcct catccagcaa cgaaaagagc tctaa                    645


<210> SEQ ID NO 356
<211> LENGTH: 214
<212> TYPE: PRT
<213> ORGANISM: Phakopsora pachyrhizi
<220> FEATURE:
<221> NAME/KEY: VARIANT
<222> LOCATION: (1)..(214)
<223> OTHER INFORMATION: ta00721.08_phapa

<400> SEQUENCE: 356

Met Lys Leu Ser Tyr Ala Tyr Leu Ile Val Leu Ile Ser Val Leu Ser
1               5                   10                  15
```

```
Ser Thr Phe Val Val Ala Glu Asp Val Ser Asp Lys Asn Ala Glu Val
            20                  25                  30

Ser Asp Ser Lys Phe Phe Gly Leu Gly Gly Leu Gly Gly Trp Gly Tyr
        35                  40                  45

Trp Gly Gly Gly Arg Phe Ala Gly Leu Gly Gly Tyr Ser Trp Leu Asn
    50                  55                  60

Pro Trp Met Gly Asn Ala Tyr Gly Phe Gly Leu Tyr Arg Gly Phe Tyr
65                  70                  75                  80

Gly Gly Trp Leu Lys Ser Ala Asp Gly His Gln Glu Arg Arg Ser Ile
                85                  90                  95

Gln Glu Leu His Asn Leu Met Ser Arg Ala Asp His Thr Val Ser Cys
            100                 105                 110

Lys Asn Lys Asn Gly Glu Val Ala His Phe Glu Thr Lys Ser Cys Leu
        115                 120                 125

Ser Ala Ala Asn Lys Leu Ala Asn Gln His Ala Ser Ser Ala Thr Cys
    130                 135                 140

Gly Ala Cys Ser Leu Ser Ile Gln Gly Pro Asn Gly Ala Leu Ser Ala
145                 150                 155                 160

Lys Ser Ile Pro Ser Ser Glu Leu Thr Lys Ala Thr Leu Asn Ile Leu
                165                 170                 175

Lys Ala Cys Ala Lys Gly Glu Ser Lys Met Leu Ala Ala Ser Glu Leu
            180                 185                 190

Glu Arg Arg Ser Pro Leu Pro Glu Glu Ile Ser Ile Ser Ile Leu Ile
        195                 200                 205

Gln Gln Arg Lys Glu Leu
    210
```

<210> SEQ ID NO 357
<211> LENGTH: 642
<212> TYPE: DNA
<213> ORGANISM: Phakopsora pachyrhizi
<220> FEATURE:
<221> NAME/KEY: misc_feature
<222> LOCATION: (1)..(642)
<223> OTHER INFORMATION: ta04963.02_phapa

<400> SEQUENCE: 357

```
atggtttact caaaggcaac cttcaccctg gtctcactcc tacctatgat cctggcccag     60

cagagcatca acaacagtga taccacaacc acggctgcta ccccggccag tcccaccaac    120

agcagcagct ctaccactac ttccactacc acctctaaca ctgccagtgg agctgctcag    180

tccttccctg cgccaacagt ctcaggaaca tcctgtggta cagcccagca gaactttaac    240

cagtgtgtta ccaaagtatc aaaggatatc tcctcatgtc cctctaccga taacacctgt    300

ctttgccaaa cgtatgcaaa cctagcctac tgttacaacg cctgtccaga tctggcatca    360

tcaggggccg gatacctgca gcagtccaca gtgaactgtg atgcagcagg tatcaagcca    420

aacgctactt ccaacgtcac caccacccct gtcacctcca ccactaacag gaacaccacc    480

aacacctcac ccatctctaa cacaaacaag aacaattcta cctcgggcaa cactgctgct    540

acatttgctg ctggaaactc caaggcaagt gggattgagg ccccgttact gagcgttgct    600

gttgttgggc tgtgtggtat cattgctagc ctatttgcat ga                       642
```

<210> SEQ ID NO 358
<211> LENGTH: 213
<212> TYPE: PRT
<213> ORGANISM: Phakopsora pachyrhizi
<220> FEATURE:
<221> NAME/KEY: VARIANT
<222> LOCATION: (1)..(213)
<223> OTHER INFORMATION: ta04963.02_phapa

<400> SEQUENCE: 358

```
Met Val Tyr Ser Lys Ala Thr Phe Thr Leu Val Ser Leu Leu Pro Met
1               5                   10                  15

Ile Leu Ala Gln Gln Ser Ile Asn Asn Ser Asp Thr Thr Thr Thr Ala
            20                  25                  30

Ala Thr Pro Ala Ser Pro Thr Asn Ser Ser Ser Ser Thr Thr Thr Ser
        35                  40                  45

Thr Thr Thr Ser Asn Thr Ala Ser Gly Ala Ala Gln Ser Phe Pro Ala
    50                  55                  60

Pro Thr Val Ser Gly Thr Ser Cys Gly Thr Ala Gln Gln Asn Phe Asn
65                  70                  75                  80

Gln Cys Val Thr Lys Val Ser Lys Asp Ile Ser Ser Cys Pro Ser Thr
                85                  90                  95

Asp Asn Thr Cys Leu Cys Gln Thr Tyr Ala Asn Leu Ala Tyr Cys Tyr
            100                 105                 110

Asn Ala Cys Pro Asp Leu Ala Ser Ser Gly Ala Gly Tyr Leu Gln Gln
        115                 120                 125

Ser Thr Val Asn Cys Asp Ala Ala Gly Ile Lys Pro Asn Ala Thr Ser
    130                 135                 140

Asn Val Thr Thr Thr Pro Val Thr Ser Thr Thr Asn Arg Asn Thr Thr
145                 150                 155                 160

Asn Thr Ser Pro Ile Ser Asn Thr Asn Lys Asn Asn Ser Thr Ser Gly
                165                 170                 175

Asn Thr Ala Ala Thr Phe Ala Ala Gly Asn Ser Lys Ala Ser Gly Ile
            180                 185                 190

Glu Ala Pro Leu Leu Ser Val Ala Val Val Gly Leu Cys Gly Ile Ile
        195                 200                 205

Ala Ser Leu Phe Ala
    210
```

<210> SEQ ID NO 359
<211> LENGTH: 639
<212> TYPE: DNA
<213> ORGANISM: Phakopsora pachyrhizi
<220> FEATURE:
<221> NAME/KEY: misc_feature
<222> LOCATION: (1)..(639)
<223> OTHER INFORMATION: ta02061.01_phapa

<400> SEQUENCE: 359

```
atgaatcaat ggttaattat tctatggatc tcacttctgg cttctcaagc cacaagaggt      60

agcgggatca ttgaaatcaa ctcaaactct ctgtcgaacg agcttatata ttgggatagt     120

aagaatgaag aaattttggg cactttaaag agtcgggaag atatggaaag actcaagaga     180

ttggggcaac ggctaagagt ctcattttca tcgagtacat tgccgctagt cgaaatcaat     240

tctacaagca gaaggtttct gaagcttact tcagaagatg aaaattttac agacctctca     300

gtctcagggt tagctataaa tcagaaaagg ttttccaaga ggtcagaggg actggggaaa     360

gagatcgttg atgcaatctt tccgattaaa ggaactgtta cgacgatcgc tgagacgata     420

aatccaaaaa aatcaatctt tccaggttct aggattttta ataagccaca cgggacgatg     480

ggaaccaatt atctggattt gacgaggaaa gatgttacaa tggcacaaat gtcaaaggcc     540
```

aagccccagg gcaatgtaat tcaggatagt atcattcaag tcctgacggc cagtcaaaga 600
caggtcagaa atcctagggt gacggttgac tccaaataa 639

<210> SEQ ID NO 360
<211> LENGTH: 212
<212> TYPE: PRT
<213> ORGANISM: Phakopsora pachyrhizi
<220> FEATURE:
<221> NAME/KEY: VARIANT
<222> LOCATION: (1)..(212)
<223> OTHER INFORMATION: ta02061.01_phapa

<400> SEQUENCE: 360

Met Asn Gln Trp Leu Ile Ile Leu Trp Ile Ser Leu Leu Ala Ser Gln
1 5 10 15

Ala Thr Arg Gly Ser Gly Ile Ile Glu Ile Asn Ser Asn Ser Leu Ser
20 25 30

Asn Glu Leu Ile Tyr Trp Asp Ser Lys Asn Glu Glu Ile Leu Gly Thr
35 40 45

Leu Lys Ser Arg Glu Asp Met Glu Arg Leu Lys Arg Leu Gly Gln Arg
50 55 60

Leu Arg Val Ser Phe Ser Ser Ser Thr Leu Pro Leu Val Glu Ile Asn
65 70 75 80

Ser Thr Ser Arg Arg Phe Leu Lys Leu Thr Ser Glu Asp Glu Asn Phe
85 90 95

Thr Asp Leu Ser Val Ser Gly Leu Ala Ile Asn Gln Lys Arg Phe Ser
100 105 110

Lys Arg Ser Glu Gly Leu Gly Lys Glu Ile Val Asp Ala Ile Phe Pro
115 120 125

Ile Lys Gly Thr Val Thr Thr Ile Ala Glu Thr Ile Asn Pro Lys Lys
130 135 140

Ser Ile Phe Pro Gly Ser Arg Ile Phe Asn Lys Pro His Gly Thr Met
145 150 155 160

Gly Thr Asn Tyr Leu Asp Leu Thr Arg Lys Asp Val Thr Met Ala Gln
165 170 175

Met Ser Lys Ala Lys Pro Gln Gly Asn Val Ile Gln Asp Ser Ile Ile
180 185 190

Gln Val Leu Thr Ala Ser Gln Arg Gln Val Arg Asn Pro Arg Val Thr
195 200 205

Val Asp Ser Lys
210

<210> SEQ ID NO 361
<211> LENGTH: 633
<212> TYPE: DNA
<213> ORGANISM: Phakopsora pachyrhizi
<220> FEATURE:
<221> NAME/KEY: misc_feature
<222> LOCATION: (1)..(633)
<223> OTHER INFORMATION: ta08296.04_phapa

<400> SEQUENCE: 361
atgcgcagct ttgtttattg tgccttgctc gtcttaattt gtcagcttgc tacaagctcg 60
cctattaatg aaagatctga ggttgaggct tccaaagagc agtcttcgga gaagtttttt 120
ccacttttcc ctcccccacc accagtgccg tttatacgcc cacctttacc accttttgga 180
tttaaagaca atcaccaaaa tgcgaagaga tccgaggttg agactgccaa agaggagtct 240
tcggagaaat tttttcccat tctacctccc cccccaccac caccattttt ccgccccccat 300

```
ctaccaccct ttggattcaa agacagccat caaaatgaga aaaggtctga ggttgctgct    360

caccaagaga gccagtcgac agagaaattt tttccagggt atggtttccc gatcctacca    420

ccaccacatc cattttttta ccaccgtcgt ccttttggtt atggcttttt tccaccacca    480

ccttttggat ttaaagacaa acaccaaaat gagaagcgat ctgaggtcga atcctctaag    540

gaaaagtcaa ctgagaagtt ttttcccagg tctcttaccg attttgccac cttttccccc    600

atttggcttc ctaaaagatg ccaagagcaa tga                                 633


<210> SEQ ID NO 362
<211> LENGTH: 210
<212> TYPE: PRT
<213> ORGANISM: Phakopsora pachyrhizi
<220> FEATURE:
<221> NAME/KEY: VARIANT
<222> LOCATION: (1)..(210)
<223> OTHER INFORMATION: ta08296.04_phapa

<400> SEQUENCE: 362

Met Arg Ser Phe Val Tyr Cys Ala Leu Leu Val Leu Ile Cys Gln Leu
1               5                   10                  15

Ala Thr Ser Ser Pro Ile Asn Glu Arg Ser Glu Val Glu Ala Ser Lys
            20                  25                  30

Glu Gln Ser Ser Glu Lys Phe Phe Pro Leu Phe Pro Pro Pro Pro Pro
        35                  40                  45

Val Pro Phe Ile Arg Pro Pro Leu Pro Pro Phe Gly Phe Lys Asp Asn
    50                  55                  60

His Gln Asn Ala Lys Arg Ser Glu Val Glu Thr Ala Lys Glu Glu Ser
65                  70                  75                  80

Ser Glu Lys Phe Phe Pro Ile Leu Pro Pro Pro Pro Pro Pro Pro Phe
                85                  90                  95

Phe Arg Pro His Leu Pro Pro Phe Gly Phe Lys Asp Ser His Gln Asn
            100                 105                 110

Glu Lys Arg Ser Glu Val Ala Ala His Gln Glu Ser Gln Ser Thr Glu
        115                 120                 125

Lys Phe Phe Pro Gly Tyr Gly Phe Pro Ile Leu Pro Pro Pro His Pro
    130                 135                 140

Phe Phe Tyr His Arg Arg Pro Phe Gly Tyr Gly Phe Phe Pro Pro Pro
145                 150                 155                 160

Pro Phe Gly Phe Lys Asp Lys His Gln Asn Glu Lys Arg Ser Glu Val
                165                 170                 175

Glu Ser Ser Lys Glu Lys Ser Thr Glu Lys Phe Phe Pro Arg Ser Leu
            180                 185                 190

Thr Asp Phe Ala Thr Phe Ser Pro Ile Trp Leu Pro Lys Arg Cys Gln
        195                 200                 205

Glu Gln
    210


<210> SEQ ID NO 363
<211> LENGTH: 633
<212> TYPE: DNA
<213> ORGANISM: Phakopsora pachyrhizi
<220> FEATURE:
<221> NAME/KEY: misc_feature
<222> LOCATION: (1)..(633)
<223> OTHER INFORMATION: ta01247.01_phapa

<400> SEQUENCE: 363
```

```
atgaatatga gaagaactgt tacaagtttt gggttaaaga gtttaacaat tttcattgga      60

gtctggcttc aactttcaac tttctcaatc gcaacgatat gtatgagtag gaaaagcagc     120

ttgaacccaa agatccttgc ctctgactgc aacatggtat tggacctcta caagcaatca     180

caatttaagt cagatgaaac agttacccta caacattctg gaaaaaacaa aaagacatgc     240

ttttcatgtc aacttgtttt cactacaagg ttagaaggag aatttcaacc aattttctct     300

aaaacggaag cgcttgaagg tataaaaagt gtcttggata catgtggagg aggacctggc     360

ctattcatga ttactcaagt cataccagat aactcaaacc caattctaaa catcactcaa     420

ccgttagtga tccaagtacg aaaagggagc ggaaaggatt gcaaggcaaa gattaagagc     480

aaaaattccc aatcaaacga aatagatgct tctttgttgg aatcaaacaa taccggattc     540

attctctcaa actctggagt ttcagatgag accgataaga aagatcccag gaatcctact     600

cgcagctttt ttgttccaat cataaggagt taa                                  633
```

```
<210> SEQ ID NO 364
<211> LENGTH: 210
<212> TYPE: PRT
<213> ORGANISM: Phakopsora pachyrhizi
<220> FEATURE:
<221> NAME/KEY: VARIANT
<222> LOCATION: (1)..(210)
<223> OTHER INFORMATION: ta01247.01_phapa

<400> SEQUENCE: 364

Met Asn Met Arg Arg Thr Val Thr Ser Phe Gly Leu Lys Ser Leu Thr
1               5                   10                  15

Ile Phe Ile Gly Val Trp Leu Gln Leu Ser Thr Phe Ser Ile Ala Thr
            20                  25                  30

Ile Cys Met Ser Arg Lys Ser Ser Leu Asn Pro Lys Ile Leu Ala Ser
        35                  40                  45

Asp Cys Asn Met Val Leu Asp Leu Tyr Lys Gln Ser Gln Phe Lys Ser
    50                  55                  60

Asp Glu Thr Val Thr Leu Gln His Ser Gly Lys Asn Lys Lys Thr Cys
65                  70                  75                  80

Phe Ser Cys Gln Leu Val Phe Thr Thr Arg Leu Glu Gly Glu Phe Gln
                85                  90                  95

Pro Ile Phe Ser Lys Thr Glu Ala Leu Glu Gly Ile Lys Ser Val Leu
            100                 105                 110

Asp Thr Cys Gly Gly Gly Pro Gly Leu Phe Met Ile Thr Gln Val Ile
        115                 120                 125

Pro Asp Asn Ser Asn Pro Ile Leu Asn Ile Thr Gln Pro Leu Val Ile
    130                 135                 140

Gln Val Arg Lys Gly Ser Gly Lys Asp Cys Lys Ala Lys Ile Lys Ser
145                 150                 155                 160

Lys Asn Ser Gln Ser Asn Glu Ile Asp Ala Ser Leu Leu Glu Ser Asn
                165                 170                 175

Asn Thr Gly Phe Ile Leu Ser Asn Ser Gly Val Ser Asp Glu Thr Asp
            180                 185                 190

Lys Lys Asp Pro Arg Asn Pro Thr Arg Ser Phe Phe Val Pro Ile Ile
        195                 200                 205

Arg Ser
    210


<210> SEQ ID NO 365
<211> LENGTH: 633
```

<212> TYPE: DNA
<213> ORGANISM: Phakopsora pachyrhizi
<220> FEATURE:
<221> NAME/KEY: misc_feature
<222> LOCATION: (1)..(633)
<223> OTHER INFORMATION: ta00656.03_phapa

<400> SEQUENCE: 365

```
atgattgcca accccgtcaa ttttgttttc ttgttgagcg tatttctgag ctttcaaatt     60

cagaatgcct caacaaaaag aggtagaggg ggaccgattg cagctctctg ccaaggaaag    120

gagcaaaatg tgaaagttat cgctacttgc agtgaaggaa aaattttatg cgagggtttg    180

gatgaaagtg gtactggaac aatgtcttgt tcagatggag gaaaactttt agaggtaaaa    240

agtgaagaag ccgctcagtg tggcgccaat ccccgttgca agaagttggc gaagggaagt    300

aaagttattg aattaggaaa ggttgtgggt gcagctctag ctgatggcaa gtccctcgca    360

cctggaagca gagcagcagt ccaaacaggg ggtaaagaag gtaaagaagg taaagagggt    420

aaagatgata aaggtggtaa agctgttgat ttggctctgg gcaagggtga tgcaaaagct    480

gctgattcag caaacggggt taaagtagat gtaaaaggca aagagttggc aaatgcgggc    540

aaggaaaaca ataaagagaa tgaggcacag aaagctacag aacctactct caatactcag    600

gctgcttcag gtggagaaga ggtaaaagca tag                                 633
```

<210> SEQ ID NO 366
<211> LENGTH: 210
<212> TYPE: PRT
<213> ORGANISM: Phakopsora pachyrhizi
<220> FEATURE:
<221> NAME/KEY: VARIANT
<222> LOCATION: (1)..(210)
<223> OTHER INFORMATION: ta00656.03_phapa

<400> SEQUENCE: 366

```
Met Ile Ala Asn Pro Val Asn Phe Val Phe Leu Leu Ser Val Phe Leu
1               5                   10                  15

Ser Phe Gln Ile Gln Asn Ala Ser Thr Lys Arg Gly Arg Gly Gly Pro
            20                  25                  30

Ile Ala Ala Leu Cys Gln Gly Lys Glu Gln Asn Val Lys Val Ile Ala
        35                  40                  45

Thr Cys Ser Glu Gly Lys Ile Leu Cys Glu Gly Leu Asp Glu Ser Gly
    50                  55                  60

Thr Gly Thr Met Ser Cys Ser Asp Gly Gly Lys Leu Leu Glu Val Lys
65                  70                  75                  80

Ser Glu Glu Ala Ala Gln Cys Gly Ala Asn Pro Arg Cys Lys Lys Leu
                85                  90                  95

Ala Lys Gly Ser Lys Val Ile Glu Leu Gly Lys Val Val Gly Ala Ala
            100                 105                 110

Leu Ala Asp Gly Lys Ser Leu Ala Pro Gly Ser Arg Ala Ala Val Gln
        115                 120                 125

Thr Gly Gly Lys Glu Gly Lys Glu Gly Lys Glu Gly Lys Asp Asp Lys
    130                 135                 140

Gly Gly Lys Ala Val Asp Leu Ala Leu Gly Lys Gly Asp Ala Lys Ala
145                 150                 155                 160

Ala Asp Ser Ala Asn Gly Val Lys Val Asp Val Lys Gly Lys Glu Leu
                165                 170                 175

Ala Asn Ala Gly Lys Glu Asn Asn Lys Glu Asn Glu Ala Gln Lys Ala
            180                 185                 190
```

```
Thr Glu Pro Thr Leu Asn Thr Gln Ala Ala Ser Gly Gly Glu Glu Val
        195                 200                 205

Lys Ala
    210


<210> SEQ ID NO 367
<211> LENGTH: 627
<212> TYPE: DNA
<213> ORGANISM: Phakopsora pachyrhizi
<220> FEATURE:
<221> NAME/KEY: misc_feature
<222> LOCATION: (1)..(627)
<223> OTHER INFORMATION: ta09267.08_phapa

<400> SEQUENCE: 367

atgcgttcac ttatcgttcc caccctttta tgcgtgctat ttattcataa atcttgcgca      60

accgttcaca ctcagtgcta caactatttt ttacaaaagg atggatgcgt tttctctgca     120

gctgatgaca gaaatcgatg ttctgcagat cccaagccca gtacagccgt cggagtggtt     180

caagcaagca acacaaatgt taaacgtcac actctggcac gacgctatga tactactcta     240

ccatctcctt ctgtgcgtgg tgaagggatt tgcggaaact ataacacagc agaagctgag     300

ggagctagtc tttgggttgg ccctaacccg gatagcacaa accctgaaga agcaggttgg     360

ctcaacaagg gaaagacatc caattgcaac aagcaattat atataataaa ccctcgcacg     420

cgtaaaactg tatacgtgaa tgtcatagac ggtcacgatt ttcagacaac gcagcctgat     480

gttggatgct tccagattgc actcacccaa aataccttcc ttcagcttga tccaacagat     540

gaagaaaaag aaaagggttc cataggatct ctcacatggg acttcaacaa ccttaatggc     600

gctagtcctc aggatggccc tgtctaa                                         627


<210> SEQ ID NO 368
<211> LENGTH: 208
<212> TYPE: PRT
<213> ORGANISM: Phakopsora pachyrhizi
<220> FEATURE:
<221> NAME/KEY: VARIANT
<222> LOCATION: (1)..(208)
<223> OTHER INFORMATION: ta09267.08_phapa

<400> SEQUENCE: 368

Met Arg Ser Leu Ile Val Pro Thr Leu Leu Cys Val Leu Phe Ile His
1               5                   10                  15

Lys Ser Cys Ala Thr Val His Thr Gln Cys Tyr Asn Tyr Phe Leu Gln
            20                  25                  30

Lys Asp Gly Cys Val Phe Ser Ala Ala Asp Asp Arg Asn Arg Cys Ser
        35                  40                  45

Ala Asp Pro Lys Pro Ser Thr Ala Val Gly Val Val Gln Ala Ser Asn
    50                  55                  60

Thr Asn Val Lys Arg His Thr Leu Ala Arg Arg Tyr Asp Thr Thr Leu
65                  70                  75                  80

Pro Ser Pro Ser Val Arg Gly Glu Gly Ile Cys Gly Asn Tyr Asn Thr
                85                  90                  95

Ala Glu Ala Glu Gly Ala Ser Leu Trp Val Gly Pro Asn Pro Asp Ser
            100                 105                 110

Thr Asn Pro Glu Glu Ala Gly Trp Leu Asn Lys Gly Lys Thr Ser Asn
        115                 120                 125

Cys Asn Lys Gln Leu Tyr Ile Ile Asn Pro Arg Thr Arg Lys Thr Val
    130                 135                 140
```

-continued

```
Tyr Val Asn Val Ile Asp Gly His Asp Phe Gln Thr Thr Gln Pro Asp
145                 150                 155                 160

Val Gly Cys Phe Gln Ile Ala Leu Thr Gln Asn Thr Phe Leu Gln Leu
                165                 170                 175

Asp Pro Thr Asp Glu Glu Lys Glu Lys Gly Ser Ile Gly Ser Leu Thr
            180                 185                 190

Trp Asp Phe Asn Asn Leu Asn Gly Ala Ser Pro Gln Asp Gly Pro Val
        195                 200                 205


<210> SEQ ID NO 369
<211> LENGTH: 627
<212> TYPE: DNA
<213> ORGANISM: Phakopsora pachyrhizi
<220> FEATURE:
<221> NAME/KEY: misc_feature
<222> LOCATION: (1)..(627)
<223> OTHER INFORMATION: ta09267.07_phapa

<400> SEQUENCE: 369

atgcgctctc ttatcattcc cgccctttta tgtgtactat ttattcataa atcttgcgca      60

accgttcaca ctcagtgcta caactatttt ttacaaaagg atggatgcgt tttctctgca     120

gctgatgaca gaaatcgatg ttctgcagat cccaagccca gtacagccgt tggagtggtt     180

caagaaagca acaaaaatgt taaaagacac actctggcac gccgttatga tactacttta     240

ccatctcctt ctatacaggg tgaaggaatt tgcggacact atgacacagc aacagctgag     300

ggagccagtc tttgggttgg tcctaaccca ggtagcacaa gacccgagga ggcaggctgg     360

cttaacaggg gaaagacatc taattgcaat aagagattat atgtaataaa ccctcgcaca     420

ggaaaaactg tctacgtaaa ggtcatagac ggccacgatt ttcagacaac acagcctgat     480

gtgggatgct tccagattgc actcacccaa aagacctttc ttgagcttga tccgactgat     540

gaagaaaagg caaaaggtgc cataggatct ctcacatggg acttcgacaa cctgcatgga     600

attagtcctc agcaaggtcc tgtatga                                        627


<210> SEQ ID NO 370
<211> LENGTH: 208
<212> TYPE: PRT
<213> ORGANISM: Phakopsora pachyrhizi
<220> FEATURE:
<221> NAME/KEY: VARIANT
<222> LOCATION: (1)..(208)
<223> OTHER INFORMATION: ta09267.07_phapa

<400> SEQUENCE: 370

Met Arg Ser Leu Ile Ile Pro Ala Leu Leu Cys Val Leu Phe Ile His
1               5                   10                  15

Lys Ser Cys Ala Thr Val His Thr Gln Cys Tyr Asn Tyr Phe Leu Gln
            20                  25                  30

Lys Asp Gly Cys Val Phe Ser Ala Ala Asp Asp Arg Asn Arg Cys Ser
        35                  40                  45

Ala Asp Pro Lys Pro Ser Thr Ala Val Gly Val Val Gln Glu Ser Asn
    50                  55                  60

Lys Asn Val Lys Arg His Thr Leu Ala Arg Arg Tyr Asp Thr Thr Leu
65                  70                  75                  80

Pro Ser Pro Ser Ile Gln Gly Glu Gly Ile Cys Gly His Tyr Asp Thr
                85                  90                  95

Ala Thr Ala Glu Gly Ala Ser Leu Trp Val Gly Pro Asn Pro Gly Ser
            100                 105                 110
```

```
Thr Arg Pro Glu Glu Ala Gly Trp Leu Asn Arg Gly Lys Thr Ser Asn
        115                 120                 125

Cys Asn Lys Arg Leu Tyr Val Ile Asn Pro Arg Thr Gly Lys Thr Val
    130                 135                 140

Tyr Val Lys Val Ile Asp Gly His Asp Phe Gln Thr Thr Gln Pro Asp
145                 150                 155                 160

Val Gly Cys Phe Gln Ile Ala Leu Thr Gln Lys Thr Phe Leu Glu Leu
                165                 170                 175

Asp Pro Thr Asp Glu Glu Lys Ala Lys Gly Ala Ile Gly Ser Leu Thr
            180                 185                 190

Trp Asp Phe Asp Asn Leu His Gly Ile Ser Pro Gln Gln Gly Pro Val
        195                 200                 205


<210> SEQ ID NO 371
<211> LENGTH: 627
<212> TYPE: DNA
<213> ORGANISM: Phakopsora pachyrhizi
<220> FEATURE:
<221> NAME/KEY: misc_feature
<222> LOCATION: (1)..(627)
<223> OTHER INFORMATION: >ta09267.04_phapa

<400> SEQUENCE: 371

atgcgttcac ttatcgttcc caccctttta tgcgtgctat ttattcataa atcttgcgca      60

accgttcaca ctcagtgcta caactatttt ttacaaaagg atggatgcgt tttctctgca     120

gctgatgaca gaaatcgatg ttctgcagat cccaagccca gtacagccgt tggagtggtt     180

caagaaagca acaaaaatgt taaaagacac actctggcac gccgttatga tactacttta     240

ccatctcctt ctatacaggg tgaaggaatt tgcggacact atgacacagc aacagctgag     300

ggagccagtc tttgggttgg tcctaaccca ggtagcacaa gacccgagga ggcaggctgg     360

cttaacaggg gaaagacatc taattgcaat aagagattat atgtaataaa ccctcgcaca     420

ggaaaaactg tctacgtaaa ggtcatagac ggccacgatt ttcagacaac acagcctgat     480

gtgggatgct tccagattgc actcacccaa aagacctttc ttgagcttga tccgactgat     540

gaagaaaagg caaaaggtgc cataggatct ctcacatggg acttcgacaa cctgcatgga     600

attagtcctc agcaaggtcc tgtatga                                         627


<210> SEQ ID NO 372
<211> LENGTH: 208
<212> TYPE: PRT
<213> ORGANISM: Phakopsora pachyrhizi
<220> FEATURE:
<221> NAME/KEY: VARIANT
<222> LOCATION: (1)..(208)
<223> OTHER INFORMATION: ta09267.04_phapa

<400> SEQUENCE: 372

Met Arg Ser Leu Ile Val Pro Thr Leu Leu Cys Val Leu Phe Ile His
1               5                   10                  15

Lys Ser Cys Ala Thr Val His Thr Gln Cys Tyr Asn Tyr Phe Leu Gln
            20                  25                  30

Lys Asp Gly Cys Val Phe Ser Ala Ala Asp Asp Arg Asn Arg Cys Ser
        35                  40                  45

Ala Asp Pro Lys Pro Ser Thr Ala Val Gly Val Val Gln Glu Ser Asn
    50                  55                  60

Lys Asn Val Lys Arg His Thr Leu Ala Arg Arg Tyr Asp Thr Thr Leu
65                  70                  75                  80
```

```
Pro Ser Pro Ser Ile Gln Gly Glu Gly Ile Cys Gly His Tyr Asp Thr
                85                  90                  95

Ala Thr Ala Glu Gly Ala Ser Leu Trp Val Gly Pro Asn Pro Gly Ser
            100                 105                 110

Thr Arg Pro Glu Glu Ala Gly Trp Leu Asn Arg Gly Lys Thr Ser Asn
        115                 120                 125

Cys Asn Lys Arg Leu Tyr Val Ile Asn Pro Arg Thr Gly Lys Thr Val
    130                 135                 140

Tyr Val Lys Val Ile Asp Gly His Asp Phe Gln Thr Thr Gln Pro Asp
145                 150                 155                 160

Val Gly Cys Phe Gln Ile Ala Leu Thr Gln Lys Thr Phe Leu Glu Leu
                165                 170                 175

Asp Pro Thr Asp Glu Glu Lys Ala Lys Gly Ala Ile Gly Ser Leu Thr
            180                 185                 190

Trp Asp Phe Asp Asn Leu His Gly Ile Ser Pro Gln Gln Gly Pro Val
        195                 200                 205


<210> SEQ ID NO 373
<211> LENGTH: 627
<212> TYPE: DNA
<213> ORGANISM: Phakopsora pachyrhizi
<220> FEATURE:
<221> NAME/KEY: misc_feature
<222> LOCATION: (1)..(627)
<223> OTHER INFORMATION: ta09267.05_phapa

<400> SEQUENCE: 373

atgcgttcac ttatcgttcc caccctttta tgcgtgctat ttattcataa atcttgcgca      60

accgttcaca ctcagtgcta caactatttt ttacaaaagg atggatgcgt tttctctgca     120

gctgatgaca gaaatcgatg ttctgcagat cccaagccca gtacagccgt tggagtggtt     180

caagaaagca acaaaaatgt taaaagacac actctggcac gccgttatga tactacttta     240

ccatctcctt ctatacaggg tgaaggaatt tgcggacact atgacacagc aacagctgag     300

ggagccagtc tttgggttgg tcctaaccca ggtagcacaa gacccgagga ggcaggctgg     360

cttaacaggg gaaagacatc taattgcaat aagagattat atgtaataaa ccctcgcaca     420

ggaaaaactg tctacgtaaa ggtcatagac ggccacgatt ttcagacaac acagcctgat     480

gtgggatgct tccagattgc actcacccaa aagacctttc ttgagcttga tccgactgat     540

gaagaaaagg caaaaggtgc cataggatct ctcacatggg acttcgacaa cctgcatgga     600

attagtcctc agcaaggtcc tgtatga                                         627


<210> SEQ ID NO 374
<211> LENGTH: 208
<212> TYPE: PRT
<213> ORGANISM: Phakopsora pachyrhizi
<220> FEATURE:
<221> NAME/KEY: VARIANT
<222> LOCATION: (1)..(208)
<223> OTHER INFORMATION: ta09267.05_phapa

<400> SEQUENCE: 374

Met Arg Ser Leu Ile Val Pro Thr Leu Leu Cys Val Leu Phe Ile His
1               5                   10                  15

Lys Ser Cys Ala Thr Val His Thr Gln Cys Tyr Asn Tyr Phe Leu Gln
            20                  25                  30

Lys Asp Gly Cys Val Phe Ser Ala Ala Asp Asp Arg Asn Arg Cys Ser
        35                  40                  45
```

-continued

```
Ala Asp Pro Lys Pro Ser Thr Ala Val Gly Val Val Gln Glu Ser Asn
    50                  55                  60

Lys Asn Val Lys Arg His Thr Leu Ala Arg Arg Tyr Asp Thr Thr Leu
65                  70                  75                  80

Pro Ser Pro Ser Ile Gln Gly Glu Gly Ile Cys Gly His Tyr Asp Thr
                85                  90                  95

Ala Thr Ala Glu Gly Ala Ser Leu Trp Val Gly Pro Asn Pro Gly Ser
            100                 105                 110

Thr Arg Pro Glu Glu Ala Gly Trp Leu Asn Arg Gly Lys Thr Ser Asn
        115                 120                 125

Cys Asn Lys Arg Leu Tyr Val Ile Asn Pro Arg Thr Gly Lys Thr Val
    130                 135                 140

Tyr Val Lys Val Ile Asp Gly His Asp Phe Gln Thr Thr Gln Pro Asp
145                 150                 155                 160

Val Gly Cys Phe Gln Ile Ala Leu Thr Gln Lys Thr Phe Leu Glu Leu
                165                 170                 175

Asp Pro Thr Asp Glu Glu Lys Ala Lys Gly Ala Ile Gly Ser Leu Thr
            180                 185                 190

Trp Asp Phe Asp Asn Leu His Gly Ile Ser Pro Gln Gln Gly Pro Val
        195                 200                 205
```

<210> SEQ ID NO 375
<211> LENGTH: 627
<212> TYPE: DNA
<213> ORGANISM: Phakopsora pachyrhizi
<220> FEATURE:
<221> NAME/KEY: misc_feature
<222> LOCATION: (1)..(627)
<223> OTHER INFORMATION: ta09267.03_phapa

<400> SEQUENCE: 375

```
atgcgttcac ttatcgttcc caccctttta tgcgtgctat ttattcataa atcttgcgca      60

accgttcaca ctcagtgcta caactatttt ttacaaaagg atggatgcgt tttctctgca     120

gctgatgaca gaaatcgatg ttctgcagat cccaagccca gtacagccgt tggagtggtt     180

caagaaagca acaaaaatgt taaaagacac actctggcac gccgttatga tactacttta     240

ccatctcctt ctatacaggg tgaaggaatt tgcggacact atgacacagc aacagctgag     300

ggagccagtc tttgggttgg tcctaaccca ggtagcacaa gacccgagga ggcaggctgg     360

cttaacaggg gaaagacatc taattgcaat aagagattat atgtaataaa ccctcgcaca     420

ggaaaaactg tctacgtaaa ggtcatagac ggccacgatt ttcagacaac acagcctgat     480

gtgggatgct tccagattgc actcacccaa aagacctttc ttgagcttga tccgactgat     540

gaagaaaagg caaaaggtgc cataggatct ctcacatggg acttcgacaa cctgcatgga     600

attagtcctc agcaaggtcc tgtatga                                         627
```

<210> SEQ ID NO 376
<211> LENGTH: 208
<212> TYPE: PRT
<213> ORGANISM: Phakopsora pachyrhizi
<220> FEATURE:
<221> NAME/KEY: VARIANT
<222> LOCATION: (1)..(208)
<223> OTHER INFORMATION: ta09267.03_phapa

<400> SEQUENCE: 376

```
Met Arg Ser Leu Ile Val Pro Thr Leu Leu Cys Val Leu Phe Ile His
1               5                   10                  15
```

```
Lys Ser Cys Ala Thr Val His Thr Gln Cys Tyr Asn Tyr Phe Leu Gln
            20                  25                  30

Lys Asp Gly Cys Val Phe Ser Ala Ala Asp Asp Arg Asn Arg Cys Ser
        35                  40                  45

Ala Asp Pro Lys Pro Ser Thr Ala Val Gly Val Val Gln Glu Ser Asn
    50                  55                  60

Lys Asn Val Lys Arg His Thr Leu Ala Arg Arg Tyr Asp Thr Thr Leu
65                  70                  75                  80

Pro Ser Pro Ser Ile Gln Gly Glu Gly Ile Cys Gly His Tyr Asp Thr
                85                  90                  95

Ala Thr Ala Glu Gly Ala Ser Leu Trp Val Gly Pro Asn Pro Gly Ser
            100                 105                 110

Thr Arg Pro Glu Glu Ala Gly Trp Leu Asn Arg Gly Lys Thr Ser Asn
        115                 120                 125

Cys Asn Lys Arg Leu Tyr Val Ile Asn Pro Arg Thr Gly Lys Thr Val
    130                 135                 140

Tyr Val Lys Val Ile Asp Gly His Asp Phe Gln Thr Thr Gln Pro Asp
145                 150                 155                 160

Val Gly Cys Phe Gln Ile Ala Leu Thr Gln Lys Thr Phe Leu Glu Leu
                165                 170                 175

Asp Pro Thr Asp Glu Glu Lys Ala Lys Gly Ala Ile Gly Ser Leu Thr
            180                 185                 190

Trp Asp Phe Asp Asn Leu His Gly Ile Ser Pro Gln Gln Gly Pro Val
        195                 200                 205
```

<210> SEQ ID NO 377
<211> LENGTH: 614
<212> TYPE: DNA
<213> ORGANISM: Phakopsora pachyrhizi
<220> FEATURE:
<221> NAME/KEY: misc_feature
<222> LOCATION: (1)..(614)
<223> OTHER INFORMATION: ta01408.01

<400> SEQUENCE: 377

```
atggaaatga ggattttgct ttttgtttgt ggttgtttct tagctgactc ttctttttca      60

tctctttggc atagttttga agcagcatca agagaagatc ttcaaggcct ttctcataac     120

atcgaagctc caagtgatat cttggaatat aaacatttcc taaagccaaa aaccattcct     180

acatcattcg attctggagt tataattgag caagcacctt tattatttag taaagctgac     240

ttttcaacag aaaaatacgg tttaaatgaa aaaagcctcg cacgcagctc aggcgttgta     300

cccaaagcag cgatgaaaga tggtgaaaag ggctataaca gcatatgtta ctcaaattcg     360

gataaagctc aaatttcaaa aggaaaaggt caattatatt acaactgtaa caatttttta     420

ccaactgttc ctgaaattcg ccagaattat tttgatccaa tagaacaatg cctaaatcaa     480

cacaagttta atggagaata tttaaatagg ctgcgaaaca accaattaga aagaccaact     540

gcacaattat cgggcattaa gcctttgatc aatagcatac ctcccggtaa caacgaagaa     600

tctgcccctg gttt                                                        614
```

<210> SEQ ID NO 378
<211> LENGTH: 204
<212> TYPE: PRT
<213> ORGANISM: Phakopsora pachyrhizi
<220> FEATURE:
<221> NAME/KEY: VARIANT
<222> LOCATION: (1)..(204)
<223> OTHER INFORMATION: ta01408.01_phapa

```
<400> SEQUENCE: 378

Met Glu Met Arg Ile Leu Leu Phe Val Cys Gly Cys Phe Leu Ala Asp
1               5                   10                  15

Ser Ser Phe Ser Ser Leu Trp His Ser Phe Glu Ala Ala Ser Arg Glu
            20                  25                  30

Asp Leu Gln Gly Leu Ser His Asn Ile Glu Ala Pro Ser Asp Ile Leu
        35                  40                  45

Glu Tyr Lys His Phe Leu Lys Pro Lys Thr Ile Pro Thr Ser Phe Asp
    50                  55                  60

Ser Gly Val Ile Ile Glu Gln Ala Pro Leu Leu Phe Ser Lys Ala Asp
65                  70                  75                  80

Phe Ser Thr Glu Lys Tyr Gly Leu Asn Glu Lys Ser Leu Ala Arg Ser
                85                  90                  95

Ser Gly Val Val Pro Lys Ala Ala Met Lys Asp Gly Glu Lys Gly Tyr
            100                 105                 110

Asn Ser Ile Cys Tyr Ser Asn Ser Asp Lys Ala Gln Ile Ser Lys Gly
        115                 120                 125

Lys Gly Gln Leu Tyr Tyr Asn Cys Asn Asn Phe Leu Pro Thr Val Pro
    130                 135                 140

Glu Ile Arg Gln Asn Tyr Phe Asp Pro Ile Glu Gln Cys Leu Asn Gln
145                 150                 155                 160

His Lys Phe Asn Gly Glu Tyr Leu Asn Arg Leu Arg Asn Asn Gln Leu
                165                 170                 175

Glu Arg Pro Thr Ala Gln Leu Ser Gly Ile Lys Pro Leu Ile Asn Ser
            180                 185                 190

Ile Pro Pro Gly Asn Asn Glu Glu Ser Ala Pro Gly
        195                 200
```